United States Patent
Coyle et al.

(10) Patent No.: US 11,104,720 B2
(45) Date of Patent: Aug. 31, 2021

(54) NUCLEIC ACIDS ENCODING A TN3 SCAFFOLD COMPRISING A CD40L-SPECIFIC MONOMER SUBUNIT

(71) Applicant: Viela Bio, Inc., Gaithersburg, MD (US)

(72) Inventors: Anthony Coyle, Boston, MA (US); Manual Baca, Gaithersburg, MD (US); Thomas Thisted, Gaitherburg, MD (US); Stacey Drabic, Gaithersburg, MD (US); Luba Grinberg, Gaithersburg, MD (US); Shabazz Novarra, Gaithersburg, MD (US); Vaheh Oganesyan, Gaithersburg, MD (US); Ronald Herbst, Gaithersburg, MD (US); David Kenneth Spencer, Gaithersburg, MD (US)

(73) Assignee: VIELA BIO, INC., Gaithersburg, MD (US)

(*) Notice: Subject to any disclaimer, the term of this patent is extended or adjusted under 35 U.S.C. 154(b) by 533 days.

(21) Appl. No.: 15/993,964

(22) Filed: May 31, 2018

(65) Prior Publication Data
US 2018/0312572 A1    Nov. 1, 2018

Related U.S. Application Data

(62) Division of application No. 14/347,016, filed as application No. PCT/US2012/059477 on Oct. 10, 2012, now Pat. No. 10,000,553.

(60) Provisional application No. 61/546,028, filed on Oct. 11, 2011.

(51) Int. Cl.
| C12N 15/11 | (2006.01) |
| C12N 5/10 | (2006.01) |
| C07K 14/78 | (2006.01) |
| C07K 16/28 | (2006.01) |
| A61K 38/39 | (2006.01) |

(52) U.S. Cl.
CPC .......... *C07K 14/78* (2013.01); *C07K 16/2875* (2013.01); *A61K 38/39* (2013.01); *C07K 2318/20* (2013.01); *C07K 2319/21* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 4,703,039 A | 10/1987 | Hawiger et al. |
| 5,474,981 A | 12/1995 | Leder et al. |
| 5,605,793 A | 2/1997 | Stemmer |
| 5,624,821 A | 4/1997 | Winter et al. |
| 5,747,035 A | 5/1998 | Presta et al. |
| 5,830,650 A | 11/1998 | Crea |
| 5,830,721 A | 11/1998 | Stemmer et al. |
| 5,866,344 A | 2/1999 | Georgiou |
| 5,869,046 A | 2/1999 | Presta et al. |
| 5,922,545 A | 7/1999 | Mattheakis et al. |
| 6,194,550 B1 | 2/2001 | Gold et al. |
| 6,699,658 B1 | 3/2004 | Wittrup et al. |
| 6,737,056 B1 | 5/2004 | Presta |
| 6,951,725 B2 | 10/2005 | Kurz et al. |
| 7,022,479 B2 | 4/2006 | Wagner |
| 7,063,943 B1 | 6/2006 | McCafferty et al. |
| 7,078,197 B2 | 7/2006 | Kurz et al. |
| 7,083,784 B2 | 8/2006 | Dall et al. |
| 7,195,880 B2 | 3/2007 | Lohse et al. |
| 10,000,553 B2 | 6/2018 | Coyle et al. |
| 2008/0004206 A1 | 1/2008 | Rosen et al. |
| 2009/0176654 A1 | 7/2009 | Cappuccilli et al. |
| 2010/0098730 A1 | 4/2010 | Lowman et al. |
| 2010/0298541 A1 | 11/2010 | Wu et al. |

FOREIGN PATENT DOCUMENTS

| CN | 101932720 A | 12/2010 |
| EP | 0439095 A2 | 7/1991 |
| JP | 2011501951 A | 1/2011 |
| WO | WO 9114438 A1 | 10/1991 |
| WO | WO 9321232 A1 | 10/1993 |
| WO | WO 9632478 A1 | 10/1996 |
| WO | WO 9743316 A1 | 11/1997 |
| WO | WO 9943713 A1 | 9/1999 |
| WO | WO 0009560 A2 | 2/2000 |
| WO | WO 2006023144 A2 | 3/2006 |
| WO | WO 2009058379 A2 | 5/2009 |
| WO | WO 2009083804 A2 | 7/2009 |
| WO | WO 2011051466 A1 | 5/2011 |
| WO | WO 2011051489 A2 | 5/2011 |

(Continued)

OTHER PUBLICATIONS

Albulescu et al. (Sep. 28, 2016) "Safety, Tolerability, and Dose-Dependent Inhibition of T-Cell-Dependent Antibody Response with MEDI4920, a Novel, Engineered CD40L Antagonist: Results of a Single-Ascending Dose Study in Healthy Volunteers", 2016 ACR/ARHP Annual Meeting, 3 Pages.

(Continued)

*Primary Examiner* — Phillip Gambel
(74) *Attorney, Agent, or Firm* — Cooley LLP

(57) ABSTRACT

The present invention provides Tenascin-3 FnIII domain-based scaffolds that specifically bind to CD40L. The invention further provides engineered variants with increased affinity for the target. The present invention is also related to engineered scaffolds as prophylactic, diagnostic, or therapeutic agents, in particular for therapeutic uses against SLE and other autoimmune diseases and conditions.

22 Claims, 52 Drawing Sheets

Specification includes a Sequence Listing.

(56) References Cited

FOREIGN PATENT DOCUMENTS

| WO | WO 2011103076 A1 | 8/2011 |
|---|---|---|
| WO | WO 2011130324 A1 | 10/2011 |
| WO | WO 2011130328 A1 | 10/2011 |
| WO | 2013/005745 A2 | 4/2013 |

OTHER PUBLICATIONS

Albulescu et al. (Oct. 4, 2018) "VI 84920, a Novel, Engineered CD40L Antagonist Decreased Disease Activity and Improved Biomarkers of Immune Activation in Patients with Active Rheumatoid Arthritis in a Phase 1 b, Multiple-Ascending Dose Proof-of-Concept Study", 2018 ACR/ARHP Annual Meeting, 3 Pages.
Karnell et al. (Apr. 24, 2019) "A CD40L-Targeting Protein Reduces Autoantibodies and Improves Disease Activity in Patients with AutoImmunity", Science Translational Medicine, 11(489):13 Pages.
Vazquez-Lombardi et al. (Oct. 2015) "Challenges and Opportunities for Non-Antibody Scaffold Drugs", Drug Discovery Today, 20(10):1271-1283.
Abcouwer, Steven F. "Müller Cell-Microglia Cross Talk Drives Neuroinflammation in Diabetic Retinopathy." Diabetes 66.2 (2017): 261-263.
Andersen, Jan Terje, et al. "Cross-species binding analyses of mouse and human neonatal Fc receptor show dramatic differences in immunoglobulin G and albumin binding." Journal of Biological Chemistry 285.7 (2010): 4826-4836.
Attwood, Teresa K. "The Babel of bioinformatics." Science 290. 5491 (2000): 471-473.
Burkly et al. "Advances in Experimental Medicine and Biology." Klower Academic/Plenum Publishers 489 (2001): 135-152.
Davidson, A., L. Budha, and B. Reddy. "The effect of anti CD40L on B cells in human systemic lupus erythematosus." Arthritis Rheum 43.271 (2000): 1229.
Definition of 'Retinopathies' by Medical Dictionary, Google, Jun. 29, 2017, 4 pages. Accessible on the Internet at URL: http://medical-dictionary.thefreedictionary.com/Retinopathies.
Elgueta, Raul, et al. "Molecular mechanism and function of CD40/CD40L engagement in the immune system." Immunological reviews 229.1 (2009): 152-172.
Emanuel, Stuart L., et al. "A fibronectin scaffold approach to bispecific inhibitors of epidermal growth factor receptor and insulin-like growth factor-I receptor." MAbs, 3.1 (2011):38-48.
Fell, H. P., et al. "Genetic construction and characterization of a fusion protein consisting of a chimeric F (ab') with specificity for carcinomas and human IL-2." The Journal of immunology 146.7 (1991): 2446-2452.
Gillies, Stephen D., et al. "Antibody-targeted interleukin 2 stimulates T-cell killing of autologous tumor cells." Proceedings of the National Academy of Sciences 89.4 (1992): 1428-1432.
International Preliminary Report on Patentability corresponding to International Patent Application No. PCT/US2012/059477, dated Apr. 15, 2014, 9 pages.
International Search Report corresponding to International Patent Application No. PCT/US2012/059477, dated Mar. 21, 2013, 5 pages.
Kalled, Susan L., et al. "Anti-CD40 ligand antibody treatment of SNF1 mice with established nephritis: preservation of kidney function." The Journal of Immunology 160.5 (1998): 2158-2165.
Karpusas, Michael, et al. "Structure of CD40 ligand in complex with the Fab fragment of a neutralizing humanized antibody." Structure 9.4 (2001): 321-329.
Law, Che-Leung, and Iqbal S. Grewal. "Therapeutic interventions targeting CD40L (CD154) and CD40: the opportunities and challenges." Therapeutic targets of the TNF superfamily. 647 (2009): 8-36.
Liossis, Stamatis-Nick C., and Petros P. Sfikakis. "Costimulation blockade in the treatment of rheumatic diseases." BioDrugs 18.2 (2004): 95-102.
Mahmoud, Tamer I., et al. "Autoimmune manifestations in aged mice arise from early-life immune dysregulation." Science translational medicine 8.361 (2016): 1-27.
Mohan, Chandra, et al. "Interaction between CD40 and its ligand gp39 in the development of murine lupus nephritis." The Journal of Immunology 154.3 (1995): 1470-1480.
Naramura, Mayumi, et al. "Mechanisms of cellular cytotoxicity mediated by a recombinant antibody-IL2 fusion protein against human melanoma cells." Immunology letters 39.1 (1993): 91-99.
National Center for Biotechnology Information "CD40 ligand [*Homo sapiens*]," GenBank Accession No. NP_000065.1, May 12, 2019, 3 pages.
National Center for Biotechnology Information "RecName: Full=CD40 ligand; Short=CD40-L; AltName: Full=T-cell antigen Gp39; AltName: Full=TNF-related activation protein; Short=TRAP; AltName: Full=Tumor necrosis factor ligand superfamily member 5; AltName: CD_antigen=CD154; Contains: RecName: Full=CD40 ligan . . . ," UniProtKB/Swiss-Prot Accession No. P29965.1, Jul. 3, 2019, 10 pages.
Peters, Anna L., Laura L. Stunz, and Gail A. Bishop. "CD40 and autoimmunity: the dark side of a great activator." Seminars in immunology. 21.5. (2009): 293-300.
Schellenberger, Volker, et al. "A recombinant polypeptide extends the in vivo half-life of peptides and proteins in a tunable manner." Nature biotechnology 27.12 (2009): 1186-1190.
Schuler, Walter, et al. "Efficacy and safety of ABI793, a novel human anti-human CD154 monoclonal antibody, in cynomolgus monkey renal allotransplantation1." Transplantation 77.5 (2004): 717-726.
Scott, Jamie K., and George P. Smith. "Searching for peptide ligands with an epitope library." Science 249.4967 (1990): 386-390.
Sickmeier, Megan, et al. "DisProt: the database of disordered proteins." Nucleic acids research 35.1 (2006): D786-D793.
Skolnick, Jeffrey, and Jacquelyn S. Fetrow. "From genes to protein structure and function: novel applications of computational approaches in the genomic era." Trends in biotechnology 18.1 (2000): 34-39.
Supplementary European Search Report corresponding to European Patent Application No. EP 12840074.4, dated Jun. 22, 2015, 2 pages.
Written Opinion corresponding to International Patent Application No. PCT/US2012/059477, dated Mar. 12, 2013, 8 pages.
Wu Herren, et al. "Stepwise in vitro affinity maturation of Vitaxin, an $\alpha v \beta 3$-specific humanized mAb." Proceedings of the National Academy of Sciences 95.11 (1998): 6037-6042.
Yellin, Michael J., et al. "Functional interactions of T cells with endothelial cells: the role of CD40L-CD40-mediated signals." Journal of Experimental Medicine 182.6 (1995): 1857-1864.
Zhao, Hong Liang, et al. "Elimination of the free sulfhydryl group in the human serum albumin (HSA) moiety of human interferon-$\alpha$2b and HSA fusion protein increases its stability against mechanical and thermal stresses." European Journal of Pharmaceutics and Biopharmaceutics 72.2 (2009): 405-411.

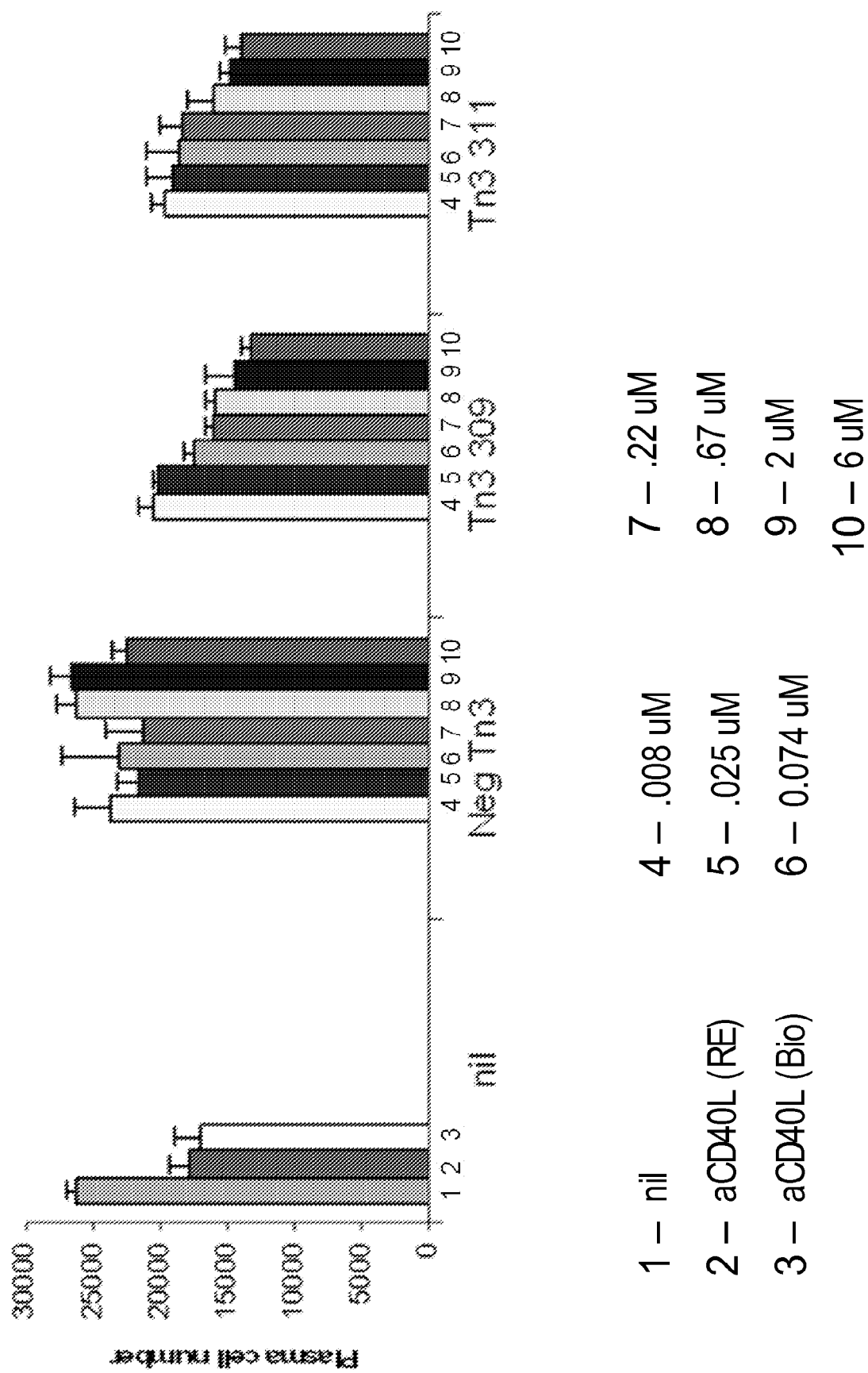

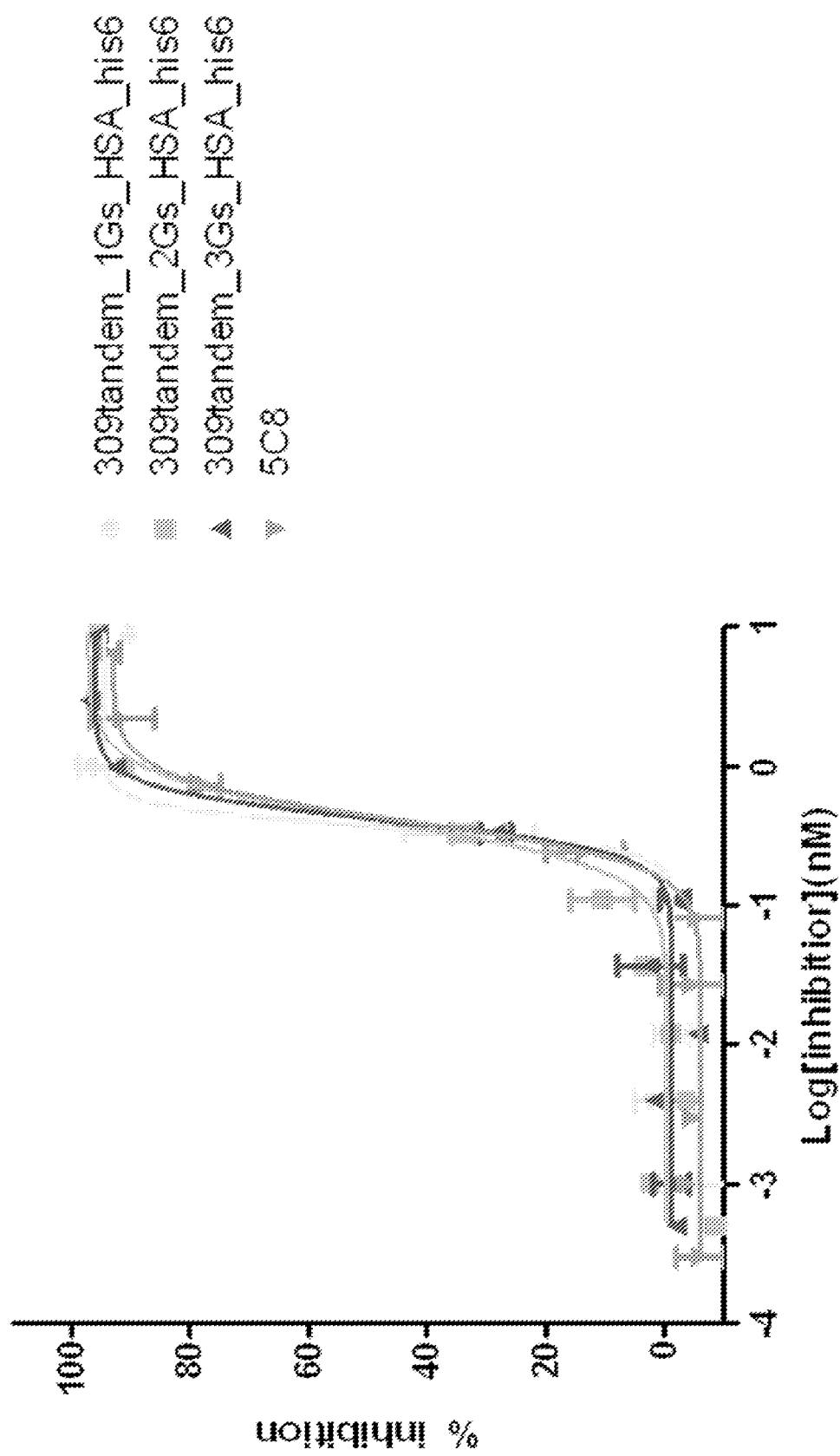

BC loop

| | | BC loop | | |
|---|---|---|---|---|
| 309 | IEVKDVTDTALITW | SDEFGHXDG | CELTYGIKDVPGDRTTID | 42 |
| 309FGwt | IEVKDVTDTALITW | SDEFGHYDG | CELTYGIKDVPGDRTTID | 42 |
| 340 | IEVKDVTDTALITW | SDDFDNYEW | CELTYGIKDVPGDRTTID | 42 |
| 341 | IEVKDVTDTALITW | SDDFADYVW | CELTYGIKDVPGDRTTID | 42 |
| 342 | IEVKDVTDTALITW | SDDFGEYVW | CELTYGIKDVPGDRTTID | 42 |
| 343 | IEVKDVTDTALITW | LDDWGSYHV | CELTYGIKDVPGDRTTID | 42 |
| 344 | IEVKDVTDTALITW | SDEVGDNVV | CELTYGIKDVPGDRTTID | 42 |
| 345 | IEVKDVTDTALITW | SDDFAEYVV | CELTYGIKDVPGDRTTID | 42 |
| 346 | IEVKDVTDTALITW | SDDFEEYVW | CELTYGIKDVPGDRTTID | 42 |
| 347 | IEVKDVTDTALITW | SDEVGQYVG | CELTYGIKDVPGDRTTID | 42 |
| 348 | IEVKDVTDTALITW | SDDIGLYVW | CELTYGIKDVPGDRTTID | 42 |
| 349 | IEVKDVTDTALITW | SDEHAEFIG | CELTYGIKDVPGDRTTID | 42 |
| consensus | IEVKDVTDTALITW | XDXXXXXXX | CELTYGIKDVPGDRTTID | 42 |

Fig. 11A

| | | | | | | | | | | | DE loop | | | | | | | | | | | | FG loop | | | | | | | | |
|---|---|---|---|---|---|---|---|---|---|---|---|---|---|---|---|---|---|---|---|---|---|---|---|---|---|---|---|---|---|---|---|
| 309 | L | W | W | H | S | A | W | Y | S | I | G | N | L | K | P | D | T | E | Y | E | V | S | L | I | C | Y | T | D | Q | E | A | G | N | P | A | K | E | T | F | T | T | 83 |
| 309FGwt | L | W | W | H | S | A | W | Y | S | I | G | N | L | K | P | D | T | E | Y | E | V | S | L | I | C | R | R | G | D | M | S | S | N | P | A | K | E | T | F | T | T | 83 |
| 340 | L | W | Y | M | A | W | Y | S | I | G | N | L | K | P | D | T | E | Y | E | V | S | L | I | C | R | R | G | D | M | S | S | N | P | A | K | E | T | F | T | T | 83 |
| 341 | L | W | W | H | S | A | W | Y | S | I | G | N | L | K | P | D | T | E | Y | E | V | S | L | I | C | R | R | G | D | M | S | S | N | P | A | K | E | T | F | T | T | 83 |
| 342 | L | W | Y | H | H | A | W | Y | S | I | G | N | L | K | P | D | T | E | Y | E | V | S | L | I | C | R | R | G | D | M | S | S | N | P | A | K | E | T | F | T | T | 83 |
| 343 | L | W | Y | H | Q | A | W | Y | S | I | G | N | L | K | P | D | T | E | Y | E | V | S | L | I | C | R | R | G | D | M | S | S | N | P | A | K | E | T | F | T | T | 83 |
| 344 | L | W | Y | H | M | A | W | Y | S | I | G | N | L | K | P | D | T | E | Y | E | V | S | L | I | C | R | R | G | D | M | S | S | N | P | A | K | E | T | F | T | T | 83 |
| 345 | L | W | W | H | S | A | W | Y | S | I | G | N | L | K | P | D | T | E | Y | E | V | S | L | I | C | R | R | G | D | M | S | S | N | P | A | K | E | T | F | T | T | 83 |
| 346 | L | W | Y | H | M | A | W | Y | S | I | G | N | L | K | P | D | T | E | Y | E | V | S | L | I | C | R | R | G | D | M | S | S | N | P | A | K | E | T | F | T | T | 83 |
| 347 | L | W | Y | H | M | A | W | Y | S | I | G | N | L | K | P | D | T | E | Y | E | V | S | L | I | C | R | R | G | D | M | S | S | N | P | A | K | E | T | F | T | T | 83 |
| 348 | L | W | F | H | Q | A | W | Y | S | I | G | N | L | K | P | D | T | E | Y | E | V | S | L | I | C | R | R | G | D | M | S | S | N | P | A | K | E | T | F | T | T | 83 |
| 349 | L | W | W | H | S | A | W | Y | S | I | G | N | L | K | P | D | T | E | Y | E | V | S | L | I | C | R | R | G | D | M | S | S | N | P | A | K | E | T | F | T | T | 83 |
| consensus | L | W | X | H | X | A | X | Y | S | I | G | N | L | K | P | D | T | E | Y | E | V | S | L | I | C | R | X | G | D | M | S | S | N | P | A | K | E | T | F | T | T | 83 |

```
MIETYNQTSP RSAATGLPIS MKIEMYLLTV FLITQMIGSA LFAVILHRRL DKIEDERNLH  60
EDEVFMKTIQ RCNTGERSLS LLNCEEIKSQ FEGFVKDIML NKEETNKENS FEMQKGDQNP 120
QIAAHVISEA SSNTTSVYLQW AEKGYFTISN LVTLENGKQ LTVKRQGLYY IYAQVTFCSN 180
REASSQAPFI ASLCLKSPGR FERTLLRAAN THSSAKPCGQ QSIHLGGVFE LQPGASVFVN 240
VTDPSQVSHG TGFTSFGLLK L 261
```

Fig. 18A

MIETYNQTSP RSAATGLPIS MKIFMYLLTV FLITQMIGSA LFAVYLHRPL DKIEDERNLH 60

EDFVFMKTIQ RCNTGERSLS LLNCEEIKSQ FEGFVKDIML NKEETKKENS FEMQKGDQNP 120

QIAAHVISEA SSKTTSVLQW AEKGYYTMSN NLVTLENGKQ LTVKRQGLYY IYAQVTFCSN 180

REASDAPFI ASLCLKSPGR FERILLRAAN THSSAKPCGQ QSIHLGGVFE LQPGASVFVN 240

VTDPSQVSHG GFTSFGLLKL 261

Fig. 18B

NUCLEIC ACIDS ENCODING A TN3 SCAFFOLD COMPRISING A CD40L-SPECIFIC MONOMER SUBUNIT

REFERENCE TO RELATED APPLICATIONS

This application is a divisional of U.S. patent application Ser. No. 14/347,016, filed Mar. 25, 2014, which is a U.S. National Stage Application of International Application Number PCT/US2012/059477, filed Oct. 10, 2012, which claims the benefit of priority of U.S. Provisional Application 61/546,028 filed on Oct. 11, 2011. Each of the above-referenced applications are incorporated herein by reference in their entireties.

REFERENCE TO SEQUENCE LISTING

This application incorporates by reference a Sequence Listing submitted with the application via EFS-Web as a test filed entitled "CD40L-101WO1_SL.txt" created on Oct. 3, 2012 and having a size of 232 kilobytes.

BACKGROUND OF THE INVENTION

Field of the Invention

The present invention relates in general to the field of antibody mimetics, specifically to scaffolds derived from the third fibronectin type III domain of human Tenascin C useful, for example, for the generation of products having novel binding characteristics. In particular, the invention relates to CD40L-specific Tn3 scaffolds, methods of making such scaffolds, and methods of use for diagnosis and treatment of systemic lupus erythematosus and other autoimmune and/or inflammatory disorders.

Background Art

This invention relates to CD40L-specific protein scaffolds that bind to CD40L, useful, for example, for the treatment of autoimmune and/or inflammatory disorders.

Biomolecules capable of specific binding to a desired target epitope are of great importance as therapeutics, research, and medical diagnostic tools. A well known example of this class of molecules is the antibody. Antibodies can be selected that bind specifically and with affinity to almost any structural epitope. However, classical antibodies are structurally complex heterotetrameric molecules with are difficult to express in simple eukaryotic systems. As a result, most antibodies are produced using complex and expensive mammalian cell expression systems.

Proteins having relatively defined three-dimensional structures, commonly referred to as protein scaffolds, may be used as reagents for the design of engineered products. One particular area in which such scaffolds are useful is the field of antibody mimetic design. Antibody mimetics, i.e., small, non-antibody protein therapeutics, capitalize on the advantages of antibodies and antibody fragments, such as high affinity binding of targets and low immunogenicity and toxicity, while avoiding some of the shortfalls, such as the tendency for antibody fragments to aggregate and be less stable than full-length IgGs.

These drawbacks can be addressed by using antibody fragments created by the removal of parts of the antibody native fold. However, this often causes aggregation when amino acid residues which would normally be buried in a hydrophobic environment such as an interface between variable and constant domain become exposed to the solvent. One example of a scaffold-based antibody mimetic is based on the structure of a Fibronectin type III domain (FnIII), a domain found widely across phyla and protein classes, such as in mammalian blood and structural proteins. The design and use of FnIII scaffolds derived from the third FnIII domain of human tenascin C is described in PCT applications PCT/US2011/032184 and PCT/US2011/032188, both of which are herein incorporated by reference in their entireties.

CD40L is a member of the TNF family of molecules which is primarily expressed on activated T cells (including Th0, Th1, and Th2 subtypes, and forms homotrimers similar to other members of this family. Further, CD40L has also been found expressed on Mast cells, and activated basophils and eosinophils. CD40L binds to the CD40 receptor (CD40R) on antigen-presenting cells (APC), which leads to many effects depending on the target cell type. In general, CD40L plays the role of a costimulatory molecule and induces activation in APC in association with T cell receptor stimulation by MHC molecules on the APC.

Signaling through the CD40 receptor by CD40L initiates a cascade of events that result in the activation of the CD40 receptor-bearing cells and optimal CD4+ T cell priming. More specifically, the cognate interaction between CD40L and the CD40 receptor promotes the differentiation of B cells into antibody secreting cells and memory B cells (Burkly, In Adv. Exp. Med. Bio., Vol. 489., D. M. Monroe, U. Hedner, M. R. Hoffman, C. Negrier, G. F. Savidge, and G. C. I. White, eds. Klower Academic/Plenum Publishers, 2001, p. 135). Additionally, the interaction between CD40L and the CD40 receptor promotes cell-mediated immunity through the activation of macrophages and dendritic cells and the generation of natural killer cells and cytotoxic T lymphocytes (see Burkly, supra).

The interaction between CD40L and the CD40 receptor has been shown to be important in several experimentally induced autoimmune diseases, such as collagen-induced arthritis, experimental allergic encephalomyelitis, oophoritis, colitis, drug-induced lupus nephritis. Specifically, it has been shown that disease induction in all of these models can be blocked with CD40L antagonists at the time of antigen administration. The blockade of disease using anti-CD40L antagonists has also been seen in animal models of spontaneous autoimmune disease, including insulin-dependent diabetes and lupus nephritis, as well as in graft-vs-host disease, transplant, pulmonary fibrosis, and atherosclerosis disease models.

Disruption of the CD40L/CD40R pathway via CD40L blockade has been shown to be beneficial in many autoimmune mediated diseases (for example, but not limited to systemic lupus erythermatosis (SLE), rheumatoid arthritis (RA), multiple sclerosis (MS), inflammatory bowel disease (IBD) and allograft rejection. For example, treatment with anti-CD40L antibodies prevented or improved nephritis in a collagen-induced arthritis mouse model (Mohan et al. J. Immuno. 154:1470). Additionally, anti-CD40L antibodies preserved renal function in SNF1 mice with established nephritis. (Kalled et al. J. Immuno. 160:2158). CD40L levels correlate closely with clinical disease severity (i.e., reduction of inflammation), and damage in target tissue in both non-humans and humans.

SLE is a progressive and sometimes fatal autoimmune disease. The diverse presentations of lupus range from rash and arthritis through anemia and thrombocytopenia to even psychosis. There is clear evidence showing that many arms of the immune system are involved in the inflammatory process leading to kidney, skin, brain disease and thrombosis. One characteristic feature of SLE is the loss of B cell tolerance and autoantibodies are prominent in patients with this disease. In lupus kidney disease, anti-double-stranded DNA autoantibodies can form antibody nucleosome complexes and settle in the renal glomerular basement membrane. These immune complexes in turn activate complement, which can lead to glomerulonephritis.

Expression of CD40R as well as CD40L has been found elevated in patients with SLE. The increased costimulatory signal likely contributes to the pathological inflammatory response found in the SLE. SLE T cells have spontaneously increased activation associated with a reduced threshold of activation to self-antigens. Further, these cells are hyporesponsive to further antigenic stimulation, are resistant to apoptosis, have increased survival after activation and have many altered intracellular signaling pathways. Following CD40R activation on APCs by T cell CD40L, both APC and T cells become activated, produce cytokines and in SLE contribute to the production of pathogenic autoantibodies and tissue injury (lupus nephritis). Blockade of the CD40R/CD40L pathway is effective, alone or in combination, in blocking disease in lupus-prone mice. In patients with SLE, a humanized anti-CD40L antibody reduced anti-dsDNA and B cells, proteinuria, and improved SLE disease severity.

However, targeting CD40L with traditional antibodies has raised significant safety concerns. For example, a study with anti-CD40L antibody 5c8 (BIOGEN®) in patients suffering with chronic refractory idiopathic thrombocytopenic purpura (ITP) was placed on hold because of reported thromboebolic complications (Davidson et al. *Arth Rheu*, 43:S271). Further, additional trials with alternative antibodies directed against CD40L gave rise to other thrombotic related complications (Davis et al. *Arth Rheu*, 43:S281; Schuler, *Transplantation*, 77:717). Given the complications with antibody-directed antagonism of CD40L, there is an unmet need to target and antagonize CD40L with a non-antibody alternative. Thus, targeting CD40L with a Tn3-based scaffold is an attractive alternative by avoiding Fab2 and/or Fc-mediated platelet aggregation and the downstream side effects.

Citation or discussion of a reference herein shall not be construed as an admission that such is prior art to the present invention.

SUMMARY OF THE INVENTION

The invention provides a Tn3 scaffold comprising a CD40L-specific monomer subunit, wherein the monomer subunit comprises seven beta strands designated A, B, C, D, E, F, and G, and six loop regions designated AB, BC, CD, DE, EF, and FG, and wherein the Tn3 scaffold specifically binds to CD40L. In some embodiments, the Tn3 scaffold comprises a single CD40L-specific monomer subunit. In other embodiments, the Tn3 scaffold comprises two CD40L-specific monomer subunits connected in tandem. In some specific embodiments, the Tn3 scaffold comprises two CD40L-specific monomer subunits which are directly connected.

In some embodiments, two CD40L-specific monomer subunits are connected by a linker. In other embodiments, the linker comprises a peptide linker, which can be a flexible peptide linker. In some embodiments, the peptide linker comprises a $(G_mX)_n$ sequence wherein X is Serine (S), Alanine (A), Glycine (G), Leu (L), Isoleucine (I), or Valine (V); m and n are integer values; m is 1, 2, 3 or 4; and, n is 1, 2, 3, 4, 5, 6, or 7. In some embodiments, the peptide linker comprises SEQ ID NO: 131, SEQ ID NO: 132, SEQ ID NO: 142 or SEQ ID NO: 143.

In some embodiments, the binding of a Tn3 scaffold comprising two CD40L-specific monomer subunits to CD40L is improved over that of a Tn3 scaffold comprising a single CD40L-specific monomer subunit. In other embodiments, the binding of a Tn3 scaffold comprising two CD40L-specific monomer subunits to CD40L improves the action on the target over that of a Tn3 scaffold comprising a single CD40L-specific monomer subunit. In other embodiments, the improvement in the binding of the Tn3 scaffold to CD40L is an improvement in binding affinity, an improvement in binding avidity, or both. In certain embodiments, the binding affinity of a Tn3 scaffold comprising two CD40L-specific monomer subunits to CD40L and the Tn3 scaffold protein stability are improved over those of a Tn3 scaffold comprising a single CD40L-specific monomer subunit. In some embodiments, the binding avidity of a Tn3 scaffold comprising two CD40L-specific monomer subunits for CD40L and the Tn3 scaffold protein stability are improved over those of a Tn3 scaffold comprising a single CD40L-specific monomer subunit.

In some embodiments, at least one CD40L-specific monomer subunit in a Tn3 scaffold is bound to a linker, or to a heterologous moiety. In other embodiments, a linker or a heterologous moiety in a Tn3 scaffold is conjugated to the N-terminus or the C-terminus of a CD40L-specific monomer subunit. In certain embodiments, the linker bound to a CD40L-specific monomer subunit in a Tn3 scaffold comprises a peptide linker, which in some embodiments can be a flexible peptide linker. This peptide linker can comprise in certain embodiments a $(GmX)_n$ sequence wherein X is Serine (S), Alanine (A), Glycine (G), Leucine (L), Isoleucine (I), or Valine (V); m and n are integers; m is 1, 2, 3 or 4; and, n is 1, 2, 3, 4, 5, 6, or 7. In some embodiments, the peptide linker bound to a CD40L-specific monomer subunit in a Tn3 scaffold comprises SEQ ID NO: 131, SEQ ID NO: 132, SEQ ID NO: 142, or SEQ ID NO: 143.

In some embodiments, the Tn3 scaffold comprises a linker which comprises a functional moiety. In some embodiments, this functional moiety is an immunoglobulin or a fragment thereof. In certain embodiments, this immunoglobulin or fragment thereof comprises an Fc domain. In some embodiments, this Fc domain fails to induce at least one FcγR-mediated effector function. In some embodiments, this at least one FcγR-mediated effector function is ADCC.

In some embodiments, the Tn3 scaffold comprises at least one CD40L-specific monomer subunit bound to a heterologous moiety. In some embodiments, this heterologous moiety comprises a composition selected from the group consisting of: a protein, a peptide, a protein domain, a linker, a drug, a toxin, a cytotoxic agent, an imaging agent, a radionuclide, a radioactive compound, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of said moieties.

In some embodiments, the Tn3 scaffold comprises at least one CD40L-specific monomer subunit conjugated to PEG. In some embodiments, the Tn3 scaffold comprises at least one CD40L-specific monomer subunit conjugated to an albumin. In certain embodiments, this albumin is human serum albumin (HSA). In other embodiments, this HSA is a variant HSA. In some specific embodiments, the amino acid sequence of the variant HSA is SEQ ID NO: 133. In other embodiments, the variant HSA has at least one improved property compared with a native HSA or a native HSA fragment. In certain embodiments, the improved property is an altered plasma half-life compared with the plasma half-life of a native HSA or a native HSA fragment. In some embodiments, the altered plasma half-life is a longer plasma half-life compared with the plasma half-life of a native HSA or a native HSA fragment. In other embodiments, the altered plasma half-life is a shorter plasma half-life compared with the plasma half-life of a native HSA or a native HSA fragment.

In some embodiments, the Tn3 scaffold is fused to an HSA variant comprising at least one amino acid substitution in HSA domain III. In other embodiments, the Tn3 scaffold is fused to an HSA variant comprising the sequence of full-length mature HSA (SEQ ID NO: 133 or 138) or a fragment thereof, except for at least one amino acid substitution, numbered relative to the position in full length mature HSA, at a position selected from the group consisting of 407, 415, 463, 500, 506, 508, 509, 511, 512, 515, 516, 521, 523, 524, 526, 535, 550, 557, 573, 574, and 580; wherein the at least one amino acid substitution does not comprise a lysine (K) to glutamic acid (E) at position 573, and wherein the Tn3 scaffold has a plasma half-life longer than the plasma half-life of a Tn3 scaffold not conjugated to such HSA variant.

In some embodiments, the Tn3 scaffold is fused to an HSA variant wherein at least one amino acid substitution, numbered relative to the position in full length mature HSA, is at a position selected from the group consisting of 463, 508, 523, and 524, wherein said Tn3 scaffold has a plasma half-life longer than the plasma half-life of a Tn3 scaffold not conjugated to said HSA variant. In some embodiments, the HSA variant comprises the sequence of full-length mature HSA (SEQ ID NO: 133 or 138) or a fragment thereof, except for at least one amino acid substitution, numbered relative to the position in full length mature HSA, selected from the group consisting of: (a) substitution of Leucine (L) at position 407 to Asparagine (N) or Tyrosine (Y); (b) substitution of Valine (V) at position 415 to Threonine (T); (c) substitution of Leucine (L) at position 463 to Asparagine (N); (d) substitution of Lysine (K) at position 500 to Arginine (R); (e) substitution of Threonine (T) at position 506 to Tyrosine (Y); (f) substitution of Threonine (T) at position 508 to Arginine (R); (g) substitution of Phenylalanine (F) at position 509 to Methionine (M) or Tryptophan (W); (h) substitution of Alanine (A) at position 511 to Phenylalanine (F); (i) substitution of Aspartic Acid (D) at position 512 to Tyrosine (Y); (j) substitution of Threonine (T) at position 515 to Glutamine (Q); (k) substitution of Leucine (L) at position 516 to Threonine (T) or Tryptophan (W); (l) substitution of Arginine (R) at position 521 to Tryptophan (W); (m) substitution of Isoleucine (I) at position 523 to Aspartic Acid (D), Glutamic Acid (E), Glycine (G), Lysine (K), or Arginine (R); (n) substitution of Lysine (K) at position 524 to Leucine (L); (o) substitution of Glutamine (Q) at position 526 to Methionine (M); (p) substitution of Histidine (H) at position 535 to Proline (P); (q) substitution of Aspartic Acid (D) at position 550 to Glutamic Acid (E); (r) substitution of Lysine (K) at position 557 to Glycine (G); (s) substitution of Lysine (K) at position 573 to Phenylalanine (F), Histidine (H), Proline (P), Tryptophan (W), or Tyrosine (Y); (t) substitution of Lysine (K) at position 574 to Asparagine (N); (u) substitution of Glutamine (Q) at position 580 to Lysine (K); and, (v) a combination of two or more of said substitutions, wherein said Tn3 scaffold has a plasma half-life longer than the plasma half-life of a Tn3 scaffold not conjugated to said HSA variant.

In some embodiments, the Tn3 scaffold is fused to an HSA variant comprising the sequence of full-length mature HSA (SEQ ID NO: 133 or 138) or a fragment thereof, except for at least one amino acid substitution, numbered relative to the position in full length mature HSA, selected from the group consisting of: (a) substitution of Leucine (L) at position 463 to Asparagine (N); (b) substitution of Threonine (T) at position 508 to Arginine (R); (c) substitution of Isoleucine (I) at position 523 to Aspartic Acid (D), Glutamic Acid (E), Glycine (G), Lysine (K), or Arginine (R); (d) substitution of Lysine (K) at position 524 to Leucine (L); and, (e) a combination of two or more of said substitutions, wherein said Tn3 scaffold has a plasma half-life longer than the plasma half-life of a Tn3 scaffold not conjugated to said HSA variant.

In some embodiments, the Tn3 scaffold comprises at least two identical CD40L-specific monomer subunits. In other embodiments, the Tn3 scaffold comprises at least two different CD40L-specific monomer subunits. In some embodiments, the Tn3 scaffold is a CD40 receptor agonist. In other embodiments, the Tn3 scaffold is a CD40 receptor antagonist.

In some embodiments, the Tn3 scaffold comprises at least two CD40L-specific monomer subunits which specifically bind to the same CD40L epitope. In other embodiments, the Tn3 scaffold comprises at least two CD40L-specific monomer subunits which specifically bind to different CD40L epitopes. In some embodiments, these different CD40L epitopes are non-overlapping epitopes. In other embodiments, these different CD40L epitopes are overlapping epitopes.

In some embodiments, the Tn3 scaffold binds to at least two CD40L molecules. In other embodiments, the Tn3 scaffold comprises a CD40L-specific monomer subunit which binds to at least two CD40L molecules.

In some embodiments, the beta strands of at least one CD40L-specific monomer subunit of the Tn3 scaffold have at least 90% sequence identity to the beta strands of SEQ ID NO: 3. In other embodiments, the Tn3 scaffold comprises a CD40L-specific monomer subunit comprising a A beta strand comprising SEQ ID NO: 11, or comprising a A beta strand comprising SEQ ID NO: 11 except for at least one mutation. In other embodiments, the Tn3 scaffold comprises a CD40L-specific monomer subunit comprising a B beta strand comprising SEQ ID NO: 12, or comprising a B beta strand comprising SEQ ID NO: 12 except for at least one mutation. In some embodiments, the Tn3 scaffold comprises a CD40L-specific monomer subunit comprising a C beta strand comprising SEQ ID NO: 13 or 14, or comprising a C beta strand comprising SEQ ID NO: 13 or 14 except for at least one mutation, and wherein the cysteine in SEQ ID NO: 13 or 14 is not substituted. In other embodiments, the Tn3 scaffold comprises a CD40L-specific monomer subunit comprising a D beta strand comprising SEQ ID NO: 15, or comprising a D beta strand comprising SEQ ID NO: 15 except for at least one mutation.

In some embodiments, the Tn3 scaffold comprises a CD40L-specific monomer subunit comprising an E beta strand comprising SEQ ID NO: 16, or comprising an E beta strand comprising SEQ ID NO: 16 except for at least one mutation. In other embodiments, the Tn3 scaffold comprises a CD40L-specific monomer subunit comprising an F beta strand comprising SEQ ID NO: 17, or comprising an F beta strand comprising SEQ ID NO: 17 except for at least one mutation, and wherein the cysteine in SEQ ID NO: 17 is not substituted. In some embodiments, the Tn3 scaffold comprises a CD40L-specific monomer subunit comprising a G beta strand comprising SEQ ID NO: 18, or comprising a G beta strand comprising SEQ ID NO: 18 except for at least one mutation.

In some embodiments, the Tn3 scaffold comprises a CD40L-specific monomer subunit comprising the amino acid sequence:

| IEV | (SEQ ID NO: 11) |
| $(X_{AB})_n$ALITW | (SEQ ID NO: 12) |
| $(X_{BC})_n$CELX$_1$YGI | (SEQ ID NO: 173) |
| $(X_{CD})_n$TTIDL | (SEQ ID NO: 15) |
| $(X_{DE})_n$YSI | (SEQ ID NO: 16) |
| $(X_{EF})_n$YEVSLIC | (SEQ ID NO: 17) |
| $(X_{FG})_n$KETFTT | (SEQ ID NO: 18) | wherein: $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively; $X_1$ represents amino acid residue A or T; and, the length of the loop n is an integer between 2 and 26.

In some embodiments, the Tn3 scaffold comprises a CD40L-specific monomer subunit, wherein the sequence of the AB loop comprises SEQ ID NO: 4 or SEQ ID NO: 136, the sequence of the CD loop comprises SEQ ID NO: 6, and the sequence of the EF loop comprises SEQ ID NO: 8 or SEQ ID NO: 137. In other embodiments, the Tn3 scaffold comprises a CD40L-specific monomer subunit, wherein the sequence of the BC loop comprises a sequence selected from the group consisting of SEQ ID NOs: 83, 84, 85, 86, 87, 88, 89, 90, 91, 92, 93, and 168. In some embodiments, the Tn3 scaffold comprises a CD40L-specific monomer subunit, wherein the sequence of the DE loop comprises a sequence selected from the group consisting of SEQ ID NOs: 94, 95, 96, 97, 98, and 169. In some embodiments, the Tn3 scaffold comprises a CD40L-specific monomer subunit, wherein the sequence of the FG loop comprises a sequence selected from the group consisting of SEQ ID NOs: 9, 99, 139, and 170.

In other embodiments, the Tn3 scaffold comprises a CD40L-specific monomer subunit, wherein the sequence of the BC loop comprises a sequence selected from the group consisting of SEQ ID NOs: 100, 101, 102, 103, 104, 105, 106, 107, 108, 109, 110, 111, 112, 113, 114, 115, 116, 117, and 174. In certain embodiments, the Tn3 scaffold comprises a CD40L-specific monomer subunit, wherein the sequence of the DE loop comprises a sequence selected from the group consisting of SEQ ID NOs: 118, 119, 120, 121, 122, 123, 124, 125, 126, 127, 128, and 175. In other embodiments, the Tn3 scaffold comprises a CD40L-specific monomer subunit, wherein the sequence of the FG loop comprises a sequence selected from the groups consisting of SEQ ID NOs: 129, 130, and 177. In certain embodiments, the Tn3 scaffold comprises a CD40L-specific monomer subunit, wherein the sequence of the AB loop comprises a sequence selected from the group consisting of SEQ ID NOs: 4 and 136.

In some embodiments, the Tn3 scaffold comprises a CD40L-specific monomer subunit, wherein the sequence of the BC loop comprises SEQ ID NO: 83, the sequence of the DE loop comprises SEQ ID NO: 94, and the sequence of the FG loop comprises SEQ ID NO: 9 or 139. In other embodiments, the Tn3 scaffold comprises a CD40L-specific monomer subunit wherein the sequence of the BC loop comprises SEQ ID NO: 83, the sequence of the DE loop comprises SEQ ID NO: 94, and the sequence of the FG loop comprises SEQ ID NO: 99. In other embodiments, the Tn3 scaffold comprises a CD40L-specific monomer subunit wherein the sequence of the BC loop comprises SEQ ID NO: 84, the sequence of the DE loop comprises SEQ ID NO: 95, and the sequence of the FG loop comprises SEQ ID NO: 9 or 139.

In some embodiments, the Tn3 scaffold comprises a CD40L-specific monomer subunit wherein the sequence of the BC loop comprises SEQ ID NO: 85, the sequence of the DE loop comprises SEQ ID NO: 94, and the sequence of the FG loop comprises SEQ ID NO: 9 or 139. In some embodiments, the Tn3 scaffold comprises a CD40L-specific monomer subunit wherein the sequence of the BC loop comprises SEQ ID NO: 86, the sequence of the DE loop comprises SEQ ID NO: 96, and the sequence of the FG loop comprises SEQ ID NO: 9 or 139. In some embodiments, the Tn3 scaffold comprises a CD40L-specific monomer subunit wherein the sequence of the BC loop comprises SEQ ID NO: 87, the sequence of the DE loop comprises SEQ ID NO: 97, and the sequence of the FG loop comprises SEQ ID NO: 9 or 139.

In some embodiments, the Tn3 scaffold comprises a CD40L-specific monomer subunit wherein the sequence of the BC loop comprises SEQ ID NO: 88, the sequence of the DE loop comprises SEQ ID NO: 95, and the sequence of the FG loop comprises SEQ ID NO: 9 or 139. In other embodiments, the Tn3 scaffold comprises a CD40L-specific monomer subunit wherein the sequence of the BC loop comprises SEQ ID NO: 89, the sequence of the DE loop comprises SEQ ID NO: 94, and the sequence of the FG loop comprises SEQ ID NO: 9 or 139. In some embodiments, the Tn3 scaffold comprises a CD40L-specific monomer subunit wherein the sequence of the BC loop comprises SEQ ID NO: 90, the sequence of the DE loop comprises SEQ ID NO: 94, and the sequence of the FG loop comprises SEQ ID NO: 9 or 139.

In other embodiments, the Tn3 scaffold comprises a CD40L-specific monomer subunit wherein the sequence of the BC loop comprises SEQ ID NO: 91, the sequence of the DE loop comprises SEQ ID NO: 95, and the sequence of the FG loop comprises SEQ ID NO: 9 or 139. In some embodiments, the Tn3 scaffold comprises a CD40L-specific monomer subunit wherein the sequence of the BC loop comprises SEQ ID NO: 92, the sequence of the DE loop comprises SEQ ID NO: 98, and the sequence of the FG loop comprises SEQ ID NO: 9 or 139. In other embodiments, the Tn3 scaffold comprises a CD40L-specific monomer subunit wherein the sequence of the BC loop comprises SEQ ID NO: 93, the sequence of the DE loop comprises SEQ ID NO: 94, and the sequence of the FG loop comprises SEQ ID NO: 9 or 139.

In some embodiments, the Tn3 scaffold comprises a CD40L-specific monomer subunit wherein the sequence of the BC loop comprises SEQ ID NO: 100, the sequence of the DE loop comprises SEQ ID NO: 118, and the sequence of the FG loop comprises SEQ ID NO: 129. In other embodiments, the Tn3 scaffold comprises a CD40L-specific monomer subunit wherein the sequence of the BC loop comprises SEQ ID NO: 101, the sequence of the DE loop comprises SEQ ID NO: 119, and the sequence of the FG loop comprises SEQ ID NO: 129. In some embodiments, the Tn3 scaffold comprises a CD40L-specific monomer subunit wherein the sequence of the BC loop comprises SEQ ID NO: 102, the sequence of the DE loop comprises SEQ ID NO: 120, and the sequence of the FG loop comprises SEQ ID NO: 129. In other embodiments, the Tn3 scaffold comprises a CD40L-specific monomer subunit wherein the sequence of the BC loop comprises SEQ ID NO: 103, the sequence of the DE loop comprises SEQ ID NO: 121, and the sequence of the FG loop comprises SEQ ID NO: 129. In some embodiments, the Tn3 scaffold comprises a CD40L-specific monomer subunit wherein the sequence of the AB loop comprises SEQ ID NO: 136.

In some embodiments, the Tn3 scaffold comprises a CD40L-specific monomer subunit wherein the sequence of the BC loop comprises SEQ ID NO: 104, the sequence of the DE loop comprises SEQ ID NO: 122, and the sequence of the FG loop comprises SEQ ID NO: 129. In other embodiments, the Tn3 scaffold comprises a CD40L-specific monomer subunit wherein the sequence of the BC loop comprises SEQ ID NO: 105, the sequence of the DE loop comprises SEQ ID NO: 121, and the sequence of the FG loop comprises SEQ ID NO: 129. In other embodiments, the Tn3 scaffold comprises a CD40L-specific monomer subunit wherein the sequence of the BC loop comprises SEQ ID NO: 106, the sequence of the DE loop comprises SEQ ID NO: 123, and the sequence of the FG loop comprises SEQ ID NO: 129. In some embodiments, the Tn3 scaffold comprises a CD40L-specific monomer subunit wherein the sequence of the AB loop comprises SEQ ID NO: 136.

In certain embodiments, the Tn3 scaffold comprises a CD40L-specific monomer subunit wherein the sequence of the BC loop comprises SEQ ID NO: 107, the sequence of the DE loop comprises SEQ ID NO: 123, and the sequence of the FG loop comprises SEQ ID NO: 129. In other embodiments, the Tn3 scaffold comprises a CD40L-specific monomer subunit wherein the sequence of the BC loop comprises SEQ ID NO: 108, the sequence of the DE loop comprises SEQ ID NO: 118, and the sequence of the FG loop comprises SEQ ID NO: 129. In some embodiments, the Tn3 scaffold comprises a CD40L-specific monomer subunit wherein the sequence of the BC loop comprises SEQ ID NO: 109, the sequence of the DE loop comprises SEQ ID NO: 123, and the sequence of the FG loop comprises SEQ ID NO: 129. In some embodiments, the sequence of the BC loop comprises SEQ ID NO: 110, the sequence of the DE loop comprises SEQ ID NO: 121, and the sequence of the FG loop comprises SEQ ID NO: 129. In some embodiments, the Tn3 scaffold comprises a CD40L-specific monomer subunit wherein the sequence of the AB loop comprises SEQ ID NO: 136.

In some embodiments, the Tn3 scaffold comprises a CD40L-specific monomer subunit wherein the sequence of the BC loop comprises SEQ ID NO: 111, the sequence of the DE loop comprises SEQ ID NO: 123, and the sequence of the FG loop comprises SEQ ID NO: 130. In other embodiments, the Tn3 scaffold comprises a CD40L-specific monomer subunit wherein the sequence of the BC loop comprises SEQ ID NO: 108, the sequence of the DE loop comprises SEQ ID NO: 121, and the sequence of the FG loop comprises SEQ ID NO: 129. In some embodiments, the Tn3 scaffold comprises a CD40L-specific monomer subunit wherein the sequence of the BC loop comprises SEQ ID NO: 112, the sequence of the DE loop comprises SEQ ID NO: 124, and the sequence of the FG loop comprises SEQ ID NO: 129. In some embodiments, the Tn3 scaffold comprises a CD40L-specific monomer subunit wherein the sequence of the BC loop comprises SEQ ID NO: 113, the sequence of the DE loop comprises SEQ ID NO: 125, and the sequence of the FG loop comprises SEQ ID NO: 129. In some embodiments, the Tn3 scaffold comprises a CD40L-specific monomer subunit wherein the sequence of the AB loop comprises SEQ ID NO: 136.

In some embodiments, the Tn3 scaffold comprises a CD40L-specific monomer subunit wherein the sequence of the BC loop comprises SEQ ID NO: 114, the sequence of the DE loop comprises SEQ ID NO: 118, and the sequence of the FG loop comprises SEQ ID NO: 129. In other embodiments, the Tn3 scaffold comprises a CD40L-specific monomer subunit wherein the sequence of the BC loop comprises SEQ ID NO: 115, the sequence of the DE loop comprises SEQ ID NO: 126, and the sequence of the FG loop comprises SEQ ID NO: 129. In some embodiments, the Tn3 scaffold comprises a CD40L-specific monomer subunit wherein the sequence of the BC loop comprises SEQ ID NO: 116, the sequence of the DE loop comprises SEQ ID NO: 127, and the sequence of the FG loop comprises SEQ ID NO: 129. In some embodiments, the Tn3 scaffold comprises a CD40L-specific monomer subunit wherein the sequence of the BC loop comprises SEQ ID NO: 117, the sequence of the DE loop comprises SEQ ID NO: 128, and the sequence of the FG loop comprises SEQ ID NO: 129. In some embodiments, the Tn3 scaffold comprises a CD40L-specific monomer subunit wherein the sequence of the AB loop comprises SEQ ID NO: 136.

In some embodiments, the Tn3 scaffold comprises a CD40L-specific monomer subunit comprising a sequence selected from the group consisting of SEQ ID NO: 20, 22, 24, 26, 28, 30, 32, 34, 36, 38, 40, 42 and 146. In some embodiments, the Tn3 scaffold comprises a CD40L-specific monomer subunit comprises the amino acid sequence: IDC-22 DNA (SEQ ID NO: 167)

$IEVKDVTDTTALITWX_1DX_2X_3X_4X_5X_6X_7X_8CELTYGIKDVPGDRTTID$ $LWX_9HX_{10}AX_{11}YSIGNLKPDTEYEVSLICRX_{12}GDMSSNPAKETFTT$ wherein: (a) $X_1$ represents amino acid residue serine (S) or leucine (L); (b) $X_2$ represents amino acid residue aspartic acid (D) or glutamic acid (E); (c) $X_3$ represents amino acid residue histidine (H), isoleucine (I), valine (V), phenylalanine (F) or tryptophan (W); (d) $X_4$ represents amino acid residue alanine (A), glycine (G), glutamic acid (E) or aspartic acid (D); (e) $X_5$ represents amino acid residue glutamic acid (E), leucine (L), glutamine (Q), serine (S), aspartic acid (D) or asparagine (N); (f) $X_6$ represents amino acid residue phenylalanine (F) or tyrosine (Y); (g) $X_7$ represents amino acid residue isoleucine (I), valine (V), histidine (H), glutamic acid (E) or aspartic acid (D); (h) $X_8$ represents amino acid residue glycine (G), tryptophan (W) or valine (V); (i) $X_9$ represents amino acid residue tryptophan (W), phenylalanine (F) or tyrosine (Y); (j) $X_{10}$ represents amino acid residue serine (S), glutamine (Q), methionine (M) or histidine (H); (k) $X_{11}$ represents amino acid residue tryptophan (W) or histidine (H); and, (l) $X_{12}$ represents amino acid residue arginine (R) or serine (S).

In some embodiments, the Tn3 scaffold comprises a CD40L-specific monomer subunit comprising a sequence selected from the group consisting of SEQ ID NO: 44, 46, 48, 50, 52, 54, 56, 58, 60, 62, 64, 66, 68, 70, 72, 74, 76, 78, 80, and 82.

In some embodiments, the Tn3 scaffold comprises a CD40L-specific monomer subunit comprising the amino acid sequence:

(SEQ ID NO: 171)
IEVX$_1$DVTDTTALITWX$_2$X$_3$RSX$_4$X$_5$X$_6$X$_7$X$_8$X$_9$X$_{10}$CELX$_{11}$YGIKDVP

GDRTTIDLX$_{12}$X$_{13}$X$_{14}$X$_{15}$YVHYSIGNLKPDTX$_{16}$YEVSLICLTTDGT

YX$_{17}$NPAKETFTT wherein:
- (a) X$_1$ represents amino acid residue lysine (K) or glutamic acid (E);
- (b) X$_2$ represents amino acid residue threonine (T) or isoleucine (I);
- (c) X$_3$ represents amino acid residue asparagine (N) or alanine (A);
- (d) X$_4$ represents amino acid residue serine (S), leucine (L), alanine (A), phenylalanine (F) or tyrosine (Y);
- (e) X$_5$ represents amino acid residue tyrosine (Y), alanine (A), glycine (G), valine (V), isoleucine (I) or serine (S);
- (f) X$_6$ represents amino acid residue tyrosine (Y), serine (S), alanine (A) or histidine (H);
- (g) X$_7$ represents amino acid residue asparagine (N), aspartic acid (D), histidine (H) or tyrosine (Y);
- (h) X$_8$ represents amino acid residue leucine (L), phenylalanine (F), histidine (H) or tyrosine (Y);
- (i) X$_9$ represents amino acid residue histidine (H), proline (P), serine (S), leucine (L) or aspartic acid (D);
- (j) X$_{10}$ represents amino acid residue glycine (G), phenylalanine (F), histidine (H) or tyrosine (Y);
- (k) X$_{11}$ represents amino acid residue alanine (A) or threonine (T);
- (l) X$_{12}$ represents amino acid residue serine (S), asparagine (N), glutamic acid (E), asparagine (R) or aspartic acid (D);
- (m) X$_{13}$ represents amino acid residue serine (S), glutamine (Q), threonine (T), asparagine (N) or alanine (A);
- (n) X$_{14}$ represents amino acid residue proline (P), valine (V), isoleucine (I) or alanine (A) or no amino acid;
- (o) X$_{15}$ represents amino acid residue isoleucine (I) or no amino acid;
- (p) X$_{16}$ represents amino acid residue glutamic acid (E) or lysine (K); and,
- (q) X$_{17}$ represents amino acid residue serine (S) or asparagine (N).

In some embodiments, the Tn3 scaffold comprises a sequence selected from the group consisting of SEQ ID NOs: 134, 135, 205, 206, 207 and 208. In other embodiments, the Tn3 scaffold consists of a sequence selected from the group consisting of SEQ ID NO: 134, 135, 205, 206, 207 and 208.

In some embodiments, the Tn3 scaffold comprises a sequence selected from the group consisting of SEQ ID NOs: 201, 202, 203, and 204. In some embodiments, the Tn3 scaffold consists of a sequence selected from the group consisting of SEQ ID NOs: 201, 202, 203, and 204. In some embodiments, the Tn3 scaffold comprises a CD40L-specific monomer subunit wherein said CD40L-specificity is towards human CD40L. In some embodiments, the Tn3 scaffold comprises a CD40L-specific monomer subunit wherein said CD40L-specificity is towards membrane bound CD40L (SEQ ID NO: 1), soluble CD40L (SEQ ID NO: 2), or a fragment thereof. In some specific embodiments, the Tn3 scaffold binds CD40L and prevents binding of CD40L to CD40.

The invention also provides a method of altering an activity in a CD40L expressing cell comprising contacting the cell with a Tn3 scaffold, wherein the Tn3 scaffold binds CD40L and prevents binding of CD40L to CD40. In some embodiments, the Tn3 scaffold binds to CD40L with an affinity ($K_d$) of about 1 μM or less, or about 500 nM or less, or about 100 nM or less, or about 50 nM or less, or about 25 nM or less, or about 10 nM or less, or about 5 nM or less, or about 2 nM or less.

In some embodiments, the Tn3 scaffold comprises a CD40L-specific monomer subunit which specifically binds to a CD40L epitope comprising amino acids located at positions 142 to 155, 200 to 230, or 247 to 251 of SEQ ID NO: 2. In some embodiments, the Tn3 scaffold comprises a CD40L-specific monomer subunit that interacts with CD40L amino acids E142, Y146, M148, N151, L155, R200, R203, and E230. In other embodiments, the Tn3 scaffold comprises a CD40L-specific monomer subunit that interacts with CD40L amino acids R203, I204, V247, H249, and T251. In other embodiments, the Tn3 scaffold comprises a CD40L-specific monomer subunit that interacts with CD40L amino acids E142, Y146, M148, N151, L155, which are located in a first CD40L molecule, and with CD40L amino acids R200, R203, and E230, which are located in a second CD40L molecule. In other embodiments, the Tn3 scaffold comprises a CD40L-specific monomer subunit that interacts with CD40L amino acids R203 and 1204, which are located in a first CD40L molecule, and with CD40L amino acids V247, H249, and T251, which are located in a second CD40L molecule.

The invention also provides polypeptides comprising one or more CD40L-specific Tn3 monomer, including but not limited to the serum albumin fusions described herein.

The invention also provides an isolated nucleic acid molecule encoding a CD40L-specific Tn3 scaffold, an expression vector comprising the nucleic acid molecule encoding a CD40L-specific Tn3 scaffold, and a host cell comprising such vector. The invention also provides a method of producing a Tn3 scaffold comprising culturing the host cell under conditions in which the CD40L-specific Tn3 scaffold encoded by the nucleic acid molecule is expressed.

The invention also provides a pharmaceutical composition comprising a CD40L-specific Tn3 scaffold and a pharmaceutically acceptable excipient. The invention also provides a method of preventing, treating, ameliorating, or managing autoimmune disease in a patient in need thereof comprising administering an effective amount of a pharmaceutical composition comprising a CD40L-specific Tn3 scaffold.

The invention also provides a method of reducing the frequency or quantity of corticosteroid administered to a patient with an autoimmune disease comprising administering to the patient a therapeutically effective amount of a pharmaceutical composition comprising a CD40L-specific Tn3 scaffold.

The autoimmune disease treated by the administration of a CD40L-specific Tn3 scaffold can be alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), comeal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arterists/giant cell arteritis, ulcerative colitis, uveitis, vasculitides such as dermatitis herpetiformis vasculitis, vitiligo, and Wegener's granulomatosis.

In some specific embodiments, the autoimmune disease treated by the administration of a CD40L-specific Tn3 scaffold is Systemic Lupus Erythematosus (SLE).

Methods of treatment with CD40L-specific Tn3 scaffolds can further comprise an additional therapy, such as immunotherapy, biological therapy, chemotherapy, radiation therapy, or small molecule drug therapy.

The invention also provides a protein crystal comprising a Tn3 scaffold consisting of SEQ ID NO: 20 in a complex with soluble CD40L (SEQ ID NO: 2) wherein the crystal has a crystal lattice in a $P2_12_12_1$ orthorhombic space group and unit cell dimensions, +/−0.1%, of a=85.69 Å, b=90.64 Å, c=95.56 Å. In some embodiments, the asymmetric unit of the crystal comprises a trimer of CD40L and three molecules of Tn3 scaffold. In other embodiments, the crystals diffract X-rays for a determination of structure coordinates to a resolution of a value equal to or less that 3.2 Å.

The invention also provides a protein crystal comprising a Tn3 scaffold consisting of SEQ ID NO: 68 in a complex with soluble CD40L (SEQ ID NO: 2) wherein the crystal has a crystal lattice in a $P2_13$ cubic space group and unit cell dimensions, +/−0.1%, of a=b=c=97.62 Å. In some embodiments, the asymmetric unit of the crystal comprises one CD40L molecule and one Tn3 scaffold molecule. In other embodiments, the crystal diffracts X-rays for a determination of structure coordinates to a resolution of a value equal to or less than 2.7 Å.

The invention also provides a protein crystal comprising a Tn3 scaffold consisting of SEQ ID NO: 28 or 146 in a complex with soluble CD40L (SEQ ID NO: 2) wherein the crystal has a crystal lattice in a P321 space group and unit cell dimensions, +/−0.1%, of a=95.53 Å, b=93.53 Å, c=66.69 Å. In some embodiments the asymmetric unit of the crystal comprises one CD40L molecule and one Tn3 scaffold molecule. In other embodiments the crystal diffracts X-rays for a determination of structure coordinates to a resolution of a value equal to or less than 2.8 Å

The invention also provides a protein crystal comprising two different Tn3 scaffolds consisting of SEQ ID NO: 68 and SEQ ID NO: 28 or 146 in a complex with soluble CD40L (SEQ ID NO: 2) wherein the crystal has a crystal lattice in a $P2_1$ cubic space group and unit cell dimensions, +/−0.1%, of a=80.32 Å, b=143.48 Å, c=111.27 Å, β=98.22 Å. In some embodiments the asymmetric unit of the crystal comprises two CD40L trimers and six of each Tn3 scaffold molecule. In other embodiments the crystal diffracts X-rays for a determination of structure coordinates to a resolution of a value equal to or less than 1.9 Å.

In some embodiments, the protein crystal is produced by using sitting-drop vapor diffusion. The invention also provides a method of making a protein crystal, comprising: (a) mixing a volume of a solution comprising a Tn3 scaffold comprising a CD40L-specific monomer subunit in a complex with CD40L with a volume of a reservoir solution comprising a precipitant; and (b) incubating the mixture obtained in step (a) in a closed container, under conditions suitable for crystallization until the protein crystal forms. In some embodiments, the method to produce the protein crystal comprises using sitting-drop vapor diffusion.

In some embodiments, the method to make a protein crystal is used to produce crystals comprising the CD40L-specific Tn3 monomer subunits of SEQ ID NO: 20, SEQ ID NO: 28, SEQ ID NO: 68 or SEQ ID NO: 146.

The invention also provides a machine-readable data storage medium comprising a data storage material encoded with machine-readable instructions for: (a) transforming data into a graphical three-dimensional representation for the structure of a portion of a protein crystal of a Tn3 scaffold comprising a CD40L-specific monomer subunit complexed with CD40L; and, (b) causing the display of said graphical three-dimensional representation. In some embodiments, such Tn3 scaffold comprises SEQ ID NO: 20, SEQ ID NO: 28, SEQ ID NO: 68 or SEQ ID NO: 146. In other embodiments, such protein crystal is:

(a) a protein crystal comprising a Tn3 scaffold consisting of SEQ ID NO: 20 in a complex with soluble CD40L (SEQ ID NO: 2) wherein the crystal has a crystal lattice in a $P2_12_12_1$ orthorhombic space group and unit cell dimensions, +/−0.10%, of a=85.69 Å, b=90.64 Å, c=95.56 Å;

(b) a protein crystal comprising a Tn3 scaffold consisting of SEQ ID NO: 68 in a complex with soluble CD40L (SEQ ID NO: 2) wherein the crystal has a crystal lattice in a P213 cubic space group and unit cell dimensions, +/−0.1%, of a=b=c=97.62 Å; or (c) a protein crystal comprising a Tn3 scaffold consisting of SEQ ID NO: 20 and a Tn3 scaffold consisting of SEQ ID NO: 68, wherein both Tn3 scaffold are in a complex with soluble CD40L (SEQ ID NO: 2)

(d) a protein crystal comprising a Tn3 scaffold consisting of SEQ ID NO: 28 or 146 in a complex with soluble CD40L (SEQ ID NO: 2) wherein the crystal has a crystal lattice in a P321 space group and unit cell dimensions, +/−0.1%, of a=95.53 Å, b=93.53 Å, c=66.69 Å

(e) a protein crystal comprising two different Tn3 scaffolds consisting of SEQ ID NO: 68 and SEQ ID NO: 28 or 146 in a complex with soluble CD40L (SEQ ID NO: 2) wherein the crystal has a crystal lattice in a $P2_1$ cubic space group and unit cell dimensions, +/−0.1%, of a=80.32 Å, b=143.48 Å, c=111.27 Å, β=98.22 Å.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 6C the inhibitory effect of human CD40L-specific monovalent Tn3 monomer scaffolds 309 and 311 on plasma cell number in T/B cell co-cultures. Tn3 scaffold 309 was also shown to bind activated primary T cells by FACS (data not shown). A D1 scaffold ("Neg Tn3") was used as control. Two monoclonal antibodies against CD40L, designated aCD40L(RE) and aCD40L(Bio) (Biogen's 5c8 anti-human CD40L monoclonal antibody) were also used as controls.

FIG. 9D shows inhibition in the human CD40L-induced CD86 expression on CD19 positive human PBMCs stimulated with Jurkat D1.1 cells. Three bivalent (309) human CD40L-specific Tn3 scaffolds were tested. Three ($G_4S$) repeats were present in the linker between the human CD40L-specific subunits (309 in this example) while the linker between the 309 subunits and the HSA was varied from 1 to 3 ($G_4S$) repeats. Biogen's 5c8 anti-human CD40L monoclonal antibody was also assayed.

FIG. 11A and FIG. 11B show a multiple sequence alignment of the parental CD40L-specific Tn3 scaffold 309, the 309FGwt variant, and the affinity optimized variants 340 to 349. Amino acid residues 1 to 42 are shown in FIG. 11A, and amino acid residues 43 to 83 are shown in FIG. 11B. The variant loops are shaded. The consensus amino acid sequence is presented below the multiple sequence alignment. The aligned sequences correspond to the amino acid sequences of Tn3 scaffold clones 309 (SEQ ID NO: 20), 309FGwt (SEQ ID NO: 22), 340 (SEQ ID NO: 24), 341 (SEQ ID NO: 26), 342 (SEQ ID NO: 28), 343 (SEQ ID NO: 30), 344 (SEQ ID NO: 32), 345 (SEQ ID NO: 34), 346 (SEQ ID NO: 36), 347 (SEQ ID NO: 38), 348 (SEQ ID NO: 40), and 349 (SEQ ID NO: 42).

FIG. 12A and FIG. 12B show as multiple sequence alignment of the parental CD40L-specific Tn3 scaffold 311, the 311K4E variant, and the affinity optimized variants 311K4E_1 to 311K4E_21. Amino acid residues 1 to 44 are shown in FIG. 12A, and amino acid residues 45 to 87 are shown in FIG. 12B. The variant loops are shaded. Amino acid variations outside the shadowed loops are boxed. A consensus sequence is presented below the multiple sequence alignment. The aligned sequences correspond to the amino acid sequences of Tn3 scaffold clones 311 (SEQ ID NO: 44), 311K4E (SEQ ID NO: 46), 311K4E_1 (SEQ ID NO: 48), 311K4E_2 (SEQ ID NO: 50), 311K4E_2 (SEQ ID NO: 52), 311K4E_3 (SEQ ID NO: 54), 311K4E_4 (SEQ ID NO: 56), 311K4E_5 (SEQ ID NO: 58), 311K4E_7 (SEQ ID NO: 60), 311K4E_8 (SEQ ID NO: 62), 311K4E_9 (SEQ ID NO: 64), 311K4E_10 (SEQ ID NO: 66), 311K4E_11 (SEQ ID NO: 68), 311K4E_12 (SEQ ID NO: 70), 311K4E_13 (SEQ ID NO: 72), 311K4E_14 (SEQ ID NO: 74), 311K4E_15 (SEQ ID NO: 76), 311K4E_16 (SEQ ID NO: 78), 311K4E_19 (SEQ ID NO: 80), 311K4E_20 (SEQ ID NO: 82), and 311K4E_21 (SEQ ID NO: 84).

FIG. 18A shows the location of the contacts between amino acids in the CD40L-specific Tn3 311K4E_12 monomer scaffold (SEQ ID NO: 68) and a trimer formed by soluble CD40L (SEQ ID NO: 2) molecules as shown in FIG. 17A. Each scaffold makes contact with 2 CD40L molecules. The CD40L sequence (SEQ ID NO: 2) is shown. Dotted underline=cytoplasmic domain; Solid underline=signal anchor type II membrane protein; Double underline=portion co-crystalized with Tn3 scaffold; Dark shading=residues on 1st CD40L that contact the Tn3; Light shading=residues on 2nd CD40L that contact the Tn3.

FIG. 18B shows the location of the contacts between amino acids in the CD40L-specific Tn3 309 monomer scaffold and CD40L trimer as shown in FIG. 17B. Each scaffold makes contact with 2 CD40L molecules. The CD40L sequence (SEQ ID NO: 2) is shown. Dotted underline=cytoplasmic domain; Solid underline=signal anchor type II membrane protein; Double underline=portion co-crystalized with Tn3 scaffold; Dark shading=residues on 1st CD40L that contact the Tn3; Light shading=residues on 2nd CD40L that contact the Tn3; double boxed residue is contact with FG loop of 309 scaffold, which likely is not conserved in clones having a wildtype FG loop.

DETAILED DESCRIPTION OF THE INVENTION

Definitions

Figure 1A:
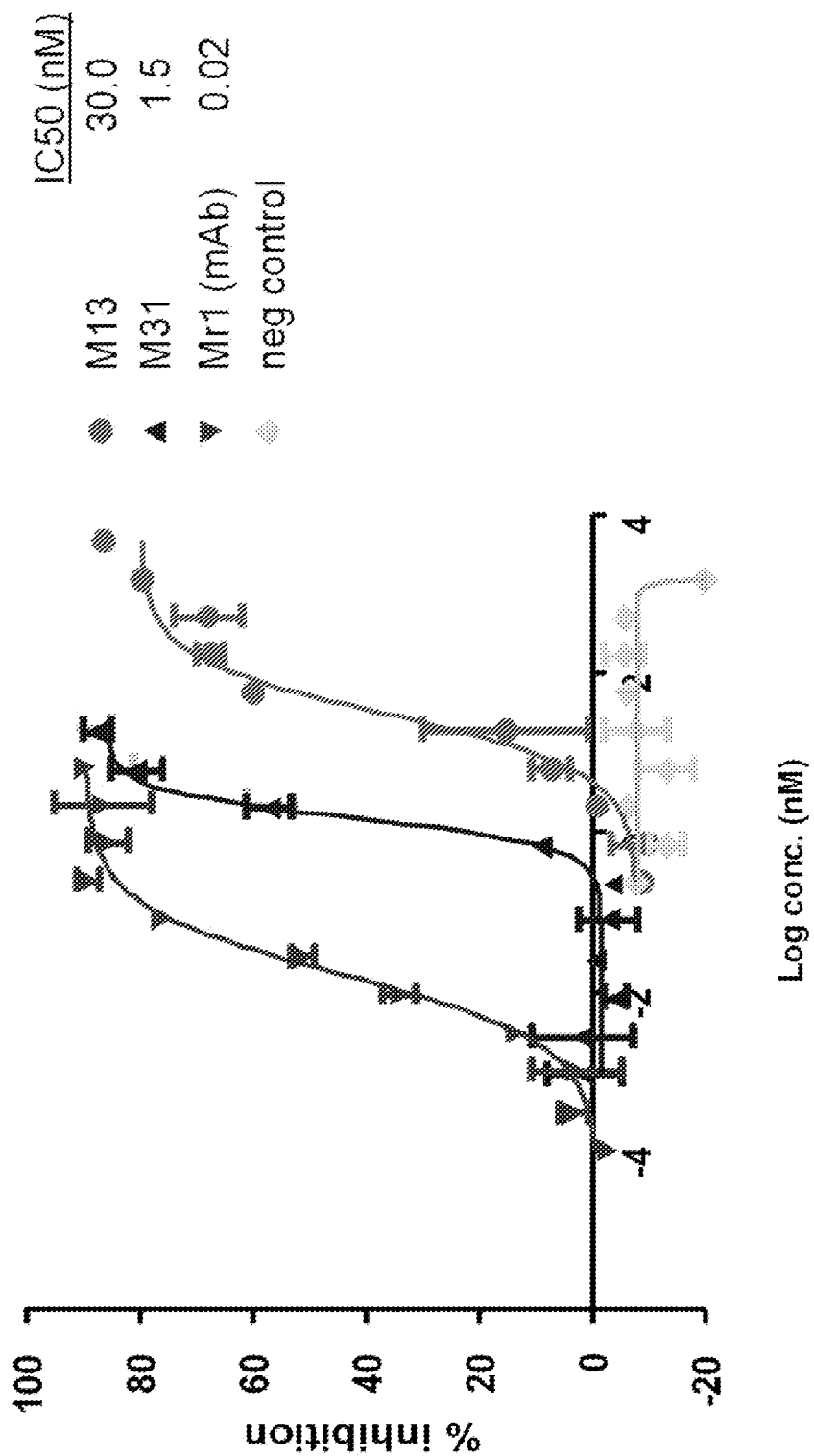
FIG. 1A shows the inhibition of murine CD40L (MuCD40L)-induced CD86 expression measured using a D10G4.1/PBMC (Peripheral Blood mononuclear Cell) assay. The M13 mouse CD40L-specific Tn3 scaffold, its M31 affinity optimized variant (approximately 20× affinity improvement), the anti-CD40L MR1 monoclonal antibody, and a negative control were assayed. $IC_{50}$ values are also shown.
Figure 1B:
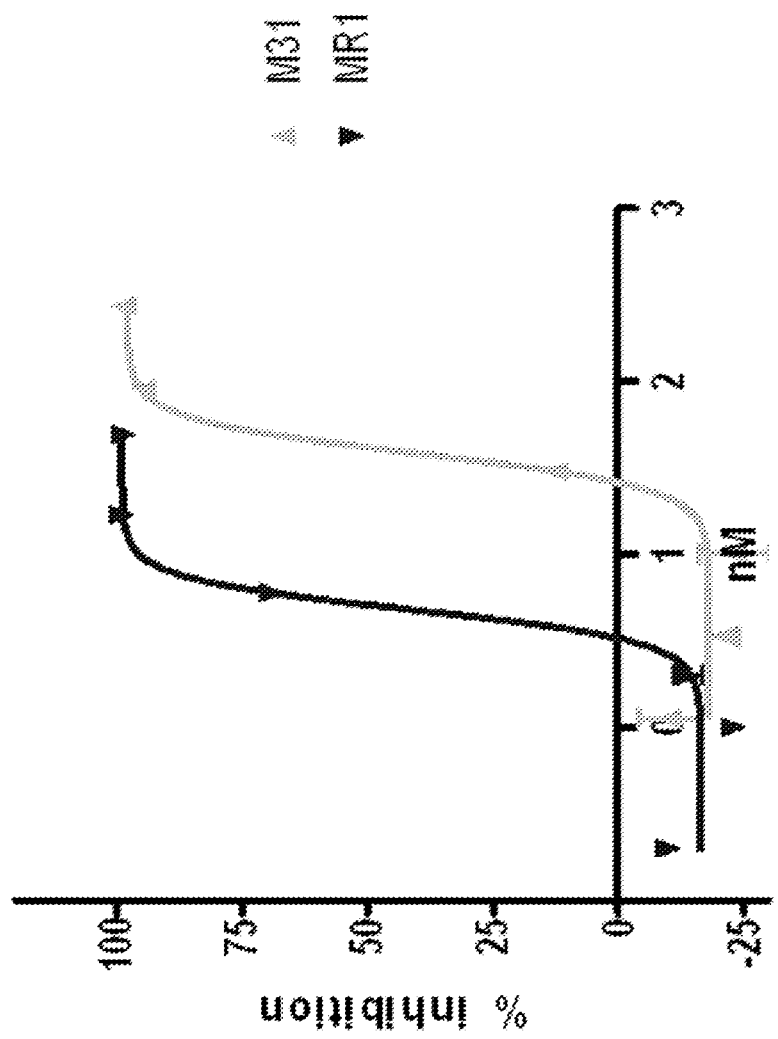
FIG. 1B shows CD40L inhibition in a murine NfkB assay. The assay uses NIHT3T cells expressing murine CD40R and containing an NfkB-Luciferase reporter construct. Addition of CD40L results in signaling (measured by luciferase activity) that is inhibited by both the MR1 anti-CD40L antibody and by the M31 CD40L-specific Tn3 scaffold.

Before describing the present invention in detail, it is to be understood that this invention is not limited to specific compositions or process steps, as such can vary. It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A," (alone) and "B" (alone). Likewise, the term "and/or" as used in a phrase such as "A, B, and/or C" is intended to encompass each of the following embodiments: A, B, and C; A, B, or C; A or C; A or B; B or C; A and C; A and B; and B and C; A (alone); B (alone); and C (alone).

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

It is understood that wherever embodiments are described herein with the language "comprising," otherwise analogous embodiments described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "epitope" as used herein refers to a protein determinant capable of binding to a scaffold of the invention. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The terms "fibronectin type III (FnIII) domain," "FnIII domain" and "FnIII scaffold" refer to polypeptides homologous to the human fibronectin type III domain having at least 7 beta strands which are distributed between two beta sheets, which themselves pack against each other to form the core of the protein, and further containing solvent exposed loops which connect the beta strands to each other. There are at least three such loops at each edge of the beta sheet sandwich, where the edge is the boundary of the protein perpendicular to the direction of the beta strands. In certain embodiments, an FnIII domain comprises 7 beta strands designated A, B, C, D, E, F, and G linked to six loop regions designated AB, BC, CD, DE, EF, and FG, wherein a loop region connects each beta strand.

The term "Tn3 scaffold" used herein, refers to molecules comprising at least one FnIII scaffold wherein the A beta strand comprises SEQ ID NO: 11, the B beta strand comprises SEQ ID NO: 12, the C beta strand SEQ ID NO: 13 or 14, the D beta strand comprises SEQ ID NO: 15, the E beta strand comprises SEQ ID NO: 16, the F beta strand comprises SEQ ID NO: 17, and the beta strand G comprises SEQ ID NO: 18, wherein at least one loop is a non-naturally occurring variant of the loops in the "parent Tn3 scaffold." In certain embodiments, one or more of the beta strands of a Tn3 module comprise at least one amino acid substitution except that the cysteine residues in the C beta strand (e.g., the cysteine in SEQ ID NOs: 13 or 14) and F beta strands (SEQ ID NO: 17) are not substituted.

The term "parent Tn3" as used herein refers to an FnIII scaffold comprising SEQ ID NO: 3, i.e., a thermally stabilized cysteine-engineered FnIII scaffold derived from the 3rd FnIII domain of human tenascin C.

The terms "multimer" or "multimeric scaffold" refer to a molecule that comprises at least two FnIII scaffolds in association. The scaffolds forming a multimeric scaffold can be linked through a linker that permits each scaffold to function independently.

The terms "monomer," "monomer subunit" or "monomer scaffold" refer to a molecule that comprises only one FnIII scaffold.

The term "CD40L-specific monomer subunit" as used herein refers to a Tn3 monomer derived from a "parent Tn3" wherein the Tn3 monomer specifically binds to CD40L or a fragment thereof, e.g., a soluble form of CD40L.

The term "DNA" refers to a sequence of two or more covalently bonded, naturally occurring or modified deoxyribonucleotides.

The term "fusion protein" refers to a protein that includes (i) one or more scaffolds of the invention joined to (ii) a second, different protein (i.e., a "heterologous" protein).

TABLE 1

Sequences and SEQ ID NOs of components of "parent Tn3"

| Name/Brief Description | Sequence | SEQ ID NO |
|---|---|---|
| Tn3 | IEVKDVTDTTALITWFKPLAEIDG<u>C</u>ELT YGIKDVPGDRTTIDLTEDENQYSIGNLK PDTEYEVSLI<u>C</u>RRGDMSSNPAKETFTT (cys residues of disulfide bond are underlined) | 3 |
| 3<sup>rd</sup> FnIII of tenascin C, AB loop (Tn3) | KDVTDTT | 4 |
| 3<sup>rd</sup> FnIII of tenascin C, BC loop (Tn3) | FKPLAEIDG | 5 |
| 3<sup>rd</sup> FnIII of tenascin C, CD loop (Tn3) | KDVPGDR | 6 |
| 3<sup>rd</sup> FnIII of tenascin C, DE loop (Tn3) | TEDENQ | 7 |
| 3<sup>rd</sup> FnIII of tenascin C, EF loop (Tn3) | GNLKPDTE | 8 |
| 3<sup>rd</sup> FnIII of tenascin C, FG loop (Tn3) | RRGDMSSNPA | 9 |
| 3<sup>rd</sup> FnIII of tenascin C, beta strand A (Tn3) | RLDAPSQIEV | 10 |
| 3<sup>rd</sup> FnIII of tenascin C, beta strand A (Tn3) N-terminal truncation | IEV | 11 |
| 3<sup>rd</sup> FnIII of tenascin C, beta strand B (Tn3) | ALITW | 12 |
| 3<sup>rd</sup> FnIII of tenascin C, beta strand C (Tn3 variant) | CELAYGI | 13 |
| 3<sup>rd</sup> FnIII of tenascin C, beta strand C (Tn3) | CELTYGI | 14 |
| 3<sup>rd</sup> FnIII of tenascin C, beta strand D (Tn3) | TTIDL | 15 |
| 3<sup>rd</sup> FnIII of tenascin C, beta strand E (Tn3) | YSI | 16 |

TABLE 1-continued

Sequences and SEQ ID NOs of components of "parent Tn3"

| Name/Brief Description | Sequence | SEQ ID NO |
|---|---|---|
| 3$^{rd}$ FnIII of tenascin C, beta strand F (Tn3) | YEVSLIC | 17 |
| 3$^{rd}$ FnIII of tenascin C, beta strand G (Tn3) | KETFTT | 18 |

The term "heterologous moiety" is used herein to indicate the addition of a composition to a Tn3 scaffold of the invention wherein the composition is not normally part of an FnIII domain. Exemplary heterologous moieties include proteins, peptides, protein domains, linkers, drugs, toxins, imaging agents, radioactive compounds, organic and inorganic polymers, and any other compositions which might provide an activity that is not inherent in the FnIII domain itself, including, but are not limited to, polyethylene glycol (PEG), a cytotoxic agent, a radionuclide, imaging agent, biotin, a dimerization domain (e.g. leucine zipper domain), human serum albumin (HSA) or an FcRn binding portion thereof, a domain or fragment of an antibody (e.g., antibody variable domain, a CH1 domain, a Ckappa domain, a Clambda domain, a CH2, or a CH3 domain), a single chain antibody, a domain antibody, an albumin binding domain, an IgG molecule, an enzyme, a ligand, a receptor, a binding peptide, a non-FnIII scaffold, an epitope tag, a recombinant polypeptide polymer, a cytokine, and the like.

The term "linker" as used herein refers to any molecular assembly that joins or connects two or more scaffolds. The linker can be a molecule whose function is to act as a "spacer" between modules in a scaffold, or it can also be a molecule with additional function (i.e., a "functional moiety"). A molecule included in the definition of "heterologous moiety" can also function as a linker.

The terms "linked" and "fused" are used interchangeably. These terms refer to the joining together of two or more scaffolds, heterologous moieties, or linkers by whatever means including chemical conjugation or recombinant means.

The terms "domain" or "protein domain" refer to a region of a protein that can fold into a stable three-dimensional structure, often independently of the rest of the protein, and which can be endowed with a particular function. This structure maintains a specific function associated with the domain's function within the original protein, e.g., enzymatic activity, creation of a recognition motif for another molecule, or to provide necessary structural components for a protein to exist in a particular environment of proteins. Both within a protein family and within related protein superfamilies, protein domains can be evolutionarily conserved regions. When describing the component of a multimeric scaffold, the terms "domain," "monomeric scaffold," "monomer subunit," and "module" can be used interchangeably. By "native FnIII domain" is meant any non-recombinant FnIII domain that is encoded by a living organism.

A "protein sequence" or "amino acid sequence" means a linear representation of the amino acid constituents in a polypeptide in an amino-terminal to carboxyl-terminal direction in which residues that neighbor each other in the representation are contiguous in the primary structure of the polypeptide.

The term "nucleic acid" refers to any two or more covalently bonded nucleotides or nucleotide analogs or derivatives. As used herein, this term includes, without limitation, DNA, RNA, and PNA. "Nucleic acid" and "polynucleotide" are used interchangeably herein.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). The term "isolated" nucleic acid or polynucleotide refers to a nucleic acid molecule, DNA or RNA that has been removed from its native environment. For example, a recombinant polynucleotide encoding, e.g., a scaffold of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

The term "pharmaceutically acceptable" refers to a compound or protein that can be administered to an animal (for example, a mammal) without significant adverse medical consequences.

The term "physiologically acceptable carrier" refers to a carrier which does not have a significant detrimental impact on the treated host and which retains the therapeutic properties of the compound with which it is administered. One exemplary physiologically acceptable carrier is physiological saline. Other physiologically acceptable carriers and their formulations are known to one skilled in the art and are described, for example, in Remington's Pharmaceutical Sciences, (18th edition), ed. A. Gennaro, 1990, Mack Publishing Company, Easton, Pa., incorporated herein by reference.

By a "polypeptide" is meant any sequence of two or more amino acids linearly linked by amide bonds (peptide bonds) regardless of length, post-translation modification, or function. "Polypeptide," "peptide," and "protein" are used interchangeably herein. Thus, peptides, dipeptides, tripeptides, or oligopeptides are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. A polypeptide can be generated in any manner, including by chemical synthesis.

Also included as polypeptides of the present invention are fragments, derivatives, analogs, or variants of the foregoing polypeptides, and any combination thereof. Variants can occur naturally or be non-naturally occurring. Non-naturally occurring variants can be produced using art-known mutagenesis techniques. Variant polypeptides can comprise conservative or non-conservative amino acid substitutions, deletions, or additions. Also included as "derivatives" are those peptides that contain one or more naturally occurring amino acid derivatives of the twenty standard amino acids.

By "randomized" or "mutated" is meant including one or more amino acid alterations, including deletion, substitution or addition, relative to a template sequence. By "randomizing" or "mutating" is meant the process of introducing, into a sequence, such an amino acid alteration. Randomization or mutation can be accomplished through intentional, blind, or spontaneous sequence variation, generally of a nucleic acid coding sequence, and can occur by any technique, for example, PCR, error-prone PCR, or chemical DNA synthesis. The terms "randomizing", "randomized", "mutating", "mutated" and the like are used interchangeably herein.

By a "cognate" or "cognate, non-mutated protein" is meant a protein that is identical in sequence to a variant protein, except for the amino acid mutations introduced into the variant protein, wherein the variant protein is randomized or mutated.

By "RNA" is meant a sequence of two or more covalently bonded, naturally occurring or modified ribonucleotides. One example of a modified RNA included within this term is phosphorothioate RNA.

The terms "scaffold of the invention" or "scaffolds of the invention" as used herein, refers to multimeric Tn3 scaffolds as well as monomeric Tn3 scaffolds. The term "target" refers to a compound recognized by a specific scaffold of the invention. The terms "target" and "antigen" are used interchangeably herein. The term "specificity" as used herein, e.g., in the terms "specifically binds" or "specific binding," refers to the relative affinity by which a Tn3 scaffold of the invention binds to one or more antigens via one or more antigen binding domains, and that binding entails some complementarity between one or more antigen binding domains and one or more antigens. According to this definition, a Tn3 scaffold of the invention is said to "specifically bind" to an epitope when it binds to that epitope more readily than it would bind to a random, unrelated epitope.

An "affinity matured" scaffold is a scaffold with one or more alterations, generally in a loop, which result in an improvement in the affinity of the Tn3 scaffold for an epitope compared to a parent Tn3 scaffold which does not possess those alteration(s).

The term "affinity" as used herein refers to a measure of the strength of the binding of a certain Tn3 scaffold of the invention to an individual epitope.

The term "avidity" as used herein refers to the overall stability of the complex between a population of Tn3 scaffolds of the invention and a certain epitope, i.e., the functionally combined strength of the binding of a plurality of Tn3 scaffolds with the antigen. Avidity is related to both the affinity of individual antigen-binding domains with specific epitopes, and also the valency of the scaffold of the invention.

The term "action on the target" refers to the binding of a Tn3 scaffold of the invention to one or more targets and to the biological effects resulting from such binding. In this respect, multiple antigen binding units in a Tn3 scaffold can interact with a variety of targets and/or epitopes and, for example, bring two targets physically closer, trigger metabolic cascades through the interaction with distinct targets, etc. With reference to CD40L, "action on the target" refers to the effect achieved, for example, by the enhancement, stimulation or activation, of one or more biological activities of CD40L.

The term "valency" as used herein refers to the number of potential antigen-binding modules, e.g., the number of FnIII modules in a scaffold of the invention. When a Tn3 scaffold of the invention comprises more than one antigen-binding module, each binding module can specifically bind, e.g., the same epitope or a different epitope, in the same target or different targets.

The term "disulfide bond" as used herein includes the covalent bond formed between two sulfur atoms. The amino acid cysteine comprises a thiol group that can form a disulfide bond or bridge with a second thiol group.

The term "immunoglobulin" and "antibody" comprises various broad classes of polypeptides that can be distinguished biochemically. Those skilled in the art will appreciate that heavy chains are classified as gamma, mu, alpha, delta, or epsilon. It is the nature of this chain that determines the "class" of the antibody as IgG, IgM, IgA IgG, or IgE, respectively. Modified versions of each of these classes are readily discernible to the skilled artisan. As used herein, the term "antibody" includes but not limited to an intact antibody, a modified antibody, an antibody VL or VL domain, a CH1 domain, a Ckappa domain, a Clambda domain, an Fc domain (see below), a CH2, or a CH3 domain.

As used herein, the term "Fc domain" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide.

As used herein, the term "modified antibody" includes synthetic forms of antibodies which are altered such that they are not naturally occurring, e.g., antibodies that comprise at least two heavy chain portions but not two complete heavy chains (as, e.g., domain deleted antibodies or minibodies); multispecific forms of antibodies (e.g., bispecific, trispecific, etc.) altered to bind to two or more antigens or to different epitopes of a single antigen). In addition, the term "modified antibody" includes multivalent forms of antibodies (e.g., trivalent, tetravalent, etc., antibodies that to three or more copies of the same antigen). (See, e.g., Antibody Engineering, Kontermann & Dubel, eds., 2010, Springer Protocols, Springer).

The term "in vivo half-life" is used in its normal meaning, i.e., the time at which 50% of the biological activity of a polypeptide is still present in the body/target organ, or the time at which the activity of the polypeptide is 50% of its initial value. As an alternative to determining functional in vivo half-life, "serum half-life" may be determined, i.e., the time at which 50% of the polypeptide molecules circulate in the plasma or bloodstream prior to being cleared. Determination of serum-half-life is often more simple than determining functional in vivo half-life and the magnitude of serum-half-life is usually a good indication of the magnitude of functional in vivo half-life. Alternative terms to serum half-life include "plasma half-life," circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

The term "increased" with respect to the functional in vivo half-life or plasma half-life is used to indicate that the relevant half-life of the polypeptide is statistically significantly increased relative to that of a reference molecule (for example an unmodified polypeptide), as determined under comparable conditions.

The term "decreased" with respect to the functional in vivo half-life or plasma half-life is used to indicate that the relevant half-life of the polypeptide is statistically significantly decreased relative to that of a reference molecule (for example an unmodified polypeptide), as determined under comparable conditions.

The term "expression" as used herein refers to a process by which a gene produces a biochemical, for example, a scaffold of the invention or a fragment thereof. The process includes any manifestation of the functional presence of the gene within the cell including, without limitation, gene knockdown as well as both transient expression and stable expression. It includes without limitation transcription of the gene into one or more mRNAs, and the translation of such mRNAs into one or more polypeptides. If the final desired product is a biochemical, expression includes the creation of that biochemical and any precursors.

An "expression product" can be either a nucleic acid, e.g., a messenger RNA produced by transcription of a gene, or a polypeptide. Expression products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "vector" or "expression vector" is used herein to mean vectors used in accordance with the present invention as a vehicle for introducing into and expressing a desired expression product in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired nucleic acid and the ability to enter and/or replicate in eukaryotic or prokaryotic cells.

The term "host cells" refers to cells that harbor vectors constructed using recombinant DNA techniques and encoding at least one expression product. In descriptions of processes for the isolation of an expression product from recombinant hosts, the terms "cell" and "cell culture" are used interchangeably to denote the source of the expression product unless it is clearly specified otherwise, i.e., recovery of the expression product from the "cells" means either recovery from spun down whole cells, or recovery from the cell culture containing both the medium and the suspended cells.

The terms "treat" or "treatment" as used herein refer to both therapeutic treatment and prophylactic or preventative measures, wherein the object is to prevent or slow down (lessen) an undesired physiological change or disorder in a subject, such as the progression of an inflammatory disease or condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

The term "treatment" also means prolonging survival as compared to expected survival if not receiving treatment. Those in need of treatment include those already with the condition or disorder as well as those prone to have the condition or disorder or those in which the condition or disorder is to be prevented.

The terms "subject," "individual," "animal," "patient," or "mammal" refer to any individual, patient or animal, in particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

The term "CD40L" as used herein refers without limitations to CD40L expressed on the surface of T-cells, recombinantly expressed CD40L, CD40L expressed and purified form E. coli or other suitable recombinant protein expression systems, aglycosylated CD40L, and soluble fragments of CD40L. As used herein, "CD40L" also refers to MegaCD40L. MEGA-CD40L™ is a high activity construct in which two trimeric CD40 ligands are artificially linked via the collagen domain of ACRP30/adiponectin. This construct very effectively simulates the natural membrane-assisted aggregation of CD40L in vivo. It provides a simple and equally potent alternative to [CD40L+enhancer] combinations (Alexis biochemicals). The term "CD40L" refers to monomeric forms of CD40L as well as oligomeric forms, e.g., trimeric CD40L.

The term "CD40L" refers both to the full length CD40L and to soluble fragments, e.g., extracellular domain forms of CD40L resulting from proteolysis. Amino acid sequences of membrane-bound and soluble forms of human CD40L (Swissprot: P29965) are shown in SEQ ID NO: 1 and SEQ ID NO: 2, respectively.

The terms "CD40L antagonist" or "antagonist" are used in the broadest sense, and includes any molecule that partially or fully inhibits, decreases or inactivates one or more biological activities of CD40L, and biologically active variants thereof, in vitro, in situ, or in vivo. For instance, a CD40L antagonist may function to partially or fully inhibit, decrease or inactivate one or more biological activities of one or more CD40L molecules, or one or more CD40L molecules bound to CD40 or other targets, in vivo, in vitro or in situ, as a result of its binding to CD40L.

The term "CD40L agonist" or "agonist" is used in the broadest sense, and includes any molecule that partially or fully enhances, stimulates or activates one or more biological activities of CD40L, and biologically active variants thereof, in vitro, in situ, or in vivo. For instance, a CD40L agonist may function to partially or fully enhance, stimulate or activate one or more biological activities of one or more CD40L molecules, or one or more CD40L molecules bound to CD40R or other targets, in vivo, in vitro or in situ, as a result of its binding to CD40L.

The term "crystal" as used herein, refers to one form of solid state of matter in which atoms are arranged in a pattern that repeats periodically in three-dimensions, typically forming a lattice.

The term "space group symmetry," as used herein, refers to the whole symmetry of the crystal that combines the translational symmetry of a crystalline lattice with the point group symmetry. A "space group" is designated by a capital letter identifying the lattice group (P, A, F, etc.) followed by the point group symbol in which the rotation and reflection elements are extended to include screw axes and glide planes. Note that the point group symmetry for a given space group can be determined by removing the cell centering symbol of the space group and replacing all screw axes by similar rotation axes and replacing all glide planes with mirror planes. The point group symmetry for a space group describes the true symmetry of its reciprocal lattice.

The term "unit cell," as used herein, means the atoms in a crystal that are arranged in a regular repeated pattern, in which the smallest repeating unit is called the unit cell. The entire structure can be reconstructed from knowledge of the unit cell, which is characterized by three lengths (a, b, and c) and three angles (α, β, and γ). The quantities a and b are the lengths of the sides of the base of the cell and γ is the angle between these two sides. The quantity c is the height of the unit cell. The angles α and β describe the angles between the base and the vertical sides of the unit cell.

The term "machine-readable data storage medium," as used herein, means a data storage material encoded with machine-readable data, wherein a machine is programmed with instructions for using such data and is capable of displaying data in the desired format, for example, a graphical three-dimensional representation of molecules or molecular complexes.

The term "X-ray diffraction pattern" means the pattern obtained from X-ray scattering of the periodic assembly of molecules or atoms in a crystal. X-ray crystallography is a technique that exploits the fact that X-rays are diffracted by crystals. X-rays have the proper wavelength (in the Angstrom range, approximately $10^{-8}$ cm) to be scattered by the electron cloud of an atom of comparable size. Based on the diffraction pattern obtained from X-ray scattering of the periodic assembly of molecules or atoms in the crystal, the electron density can be reconstructed. Additional phase information can be extracted either from the diffraction data or from supplementing diffraction experiments to complete the reconstruction (the phase problem in crystallography). A model is the progressively built into the experimental electron density, refined against the data to produce an accurate molecular structure. X-ray structure coordinates define a unique configuration of points in space. Those of skill in the art understand that a set of structure coordinates for a protein or a protein-ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a configuration of points can be defined by increasing or decreasing the distances between coordinates by a scalar factor, while keeping the angles essentially the same.

The term "crystal structure," as used herein, refers to the three-dimensional or lattice spacing arrangement of repeating atomic or molecular units in a crystalline material. The crystal structure of a crystalline material can be determined by X-ray crystallographic methods, see, for example, "Principles of Protein X-Ray Crystallography" by Jan Drenth, Springer Advanced Texts in Chemistry, Springer Verlag, 2nd ed., February 199, ISBN: 0387985875, and "Introduction to Macromolecular Crystallography" by Alexander McPherson, Wiley-Liss, Oct. 18, 2002, ISBN: 0471251224.

The term "effector function" refers to those biological activities of an antibody or antibody fragment attributable to the Fc region (a native Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; downregulation of cell surface receptors (e.g., B cell receptors); and B cell activation.

The term "antibody-dependent cell-mediate cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cells with cytotoxins.

The term "Fc receptor" or "FcR" describes a receptor that binds to the Fc region of an antibody. The FcR can be a native sequence human FcR. The FcR can bind to an IgG antibody (a gamma receptor) and includes receptors of the FcγRI, FcγRII and FcγRIII subclasses, including allelic variants and alternatively spliced forms of these receptors. The term also includes the neonatal receptor FcRn.

The term "consensus sequence" refers to a protein sequence showing the most common amino acids at a particular position after multiple sequences are aligned. A consensus sequence is a way of representing the results of a multiple sequence alignment, where related sequences are compared to each other. The consensus sequence shows which residues are most abundant in the alignment at each position, and the degree of variability at each position.

INTRODUCTION

CD40L (also known as CD154, CD40 ligand, gp39 or TBAM) is a 33 kDa, Type II membrane glycoprotein (Swiss-ProtAcc-No P29965). Additionally, shorter 18 kDa CD40L soluble forms exist, (also known as sCD40L or soluble CD40L). These soluble forms of CD40L are generated by proteolytic processing of the membrane bound protein, but the cellular activity of the soluble species is weak in the absence of higher order oligomerization (e.g., trimerization).

The present invention provides a family of recombinant, non-naturally occurring protein scaffolds (Tn3 scaffolds) capable of binding to CD40L. In particular, the proteins described herein can be used to display defined loops which are analogous to the complementarity-determining regions ("CDRs") of an antibody variable region. These loops can be subjected to randomization or restricted evolution to generate diversity capable of binding to a multitude of target compounds. The Tn3 scaffolds can be used as monomers or can be assembled into multimer scaffolds capable of binding to CD40L.

In specific embodiments, the invention provides CD40L-specific binders which are useful for preventing ameliorating, detecting, diagnosing, or monitoring diseases, such as but not limited to autoimmune disease. In other specific embodiments, CD40L-specific Tn3 scaffolds of the invention are useful for the treatment of autoimmune diseases and conditions. In some embodiments, autoimmune diseases may include, but are not limited to systemic lupus erythematosis (SLE), rheumatoid arthritis (RA), multiple sclerosis (MS), inflammatory bowel disease (IBD) and allograft rejection.

The Tn3 scaffolds of the invention comprise CD40L-specific monomer subunits derived from the third FnIII domain of human tenascin C, in which at least one non-naturally occurring intramolecular disulfide bond has been engineered. The monomer subunits that make up the Tn3 scaffolds of the invention correctly fold independently of each other, retain their binding specificity and affinity, and each of the monomeric scaffolds retains its functional properties. When monomer subunits are assembled in high valency multimeric Tn3 scaffolds the monomer subunits correctly fold independently of each other, retain their binding specificity and affinity, and each one of the monomers retains its functional properties.

Tn3 scaffolds of the invention comprising more than one monomer subunit can bind to multiple epitopes, e.g., (i) bind to multiple epitopes in a single target, (ii) bind to a single epitope in multiple targets, (iii) bind to multiple epitopes located on different subunits of one target, or (iv) bind to multiple epitopes on multiple targets, thus increasing avidity.

In addition, due to the possibility of varying the distance between multiple monomers via linkers, multimeric Tn3 scaffolds are capable of binding to multiple target molecules on a surface (either on the same cell/surface or in different cells/surfaces). As a result of their ability to bind simultaneously to more than one target, a Tn3 multimeric scaffold of the invention can be used to modulate multiple pathways, cross-link receptors on a cell surface, bind cell surface receptors on separate cells, and/or bind target molecules or cells to a substrate.

In addition, the present invention provides affinity matured scaffolds wherein the affinity of a scaffold for a specific target is modulated via mutation. Also, the invention provides methods to produce the scaffolds of the invention as well as methods to engineer scaffolds with desirable physicochemical, pharmacological, or immunological properties. Furthermore, the present invention provides uses for such scaffolds and methods for therapeutic, prophylactic, and diagnostic use.

The FnIII Structural Motif

The Tn3 scaffolds of the present invention are based on the structure of a type III fibronectin module (FnIII), a domain found widely across all three domains of life and viruses, and in multitude of protein classes. In specific embodiments, the scaffolds of the invention are derived from the third FnIII domain of human tenascin C (see International Application No. International Application No. PCT/US2008/012398, published as WO 2009/058379; PCT/US2011/032184, published as WO 2011/130324; and International Application No. PCT/US2011/032188, published as WO2011130328).

In one specific embodiment, the Tn3 scaffolds of the invention comprise a CD40L-specific monomer subunit derived from a parent Tn3 scaffold. The overall tridimensional fold of the monomer is closely related to that of the smallest functional antibody fragment, the variable region of the heavy chain (VH), which in the single domain antibodies of camels and camelids (e.g., llamas) comprises the entire antigen recognition unit.

The Tn3 monomer subunits of the invention and the native FnIII domain from tenascin C are characterized by the same tridimensional structure, namely a beta-sandwich structure with three beta strands (A, B, and E) on one side and four beta strands (C, D, F, and G) on the other side, connected by six loop regions. These loop regions are designated according to the beta-strands connected to the N- and C-terminus of each loop. Accordingly, the AB loop is located between beta strands A and B, the BC loop is located between strands B and C, the CD loop is located between beta strands C and D, the DE loop is located between beta strands D and E, the EF loop is located between beta strands E and F, and the FG loop is located between beta strands F and G. FnIII domains possess solvent exposed loops tolerant of randomization, which facilitates the generation of diverse pools of protein scaffolds capable of binding specific targets with high affinity.

In one aspect of the invention, Tn3 monomer subunits are subjected to directed evolution designed to randomize one or more of the loops which are analogous to the complementarity-determining regions (CDRs) of an antibody variable region. Such a directed evolution approach results in the production of antibody-like molecules with high affinities for targets of interest, e.g., CD40L.

In addition, in some embodiments the Tn3 scaffolds described herein can be used to display defined exposed loops (for example, loops previously randomized and selected on the basis of target binding) in order to direct the evolution of molecules that bind to such introduced loops. This type of selection can be carried out to identify recognition molecules for any individual CDR-like loop or, alternatively, for the recognition of two or all three CDR-like loops combined into a nonlinear epitope binding moiety. A set of three loops (designated BC, DE, and FG), which can confer specific target binding, run between the B and C strands; the D and E strands, and the F and G beta strands, respectively. The BC, DE, and FG loops of the third FnIII domain of human tenascin C are 9, 6, and 10 amino acid residues long, respectively. The length of these loops falls within the narrow range of the cognate antigen-recognition loops found in antibody heavy chains, that is, 7-10, 4-8, and 4-28 amino acids in length, respectively. Similarly, a second set of loops, the AB, CD, and EF loops (7, 7, and 8, amino acids in length respectively) run between the A and B beta strands; the C and D beta strands; and the E and F beta strands, respectively.

Once randomized and selected for high affinity binding to a target, the loops in the Tn3 monomer scaffold may make contacts with targets equivalent to the contacts of the cognate CDR loops in antibodies. Accordingly, in some embodiments the AB, CD, and EF loops are randomized and selected for high affinity binding to one or more targets, e.g., CD40L. In some embodiments, this randomization and selection process may be performed in parallel with the randomization of the BC, DE, and FG loops, whereas in other embodiments this randomization and selection process is performed in series.

CD40L-Specific Monomeric Subunits

The invention provides CD40L-specific recombinant, non-naturally occurring Tn3 scaffolds comprising, a plurality of beta strand domains linked to a plurality of loop regions, wherein one or more of said loop regions vary by deletion, substitution or addition of at least one amino acid from the cognate loops in wild type Tn3 (SEQ ID NO: 3) (see TABLE 1).

To generate improved CD40L-specific Tn3 monomer subunits with novel binding characteristics, parent Tn3 is subjected to amino acid additions, deletions or substitutions. It will be understood that, when comparing the sequence of a CD40L-specific Tn3 monomer subunit to the sequence of parent Tn3, the same definition of the beta strands and loops is utilized. In some embodiments, the CD40L-specific Tn3 monomer subunits of the invention comprise the amino acid sequence:

| | |
|---|---|
| IEV | (SEQ ID NO: 11) |
| $(X_{AB})_n$ALITW | (SEQ ID NO: 12) |
| $(X_{BC})_n$CELX$_1$YGI | (SEQ ID NO: 173) |
| $(X_{CD})_n$TTIDL | (SEQ ID NO: 15) |
| $(X_{DE})_n$YSI | (SEQ ID NO: 16) |
| $(X_{EF})_n$YEVSLIC | (SEQ ID NO: 17) |
| $(X_{FG})_n$KETFTT | (SEQ ID NO: 18) | wherein:

(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;

(b) $X_1$ represents amino acid residue alanine (A) or threonine (T); and, (c) length of the loop n is an integer between 2 and 26.

TABLE 2

Loop Sequences of Tn3 Clones Used in These Studies

| Clone | AB Loop SEQ ID NO | BC Loop SEQ ID NO | CD Loop SEQ ID NO | DE Loop SEQ ID NO | EF Loop SEQ ID NO | FG Loop SEQ ID NO* |
|---|---|---|---|---|---|---|
| PARENT Tn3 | | | | | | |
| Tn3 | 4 | 5 | 6 | 7 | 8 | 9 |
| 309 FAMILY | | | | | | |
| 309FGwt | 4 | 83 | 6 | 94 | 8 | 9 |
| 309 | 4 | 83 | 6 | 94 | 8 | 99 |
| 340 | 4 | 84 | 6 | 95 | 8 | 9 |
| 341 | 4 | 85 | 6 | 94 | 8 | 9 |
| 342 | 4 | 86 | 6 | 96 | 8 | 9 |
| 343 | 4 | 87 | 6 | 97 | 8 | 9 |
| 344 | 4 | 88 | 6 | 95 | 8 | 9 |
| 345 | 4 | 89 | 6 | 94 | 8 | 9 |
| 346 | 4 | 90 | 6 | 94 | 8 | 9 |
| 347 | 4 | 91 | 6 | 95 | 8 | 9 |
| 348 | 4 | 92 | 6 | 98 | 8 | 9 |
| 349 | 4 | 93 | 6 | 94 | 8 | 9 |
| 309FGwt consensus | 4 | 168 | 6 | 169 | 8 | 170 |
| 311 FAMILY** | | | | | | |
| 311 | 4 | 100 | 6 | 118 | 8 | 129 |
| 311K4E | 136 | 100 | 6 | 118 | 137 | 129 |
| 311K4E_1 | 136 | 101 | 6 | 119 | 8 | 129 |
| 311K4E_2 | 136 | 102 | 6 | 120 | 8 | 129 |
| 311K4E_3† | 136 | 103 | 6 | 121 | 8 | 129 |
| 311K4E_4† | 136 | 104 | 6 | 122 | 8 | 129 |
| 311K4E_5† | 136 | 105 | 6 | 121 | 8 | 129 |
| 311K4E_7 | 136 | 106 | 6 | 123 | 8 | 129 |
| 311K4E_8† | 136 | 107 | 6 | 123 | 8 | 129 |
| 311K4E_9 | 136 | 108 | 6 | 118 | 8 | 129 |
| 311K4E_10† | 136 | 109 | 6 | 123 | 8 | 129 |
| 311K4E_11 | 136 | 110 | 6 | 121 | 8 | 129 |
| 311K4E_12† | 136 | 111 | 6 | 123 | 8 | 130 |
| 311K4E_13 | 136 | 108 | 6 | 121 | 8 | 129 |
| 311K4E_14 | 136 | 112 | 6 | 124 | 8 | 129 |
| 311K4E_15 | 136 | 113 | 6 | 125 | 8 | 129 |
| 311K4E_16 | 136 | 114 | 6 | 118 | 8 | 129 |
| 311K4E_19 | 136 | 115 | 6 | 126 | 8 | 129 |
| 311K4E_20 | 136 | 116 | 6 | 127 | 8 | 129 |
| 311K4E_21 | 136 | 117 | 6 | 128 | 8 | 129 |
| 311 consensus | 173 | 174 | 6 | 175 | 176 | 177 |

†Clones comprising a C beta strand having the sequence CELAYGI (SEQ ID NO: 14), all other clones comprise a C beta strand having the sequence CELTYGI (SEQ ID NO: 13).
*In some variants in the 309 family, e.g., 342, the FG loop can be replaced with SEQ ID NO: 139.
**In some variants in the 311 family, the BC loop can be engineered to replace the tyrosine at position 21. It is specifically contemplated that the replacement amino acid residues can have a small side chain.

In some embodiments, the CD40L-specific Tn3 monomer subunits of the invention consist of the amino acid sequence:

```
IEV                  (SEQ ID NO: 11)

(X_AB)_n ALITW       (SEQ ID NO: 12)

(X_BC)_n CELX_1 YGI  (SEQ ID NO: 173)

(X_CD)_n TTIDL       (SEQ ID NO: 15)

(X_DE)_n YSI         (SEQ ID NO: 16)

(X_EF)_n YEVSLIC     (SEQ ID NO: 17)

(X_FG)_n KETFTT      (SEQ ID NO: 18)
``` wherein:
(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;
(b) $X_1$ represents amino acid residue alanine (A) or threonine (T); and,
(c) length of the loop n is an integer between 2 and 26.

In one embodiment, the beta strands of the CD40L-specific Tn3 monomer scaffold have at least 90% sequence identity to the beta strands of the parent Tn3 scaffold (SEQ ID NO: 3). To calculate such percentage of sequence identify, amino acid sequences are aligned applying methods known in the art. The percentage of sequence identity is defined as the ratio between (a) the number of amino acids located in beta strands which are identical in the sequence alignment and (b) the total number of amino acids located in beta strands.

In one embodiment, the sequence of the AB loop comprises SEQ ID NO: 4 or SEQ ID NO: 136. In another embodiment, the sequence of the CD loop comprises SEQ ID NO: 6. In another embodiment, the sequence of the EF loop comprises SEQ ID NO: 8 or SEQ ID NO: 137. In one embodiment, the sequence of the AB loop consists of SEQ ID NO: 4 or SEQ ID NO: 136. In another embodiment, the sequence of the CD loop consists of SEQ ID NO: 6. In another embodiment, the sequence of the EF loop consists of SEQ ID NO: 8 or SEQ ID NO: 137.

In one embodiment, the sequence of the BC loop comprises a sequence selected from the group consisting of SEQ ID NOs: 83, 84, 85, 86, 87, 88, 89, 90, 91, 92 and 93. In another embodiment, the sequence of the BC loop consists of a sequence selected from the group consisting of SEQ ID NOs: 83, 84, 85, 86, 87, 88, 89, 90, 91, 92 and 93.

In one embodiment, the sequence of the DE loop comprises a sequence selected from the group consisting of SEQ ID NOs: 94, 95, 96, 97 and 98. In another embodiment, the sequence of the DE loop consists of a sequence selected from the group consisting of SEQ ID NOs: 94, 95, 96, 97 and 98.

In one embodiment, the sequence of the FG loop comprises a sequence selected from the group consisting of SEQ ID NOs: 9, 99, and 139. In another embodiment, the sequence of the FG loop consists of a sequence selected from the group consisting of SEQ ID NOs: 9, 99, and 139.

In one embodiment, the sequence of the BC loop comprises a sequence selected from the group consisting of SEQ ID NOs: 100, 101, 102, 103, 104, 105, 106, 107, 108, 109, 110, 111, 112, 113, 114, 115, 116 and 117. In another embodiment, the sequence of the BC loop consists of a sequence selected from the group consisting of SEQ ID NOs: 100, 101, 102, 103, 104, 105, 106, 107, 108, 109, 110, 111, 112, 113, 114, 115, 116 and 117.

In some embodiments, the sequence of the DE loop comprises a sequence selected from the group consisting of SEQ ID NOs: 118, 119, 120, 121, 122, 123, 124, 125, 126, 127 and 128. In other embodiments, the sequence of the DE loop consists of a sequence selected from the group consisting of SEQ ID NOs: 118, 119, 120, 121, 122, 123, 124, 125, 126, 127 and 128.

In some embodiments, the sequence of the FG loop comprises a sequence selected from the groups consisting of SEQ ID NOs: 129 and 130. In other embodiments, the sequence of the FG loop consists of a sequence selected from the groups consisting of SEQ ID NOs: 129 and 130.

In some embodiments, the sequence of the BC loop comprises SEQ ID NO: 83, the sequence of the DE loop comprises SEQ ID NO: 94, and the sequence of the FG loop comprises SEQ ID NO: 9 or 139. In some embodiments, the sequence of the BC loop consists of SEQ ID NO: 83, the sequence of the DE loop consists of SEQ ID NO: 94, and the sequence of the FG loop consists of SEQ ID NO: 9 or 139.

In some embodiments, the sequence of the BC loop comprises SEQ ID NO: 83, the sequence of the DE loop comprises SEQ ID NO: 94, and the sequence of the FG loop comprises SEQ ID NO: 99. In other embodiments, the sequence of the BC loop consists of SEQ ID NO: 83, the sequence of the DE loop consists of SEQ ID NO: 94, and the sequence of the FG loop consists of SEQ ID NO: 99.

In some embodiments, the sequence of the BC loop comprises SEQ ID NO: 84, the sequence of the DE loop comprises SEQ ID NO: 95, and the sequence of the FG loop comprises SEQ ID NO: 9 or 139. In other embodiments, the sequence of the BC loop consists of SEQ ID NO: 84, the sequence of the DE loop consists of SEQ ID NO: 95, and the sequence of the FG loop consists of SEQ ID NO: 9 or 139.

In some embodiments, the sequence of the BC loop comprises SEQ ID NO: 85, the sequence of the DE loop comprises SEQ ID NO: 94, and the sequence of the FG loop comprises SEQ ID NO: 9 or 139. In other embodiments, the sequence of the BC loop consists of SEQ ID NO: 85, the sequence of the DE loop consists of SEQ ID NO: 94, and the sequence of the FG loop consists of SEQ ID NO: 9 or 139.

In some embodiments, the sequence of the BC loop comprises SEQ ID NO: 86, the sequence of the DE loop comprises SEQ ID NO: 96, and the sequence of the FG loop comprises SEQ ID NO: 9 or 139. In other embodiments, the sequence of the BC loop consists of SEQ ID NO: 86, the sequence of the DE loop consists of SEQ ID NO: 96, and the sequence of the FG loop consists of SEQ ID NO: 9 or 139.

In some embodiments, the sequence of the BC loop comprises SEQ ID NO: 87, the sequence of the DE loop comprises SEQ ID NO: 97, and the sequence of the FG loop comprises SEQ ID NO: 9 or 139. In other embodiments, the sequence of the BC loop consists of SEQ ID NO: 87, the sequence of the DE loop consists of SEQ ID NO: 97, and the sequence of the FG loop consists of SEQ ID NO: 9 or 139.

In some embodiments, the sequence of the BC loop comprises SEQ ID NO: 88, the sequence of the DE loop comprises SEQ ID NO: 95, and the sequence of the FG loop comprises SEQ ID NO: 9 or 139. In other embodiments, the sequence of the BC loop consists of SEQ ID NO: 88, the sequence of the DE loop consists of SEQ ID NO: 95, and the sequence of the FG loop consists of SEQ ID NO: 9 or 139.

In some embodiments, the sequence of the BC loop comprises SEQ ID NO: 89, the sequence of the DE loop comprises SEQ ID NO: 94, and the sequence of the FG loop comprises SEQ ID NO: 9 or 139. In other embodiments, sequence of the BC loop consists of SEQ ID NO: 89, the sequence of the DE loop consists of SEQ ID NO: 94, and the sequence of the FG loop consists of SEQ ID NO: 9 or 139.

In some embodiments, the sequence of the BC loop comprises SEQ ID NO: 90, the sequence of the DE loop comprises SEQ ID NO: 94, and the sequence of the FG loop comprises SEQ ID NO: 9 or 139. In other embodiments, the sequence of the BC loop consists of SEQ ID NO: 90, the sequence of the DE loop consists of SEQ ID NO: 94, and the sequence of the FG loop consists of SEQ ID NO: 9 or 139.

In some embodiments, the sequence of the BC loop comprises SEQ ID NO: 91, the sequence of the DE loop comprises SEQ ID NO: 95, and the sequence of the FG loop comprises SEQ ID NO: 9 or 139. In other embodiments, the sequence of the BC loop consists of SEQ ID NO: 91, the sequence of the DE loop consists of SEQ ID NO: 95, and the sequence of the FG loop consists of SEQ ID NO: 9 or 139.

In some embodiments, the sequence of the BC loop comprises SEQ ID NO: 92, the sequence of the DE loop comprises SEQ ID NO: 98, and the sequence of the FG loop comprises SEQ ID NO: 9 or 139. In other embodiments, the sequence of the BC loop consists of SEQ ID NO: 92, the sequence of the DE loop consists of SEQ ID NO: 98, and the sequence of the FG loop consists of SEQ ID NO: 9 or 139.

In some embodiments, the sequence of the BC loop comprises SEQ ID NO: 93, the sequence of the DE loop comprises SEQ ID NO: 94, and the sequence of the FG loop comprises SEQ ID NO: 9 or 139. In other embodiments, the sequence of the BC loop consists of SEQ ID NO: 93, the sequence of the DE loop consists of SEQ ID NO: 94, and the sequence of the FG loop consists of SEQ ID NO: 9 or 139.

In some embodiments, the sequence of the BC loop comprises SEQ ID NO: 168, the sequence of the DE loop comprises SEQ ID NO: 169, and the sequence of the FG loop comprises SEQ ID NO: 170. In other embodiments, sequence of the BC loop consists of SEQ ID NO: 168, the sequence of the DE loop consists of SEQ ID NO: 169, and the sequence of the FG loop consists of SEQ ID NO: 170.

In some embodiments, the sequence of the BC loop comprises SEQ ID NO: 100, the sequence of the DE loop comprises SEQ ID NO: 118, and the sequence of the FG loop comprises SEQ ID NO: 129. In other embodiments, the sequence of the BC loop consists of SEQ ID NO: 100, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 101, the sequence of the DE loop comprises SEQ ID NO: 119, and the sequence of the FG loop comprises SEQ ID NO: 129. In other embodiments, the sequence of the AB loop consists of SEQ ID NO: 136, the sequence of the BC loop consists of SEQ ID NO: 101, the sequence of the DE loop consists of SEQ ID NO: 119, and the sequence of the FG loop consists of SEQ ID NO: 129.

In some embodiments, the sequence of the AB loop comprises SEQ ID NO: 136, the sequence of the BC loop comprises SEQ ID NO: 102, the sequence of the DE loop comprises SEQ ID NO: 120, and the sequence of the FG loop comprises SEQ ID NO: 129. In other embodiments, the sequence of the AB loop consists of SEQ ID NO: 136, the sequence of the BC loop consists of SEQ ID NO: 102, the sequence of the DE loop consists of SEQ ID NO: 120, and the sequence of the FG loop consists of SEQ ID NO: 129.

In some embodiments, the sequence of the AB loop comprises SEQ ID NO: 136, the sequence of the BC loop comprises SEQ ID NO: 103, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 103, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 104, the sequence of the DE loop comprises SEQ ID NO: 122, and the sequence of the FG loop comprises SEQ ID NO: 129. In other embodiments, the sequence of the AB loop consists of SEQ ID NO: 136, the sequence of the BC loop consists of SEQ ID NO: 104, the sequence of the DE loop consists of SEQ ID NO: 122, and the sequence of the FG loop consists of SEQ ID NO: 129.

In some embodiments, the sequence of the AB loop comprises SEQ ID NO: 136, the sequence of the BC loop comprises SEQ ID NO: 105, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 105, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 106, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 106, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 107, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 107, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 108, the sequence of the DE loop comprises SEQ ID NO: 118, and the sequence of the FG loop comprises SEQ ID NO: 129. In other embodiments, the sequence of the AB loop consists of SEQ ID NO: 136, the sequence of the BC loop consists of SEQ ID NO: 108, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 109, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 109, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 110, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 110, the sequence of the DE loop consists of s SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 111, the sequence of the DE loop comprises SEQ ID NO: 123, and the sequence of the FG loop comprises SEQ ID NO: 130. In other embodiments, the sequence of the AB loop consists of SEQ ID NO: 136, the sequence of the BC loop consists of SEQ ID NO: 111, the sequence of the DE loop consists of SEQ ID NO: 123, and the sequence of the FG loop consists of SEQ ID NO: 130.

In some embodiments, the sequence of the AB loop comprises SEQ ID NO: 136, the sequence of the BC loop comprises SEQ ID NO: 108, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 108, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 112, the sequence of the DE loop comprises SEQ ID NO: 124, and the sequence of the FG loop comprises SEQ ID NO: 129. In other embodiments, the sequence of the AB loop consists of SEQ ID NO: 136, the sequence of the BC loop consists of SEQ ID NO: 112, the sequence of the DE loop consists of SEQ ID NO: 124, and the sequence of the FG loop consists of SEQ ID NO: 129.

In some embodiments, the sequence of the AB loop comprises SEQ ID NO: 136, the sequence of the BC loop comprises SEQ ID NO: 113, the sequence of the DE loop comprises SEQ ID NO: 125, and the sequence of the FG loop comprises SEQ ID NO: 129. In other embodiments, the sequence of the AB loop consists of SEQ ID NO: 136, the sequence of the BC loop consists of SEQ ID NO: 113, the sequence of the DE loop consists of SEQ ID NO: 125, and the sequence of the FG loop consists of SEQ ID NO: 129.

In some embodiments, the sequence of the AB loop comprises SEQ ID NO: 136, the sequence of the BC loop comprises SEQ ID NO: 114, the sequence of the DE loop comprises SEQ ID NO: 118, and the sequence of the FG loop comprises SEQ ID NO: 129. In other embodiments, the sequence of the AB loop consists of SEQ ID NO: 136, the sequence of the BC loop consists of SEQ ID NO: 114, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 115, the sequence of the DE loop comprises SEQ ID NO: 126, and the sequence of the FG loop comprises SEQ ID NO: 129. In other embodiments, the sequence of the AB loop consists of SEQ ID NO: 136, the sequence of the BC loop consists of SEQ ID NO: 115, the sequence of the DE loop consists of SEQ ID NO: 126, and the sequence of the FG loop consists of SEQ ID NO: 129.

In some embodiments, the sequence of the AB loop comprises SEQ ID NO: 136, the sequence of the BC loop comprises SEQ ID NO: 116, the sequence of the DE loop comprises SEQ ID NO: 127, and the sequence of the FG loop comprises SEQ ID NO: 129. In other embodiments, the sequence of the AB loop consists of SEQ ID NO: 136, the sequence of the BC loop consists of SEQ ID NO: 116, the sequence of the DE loop consists of SEQ ID NO: 127, and the sequence of the FG loop consists of SEQ ID NO: 129.

In some embodiments, the sequence of the AB loop comprises SEQ ID NO: 136, the sequence of the BC loop comprises SEQ ID NO: 117, the sequence of the DE loop comprises SEQ ID NO: 128, and the sequence of the FG loop comprises SEQ ID NO: 129. In other embodiments, the sequence of the AB loop consists of SEQ ID NO: 136, the sequence of the BC loop consists of SEQ ID NO: 117, the sequence of the DE loop consists of SEQ ID NO: 128, and the sequence of the FG loop consists of SEQ ID NO: 129.

In some embodiments, the sequence of the BC loop comprises SEQ ID NO: 174, the sequence of the DE loop comprises SEQ ID NO: 175, and the sequence of the FG loop comprises SEQ ID NO: 177. In other embodiments, the sequence of the BC loop consists of SEQ ID NO: 174, the sequence of the DE loop consists of SEQ ID NO: 175, and the sequence of the FG loop consists of SEQ ID NO: 177.

In some embodiments, the CD40L-specific monomer subunit comprises a sequence selected from the group consisting of SEQ ID NO: 20, 22, 24, 26, 28, 30, 32, 34, 36, 38, 40, 42 and 146. In other embodiments, the CD40L-specific monomer subunit consists of a sequence selected from the group consisting of SEQ ID NO: 20, 22, 24, 26, 28, 30, 32, 34, 36, 38, 40, 42 and 146.

In some embodiments, the CD40L-specific monomer subunit comprises SEQ ID NO: 28 or 146. In other embodiments, the CD40L-specific monomer subunit consists of SEQ ID NO: 28 or 146.

In some embodiments, the CD40L-specific Tn3 monomer subunits of the invention comprise the amino acid sequence:

(SEQ ID NO: 167)
IEVKDVTDTTALITWX$_1$DX$_2$X$_3$X$_4$X$_5$X$_6$X$_7$X$_8$CELTYGIKDVPGDRTTID

LWX$_9$HX$_{10}$AX$_{11}$YSIGNLKPDTEYEVSLICRX$_{12}$GDMSSNPAKETFTT wherein:
(a) X$_1$ represents amino acid residue serine (S) or leucine (L);
(b) X$_2$ represents amino acid residue aspartic acid (D) or glutamic acid (E);
(c) X$_3$ represents amino acid residue histidine (H), isoleucine (I), valine (V), phenylalanine (F) or tryptophan (W);
(d) X$_4$ represents amino acid residue alanine (A), glycine (G), glutamic acid (E) or aspartic acid (D);
(e) X$_5$ represents amino acid residue glutamic acid (E), leucine (L), glutamine (Q), serine (S), aspartic acid (D) or asparagine (N);
(f) X$_6$ represents amino acid residue phenylalanine (F) or tyrosine (Y);
(g) X$_7$ represents amino acid residue isoleucine (I), valine (V), histidine (H), glutamic acid (E) or aspartic acid (D);
(h) X$_8$ represents amino acid residue glycine (G), tryptophan (W) or valine (V);
(i) X$_9$ represents amino acid residue tryptophan (W), phenylalanine (F) or tyrosine (Y);
(j) X$_{10}$ represents amino acid residue serine (S), glutamine (Q), methionine (M) or histidine (H);
(k) X$_{11}$ represents amino acid residue tryptophan (W) or histidine (H); and,
(l) X$_{12}$ represents amino acid residue arginine (R) or serine (S).

In some embodiments, the CD40L-specific Tn3 monomer subunits of the invention consist of the amino acid sequence: IDC-29 DNA (SEQ ID NO: 167)
IEVKDVTDTTALITWX$_1$DX$_2$X$_3$X$_4$X$_5$X$_6$X$_7$X$_8$CELTYGIKDVPGDRTTID

LWX$_9$HX$_{10}$AX$_{11}$YSIGNLKPDTEYEVSLICRX$_{12}$GDMSSNPAKETFTT wherein:
(a) X$_1$ represents amino acid residue serine (S) or leucine (L);
(b) X$_2$ represents amino acid residue aspartic acid (D) or glutamic acid (E);
(c) X$_3$ represents amino acid residue histidine (H), isoleucine (I), valine (V), phenylalanine (F) or tryptophan (W);
(d) X$_4$ represents amino acid residue alanine (A), glycine (G), glutamic acid (E) or aspartic acid (D);
(e) X$_5$ represents amino acid residue glutamic acid (E), leucine (L), glutamine (Q), serine (S), aspartic acid (D) or asparagine (N);
(f) X$_6$ represents amino acid residue phenylalanine (F) or tyrosine (Y);
(g) X$_7$ represents amino acid residue isoleucine (I), valine (V), histidine (H), glutamic acid (E) or aspartic acid (D);
(h) X$_8$ represents amino acid residue glycine (G), tryptophan (W) or valine (V);
(i) X$_9$ represents amino acid residue tryptophan (W), phenylalanine (F) or tyrosine (Y);
(j) X$_{10}$ represents amino acid residue serine (S), glutamine (Q), methionine (M) or histidine (H);
(k) X$_{11}$ represents amino acid residue tryptophan (W) or histidine (H); and,
(l) X$_{12}$ represents amino acid residue arginine (R) or serine (S).

In some embodiments, the CD40L-specific monomer subunit comprises a sequence selected from the group consisting of SEQ ID NO: 44, 46, 48, 50, 52, 54, 56, 58, 60, 62, 64, 66, 68, 70, 72, 74, 76, 78, 80, and 82. In some embodiments, the CD40L-specific monomer subunit consists of a sequence selected from the group consisting of SEQ ID NO: 44, 46, 48, 50, 52, 54, 56, 58, 60, 62, 64, 66, 68, 70, 72, 74, 76, 78, 80, and 82.

In some embodiments, the CD40L-specific Tn3 monomer subunits of the invention comprise the amino acid sequence:

(SEQ ID NO: 171)
$IEVX_1DVTDTTALITWX_2X_3RSX_4X_5X_6X_7X_8X_9X_{10}CELX_{11}YGIKDVP$ $GDRTTIDLX_{12}X_{13}X_{14}X_{15}YVHYSIGNLKPDTX_{16}YEVSLICLTTDGT$ $YX_{17}NPAKETFTT$ wherein:

(a) $X_1$ represents amino acid residue lysine (K) or glutamic acid (E);
(b) $X_2$ represents amino acid residue threonine (T) or isoleucine (I);
(c) $X_3$ represents amino acid residue asparagine (N) or alanine (A);
(d) $X_4$ represents amino acid residue serine (S), leucine (L), alanine (A), phenylalanine (F) or tyrosine (Y);
(e) $X_5$ represents amino acid residue tyrosine (Y), alanine (A), glycine (G), valine (V), isoleucine (I) or serine (S);
(f) $X_6$ represents amino acid residue tyrosine (Y), serine (S), alanine (A) or histidine (H);
(g) $X_7$ represents amino acid residue asparagine (N), aspartic acid (D), histidine (H) or tyrosine (Y);
(h) $X_8$ represents amino acid residue leucine (L), phenylalanine (F), histidine (H) or tyrosine (Y);
(i) $X_9$ represents amino acid residue histidine (H), proline (P), serine (S), leucine (L) or aspartic acid (D);
(j) $X_{10}$ represents amino acid residue glycine (G), phenylalanine (F), histidine (H) or tyrosine (Y);
(k) $X_{11}$ represents amino acid residue alanine (A) or threonine (T);
(l) $X_{12}$ represents amino acid residue serine (S), asparagine (N), glutamic acid (E), asparagine (R) or aspartic acid (D);
(m) $X_{13}$ represents amino acid residue serine (S), glutamine (Q), threonine (T), asparagine (N) or alanine (A);
(n) $X_{14}$ represents amino acid residue proline (P), valine (V), isoleucine (I) or alanine (A) or no amino acid;
(o) $X_{15}$ represents amino acid residue isoleucine (I) or no amino acid;

(p) $X_{16}$ represents amino acid residue glutamic acid (E) or lysine (K); and, (q) $X_{17}$ represents amino acid residue serine (S) or asparagine (N).

In some embodiments, the CD40L-specific Tn3 monomer subunits of the invention consist of the amino acid sequence:

(SEQ ID NO: 171)
$IEVX_1DVTDTTALITWX_2X_3RSX_4X_5X_6X_7X_8X_9X_{10}CELX_{11}YGIKDVP$ $GDRTTIDLX_{12}X_{13}X_{14}X_{15}YVHYSIGNLKPDTX_{16}YEVSLICLTTDGT$ $YX_{17}NPAKETFTT$ wherein:

(a) $X_1$ represents amino acid residue lysine (K) or glutamic acid (E);
(b) $X_2$ represents amino acid residue threonine (T) or isoleucine (I);
(c) $X_3$ represents amino acid residue asparagine (N) or alanine (A);
(d) $X_4$ represents amino acid residue serine (S), leucine (L), alanine (A), phenylalanine (F) or tyrosine (Y);
(e) $X_5$ represents amino acid residue tyrosine (Y), alanine (A), glycine (G), valine (V), isoleucine (I) or serine (S);
(f) $X_6$ represents amino acid residue tyrosine (Y), serine (S), alanine (A) or histidine (H);
(g) $X_7$ represents amino acid residue asparagine (N), aspartic acid (D), histidine (H) or tyrosine (Y);
(h) $X_8$ represents amino acid residue leucine (L), phenylalanine (F), histidine (H) or tyrosine (Y);
(i) $X_9$ represents amino acid residue histidine (H), proline (P), serine (S), leucine (L) or aspartic acid (D);
(j) $X_{10}$ represents amino acid residue glycine (G), phenylalanine (F), histidine (H) or tyrosine (Y);
(k) $X_{11}$ represents amino acid residue alanine (A) or threonine (T);
(l) $X_{12}$ represents amino acid residue serine (S), asparagine (N), glutamic acid (E), asparagine (R) or aspartic acid (D);
(m) $X_{13}$ represents amino acid residue serine (S), glutamine (Q), threonine (T), asparagine (N) or alanine (A);
(n) $X_{14}$ represents amino acid residue proline (P), valine (V), isoleucine (I) or alanine (A) or no amino acid;
(o) $X_{15}$ represents amino acid residue isoleucine (I) or no amino acid;

(p) $X_{16}$ represents amino acid residue glutamic acid (E) or lysine (K); and, (q) $X_{17}$ represents amino acid residue serine (S) or asparagine (N).

In some embodiments, a CD40L-specific monomer scaffold comprise a Tn3 module wherein one or more of the beta strands comprise at least one amino acid substitution except that the cysteine residues in the C and F beta strands (SEQ ID NOs: 13 or 14; and SEQ ID NO: 17, respectively) may not be substituted.

The loops connecting the various beta strands of a CD40L-specific monomer subunit can be randomized for length and/or sequence diversity. In one embodiment, a CD40L-specific monomer subunit has at least one loop that is randomized for length and/or sequence diversity. In one embodiment, at least one, at least two, at least three, at least four, at least five or at least six loops of a CD40L-specific monomer subunit are randomized for length and/or sequence diversity. In one embodiment, at least one loop of a CD40L-specific monomer subunit is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or at least all three of loops AB, CD, and EF are randomized while at least one, at least two, or all three of loops BC, DE, and FG are randomized for length and/or sequence diversity. In still another embodiment, at least one, at least two, at least three of loops, at least 4, at least five, or all six of loops AB, CD, EF, BC, DE, and FG are randomized for length or sequence diversity.

In some embodiments, one or more residues within a loop are held constant while other residues are randomized for length and/or sequence diversity. In some embodiments, one or more residues within a loop are held to a predetermined and limited number of different amino acids while other residues are randomized for length and/or sequence diversity. Accordingly, a CD40L-specific monomer subunit of the invention can comprise one or more loops having a degenerate consensus sequence and/or one or more invariant amino acid residues.

In one embodiment, the CD40L-specific monomer subunit of the invention comprises an AB loop which is randomized. In another embodiment, the CD40L-specific monomer subunit of the invention comprises a BC loop which is randomized. In one embodiment, the CD40L-specific monomer subunit of the invention comprises a CD loop which is randomized. In one embodiment, the CD40L- specific monomer subunit of the invention comprises a DE loop which is randomized. In one embodiment, the CD40L-specific monomer subunit of the invention comprises an EF loop which is randomized.

In certain embodiments, the CD40L-specific monomer subunit of the invention comprises a FG loop which is held to be at least one amino acid residue shorter than the cognate FG loop of the third FnIII domain of human tenascin C and is further randomized at one or more positions.

In specific embodiments, at least one of loops BC, DE, and FG is randomized, wherein the A beta strand comprises SEQ ID NO:10 or 11, the B beta strand comprises SEQ ID NO:12, the C beta strand comprises SEQ ID NO:13 or 14, the D beta strand comprises SEQ ID NO:15, the E beta strand comprises SEQ ID NO:16, the F beta strand comprises SEQ ID NO:17, and the G beta strand comprises SEQ ID NO:18, the AB loop comprises SEQ ID NO:4 or 136, the CD loop comprises SEQ ID NO:6 and the EF loop comprises SEQ ID NO:8 or 137.

In other specific embodiments, at least one of loops AB, CD, and EF are randomized, wherein the A beta strand comprises SEQ ID NO:10 or 11, the B beta strand comprises SEQ ID NO:12, the C beta strand comprises SEQ ID NO:13 or 14, the D beta strand comprises SEQ ID NO:15, the E beta strand comprises SEQ ID NO:16, the F beta strand comprises SEQ ID NO:17, and the G beta strand comprises SEQ ID NO:18, the BC loop comprises SEQ ID NO:5, the DE loop comprises SEQ ID NO:7 and the FG loop comprises SEQ ID NO:9 or 139.

Enhanced Scaffold Stability

The stability of Tn3 scaffolds of the invention may be increased by many different approaches. In some embodiments, Tn3 scaffolds of the invention can be stabilized by elongating the N- and/or C-terminal regions. The N- and/or C-terminal regions can be elongated by 1, 2, 3, 4, 5, 6, 7, 8, 9, 10 or more than 10 amino acids. In other embodiments, the Tn3 scaffolds of the invention can be stabilized by introducing an alteration that increases serum half-life, as described herein. In yet another embodiment, the Tn3 scaffolds of the invention comprise an addition, deletion or substitution of at least one amino acid residue to stabilize the hydrophobic core of the scaffold.

Tn3 scaffolds of the invention can be effectively stabilized by engineering non-natural disulfide bonds as disclosed in International Patent Application No. PCT/US2011/032184. In some embodiments, scaffolds of the invention comprise non-naturally occurring disulfide bonds, as described in PCT Publication No: WO 2009/058379. A bioinformatics approach may be utilized to identify candidate positions suitable for engineering disulfide bonds.

In one embodiment, a Tn3 monomer subunit of the invention comprises at least one, at least two, at least three, at least four, or at least five non-naturally occurring intramolecular disulfide bonds. In one embodiment, a Tn3 monomer subunit of the invention comprises at least one non-naturally occurring intramolecular disulfide bond, wherein said at least one non-naturally occurring disulfide bond stabilizes the monomer. In yet another embodiment, Tn3 scaffolds of the invention comprise at least one non-naturally occurring disulfide bond, wherein the bond is located between two distinct monomer or multimer Tn3 scaffolds, i.e., the disulfide bond is an intermolecular disulfide bond. For example, a disulfide bond can link distinct scaffolds (for example, two CD40L-specific monomer scaffolds), a Tn3 scaffold and a linker, a Tn3 scaffold and an Fc domain, or a Tn3 scaffold and an antibody or fragment thereof.

In some embodiments, Tn3 scaffolds of the invention comprise at least one non-naturally occurring intermolecular disulfide bond that links a Tn3 monomer subunit and an isolated heterologous moiety, a Tn3 monomer subunit and a heterologous moiety fused or conjugated to the same Tn3 scaffold, or a Tn3 monomer subunit and a heterologous moiety fused or conjugated to a different Tn3 scaffold.

In some embodiments, Tn3 scaffolds of the invention comprise a disulfide bond that forms a Tn3 multimeric scaffold of at least 2, at least 3, at least 4 or more monomer subunits.

In another embodiment, Tn3 scaffolds of the invention may comprise an elongation of the N and/or C terminal regions. In one embodiment, the Tn3 scaffold of the invention comprises an alteration to increase serum half-life, as described herein. In yet another embodiment, the scaffolds of the invention comprise an addition, deletion or substitution of at least one amino acid residue to stabilize the hydrophobic core of the scaffold.

Stability Measurements

The stability of the Tn3 monomer subunits of the invention, isolated or as part of a multimeric Tn3 scaffold, can be readily measured by techniques well known in the art, such as thermal (Tm) and chaotropic denaturation (such as treatment with urea, or guanidine salts), protease treatment (such as treatment with thermolysin) or another art accepted methodology to determine protein stability. A comprehensive review of techniques used to measure protein stability can be found, for example in "Current Protocols in Molecular Biology" and "Current Protocols in Protein Science" by John Wiley and Sons. 2007. Multimeric Tn3 Scaffolds One aspect of the present invention provides multimeric Tn3 scaffolds comprising at least two Tn3 monomer subunits of the invention joined in tandem, and wherein at least one of the monomers is a CD40L-specific monomer subunit. Such multimeric Tn3 scaffolds can be assembled in multiple formats. In a specific aspect, the invention provides multimeric Tn3 scaffolds, wherein at least two CD40L-specific monomer subunits are connected in tandem via a peptide linker. In some embodiments, the multimeric Tn3 scaffold exhibits an increase in the valency and/or avidity of target binding, or other action of the target(s). In some embodiments, the increase in valency and/or avidity of target binding is accomplished when multiple monomer subunits bind to the same target. In some embodiments, the increase in valency improves a specific action on the target, such as increasing the dimerization of a target protein.

In a specific embodiment, a multimeric Tn3 scaffold of the invention comprises at least two CD40L-specific monomer subunits connected in tandem, wherein each CD40L-specific monomer subunit binds at least one target, and wherein each CD40L-specific monomer subunit comprises a plurality of beta strands linked to a plurality of loop regions, wherein at least one loop is a non-naturally occurring variant of the cognate loop in the parent Tn3 scaffold (SEQ ID NO: 3).

In one embodiment, multimeric Tn3 scaffolds are generated through covalent binding between CD40L-specific monomer subunits, for example, by directly linking the CD40L-specific monomer subunits, or by the inclusion of a linker, e.g., a peptide linker. In particular examples, covalently bonded Tn3 scaffolds are generated by constructing fusion genes that encode the CD40L-specific monomer subunits or, alternatively, by engineering codons for cysteine residues into CD40L-specific monomer subunits and allowing disulfide bond formation to occur between the expression products.

In one embodiment, multimeric Tn3 scaffolds of the invention comprise at least two CD40L-specific monomer subunits that are connected directly to each other without any additional intervening amino acids. In another embodiment, multimeric Tn3 scaffolds of the invention comprise at least two CD40L-specific monomer subunits that are connected in tandem via a linker, e.g., a peptide linker.

In a specific embodiment, multimeric Tn3 scaffolds of the invention comprise at least two CD40L-specific monomer subunits that are connected in tandem via a peptide linker, wherein the peptide linker comprises 1 to about 1000, or 1 to about 500, or 1 to about 250, or 1 to about 100, or 1 to about 50, or 1 to about 25, amino acids. In a specific embodiment, the multimeric Tn3 scaffold comprises at least two CD40L-specific monomer subunits that are connected in tandem via a peptide linker, wherein the peptide linker comprises 1 to about 20, or 1 to about 15, or 1 to about 10, or 1 to about 5, amino acids.

In a specific embodiment, the multimeric Tn3 scaffold comprises at least two CD40L-specific monomer subunits that are connected in tandem via a linker, e.g., a peptide linker, wherein the linker is a functional moiety. The functional moiety will be selected based on the desired function and/or characteristics of the multimeric Tn3 scaffold. For example, a functional moiety useful for purification (e.g., a histidine tag) may be used as a linker. Functional moieties useful as linkers include, but are not limited to, polyethylene glycol (PEG), a cytotoxic agent, a radionuclide, imaging agent, biotin, a dimerization domain, human serum albumin (HSA) or an FcRn binding portion thereof, a domain or fragment of an antibody, a single chain antibody, a domain antibody, an albumin binding domain, an IgG molecule, an enzyme, a ligand, a receptor, a binding peptide, a non-Tn3 scaffold, an epitope tag, a recombinant polypeptide polymer, a cytokine, and the like. Specific peptide linkers and functional moieties which may be used as linkers are disclosed infra.

In specific embodiments, the functional moiety is an immunoglobulin or a fragment thereof. In some embodiments, the immunoglobulin or fragment thereof comprises an Fc domain. In some embodiments, the Fc domain fails to induce at least one FcγR-mediated effector function, such as ADCC (Antibody-dependent cell-mediated cytotoxicity). It is known in the art that the Fc domain maybe altered to reduce or eliminate at least one FcγR-mediated effector function, see, for example, U.S. Pat. Nos. 5,624,821 and 6,737,056.

In some embodiments, the multimeric Tn3 scaffold comprises at least two CD40L-specific monomer subunits that are connected via one or more linkers, wherein the linkers interposed between each CD40L-specific monomer subunit can be the same linkers or different linkers. In some embodiments, a linker can comprise multiple linkers, which can be the same linker or different linkers. In some embodiments, when a plurality of linkers are concatenated, some or all the linkers can be functional moieties.

Scaffold Binding Stoichiometry

In some embodiments, a monomeric or multimeric Tn3 scaffold can comprise a CD40L-specific monomer subunit specific for different epitopes, which can be different epitopes on a single CD40L molecule or on different CD40L target molecules. In some embodiments, a multimeric Tn3 scaffold can comprise CD40L-specific monomer subunits wherein each subunit targets one or more different epitopes on one or more CD40L molecules.

In other embodiments, a monomeric or multimeric Tn3 scaffold can bind two or more different epitopes on the same CD40L molecule. In some embodiments, the different epitopes are non-overlapping epitopes. In other embodiments, the different epitopes are overlapping epitopes.

In yet another specific embodiment, a monomeric or multimeric Tn3 scaffold can bind one or more epitopes on a CD40L molecule and additionally bind one or more epitopes on a second CD40L molecule. In some embodiments, the different target molecules are part of an oligomeric complex, e.g, a trimeric CD40L complex.

In still another specific embodiment, a monomeric or multimeric Tn3 scaffold can bind to a single epitope on a CD40L trimer. In yet another embodiment, a monomeric or multimeric Tn3 scaffold can bind to the same epitope on at least two CD40L trimers.

In certain embodiments, a monomeric or multimeric Tn3 scaffold can bind the same epitope on two or more copies of a CD40L molecule on an adjacent cell surface. In certain embodiments, a monomeric or multimeric Tn3 scaffold can bind the same epitope on two or more copies of a CD40L molecule in solution. In some embodiments, a monomeric or multimeric Tn3 scaffold can bind to the same epitope or different epitopes on CD40L with the same or different binding affinities and/or avidities.

In another embodiment, a monomeric or multimeric Tn3 scaffolds can bind to epitopes on one or more copies of CD40L and achieve or enhance (e.g., synergistically) a desired action on the target, e.g., prevent binding to a receptor or prevent oligomerization.

In addition, when a monomeric or multimeric Tn3 scaffold of the invention comprises a plurality of CD40L-specific monomer subunits, e.g., different monomers wherein each monomer targets different epitopes on CD40L, such monomer subunits can be arranged according to a certain pattern or special orientation to achieve or enhance a certain biological effect. Such combinations of monomeric subunits can be assembled and subsequently evaluated using methods known in the art.

Fusions

The invention provides Tn3 scaffolds wherein at least one CD40L-specific monomer subunit can be fused to a heterologous moiety. In this context the heterologous moiety is not used to link the scaffolds as a spacer but may provide additional functionality to the Tn3 scaffold. In some embodiments, a heterologous moiety can also function as a linker. The present invention encompasses the use of Tn3 scaffolds conjugated or fused to one or more heterologous moieties, including but not limited to, peptides, polypeptides, proteins, fusion proteins, nucleic acid molecules, small molecules, mimetic agents, synthetic drugs, inorganic molecules, and organic molecules. Accordingly, the invention provides polypeptides comprising one or more CD40L-specific Tn3 monomer, including but not limited to the fusion proteins described herein.

The present invention encompasses the use of Tn3 scaffolds recombinantly fused or chemically conjugated to a heterologous protein or polypeptide or fragment thereof. Conjugation includes both covalent and non-covalent conjugation. In some embodiments, a Tn3 scaffold can be fused or chemically conjugated to a polypeptide of at least 10, at least 20, at least 30, at least 40, at least 50, at least 60, at least 70, at least 80, at least 90, at least 100, at least 200, at least 300, at least 500, or at least 1000 amino acids) to generate fusion proteins.

The fusion or conjugation of a Tn3 scaffold to one or more heterologous moieties can be direct, i.e., without a linker interposed between a Tn3 scaffold and a heterologous moiety, or via one or more linker sequences described herein. In some embodiments, scaffolds can be used to target heterologous polypeptides to particular cell types, either in vitro or in vivo, by fusing or conjugating the Tn3 scaffolds to antibodies specific for particular cell surface receptors in the target cells.

Tn3 scaffolds fused or conjugated to heterologous polypeptides can also be used in in vitro immunoassays and purification methods using methods known in the art. See, e.g., International Publication No. WO 93/21232; European Patent No. EP 439,095; Naramura et al., Immunol. Lett. 39:91-99, 1994; U.S. Pat. No. 5,474,981; Gillies et al., PNAS 89:1428-1432, 1992; and Fell et al., J. Immunol. 146:2446-2452, 1991, which are incorporated by reference in their entireties.

In some embodiments, the Tn3 scaffolds can be integrated with the human immune response by fusing or conjugating a scaffold with an immunoglobulin or domain thereof including, but not limited to, the constant region of an IgG (Fc), e.g., through the N or C-terminus. Similarly, a fusion between a Tn3 scaffold and a complement protein, such as C1q, can be used to target cells.

Various publications describe methods for obtaining physiologically active molecules whose half-lives are modified by introducing an FcRn-binding polypeptide into the molecules (see, e.g., WO 97/43316; U.S. Pat. Nos. 5,869,046; 5,747,035; WO 96/32478; and WO 91/14438), by fusing the molecules with antibodies whose FcRn-binding affinities are preserved but affinities for other Fc receptors have been greatly reduced (see, e.g., WO 99/43713), or by fusing the molecules with FcRn binding domains of antibodies (see, e.g., WO 00/09560; U.S. Pat. No. 4,703,039). Specific techniques and methods of increasing half-life of physiologically active molecules can also be found in U.S. Pat. No. 7,083,784. Specifically, it is contemplated that the Tn3 scaffolds can be fused to an Fc region from an IgG, wherein the Fc region comprises amino acid residue mutations M252Y/S254T/T256E or H433K/N434F/Y436H, wherein amino acid positions are designated according to the Kabat numbering schema. It is specifically contemplated the fusion of a Tn3 scaffold to an Fc domain variant not capable of inducing ADCC.

In some embodiments, the half-life of the Tn3 scaffold can be increased by genetically fusing the Tn3 scaffold with an intrinsically unstructured recombinant polypeptide (e.g., an XTEN™ polypeptide) or by conjugation with polyethylene glycol (PEG).

In some embodiments, the Tn3 scaffold can be fused with molecules that increase or extend in vivo or serum half-life. In some embodiments, the scaffold can be fused or conjugated with albumin, such as human serum albumin (HSA), a neonatal Fc receptor (FcRn) binding fragment thereof, PEG, polysaccharides, antibodies, complement, hemoglobin, a binding peptide, lipoproteins and other factors to increase its half-life in the bloodstream and/or its tissue penetration. Any of these fusions may be generated by standard techniques, for example, by expression of the fusion protein from a recombinant fusion gene constructed using publicly available gene sequences.

In some embodiments, a property of the Tn3 scaffold can be improved by conjugation or fusion to an HSA variant, i.e., a molecule derived from full length HSA (SEQ ID NO: 139) comprising at least an amino acid substitution, a deletion, or a sequence truncation.

In some embodiments, the property improved by conjugation with an HSA variant is plasma half-life. The improvement in plasma half-life of the Tn3 scaffold can be an alteration in that property such as an increase or decrease in plasma half-life, or changes in other pharmacokinetic parameters. In some embodiments, the HSA variant is a mutant derived from full length HSA (SEQ ID NO: 138). In a specific embodiment, the HSA variant comprises a substitution of cysteine at position 34 to serine (SEQ ID NO: 133). HSA variants that can be used to modify the plasma half-life of a Tn3 scaffold are described, e.g., in International Publications WO 2011/103076 and WO 2011/051489, both of which are incorporated by reference in their entireties. In some embodiments, the plasma half-life of a Tn3 scaffold of the invention is increased by fusing it with an HSA variant comprising at least one amino acid substitution in domain III of HSA.

In some embodiments, the Tn3 scaffold of the invention comprises an HSA variant comprising the sequence of full-length mature HSA (SEQ ID NO: 138) or a fragment thereof, except for at least one amino acid substitution, numbered relative to the position in full length mature HSA, at a position selected from the group consisting of 407, 415, 463, 500, 506, 508, 509, 511, 512, 515, 516, 521, 523, 524, 526, 535, 550, 557, 573, 574, and 580; wherein the at least one amino acid substitution does not comprise a lysine (K) to glutamic acid (E) at position 573, and wherein the Tn3 scaffold has a plasma half-life longer than the plasma half-life of a Tn3 scaffold not conjugated to the HSA variant.

In some other embodiments, at least one amino acid substitution, numbered relative to the position in full length mature HSA, is at a position selected from the group consisting of 463, 508, 523, and 524, wherein the Tn3 scaffold has a plasma half-life longer than the plasma half-life of a Tn3 scaffold not conjugated to the HSA variant.

In other embodiments, a Tn3 scaffold of the invention comprises an HSA variant comprising the sequence of full-length mature HSA (SEQ ID NO: 133 or 138) or a fragment thereof, except for at least one amino acid substitution, numbered relative to the position in full length mature HSA, selected from the group consisting of:

(a) substitution of Leucine (L) at position 407 to Asparagine (N) or Tyrosine (Y);
(b) substitution of Valine (V) at position 415 to Threonine (T);
(c) substitution of Leucine (L) at position 463 to Asparagine (N);
(d) substitution of Lysine (K) at position 500 to Arginine (R);
(e) substitution of Threonine (T) at position 506 to Tyrosine (Y);
(f) substitution of Threonine (T) at position 508 to Arginine (R);
(g) substitution of Phenylalanine (F) at position 509 to Methionine (M) or Tryptophan (W);
(h) substitution of Alanine (A) at position 511 to Phenylalanine (F);
(i) substitution of Aspartic Acid (D) at position 512 to Tyrosine (Y);
(j) substitution of Threonine (T) at position 515 to Glutamine (Q);
(k) substitution of Leucine (L) at position 516 to Threonine (T) or Tryptophan (W);
(l) substitution of Arginine (R) at position 521 to Tryptophan (W);
(m) substitution of Isoleucine (I) at position 523 to Aspartic Acid (D), Glutamic Acid (E), Glycine (G), Lysine (K), or Arginine (R);
(n) substitution of Lysine (K) at position 524 to Leucine (L);

(o) substitution of Glutamine (Q) at position 526 to Methionine (M);
(p) substitution of Histidine (H) at position 535 to Proline (P);
(q) substitution of Aspartic Acid (D) at position 550 to Glutamic Acid (E);
(r) substitution of Lysine (K) at position 557 to Glycine (G);
(s) substitution of Lysine (K) at position 573 to Phenylalanine (F), Histidine (H), Proline (P), Tryptophan (W), or Tyrosine (Y);
(t) substitution of Lysine (K) at position 574 to Asparagine (N);
(u) substitution of Glutamine (Q) at position 580 to Lysine (K); and,
(v) a combination of two or more of said substitutions,
wherein said Tn3 scaffold has a plasma half-life longer than the plasma half-life of a Tn3 scaffold not conjugated to said HSA variant.

In some embodiments, the Tn3 scaffold comprises a HSA variant which comprises the sequence of full-length mature HSA (SEQ ID NO: 133 or 138) or a fragment thereof, except for at least one amino acid substitution, numbered relative to the position in full length mature HSA, selected from the group consisting of
(a) substitution of Leucine (L) at position 463 to Asparagine (N);
(b) substitution of Threonine (T) at position 508 to Arginine (R);
(c) substitution of Isoleucine (I) at position 523 to Aspartic Acid (D), Glutamic Acid (E), Glycine (G), Lysine (K), or Arginine (R);
(d) substitution of Lysine (K) at position 524 to Leucine (L); and,
(e) a combination of two or more of said substitutions,
wherein said Tn3 scaffold has a plasma half-life longer than the plasma half-life of a Tn3 scaffold not conjugated to said HSA variant.

Moreover, the Tn3 scaffolds of the invention can be fused to marker sequences, such as a peptide to facilitate purification. In some embodiments, the marker amino acid sequence is a poly-histidine peptide (His-tag), e.g., a octa-histidine-tag (His-8-tag) or hexa-histidine-tag (His-6-tag) such as the tag provided in a pQE expression vector (QIAGEN®, Inc., 9259 Eton Avenue, Chatsworth, Calif., 91311), among other vectors, many of which are commercially available. As described in Gentz et al., Proc. Natl. Acad. Sci. USA 86:821-824, 1989, for instance, poly-histidine provides for convenient purification of the fusion protein. Other peptide tags useful for purification include, but are not limited to, a hemagglutinin ("HA") tag, which corresponds to an epitope derived from the influenza hemagglutinin protein (see, e.g., Wilson et al., Cell 37:767, 1984), a FLAG® tag, a STREP-TAG®, a myc-tag, a V5 tag, a GFP-tag, an AU1-tag, an AU5-tag, an ECS-tag, a GST-tag, or an OLLAS tag.

Additional fusion proteins comprising Tn3 scaffolds of the invention may be generated through the techniques of gene-shuffling, motif-shuffling, exon-shuffling, and/or codon-shuffling (collectively referred to as "DNA shuffling").

DNA shuffling may be employed to alter the action of Tn3 scaffolds on the target (e.g., generate scaffolds with higher affinities and lower dissociation rates). Tn3 scaffolds may be altered by random mutagenesis by error-prone PCR, random nucleotide insertion, or other methods prior to recombination. One or more portions of a polynucleotide encoding a scaffold, which bind to a specific target may be recombined with one or more components, motifs, sections, parts, domains, fragments, etc. of one or more heterologous molecules.

Antibody and Fc Domain Fusions

In some embodiments, the Tn3 scaffold of the invention comprises a CD40L-specific monomer subunit fused to a domain or fragment of an antibody (e.g., an IgG), including, but not limited to, an Fc domain.

In some embodiments, only one CD40L-specific monomer subunit is conjugated or fused to a domain or fragment of an antibody. For instance, a single a CD40L-specific monomer subunit can be fused to the N-terminus of a polypeptide of a domain or fragment of an antibody (e.g., a heavy chain or a light chain of an antibody). In other embodiments, Tn3 scaffolds are created by fusing or conjugating one or more CD40L-specific monomer subunits to the N-terminus and/or the C-terminus a polypeptide of a domain or fragment of an antibody (e.g., a heavy chain and/or a light chain of an antibody, or an Fc domain).

In some embodiments, some or all the a CD40L-specific monomer subunits fused to a domain or fragment of an antibody are identical. In some other embodiments, some or all the a CD40L-specific monomer subunit fused to a domain or fragment of an antibody are different.

In a specific embodiment, the Tn3 scaffold of the invention comprises one CD40L-specific monomer subunit fused to an Fc domain. In other embodiments, the Tn3 scaffold of the invention comprises at least two CD40L-specific monomer subunits fused to an Fc domain. In one specific embodiment, two of the CD40L-specific monomer subunits fused to an Fc domain are identical. In one specific embodiment, two of the CD40L-specific monomer subunits fused to an Fc domain are different. In one specific embodiment, two CD40L-specific monomer subunits fused to an Fc domain are connected to each other in tandem, and one of the CD40L-specific monomer subunits is fused to the Fc domain.

In some embodiments, different Tn3 scaffolds of the invention can be dimerized by the use of Fc domain mutations which favor the formation of heterodimers. It is known in the art that variants of the Fc region (e.g., amino acid substitutions and/or additions and/or deletions) enhance or diminish effector function of the antibody and can alter the pharmacokinetic properties (e.g. half-life) of the antibody. Thus, in certain embodiments, the Tn3 scaffolds of the invention comprise Fc domain(s) that comprise an altered Fc region in which one or more alterations have been made in the Fc region in order to change functional and/or pharmacokinetic properties of the Tn3 scaffold. In certain embodiments, the Tn3 scaffolds of the invention comprise Fc domain(s) that comprise an altered Fc region in which one or more alterations have been made in the Fc region in order reduce or eliminate at least one FcγR-mediated effector function.

It is also known that the glycosylation of the Fc region can be modified to increase or decrease effector function and/or anti-inflammatory activity. Accordingly, in one embodiment a Tn3 scaffold of the invention comprise an Fc region with altered glycosylation of amino acid residues in order to change cytotoxic and/or anti-inflammatory properties of the Tn3 scaffolds.

Tn3 Scaffold Topologies

The Tn3 scaffolds of the invention can be fused to the C-terminus of the Fc domains, antibody light chains, and antibody heavy chains in any suitable spatial arrangement.

See, e.g., International Publication PCT/US2011/032184 for a detailed description of contemplated scaffold topologies.

Generation of Scaffolds of the Invention

The Tn3 scaffolds described herein may be used in any technique for evolving new or improved target binding proteins. In one particular example, the target is immobilized on a solid support, such as a column resin or microtiter plate well, and the target contacted with a library of candidate scaffold-based binding proteins. Such a library may consist of clones constructed from a Tn3 scaffold, through randomization of the sequence and/or the length of the CDR-like loops.

In this regard, bacteriophage (phage) display is one well known technique which allows one to screen large oligopeptide libraries to identify member(s) of those libraries which are capable of specifically binding to a target. Phage display is a technique by which variant polypeptides are displayed as fusion proteins to the coat protein on the surface of bacteriophage particles (Scott, J. K. and Smith, G. P. (1990) Science 249: 386). A bioinformatics approach may be employed to determine the loop length and diversity preferences of naturally occurring FnIII domains. Using this analysis, the preferences for loop length and sequence diversity may be employed to develop a "restricted randomization" approach. In this restricted randomization, the relative loop length and sequence preferences are incorporated into the development of a library strategy. Integrating the loop length and sequence diversity analysis into library development results in a restricted randomization (i.e. certain positions within the randomized loop are limited in which amino acid could reside in that position).

The invention also provides recombinant libraries comprising diverse populations of non-naturally occurring Tn3 scaffolds. In one embodiment, the libraries comprise non-naturally occurring Tn3 scaffolds comprising, a plurality of beta strand domains linked to a plurality of loop regions, wherein one or more of said loops vary by deletion, substitution or addition by at least one amino acid. In a specific embodiment, the libraries comprise Tn3 scaffolds derived from the wild type Tn3 scaffold.

As detailed above, the loops connecting the various beta strands of the scaffolds may be randomized for length and/or sequence diversity. In one embodiment, the libraries of the invention comprise Tn3 scaffolds having at least one loop that is randomized for length and/or sequence diversity. In one embodiment, at least one, at least two, at least three, at least four, at least five or at least six loops of the Tn3 scaffolds are randomized for length and/or sequence diversity. In one embodiment, at least one loop is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or at least all three of loops AB, CD, and EF are randomized while at least one, at least two, or all three of loops BC, DE, and FG are randomized for length and/or sequence diversity.

In a specific embodiment, the libraries of the invention comprise FnIII scaffolds, wherein the A beta strand comprises SEQ ID NO: 10 or 11, the B beta strand comprises SEQ ID NO: 12, the C beta strand comprises SEQ ID NO: 13 or 14, the D beta strand comprises SEQ ID NO: 15, the E beta strand comprises SEQ ID NO: 16, the F beta strand comprises SEQ ID NO: 17, and the G beta strand comprises SEQ ID NO: 18.

In a specific embodiment, the libraries of the invention comprise FnIII scaffolds, wherein the A beta strand consists of SEQ ID NO: 10 or 11, the B beta strand consists of SEQ ID NO: 12, the C beta strand consists of SEQ ID NO: 13 or 14, the D beta strand consists of SEQ ID NO: 15, the E beta strand consists of SEQ ID NO: 16, the F beta strand consists of SEQ ID NO: 17, and the G beta strand consists of SEQ ID NO: 18.

In a specific embodiment, the libraries of the invention comprise FnIII scaffolds, wherein the A beta strand consists essentially of SEQ ID NO: 10 or 11, the B beta strand consists essentially of SEQ ID NO: 12, the C beta strand consists essentially of SEQ ID NO: 13 or 14, the D beta strand consists essentially of SEQ ID NO: 15, the E beta strand consists essentially of SEQ ID NO: 16, the F beta strand consists essentially of SEQ ID NO: 17, and the G beta strand consists essentially of SEQ ID NO: 18.

As detailed above, one or more residues within a loop may be held constant while other residues are randomized for length and/or sequence diversity. Optionally or alternatively, one or more residues within a loop may be held to a predetermined and limited number of different amino acids while other residues are randomized for length and/or sequence diversity. Accordingly, libraries of the invention comprise Tn3 scaffolds that may comprise one or more loops having a degenerate consensus sequence and/or one or more invariant amino acid residues. In another embodiment, the libraries of the invention comprise Tn3 scaffolds having BC loops which are randomized. In another embodiment, the libraries of the invention comprise Tn3 scaffolds having BC loops which are randomized. In still another embodiment, the libraries of the invention comprise Tn3 scaffolds having BC loops which are randomized.

In one embodiment the libraries of the invention comprise Tn3 scaffolds having DE loops which are randomized. In one embodiment, the libraries of the invention comprise Tn3 scaffolds having FG loops which are randomized. In another embodiment, the libraries of the invention comprise FnIII scaffolds having FG loops which are randomized.

In a specific embodiment, the libraries of the invention comprise scaffolds, wherein the scaffolds comprise the amino acid sequence:

| | |
|---|---|
| IEV | (SEQ ID NO: 11) |
| $(X_{AB})_n$ALITW | (SEQ ID NO: 12) |
| $(X_{BC})_n$CELX$_1$YGI | (SEQ ID NO: 173) |
| $(X_{CD})_n$TTIDL | (SEQ ID NO: 15) |
| $(X_{DE})_n$YSI | (SEQ ID NO: 16) |
| $(X_{EF})_n$YEVSLIC | (SEQ ID NO: 17) |
| $(X_{FG})_n$KETFTT | (SEQ ID NO: 18) | wherein:

(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;

(b) $X_1$ represents amino acid residue A or T; and, (c) length of the loop n is an integer between 2 and 26.

In some embodiments, the libraries of the invention comprise CD40L-specific Tn3 monomer subunits of the invention comprising the amino acid sequence:

(SEQ ID NO: 167)
IEVKDVTDTTALITWX$_1$DX$_2$X$_3$X$_4$X$_5$X$_6$X$_7$X$_8$CELTYGIKDVPGDRTTID

LWX$_9$HX$_{10}$AX$_{11}$YSIGNLKPDTEYEVSLICRX$_{12}$GDMSSNPAKETFTT wherein:

(a) X$_1$ represents amino acid residue serine (S) or leucine (L);
(b) X$_2$ represents amino acid residue aspartic acid (D) or glutamic acid (E);
(c) X$_3$ represents amino acid residue histidine (H), isoleucine (I), valine (V), phenylalanine (F) or tryptophan (W);
(d) X$_4$ represents amino acid residue alanine (A), glycine (G), glutamic acid (E) or aspartic acid (D);
(e) X$_5$ represents amino acid residue glutamic acid (E), leucine (L), glutamine (Q), serine (S), aspartic acid (D) or asparagine (N);
(f) X$_6$ represents amino acid residue phenylalanine (F) or tyrosine (Y);
(g) X$_7$ represents amino acid residue isoleucine (I), valine (V), histidine (H), glutamic acid (E) or aspartic acid (D);
(h) X$_8$ represents amino acid residue glycine (G), tryptophan (W) or valine (V);
(i) X$_9$ represents amino acid residue tryptophan (W), phenylalanine (F) or tyrosine (Y);
(j) X$_{10}$ represents amino acid residue serine (S), glutamine (Q), methionine (M) or histidine (H);
(k) X$_{11}$ represents amino acid residue tryptophan (W) or histidine (H); and,
(l) X$_{12}$ represents amino acid residue arginine (R) or serine (S).

In some embodiments, the libraries of the invention comprise CD40L-specific Tn3 monomer subunits of the invention comprising the amino acid sequence:

(SEQ ID NO: 171)
IEVX$_1$DVTDTTALITWX$_2$X$_3$RSX$_4$X$_5$X$_6$X$_7$X$_8$X$_9$X$_{10}$CELX$_{11}$YGIKDVP

GDRTTIDLX$_{12}$X$_{13}$X$_{14}$X$_{15}$YVHYSIGNLKPDTX$_{16}$YEVSLICLTTDGT

YX$_{17}$NPAKETFTT wherein:

(a) X$_1$ represents amino acid residue lysine (K) or glutamic acid (E);
(b) X$_2$ represents amino acid residue threonine (T) or isoleucine (I);
(c) X$_3$ represents amino acid residue asparagine (N) or alanine (A);
(d) X$_4$ represents amino acid residue serine (S), leucine (L), alanine (A), phenylalanine (F) or tyrosine (Y);
(e) X$_5$ represents amino acid residue tyrosine (Y), alanine (A), glycine (G), valine (V), isoleucine (I) or serine (S);
(f) X$_6$ represents amino acid residue tyrosine (Y), serine (S), alanine (A) or histidine (H);
(g) X$_7$ represents amino acid residue asparagine (N), aspartic acid (D), histidine (H) or tyrosine (Y);
(h) X$_8$ represents amino acid residue leucine (L), phenylalanine (F), histidine (H) or tyrosine (Y);
(i) X$_9$ represents amino acid residue histidine (H), proline (P), serine (S), leucine (L) or aspartic acid (D);
(j) X$_{10}$ represents amino acid residue glycine (G), phenylalanine (F), histidine (H) or tyrosine (Y);
(k) X$_{11}$ represents amino acid residue alanine (A) or threonine (T);
(l) X$_{12}$ represents amino acid residue serine (S), asparagine (N), glutamic acid (E), asparagine (R) or aspartic acid (D);
(m) X$_{13}$ represents amino acid residue serine (S), glutamine (Q), threonine (T), asparagine (N) or alanine (A);
(n) X$_{14}$ represents amino acid residue proline (P), valine (V), isoleucine (I) or alanine (A) or no amino acid;
(o) X$_{15}$ represents amino acid residue isoleucine (I) or no amino acid;
(p) X$_{16}$ represents amino acid residue glutamic acid (E) or lysine (K); and,
(q) X$_{17}$ represents amino acid residue serine (S) or asparagine (N).

The invention further provides methods for identifying a recombinant Tn3 scaffold that binds a target, e.g., CD40L, and has increased stability or improved action on the target, e.g., CD40L, as compared to a parent Tn3 scaffold by screening the libraries of the invention.

In certain embodiments, the method for identifying a recombinant Tn3 scaffold having increased protein stability as compared to a parent Tn3 scaffold, and which specifically binds a target, comprises:

contacting the target ligand with a library of the invention under conditions suitable for forming a scaffold:target ligand complex;

obtaining from the complex, the scaffold that binds the target ligand;

determining if the stability of the scaffold obtained in step (b) is greater than that of the wild type Tn3 scaffold.

The same method can be used to identify a recombinant Tn3 scaffold with improved binding affinity, avidity, etc. to the target. In one embodiment, in step (a) the scaffold library of the invention is incubated with immobilized target. In one embodiment, in step (b) the scaffold:target ligand complex is washed to remove non-specific binders, and the tightest binders are eluted under very stringent conditions and subjected to PCR to recover the sequence information. It is specifically contemplated that the binders and/or sequence information obtained in step (b) can be used to create a new library using the methods disclosed herein or known to one of skill in the art, which may be used to repeat the selection process, with or without further mutagenesis of the sequence. In some embodiments, a number of rounds of selection may be performed until binders of sufficient affinity for the antigen are obtained.

A further embodiment of the invention is a collection of isolated nucleic acid molecules encoding a library comprising the scaffolds of the invention and as described above.

The scaffolds of the invention may be subjected to affinity maturation. In this art-accepted process, a specific binding protein is subject to a scheme that selects for increased affinity for a specific target (see Wu et al., Proc. Natl. Acad. Sci. USA. 95(11):6037-42). The resultant scaffolds of the invention may exhibit binding characteristics at least as high as compared to the scaffolds prior to affinity maturation.

The invention also provides methods of identifying the amino acid sequence of a protein scaffold capable of binding to target so as to form a scaffold:target complex. In one embodiment, the method comprises: (a) contacting a library of the invention with an immobilized or separable target; (b) separating the scaffold:target complexes from the free scaffolds; (c) causing the replication of the separated scaffolds of (b) so as to result in a new polypeptide display library distinguished from that in (a) by having a lowered diversity and by being enriched in displayed scaffolds capable of binding the target; d) optionally repeating steps (a), and (b) with the new library of (c); and e) determining the nucleic acid sequence of the region encoding the displayed scaffold of a species from (d) and hence deducing the peptide sequence capable of binding to the target.

In another embodiment, the Tn3 scaffolds of the invention may be further randomized after identification from a library screen. In one embodiment, methods of the invention comprise further randomizing at least one, at least two, at least three, at least four, at least five or at least six loops of a scaffold identified from a library using a method described herein. In another embodiment, the further randomized scaffold is subjected to a subsequent method of identifying a scaffold capable of binding a target. This method comprises (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said further randomized scaffold and hence, deducing the peptide sequence capable of binding to the target.

In a further embodiment, the further randomized scaffolds comprise at least one, at least two, at least three, at least four, at least five, or at least six randomized loops which were previously randomized in the first library. In an alternate further embodiment, the further randomized scaffolds comprise at least one, at least two, at least three, at least four, at least five, or at least six randomized loops which were not previously randomized in the first library.

The invention also provides a method for obtaining at least two Tn3 scaffolds that bind to at least one or more targets. This method allows for the screening of agents that act cooperatively to elicit a particular response. It may be advantageous to use such a screen when an agonistic activity requiring the cooperation of more than one scaffold is required. This method allows for the screening of cooperative agents without the reformatting of the library to form multimeric complexes. In one embodiment, the method of the invention comprises contacting a target ligand with a library of the invention under conditions that allow a scaffold:target ligand complex to form, engaging said scaffolds with a crosslinking agent (defined as an agent that brings together, in close proximity, at least two identical or distinct scaffolds) wherein the crosslinking of the scaffolds elicits a detectable response and obtaining from the complex, said scaffolds that bind the target. In a further embodiment, the crosslinking agent is a scaffold specific antibody, or fragment thereof, an epitope tag specific antibody of a fragment thereof, a dimerization domain, such as Fc region, a coiled coil motif (for example, but not limited to, a leucine zipper), a chemical crosslinker, or another dimerization domain known in the art.

The invention also provides methods of detecting a compound utilizing the Tn3 scaffolds of the invention. Based on the binding specificities of the Tn3 scaffolds obtained by library screening, it is possible to use such Tn3 scaffolds in assays to detect the specific target in a sample, such as for diagnostic methods. In one embodiment, the method of detecting a compound comprises contacting said compound in a sample with a Tn3 scaffold of the invention, under conditions that allow a compound: scaffold complex to form and detecting said scaffold, thereby detecting said compound in a sample. In further embodiments, the scaffold is labeled (i.e., radiolabel, fluorescent, enzyme-linked or colorimetric label) to facilitate the detection of the compound.

The invention also provides methods of capturing a compound utilizing the Tn3 scaffolds of the invention. Based on the binding specificities of the Tn3 scaffolds obtained by library screening, it is possible to use such Tn3 scaffolds in assays to capture the specific target in a sample, such as for purification methods. In one embodiment, the method of capturing a compound in a sample comprises contacting said compound in a sample with a scaffold of the invention under conditions that allow the formation of a compound:scaffold complex and removing said complex from the sample, thereby capturing said compound in said sample. In further embodiments, the Tn3 scaffold is immobilized to facilitate the removing of the compound:scaffold complex.

In some embodiments, Tn3 scaffolds isolated from libraries of the invention comprise at least one, at least two, at least four, at least five, at least six, or more randomized loops. In some embodiments, isolated Tn3 scaffold loop sequences may be swapped from a donor scaffold to any loop in a FnIII receiver scaffold included, but not limited to, a Tn3 receiver scaffold (for example, an FG loop sequence from a donor scaffold may be transferred to any loop in a receiver FnIII scaffold). In specific embodiments, isolated loop sequences may be transferred to the cognate loop in the receiving scaffold (for example, an FG loop sequence from a donor scaffold may be transferred to an FnIII receiver scaffold in the FG loop position). In some embodiments, isolated loop sequences may be "mix and matched" randomly with various receiver scaffolds.

In other embodiments, isolated Tn3 scaffolds sequences may be identified by the loop sequence. For example, a library is used to pan against a particular target and a collection of specific binders are isolated. The randomized loop sequences may be characterized as specific sequences independently of the Tn3 scaffold background (i.e., the scaffold that binds target X wherein said scaffold comprises an FG loop sequence of SEQ ID NO:X). In alternative embodiments, where a scaffold exhibits two loop sequences that bind target X, the loop sequences may be characterized as binding target X in the absence of the scaffold sequence. In other words, it is contemplated that scaffolds isolated from a library that bind a particular target may be expressed as the variable loop sequences that bind that target independent of the scaffold backbone. This process would be analogous to the concept of CDRs in variable regions of antibodies.

Affinity Maturation

The development of Tn3 scaffolds of the invention may involve one or more in vitro or in vivo affinity maturation steps. In some embodiments, Tn3 monomer subunits can undergo a single step of affinity maturation. In other embodiments, Tn3 monomer subunits can under two or more steps of affinity maturation. Any affinity maturation approach can be employed that results, in general, in amino acid changes in a parent Tn3 scaffold, or specifically amino acid changes in a parent Tn3 scaffold's loops that improve the binding of the affinity matured Tn3 scaffold to the desired antigen.

These amino acid changes can, for example, be achieved via random mutagenesis, "walk though" mutagenesis, and "look through" mutagenesis. Such mutagenesis can be achieved by using, for example, error-prone PCR, "mutator" strains of yeast or bacteria, incorporation of random or defined nucleic acid changes during ab initio synthesis of all or part of a FnIII-based binding molecule. Methods for performing affinity maturation and/or mutagenesis are described, for example, in U.S. Pat. Nos. 7,195,880; 6,951, 725; 7,078,197; 7,022,479; 5,922,545; 5,830,721; 5,605, 793, 5,830,650; 6,194,550; 6,699,658; 7,063,943; 5,866,344 and PCT Publication WO06023144.

Such affinity maturation methods may further require that the stringency of the antigen-binding screening assay is increased to select for Tn3 scaffolds with improved affinity for an antigen. Art recognized methods for increasing the stringency of a protein-protein interaction assay can be used here. In one embodiment, one or more of the assay conditions are varied (for example, the salt concentration of the assay buffer) to reduce the affinity of the Tn3 scaffold for the desired antigen. In another embodiment, the length of time permitted for the Tn3 scaffold to bind to the desired antigen is reduced.

In another embodiment, a competitive binding step can be added to the protein-protein interaction assay. For example, the Tn3 scaffold can be first allowed to bind to a desired immobilized antigen. A specific concentration of non-immobilized antigen is then added which serves to compete for binding with the immobilized antigen such that the Tn3 scaffolds with the lowest affinity for antigen are eluted from the immobilized antigen resulting in selection of Tn3 scaffolds with improved antigen binding affinity. The stringency of the assay conditions can be further increased by increasing the concentration of non-immobilized antigen is added to the assay.

Screening methods may also require multiple rounds of selection to enrich for one or more Tn3 scaffolds with improved antigen binding. In one embodiment, at each round of selection further amino acid mutations are introduce into the Tn3 scaffold. In another embodiment, at each round of selection the stringency of binding to the desired antigen is increased to select for Tn3 scaffolds with increased affinity for antigen.

In some embodiments, affinity maturation is performed by saturation mutagenesis of portions of the BC, DE, and FG loops of Tn3. In some embodiments, saturation mutagenesis is performed using Kunkel mutagenesis. In other embodiments, saturation mutagenesis is performed by using PCR.

In some embodiments, at least one, at least two, at least three, at least four, at least five, or more than five rounds of affinity maturation are applied. In some embodiments, saturation mutagenesis is applied to only one loop, whereas in some other embodiments, only one loop or a portion of a loop is mutated during one round of affinity maturation. In some embodiments, more than one loop or portions of one or more than loop are mutated during the same round of affinity maturation.

In other embodiments, the BC, DE, and FG loops mutated simultaneously during the same round of affinity maturation.

In the case of the monomers to assemble into multimeric Tn3 scaffolds binding to different epitopes of the same target, each binding specificity can be screened independently.

In some embodiments, the loops are randomized using a phage display library. In some embodiments, the binding of a Tn3 scaffold to a desired target can be determined using methods recognized in the art. Also, the amino acid sequences of the Tn3 scaffolds identified in the screens can be determined using art recognized methods.

In some embodiments, the monomeric affinity matured scaffolds of the invention exhibit an increased in affinity for CD40L of at least 5-fold, at least 10-fold, at least 20-fold, at least 40-fold, at least 60-fold, at least 80-fold, or at least 100-fold or more compared to the same Tn3 scaffold prior to affinity maturation, as measured by Surface Plasmon Resonance or by other assays known in the art. In some embodiments, the monomeric affinity matured scaffolds of the invention have a dissociation constant ($K_d$) of less than 5 µM, less than 1 µM, less than 500 µM, less than 250 µM, less than 100 µM, or less than 50 µM, as measured by Surface Plasmon Resonance or by other assays known in the art.

These affinity maturation methods can be applied to develop Tn3 scaffolds with desirable improved binding properties such as increased affinity or other desirable characteristics, such as favorable pharmacokinetic properties, high potency, low immunogenicity, increased or decreased cross-reactivity, etc.

Generation of Tandem Repeats

Linking of tandem constructs, a dimer formed by linking two CD40L-specific monomer subunits, may be generated by ligation of oligonucleotides at restriction sites using restriction enzymes known in the art, including but not limited to type II and type IIS restriction enzymes.

The multimeric Tn3 scaffolds of the invention may comprise a linker at the C-terminus and/or the N-terminus and/or between domains as described herein. Further, scaffolds of the invention comprising at least 1, at least 2, at least 3, at least 4, at least 5, at least 6, at least 7, at least 8 or polypeptide scaffolds may be fused or conjugated to a dimerization domain, including but not limited to an antibody moiety selected from:

(i) a Fab fragment, having VL, CL, VH and CH1 domains;
(ii) a Fab' fragment, which is a Fab fragment having one or more cysteine residues at the C-terminus of the CH1 domain;
(iii) a Fd fragment having VH and CH1 domains;
(iv) a Fd' fragment having VH and CH1 domains and one or more cysteine residues at the C-terminus of the CH1 domain;
(v) a Fv fragment having the VL and VH domains of a single arm of an antibody;
(vi) a dAb fragment which consists of a VH domain;
(vii) isolated CDR regions;
(viii) F(ab')2 fragments, a bivalent fragment including two Fab' fragments linked by a disulphide bridge at the hinge region;
(ix) single chain antibody molecules (e.g., single chain Fv; scFv);
(x) a "diabody" with two antigen binding sites, comprising a heavy chain variable domain (VH) connected to a light chain variable domain (VL) in the same polypeptide chain;
(xi) a "linear antibody" comprising a pair of tandem Fd segments (VH-CH1-VH-CH1) which, together with complementary light chain polypeptides, form a pair of antigen binding regions;
(xii) a full length antibody; and
(xiii) an Fc region comprising CH2-CH3, which may further comprise all or a portion of a hinge region and/or a CH1 region.

Tn3 Scaffold Production

Recombinant expression of a Tn3 scaffold of the invention requires construction of an expression vector containing a polynucleotide that encodes the Tn3 scaffold. Once a polynucleotide encoding a Tn3 scaffold has been obtained, the vector for the production of the Tn3 scaffold may be produced by recombinant DNA technology using techniques well known in the art. Thus, methods for preparing a protein by expressing a polynucleotide containing a Tn3 scaffold encoding nucleotide sequence are described herein. Methods that are well known to those skilled in the art can be used to construct expression vectors containing scaffold polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a Tn3 scaffold of the invention, operably linked to a promoter.

The expression vector is transferred to a host cell by conventional techniques and the transfected cells are then cultured by conventional techniques to produce a Tn3 scaffold of the invention. Thus, the invention includes host cells containing a polynucleotide encoding a scaffold of the invention, operably linked to a heterologous promoter. Suitable host cells include, but are not limited to, microorganisms such as bacteria (e.g., E. coli and B. subtilis).

A variety of host-expression vector systems may be utilized to express the Tn3 scaffolds of the invention. Such host-expression systems represent vehicles by which the coding sequences of interest may be produced and subsequently purified, but also represent cells which may, when transformed or transfected with the appropriate nucleotide coding sequences, express a scaffold of the invention in situ. These include but are not limited to microorganisms such as bacteria (e.g., E. coli and B. subtilis) transformed with recombinant bacteriophage DNA, plasmid DNA or cosmid DNA expression vectors containing scaffold coding sequences or mammalian cell systems (e.g., COS, CHO, BHK, 293, NSO, and 3T3 cells).

Methods useful for the production of the Tn3 scaffolds of the invention are disclosed, for example, in International Patent Application Publication No WO 2009/058379. Once a scaffold of the invention has been produced by recombinant expression, it may be purified by any method known in the art for purification of a protein.

In some embodiments, scaffolds of the invention can be produced in an aglycosylated form by replacing amino acid residues that can be glycosylated during recombinant expression. In one specific embodiment, serine amino acids in a glycine-serine linker (e.g., SEQ ID NO: 131 or SEQ ID NO: 132) can be replaced by other amino acids residues such as alanine, glycine, leucine, isoleucine or valine (see, e.g., SEQ ID NOs: 140, 141, 142 and 143) in order to prevent glycosylation during recombinant expression. In some specific embodiments, an N-glycosylation site is removed from a Tn3 scaffolds of the invention. In other embodiments, a scaffold of the invention can be deglycosylated after recombinant expression. Methods of in vitro deglycosylation after recombinant expression using, e.g., enzymatic cocktails are known in the art (for example, the PFGase F, Enodo F Multi, Orela O-linked Glycan Release, Enzymatic CarboRelease, and Enzymatic DeGlycoMx deglycosylation kits marketed by QA-bio, Palm Desert, Calif.).

Production of the Tn3 scaffolds of the invention in the research laboratory can be scaled up to produce scaffolds in analytical scale reactors or production scale reactors, as described in U.S. Patent Publication No. US 2010-0298541 A1.

Scalable Production of Secreted Tn3 Scaffolds

The Tn3 scaffolds of the invention can be produced intracellularly or as a secreted form. In some embodiments, the secreted scaffolds are properly folded and fully functional. Tn3 scaffolds of the invention can be produced by a scalable process. In some embodiments, scaffolds can be produced by a scalable process of the invention in the research laboratory that can be scaled up to produce the scaffolds of the invention in analytical scale bioreactors (for example, but not limited to 5 L, 10 L, 15 L, 30 L, or 50 L bioreactors). In other embodiments, the Tn3 scaffolds can be produced by a scalable process of the invention in the research laboratory that can be scaled up to produce the Tn3 scaffolds of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory.

Linkers

The monomer subunits in a multimeric Tn3 scaffold can be connected by protein and/or nonprotein linkers, wherein each linker is fused to at least two monomer subunits. A suitable linker can consist of a protein linker, a nonprotein linker, and combinations thereof. Combinations of linkers can be homomeric or heteromeric. In some embodiments, a multimeric Tn3 scaffold of the invention comprises a plurality of monomer subunits wherein are all the linkers are identical. In other embodiments, a multimeric Tn3 scaffold comprises a plurality of monomer subunits wherein at least one of the linkers is functionally or structurally different from the rest of the linkers. In some embodiments, linkers can themselves contribute to the activity of a multimeric Tn3 scaffold by participating directly or indirectly in the binding to a target.

In some embodiments, the protein linker is a polypeptide. The linker polypeptide should have a length, which is adequate to link two or more monomer subunits in such a way that they assume the correct conformation relative to one another so that they retain the desired activity.

In one embodiment, the polypeptide linker comprises 1 to about 1000 amino acids residues, 1 to about 50 amino acid residues, 1-25 amino acid residues, 1-20 amino acid residues, 1-15 amino acid residues, 1-10 amino acid residues, 1-5 amino acid residues, 1-3 amino acid residues. The invention further provides nucleic acids, such as DNA, RNA, or combinations of both, encoding the polypeptide linker sequence. The amino acid residues selected for inclusion in the polypeptide linker should exhibit properties that do not interfere significantly with the activity or function of the multimeric Tn3 scaffold of the invention. Thus, a polypeptide linker should on the whole not exhibit a charge which would be inconsistent with the activity or function of the Tn3 multimeric scaffold of the invention, or interfere with internal folding, or form bonds or other interactions with amino acid residues in one or more of the monomer subunits which would seriously impede the binding of the multimeric Tn3 scaffold of the invention to CD40L.

The use of naturally occurring as well as artificial peptide linkers to connect polypeptides into novel linked fusion polypeptides is well known in the literature. Accordingly, the linkers fusing two or more monomer subunits are natural linkers, artificial linkers, or combinations thereof. In some embodiments, the amino acid sequences of all peptide linkers present in a Tn3 multimeric scaffold of the invention are identical. In other embodiments, the amino acid sequences of at least two of the peptide linkers present in a multimeric Tn3 scaffold of the invention are different.

In some embodiments, a polypeptide linker possesses conformational flexibility. In some embodiments, a polypeptide linker sequence comprises a $(G-G-G-G-X)_m$ amino acid sequence where X is Alanine (A), Serine (S), Glycine (G), Isoleucine (I), Leucine (L) or Valine (V) and m is a positive integer (see, e.g., SEQ ID NO: 209). In a specific embodiment, a polypeptide linker sequence comprises a $(G-G-G-G-S)_m$ amino acid sequence where m is a positive integer (see, e.g., SEQ ID NO: 147). In another specific embodiment, a polypeptide linker sequence comprises a $(G-G-G-G-G)_m$ amino acid sequence where m is a positive integer (see, e.g., SEQ ID NO: 148). In still another specific embodiment, a polypeptide linker sequence comprises a (G-G-G-G-A)$_m$ amino acid sequence where m is a positive integer (see, e.g., SEQ ID NO: 149). In some embodiments, a polypeptide linker is an inherently unstructured natural or artificial polypeptide (see, e.g., Schellenberger et al., Nature Biotechnol. 27:1186-1190, 2009; see also, Sickmeier et al., Nucleic Acids Res. 35:D786-93, 2007).

The peptide linker can be modified in such a way that an amino acid residue comprising an attachment group for a non-polypeptide moiety is introduced. Examples of such amino acid residues may be a cysteine residue (to which the non-polypeptide moiety is then subsequently attached) or the amino acid sequence may include an in vivo N-glycosylation site (thereby attaching a sugar moiety (in vivo) to the peptide linker).

In some embodiments, the amino acid sequences of all peptide linkers present in the polypeptide multimer are identical. Alternatively, the amino acid sequences of all peptide linkers present in the polypeptide multimer may be different.

Labeling or Conjugation of Tn3 Scaffolds

The Tn3 scaffolds of the invention can be used in non-conjugated form or conjugated to at least one of a variety of heterologous moieties to facilitate target detection or for imaging or therapy. The Tn3 scaffolds of the can be labeled or conjugated either before or after purification, when purification is performed.

Many heterologous moieties lack suitable functional groups to which Tn3 scaffolds of the invention can be linked. Thus, in some embodiments, the effector molecule is attached to the scaffold through a linker, wherein the linker contains reactive groups for conjugation. In some embodiments, the heterologous moiety conjugated to a Tn3 scaffold of the invention can function as a linker. In other embodiments, the moiety is conjugated to the Tn3 scaffold via a linker that can be cleavable or non-cleavable. In one embodiment, the cleavable linking molecule is a redox cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides.

In some embodiments, Tn3 scaffolds of the invention are engineered to provide reactive groups for conjugation. In such scaffolds, the N-terminus and/or C-terminus can also serve to provide reactive groups for conjugation. In other embodiments, the N-terminus can be conjugated to one moiety (such as, but not limited to PEG) while the C-terminus is conjugated to another moiety (such as, but not limited to biotin), or vice versa.

The term "polyethylene glycol" or "PEG" means a polyethylene glycol compound or a derivative thereof, with or without coupling agents, coupling or activating moieties (e.g., with thiol, triflate, tresylate, aziridine, oxirane, N-hydroxysuccinimide or a maleimide moiety). The term "PEG" is intended to indicate polyethylene glycol of a molecular weight between 500 and 150,000 Da, including analogues thereof, wherein for instance the terminal OH-group has been replaced by a methoxy group (referred to as mPEG).

The Tn3 scaffolds of the invention can be derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a specific embodiment, the PEGs employed have molecular weights ranging from 5,000 daltons to about 20,000 daltons. PEGs coupled to the scaffolds of the invention can be either branched or unbranched. See, for example, Monfardini, C. et al. 1995 Bioconjugate Chem 6:62-69. PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), carbonyldiimidazole, an anhydride reagent (for example, a dihalo succinic anhydride, such as dibromosuccinic anhydride), acyl azide, p-diazoniumbenzyl ether, 3-(p-diazoniumphenoxy)-2-hydroxypropylether) and the like. The activated polymer is then reacted with a polypeptide as described herein to produce a polypeptide derivatized with a polymer. Alternatively, a functional group in the Tn3 scaffolds of the invention can be activated for reaction with the polymer, or the two groups can be joined in a concerted coupling reaction using known coupling methods. It will be readily appreciated that the polypeptides of the invention can be derivatized with PEG using a myriad of other reaction schemes known to and used by those of skill in the art. A PEG can be coupled to a scaffold of the invention at one or more functional groups at either end of the Tn3 scaffold or within the Tn3 scaffold. In certain embodiments, the PEG is coupled at either the N-terminus or the C-terminus.

In other embodiments, Tn3 scaffolds of the invention, analogs or derivatives thereof may be conjugated to a diagnostic or detectable agent. Such Tn3 scaffolds can be useful for monitoring or prognosing the development or progression of a disease as part of a clinical testing procedure, such as determining the efficacy of a particular therapy.

The present invention further encompasses uses of Tn3 scaffolds conjugated to a therapeutic moiety. A Tn3 scaffold may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Assaying Tn3 Scaffolds

The binding affinity and other binding properties of a Tn3 scaffold to an antigen may be determined by a variety of in vitro assay methods known in the art including for example, equilibrium methods (e.g., enzyme-linked immunoabsorbent assay (ELISA) or kinetics (e.g., BIACORE® analysis), and other methods such as indirect binding assays, competitive binding assays, gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999).

In some embodiments, Tn3 scaffolds of the invention specifically bind a target with specific kinetics. In some embodiments, Tn3 scaffolds of the invention may have a dissociation constant or $K_d$ ($k_{off}/k_{on}$) of less than $1\times10^{-2}$M, $1\times10^{-3}$M, $1\times10^{-4}$M, $1\times10^{-5}$M, $1\times10^{-6}$M, $1\times10^{-7}$M, $1\times10^{-8}$M, $1\times10^{-9}$M, $1\times10^{-10}$M, $1\times10^{-11}$M, $1\times10^{-12}$M, $1\times10^{-13}$M, $1\times10^{-14}$M or less than $1\times10^{-15}$M. In specific embodiments, Tn3 scaffolds of the invention have a $K_d$ of 500 µM, 100 µM, 500 nM, 100 nM, 1 nM, 500 pM, 100 pM or less as determined by a BIAcore Assay® or by other assays known in the art.

In an alternative embodiment, the affinity of the Tn3 scaffolds of the invention is described in terms of the association constant ($K_a$), which is calculated as the ratio $k_{on}/k_{off}$, of at least $1\times10^2$M$^{-1}$, $1\times10^3$M$^{-1}$, $1\times10^4$M$^{-1}$, $1\times10^5$M$^{-1}$, $1\times10^6$M$^{-7}$, $1\times10^7$M$^{-1}$, $1\times10^8$M$^{-1}$, $1\times10^9$M$_{-1}$, $1\times10^{10}$M$^{-1}$ $1\times10^{11}$M$^{-1}$ $1\times10^{12}$M$^{-1}$, $1\times10^{13}$M$^{-1}$, $1\times10^{14}$M$^{-1}$, $1\times10^{15}$M$^{-1}$, or at least $5\times10^{15}$ M$^{-1}$.

In certain embodiments the rate at which the Tn3 scaffolds of the invention dissociate from a target epitope may be more relevant than the value of the $K_d$ or the $K_a$. In some embodiments, the Tn3 scaffolds of the invention have a $k_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In certain other embodiments, the rate at which the Tn3 scaffolds of the invention associate with a target epitope may be more relevant than the value of the $K_d$ or the $K_a$. In this instance, the Tn3 scaffolds of the invention bind to a target with a $k_{on}$ rate of at least $10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$s$^{-1}$, at least $5\times10^7$ M$^{-1}$s$^{-1}$, or at least $10^8$ M$^{-1}$s$^{-1}$, or at least $10^9$ M$^{-1}$s$^{-1}$.

Tn3 scaffolds of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

CD40L-Specific Tn3 Scaffolds

The invention provides Tn3 scaffolds that specifically bind to CD40L. In specific embodiments, scaffolds of the invention specifically bind to human CD40L. In other specific embodiments, Tn3 scaffolds of the invention bind to CD40L homologs from mouse, chicken, Rhesus, cynomolgus, rat, or rabbit. In some embodiments, Tn3 scaffolds of the invention bind to an exposed epitope of CD40L. Such embodiments include CD40L endogenously expressed on cells and/or cells transfected to ectopically express the receptor.

In some embodiments, Tn3 scaffolds of the invention recognize epitopes displayed on a monomeric CD40L. In other embodiments, Tn3 scaffolds of the invention recognize epitopes displayed on a trimeric form of CD40L. In other embodiments, Tn3 scaffolds of the invention recognize epitopes displayed on a membrane bound CD40L. In other embodiments, Tn3 scaffolds of the invention recognize epitopes displayed on soluble CD40L.

In yet other embodiments, Tn3 scaffolds of the invention bind monomeric CD40L and prevent or interfere with oligomerization of CD40L molecules. In yet other embodiments, scaffolds of the invention reduce or inhibit interaction of CD40L with CD40. In other embodiments, Tn3 scaffolds of the invention agonize cellular signaling mediated by CD40L. In yet other embodiments, Tn3 scaffolds of the invention antagonize cellular signaling mediated by CD40L.

The invention also provides methods of modulating CD40L activity using the Tn3 scaffolds described herein. In some embodiments, methods of the invention comprise contacting a CD40L with CD40L-specific scaffolds and blocking the interaction between CD40 and CD40L. In other embodiments, methods of the invention comprise contacting a cell expressing CD40L with a CD40L-specific Tn3 scaffold and preventing proteolytic cleavage of CD40L from the cell surface. In other embodiments, methods of the invention comprise contacting a CD40L monomer with a CD40L-specific Tn3 scaffold and preventing CD40L oligomerization. In other embodiments, dimerization or oligomerization of CD40L may be achieved through the use of multimeric Tn3 scaffolds.

In some embodiments, methods of the invention comprise the administration of a CD40L specific scaffold that reduces a CD40-mediated immune response (see, e.g., Elqueta et al. 229: 152-172, 2009), or a downstream signaling pathway initiated by CD40 binding to CD40L, as measured by routine assays known in the art.

Without wishing to be bound by any particular theory, CD40L scaffolds of the present invention could function by preventing binding of CD40L to CD40, by binding and sequestering soluble CD40L, by altering the interaction of CD40L with CD40 but not preventing binding, by preventing or enhancing metalloprotease-mediated enzymatic cleavage of CD40L from the cell surface to yield soluble CD40L, by preventing or enhancing cell surface CD40L endocytosis, etc.

Specific CD40L Binding Sequences

In some embodiments, the Tn3 scaffold of the invention comprise CD40L-specific monomer subunits comprising at least one, at least two, at least three, at least four, at least five, or at least six loop sequences that bind to CD40L.

In some embodiments, CD40L-specific monomer subunits comprise at least one, at least two, at least three, at least four, at least five, or at least six loop sequences of CD40L-binding monomer clones selected from: 309 (parental 309 family clone isolated from naive Tn3 library; SEQ ID NO: 20), 309FGwt (parental 309 clone with humanized FG loop; SEQ ID NO: 22), 340 (affinity matured 309 clone; SEQ ID NO: 24), 341 (affinity matured 309 clone; SEQ ID NO: 26), 342 (affinity matured 309 clone; SEQ ID NO: 28 or SEQ ID NO: 146), 343 (affinity matured 309 clone; SEQ ID NO: 30), 344 (affinity matured 309 clone; SEQ ID NO: 32), 345 (affinity matured 309 clone; SEQ ID NO: 34), 346 (affinity matured 309 clone; SEQ ID NO: 36), 347 (affinity matured 309 clone; SEQ ID NO: 38), 348 (affinity matured 309 clone; SEQ ID NO: 40), 349 (affinity matured 309 clone; SEQ ID NO: 42), 311 (parental 311 family clone isolated from naive Tn3 library; SEQ ID NO: 44), 311K4E (variant 311 family clone from first round of affinity maturation; SEQ ID NO: 46); 311K4E_1 (variant 311 family clone from second round of affinity maturation; SEQ ID NO: 48), 311K4E_2 (variant 311 family clone from second round of affinity maturation; SEQ ID NO: 50), 311K4E_3 (variant 311 family clone from second round of affinity maturation; SEQ ID NO: 52), 311K4E_4 (variant 311 family clone from second round of affinity maturation; SEQ ID NO: 54), 311K4E_5 (variant 311 family clone from second round of affinity maturation; SEQ ID NO: 56), 311K4E_7 (variant 311 family clone from second round of affinity maturation; SEQ ID NO: 58), 311K4E_8 (variant 311 family clone from second round of affinity maturation; SEQ ID NO: 60), 311K4E_9 (variant 311 family clone from second round of affinity maturation; SEQ ID NO: 62), 311K4E_10 (variant 311 family clone from second round of affinity maturation;

SEQ ID NO: 64), 311K4E_11 (variant 311 family clone from second round of affinity maturation; SEQ ID NO: 66), 311K4E_12 (variant 311 family clone from second round of affinity maturation; SEQ ID NO: 68), 311K4E_13 (variant 311 family clone from second round of affinity maturation; SEQ ID NO: 70), 311K4E_14 (variant 311 family clone from second round of affinity maturation; SEQ ID NO: 72), 311K4E_15 (variant 311 family clone from second round of affinity maturation; SEQ ID NO: 74), 311K4E_16 (variant 311 family clone from second round of affinity maturation; SEQ ID NO: 76), 311K4E_19 (variant 311 family clone from second round of affinity maturation; SEQ ID NO: 78), 311K4E_20 (variant 311 family clone from second round of affinity maturation; SEQ ID NO: 80), and 311K4E_21 (variant 311 family clone from second round of affinity maturation; SEQ ID NO: 82).

In some embodiments, CD40L-specific monomer subunits comprise at least one loop sequence selected from the loop sequences listed in TABLE 2. In other embodiments, CD40L-specific monomer subunits comprise at least one BC loop sequence selected from the BC loop sequences listed in TABLE 2. In other embodiments, CD40L-specific monomer subunits comprise at least one DE loop sequence selected from the DE loop sequences listed in TABLE 2. In other embodiments, CD40L-specific monomer subunits comprise at least one FG loop sequence selected from the FG loop sequences listed in TABLE 2.

In some embodiments, CD40L-specific monomer subunits comprise a BC loop sequence selected from the BC loop sequences listed in TABLE 2; and a DE loop sequence selected from the DE loop sequences listed in TABLE 2. In other embodiments, CD40L-specific monomer subunits comprise a BC loop sequence selected from the BC loop sequences listed in TABLE 2; and an FG loop sequence selected from the FG loop sequences listed in TABLE 2. In other embodiments, CD40L-specific monomer subunits comprise a DE loop sequence selected from the DE loop sequences listed in TABLE 2; and an FG loop sequence selected from the FG loop sequences listed in TABLE 2. In some embodiments, a CD40L-specific monomer subunits comprises loop sequences corresponding to loop sequences from one, two or three different Tn3 clones.

In certain embodiments, where the CD40L-specific monomer scaffold sequence contains a linker and/or a Histidine tag (e.g., a His-8 tag) at the C-terminus of the sequence, or additional N-terminal amino acids, these C-terminal linker and/or Histidine tag and additional N-terminal amino acids can be removed, the corresponding amino acid sequence thus containing a deletion of the C-terminal linker and His tag sequences and the N-terminal additional amino acid or amino acids.

In some embodiments, the CD40L-specific Tn3 scaffold comprises a single monomer subunit, e.g., the 342 clone sequence (affinity matured 309 clone; SEQ ID NO: 28 and/or SEQ ID NO: 146). In other embodiments, the CD40L-specific scaffold comprises more than one monomer subunits, e.g., two 342 clone monomer subunits (SEQ ID NO: 28 and/or SEQ ID NO: 146) in tandem (see, e.g., SEQ ID NO: 135). In specific embodiments, Tn3 scaffolds of the invention are conjugated to a variant HSA (see, e.g., SEQ ID NO: 134 and SEQ ID NO: 135). In further embodiments, the HSA can be conjugated at either the N-terminus or the C-terminus of the multimeric Tn3 scaffold.

In a specific embodiment, the CD40L-specific Tn3 scaffold comprises a single 311K4E_12 monomer subunit, a GS linker, and a C34S HSA variant (see, e.g., SEQ ID NO: 201). In another specific embodiment, the CD40L-specific Tn3 scaffold comprises a single 311K4E_12 monomer subunit with a beta strand C CELTYG variant, an all glycine linker, and a C34S HSA variant (see, e.g., SEQ ID NO: 202). In another specific embodiment, the CD40L-specific Tn3 scaffold comprises two 311K4E_12 subunits in tandem, and two GS linkers, wherein one GS linker connects the subunits to each other and a second GS linker connects one subunit to a C34S HSA variant (see, e.g., SEQ ID NO: 203). In yet another specific embodiment, the CD40L-specific Tn3 scaffold comprises two 311K4E_12 subunits in tandem, and two all glycine linkers, wherein one all glycine linker connects the subunits to each other and a second all glycine linker connects one subunit to a C34S HSA variant (see, e.g., SEQ ID NO: 204).

In one specific embodiment, the CD40L-specific Tn3 scaffold comprises two 309 subunits connected in tandem via a GS linker (see, e.g., SEQ ID NO: 205). In another specific embodiment, the CD40L-specific Tn3 scaffold comprises a single 309 subunit connected to a C34S HSA variant (see, e.g., SEQ ID NO: 206). In another specific embodiment, the CD40L-specific Tn3 scaffold comprises two 309 subunits in tandem, and two GS linkers, wherein one GS linker connects the subunits to each other and a second GS linker connects one subunit to a C34S HSA variant (see, e.g., SEQ ID NO: 207).

In a specific embodiment, the CD40L-specific Tn3 scaffold comprises a single 342 monomer subunit, a GS linker, and a C34S HSA variant (see, e.g., SEQ ID NO: 134). In another specific embodiment, the CD40L-specific Tn3 scaffold comprises a single 342 monomer subunit, an all glycine linker, and a C34S HSA variant (see, e.g., SEQ ID NO: 144). In another specific embodiment, the CD40L-specific Tn3 scaffold comprises two 342 subunits in tandem, and two GS linkers, wherein one GS linker connects the subunits to each other and a second GS linker connects one subunit to a C34S HSA variant (see, e.g., SEQ ID NO: 135). In yet another specific embodiment, the CD40L-specific Tn3 scaffold comprises two 342 subunits in tandem, and two all glycine linkers, wherein one all glycine linker connects the subunits to each other and a second all glycine linker connects one subunit to a C34S HSA variant (see, e.g., SEQ ID NO: 145). In yet another specific embodiment, the CD40L-specific Tn3 scaffold comprises two 342 subunits connected in tandem by a GS linker (see, e.g., SEQ ID NO: 208).

In a specific embodiment, the CD40L-specific Tn3 scaffold comprises In another specific embodiment, the CD40L-specific Tn3 scaffold comprises a 311 subunit, or a subunit derived from 311 (e.g., 311K4E_12) and a 309 subunit, or a subunit derived from 309 (e.g., 342) in tandem and two GS linkers, wherein one GS linker connects the subunits to each other and a second GS linker connects one subunit to a C34S HSA variant (see, e.g., SEQ ID NO: 135). In yet another specific embodiment, the CD40L-specific Tn3 scaffold comprises a 311 subunit, or a subunit derived from 311 (e.g., 311K4E_12) and a 309 subunit, or a subunit derived from 309 (e.g., 342) in tandem, and two all glycine linkers, wherein one all glycine linker connects the subunits to each other and a second all glycine linker connects one subunit to a C34S HSA variant (see, e.g., SEQ ID NO: 145).

Figure 2A:
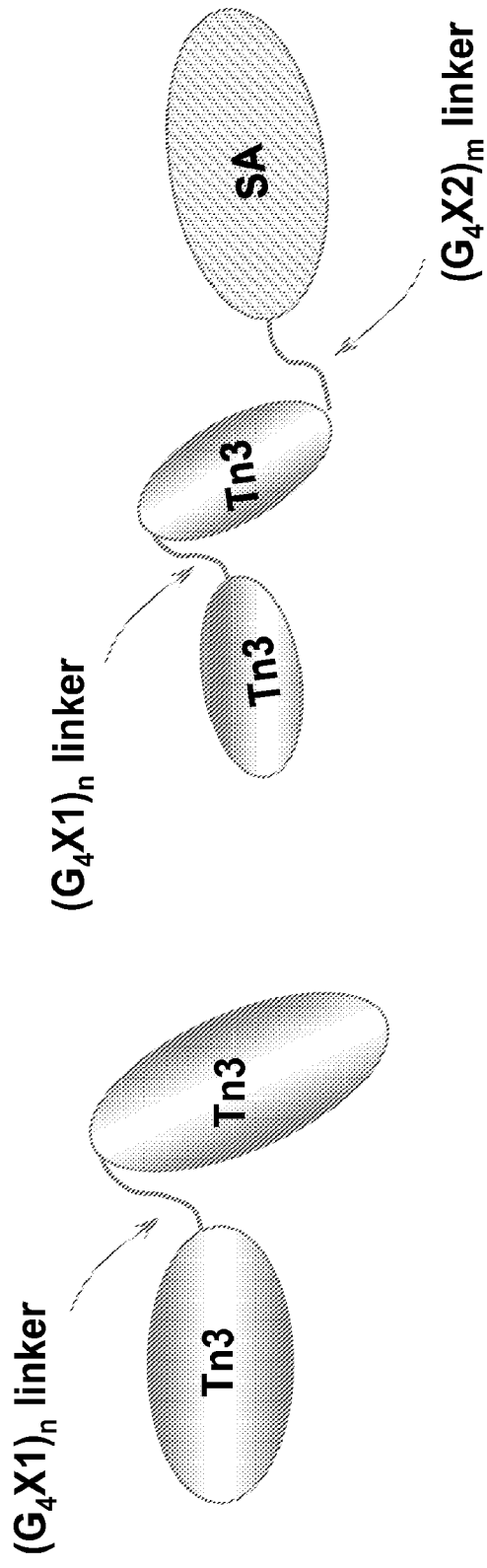
FIG. 2A shows the design of CD40L-specific tandem bivalent Tn3 scaffolds and Serum Albumin (SA) fusion constructs.
Figure 2B:
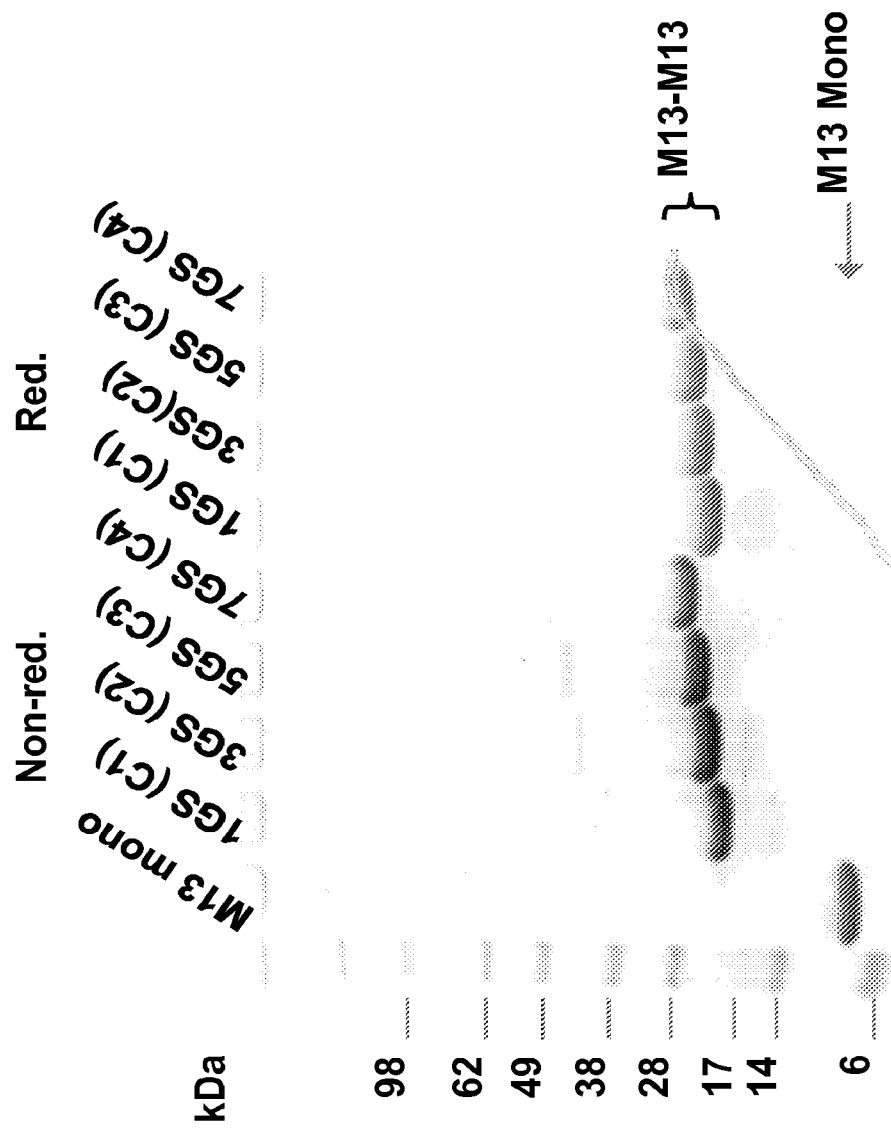
FIG. 2B shows the SDS-PAGE analysis of a purified monovalent M13 construct (CD40L-specific Tn3 construct), or tandem bivalent scaffolds with linkers containing 1, 3, 5 or 7 Gly$_4$Ser units (denoted as GS) joining two M13 Tn3 monomer subunits. The monovalent M13 construct was run in lane 2, the dimeric construct with 1 GS unit (C1) was run in lanes 3 and 7, the dimeric constrict with 3 GS units (C2) was run in lanes 4 and 8, the dimeric construct with 5 GS units (C3) was run in lanes 5 and 9, and the dimeric construct with 7 GS units (C4) was run in lanes 6 and 10. Samples were run either non-reduced conditions (lanes 2-6) or reduced conditions (lanes 7-10).
Figure 2C:
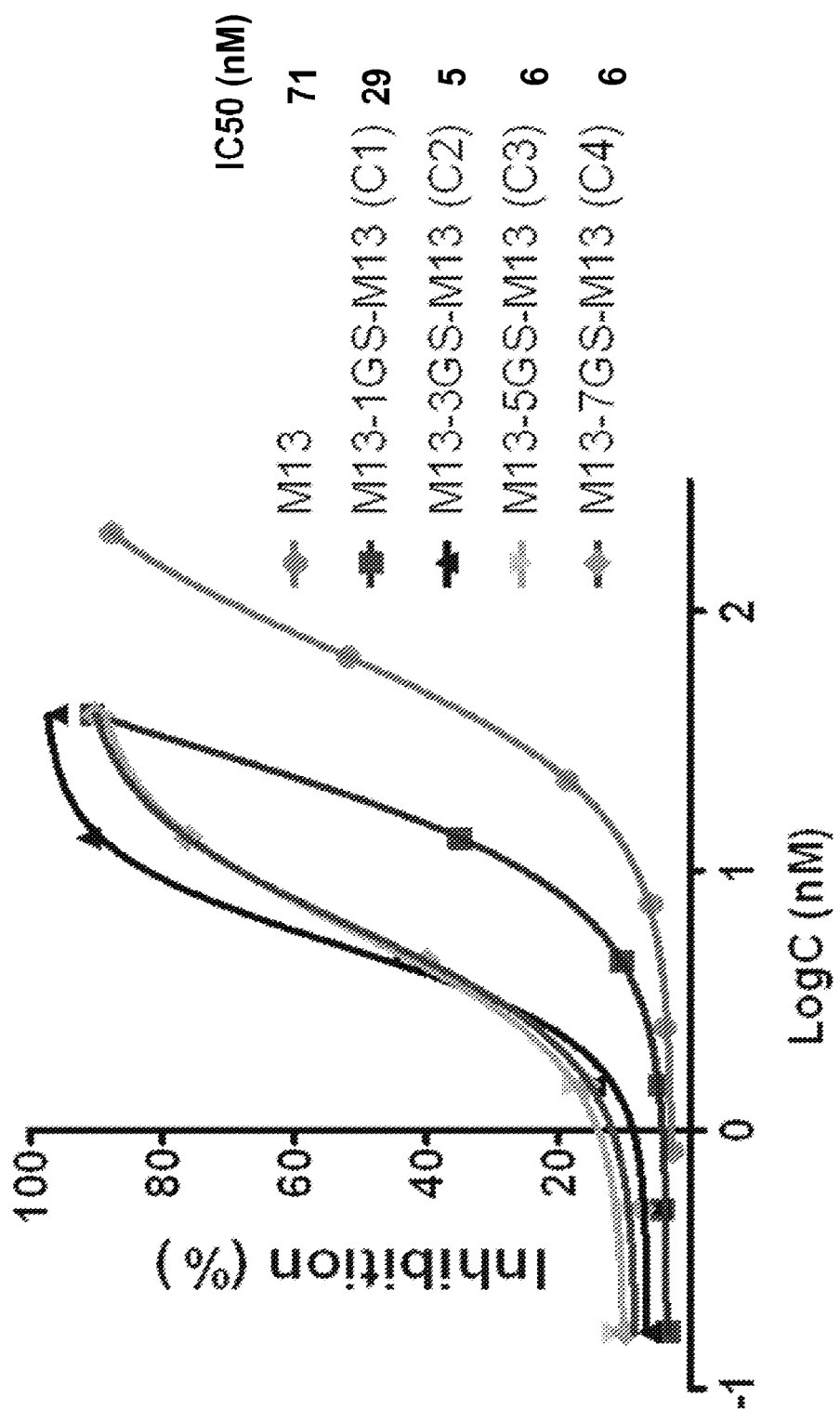
FIG. 2C shows the competitive inhibition of murine CD40L binding to murine CD40 receptor immobilized on a biosensor chip by murine CD40L-specific monovalent (M13) or bivalent tandem scaffolds (M13-xGS-M13, wherein x is 1, 3, 5 or 7, corresponding to bivalent scaffolds with linkers containing 1, 3, 5 or 7 Gly4Ser units). The half maximal inhibitory concentration ($IC_{50}$) for the various constructs is also indicated.
Figure 2D:
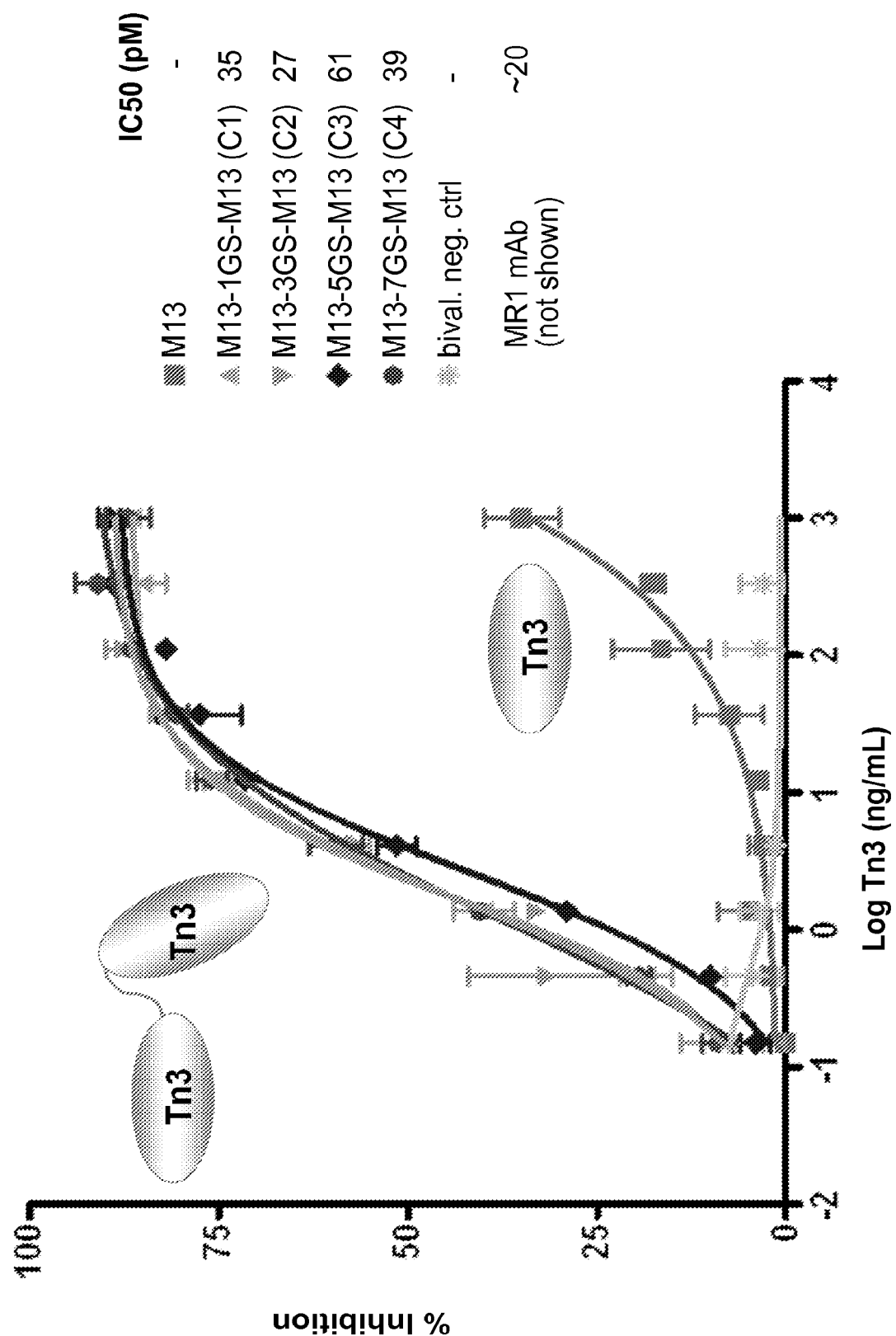
FIG. 2D shows the inhibitory effect of murine CD40L-specific Tn3 monovalent (M13) and bivalent tandem scaffolds, on murine CD40L-induced CD86 expression on B cells. $IC_{50}$ values are provided for all Tn3 constructs and for the MR1 anti-murine CD40L antibody.
Figure 9A:
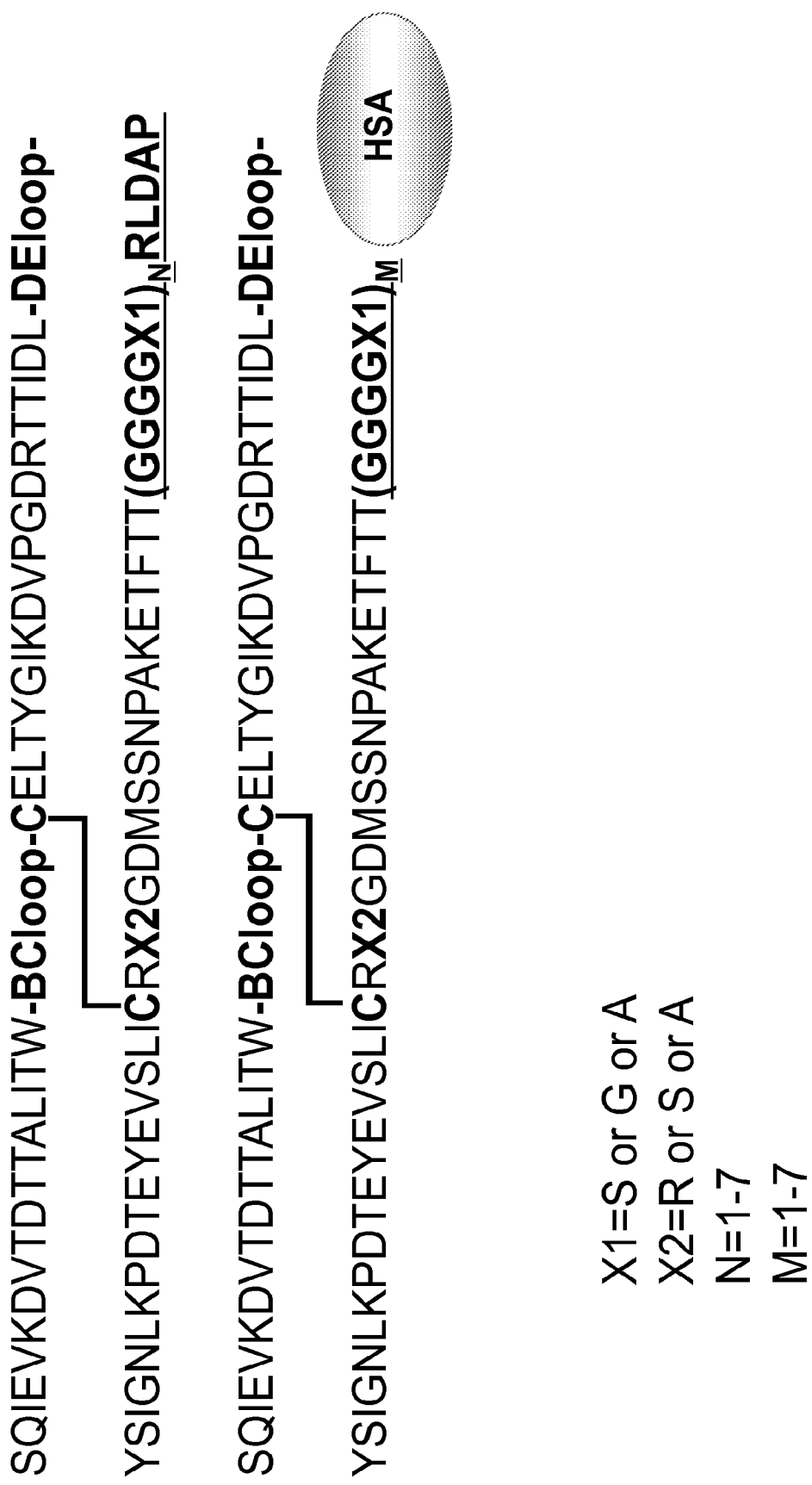
FIG. 9A shows the design of a representative human CD40L-specific tandem bivalent Tn3 scaffold fused to human serum albumin (HSA) (e.g., SEQ ID NO:135 or SEQ ID NO:145). "GGGGG" (SEQ ID NO: 148) and "GGGGA" (SEQ ID NO: 149) are alternative linkers to the "GGGGS" linkers (SEQ ID NO: 147).

Examples of CD40L-specific tandem bivalent Tn3 scaffolds and Serum Albumin (SA) fusions are shown in FIG. 2A (also see FIG. 9A). Although specific linkers are provided in FIG. 2A, other linkers are contemplated as provided herein. Although wild type mature SA may be used, e.g., murine serum albumin (MSA) or human serum albumin (HSA), it is contemplated that one or more Cysteine (C)

amino acid residues in the mature SA may be substituted, for example with Serine (S), Alanine (A), Glycine (G), etc.

Representative constructs are shown below. The sequence of the SA is underlined. Linkers are boxed. It will be understood that numerous variations are within the scope of the invention. For example, the linkers may be altered (several non-limited examples are provided herein), the first one or two N-terminal amino acid residues (SQ) may be absent and/or substituted with alternative amino acid residues, a tag (e.g., 6×His tag) may be incorporated, alternative CD40L-specific scaffolds (e.g., those based on the 10$^{th}$ Fn3 domain of fibronectin) may be utilized in a similar construct, etc.

342 Monovalent HSA construct 1 (SEQ ID NO: 134)
[342 monomer]-(G$_4$S)$_2$ linker-HSA$_{C34S}$

SQIEVKDVTDTTALITWSDDFGEYVWCELTYGIKDVPGDRTTIDLWYHHAHYSIGNLKPD

TEYEVSLICRSGDMSSNPAKETFTT GGGGSGGGGS DAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL

342 Monovalent HSA construct 2 (SEQ ID NO: 144)
[342 monomer]-G$_{10}$ linker-HSA$_{C34S}$:

SQIEVKDVTDTTALITWSDDFGEYVWCELTYGIKDVPGDRTTIDLWYHHAHYSIGNLKPD

TEYEVSLICRSGDMSSNPAKETFTT GGGGSGGGGS DAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL

342 Bivalent HSA Construct 1 (SEQ ID NO: 135)
[342 monomer]-(G$_4$S)$_3$ linker-[342 monomer]-(G$_4$S)$_2$ linker-HSA$_{C34S}$:

SQIEVKDVTDTTALITWSDDFGEYVWCELTYGIKDVPGDRTTIDLWYHHAHYSIGNLKPD

TEYEVSLICRSGDMSSNPAKETFTT GGGGSGGGGSGGGGS RLDAPSQIEVKDVTDTTALI

TWSDDFGEYVWCELTYGIKDVPGDRTTIDLWYHHAHYSIGNLKPDTEYEVSLICRSGDMS

SNPAKETFTT GGGGSGGGGS DAHKSEVAHRFKDLGEENFKALVLIAFAQYLQQSPFEDHV

KLVNEVTEFAKTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFYAPELLFFAKR

YKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCE

KPLLEKSHCIAEVENDEMPADLPSLAADFVESKDVCKNYAEAKDVFLGMFLYEYARRHPD
YSVVLLLRLAKTYETTLEKCCAAADPHECYAKVFDEFKPLVEEPQNLIKQNCELFEQLGE
YKFQNALLVRYTKKVPQVSTPTLVEVSRNLGKVGSKCCKHPEAKRMPCAEDYLSVVLNQL
CVLHEKTPVSDRVTKCCTESLVNRRPCFSALEVDETYVPKEFNAETFTFHADICTLSEKE
RQIKKQTALVELVKHKPKATKEQLKAVMDDFAAFVEKCCKADDKETCFAEEGKKLVAASQ
AALGL

342 Bivalent HSA Construct 2 (SEQ ID NO: 145)
[342 monomer]-G$_{15}$ linker-[342 monomer]-G$_{10}$ linker-HSA$_{C34S}$:

SQIEVKDVTDTTALITWSDDFGEYVWCELTYGIKDVPGDRTTIDLWYHHAHYSIGNLKPD
TEYEVSLICRSGDMSSNPAKETFTTGGGGGGGGGGGGGGGRLDAPSQIEVKDVTDTTALI
TWSDDFGEYVWCELTYGIKDVPGDRTTIDLWYHHAHYSIGNLKPDTEYEVSLICRSGDMS
SNPAKETFTTGGGGGGGGGGDAHKSEVAHRFKDLGEENFKALVLIAFAQYLQQSPFEDHV
KLVNEVTEFAKTCVADESAENCDKSLHTLFGDKLCTVATLRETYGEMADCCAKQEPERNE
CFLQHKDDNPNLPRLVRPEVDVMCTAFHDNEETFLKKYLYEIARRHPYFYAPELLFFAKR
YKAAFTECCQAADKAACLLPKLDELRDEGKASSAKQRLKCASLQKFGERAFKAWAVARLS
QRFPKAEFAEVSKLVTDLTKVHTECCHGDLLECADDRADLAKYICENQDSISSKLKECCE
KPLLEKSHCIAEVENDEMPADLPSLAADFVESKDVCKNYAEAKDVFLGMFLYEYARRHPD
YSVVLLLRLAKTYETTLEKCCAAADPHECYAKVFDEFKPLVEEPQNLIKQNCELFEQLGE
YKFQNALLVRYTKKVPQVSTPTLVEVSRNLGKVGSKCCKHPEAKRMPCAEDYLSVVLNQL
CVLHEKTPVSDRVTKCCTESLVNRRPCFSALEVDETYVPKEFNAETFTFHADICTLSEKE
RQIKKQTALVELVKHKPKATKEQLKAVMDDFAAFVEKCCKADDKETCFAEEGKKLVAASQ
AALGL

311K4E_12 Monovalent HSA Construct 1 (SEQ ID NO: 201)
[311K4E_12 monomer]-(G$_4$S)$_2$ linker-HSA$_{C34S}$:

SQIEVEDVTDTTALITWTNRSSYSNLHGCELAYGIKDVPGDRTTIDLNQPYVHYSIGNLK
PDTEYEVSLICLTTDGTYNNPAKETFTTGGGGSGGGGSDAHKSEVAHRFKDLGEENFKAL
VLIAFAQYLQQSPFEDHVKLVNEVTEFAKTCVADESAENCDKSLHTLFGDKLCTVATLRE
TYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCAS
LQKFGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNYAEA
KDVFLGMFLYEYARRHPDYSVVLLLRLAKTYETTLEKCCAAADPHECYAKVFDEFKPLVE
EPQNLIKQNCELFEQLGEYKFQNALLVRYTKKVPQVSTPTLVEVSRNLGKVGSKCCKHPE
AKRMPCAEDYLSVVLNQLCVLHEKTPVSDRVTKCCTESLVNRRPCFSALEVDETYVPKEF
NAETFTFHADICTLSEKERQIKKQTALVELVKHKPKATKEQLKAVMDDFAAFVEKCCKAD
DKETCFAEEGKKLVAASQAALGL

311K4E_12 Monovalent HSA Construct 2 (SEQ ID NO: 202)
[311K4E_12 monomer]-G$_{10}$ linker-HSA$_{C34S}$:

SQIEVEDVTDTTALITWTNRSSYSNLHGCELTYGIKDVPGDRTTIDLNQPYVHYSIGNLK
PDTEYEVSLICLTTDGTYNNPAKETFTTGGGGGGGGGGDAHKSEVAHRFKDLGEENFKAL
VLIAFAQYLQQSPFEDHVKLVNEVTEFAKTCVADESAENCDKSLHTLFGDKLCTVATLRE

TYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCAS
LQKFGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNYAEA
KDVFLGMFLYEYARRHPDYSVVLLLRLAKTYETTLEKCCAAADPHECYAKVFDEFKPLVE
EPQNLIKQNCELFEQLGEYKFQNALLVRYTKKVPQVSTPTLVEVSRNLGKVGSKCCKHPE
AKRMPCAEDYLSVVLNQLCVLHEKTPVSDRVTKCCTESLVNRRPCFSALEVDETYVPKEF
NAETFTFHADICTLSEKERQIKKQTALVELVKHKPKATKEQLKAVMDDFAAFVEKCCKAD
DKETCFAEEGKKLVAASQAALGL

311K4E_12 Bivalent HSA Construct 1 (SEQ ID NO: 203)
[311K4E_12 monomer]-G₄S₃ linker-[311K4E_12 monomer]-(G₄S)₂
linker-HSA$_{C34S}$:

SQIEVEDVTDTTALITWTNRSSYSNLHGCELAYGIKDVPGDRTTIDLNQPYVHYSIGNLK
PDTEYEVSLICLTTDGTYNNPAKETFTI`GGGGSGGGGSGGGGS`RLDAPSQIEVEDVTDTT
ALITWTNRSSYSNLHGCELAYGIKDVPGDRTTIDLNQPYVHYSIGNLKPDTEYEVSLICL
TTDGTYNNPAKETFTTGGGGSGGGGSDAHKSEVAHRFKDLGEENFKALVLIAFAQYLQQS
PFEDHVKLVNEVTEFAKTCVADESAENCDKSLHTLFGDKLCTVATLRETYGEMADCCAKQ
EPERNECFLQHKDDNPNLPRLVRPEVDVMCTAFHDNEETFLKKYLYEIARRHPYFYAPEL
LFFAKRYKAAFTECCQAADKAACLLPKLDELRDEGKASSAKQRLKCASLQKFGERAFKAW
AVARLSQRFPKAEFAEVSKLVTDLTKVHTECCHGDLLECADDRADLAKYICENQDSISSK
LKECCEKPLLEKSHCIAEVENDEMPADLPSLAADFVESKDVCKNYAEAKDVFLGMFLYEY
ARRHPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAEDYLS
VVLNQLCVLHEKTPVSDRVTKCCTESLVNRRPCFSALEVDETYVPKEFNAETFTFHADIC
TLSEKERQIKKQTALVELVKHKPKATKEQLKAVMDDFAAFVEKCCKADDKETCFAEEGKK
LVAASQAALGL

311K4E_12 Bivalent HSA Construct 2 (SEQ ID NO: 204)
[311K4E_12 monomer]-G15 linker-[311K4E_12 monomer]-G₁₀
linker-HSA$_{C34S}$:

SQIEVEDVTDTTALITWTNRSSYSNLHGCELTYGIKDVPGDRTTIDLNQPYVHYSIGNLK
PDTEYEVSLICLTTDGTYNNPAKETFTI`GGGGGGGGGGGGGGG`RLDAPSQIEVEDVTDTT
ALITWTNRSSYSNLHGCELAYGIKDVPGDRTTIDLNQPYVHYSIGNLKPDTEYEVSLICL
TTDGTYNNPAKETFTI`GGGGGGGGGG`DAHKSEVAHRFKDLGEENFKALVLIAFAQYLQQS
PFEDHVKLVNEVTEFAKTCVADESAENCDKSLHTLFGDKLCTVATLRETYGEMADCCAKQ
EPERNECFLQHKDDNPNLPRLVRPEVDVMCTAFHDNEETFLKKYLYEIARRHPYFYAPEL
LFFAKRYKAAFTECCQAADKAACLLPKLDELRDEGKASSAKQRLKCASLQKFGERAFKAW
AVARLSQRFPKAEFAEVSKLVTDLTKVHTECCHGDLLECADDRADLAKYICENQDSISSK
LKECCEKPLLEKSHCIAEVENDEMPADLPSLAADFVESKDVCKNYAEAKDVFLGMFLYEY
ARRHPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAEDYLS
VVLNQLCVLHEKTPVSDRVTKCCTESLVNRRPCFSALEVDETYVPKEFNAETFTFHADIC

-continued

TLSEKERQIKKQTALVELVKHKPKATKEQLKAVMDDFAAFVEKCCKADDKETCFAEEGKK

LVAASQAALGL

Pharmaceutical Compositions

In another aspect, the present invention provides a composition, for example, but not limited to, a pharmaceutical composition, containing one or a combination of Tn3 scaffolds of the present invention, formulated together with a pharmaceutically acceptable carrier. Such compositions may include one or a combination of, for example, but not limited to two or more different Tn3 scaffolds of the invention. For example, a pharmaceutical composition of the invention may comprise a combination of Tn3 scaffolds that bind to different epitopes on the target antigen or that have complementary activities. In a specific embodiment, a pharmaceutical composition comprises a single monomer Tn3 scaffold of the invention. In a specific embodiment, a pharmaceutical composition comprises a multimeric Tn3 scaffold of the invention. In still another specific embodiment, a pharmaceutical composition comprises dimer Tn3 scaffold of the invention.

Pharmaceutical compositions of the invention also can be administered in combination therapy, such as, combined with other agents. For example, the combination therapy can include a Tn3 scaffold of the present invention combined with at least one other therapy wherein the therapy may be immunotherapy, chemotherapy, radiation treatment, or drug therapy. The pharmaceutical compounds of the invention may include one or more pharmaceutically acceptable salts.

Methods of Using Scaffolds

The Tn3 scaffolds of the present invention have in vitro and in vivo diagnostic and therapeutic utilities. For example, these molecules can be administered to cells in culture, e.g., in vitro or ex vivo, or in a subject, e.g., in vivo, to treat, prevent or diagnose a variety of disorders.

The invention also provides methods of using the Tn3 scaffolds of the invention. The present invention also encompasses the use of the Tn3 scaffolds of the invention for the prevention, diagnosis, management, treatment or amelioration of one or more symptoms associated with diseases, disorders of diseases or disorders, including but not limited to cancer, inflammatory and autoimmune diseases, infectious diseases either alone or in combination with other therapies. The invention also encompasses the use of the Tn3 scaffolds of the invention conjugated or fused to a moiety (e.g., therapeutic agent or drug) for prevention, management, treatment or amelioration of one or more symptoms associated with diseases, disorders or infections, including but not limited to cancer, inflammatory and autoimmune diseases, infectious diseases either alone or in combination with other therapies.

The invention also provides methods of targeting epitopes not easily accomplished with traditional antibodies. For example, in one embodiment, the Tn3 scaffolds the invention may be used to first target an adjacent antigen and while binding, another binding domain may engage the cryptic antigen.

The invention also provides methods of using the Tn3 scaffolds to bring together distinct cell types. In one embodiment, the proteins of the invention may bind a target cell with one binding domain and recruit another cell via another binding domain. In another embodiment, the first cell may be a cancer cell and the second cell is an immune effector cell such as an NK cell. In another embodiment, the Tn3 scaffolds of the invention may be used to strengthen the interaction between two distinct cells, such as an antigen presenting cell and a T cell to possibly boost the immune response.

The invention also provides methods of using the Tn3 scaffolds to deplete a cell population. In one embodiment, methods of the invention are useful in the depletion of the following cell types: eosinophil, basophil, neutrophil, T cell, B cell, mast cell, monocytes and tumor cells.

The invention also provides methods of using Tn3 scaffolds as diagnostic reagents. Such diagnostic reagents are could be used to test for the presence or absence of CD40L, the presence of CD40 receptor, the binding efficiency of CD40L to CD40 receptor, free CD40L in a patient, free CD40L in a sample, or bound CD40L to CD40 receptor in a sample.

The Tn3 scaffolds of the invention and compositions comprising the same are useful for many purposes, for example, as therapeutics against a wide range of chronic and acute diseases and disorders including, but not limited to, autoimmune and/or inflammatory diseases. The compositions and methods of the invention described herein are useful for the prevention or treatment of autoimmune disorders and/or inflammatory disorders.

Examples of autoimmune and/or inflammatory disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), comeal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacterial infections. The compositions and methods of the invention can be used with one or more conventional therapies that are used to prevent, manage or treat the above diseases.

The invention provides methods for preventing, managing, treating or ameliorating cancer, autoimmune, inflammatory or infectious diseases or one or more symptoms or one or more symptoms thereof, said methods comprising administering to a subject in need thereof one or more Tn3 scaffolds of the invention in combination with one or more of therapeutic agents that are not cancer therapeutics (a.k.a., non-cancer therapies).

Examples of such agents include, but are not limited to, anti-emetic agents, anti-fungal agents, anti-bacterial agents, such as antibiotics, anti-inflammatory agents, and antiviral agents. Non-limiting examples of anti-emetic agents include metopimazin and metochlopramide. Non-limiting examples of antifungal agents include azole drugs, imidazole, triazoles, polyene, amphotericin and ryrimidine. Non-limiting examples of anti-bacterial agents include dactinomycin, bleomycin, erythromycin, penicillin, mithramycin, cephalosporin, imipenem, axtreonam, vancomycin, cycloserine, bacitracin, chloramphenicol, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketoconazole, isoniazid, metronidazole and pentamidine. Non-limiting examples of antiviral agents include nucleoside analogs (e.g., zidovudine, acyclovir, gangcyclovir, vidarbine, idoxuridine, trifluridine and ribavirin), foscaret, amantadine, rimantadine, saquinavir, indinavir, ritonavir, interferon ("IFN")-$\alpha,\beta$ or $\gamma$ and AZT. Non-limiting examples of anti-inflammatory agents include non-steroidal anti-inflammatory drugs ("NSAIDs"), steroidal anti-inflammatory drugs, beta-agonists, anti-cholinergic agents and methylxanthines.

In one embodiment, the invention comprises compositions capable of treating chronic inflammation. In one embodiment, the compositions are useful in the targeting of immune cells for destruction or deactivation. In one embodiment, the compositions are useful in targeting activated T cells, dormant T cells, B cells, neutrophils, eosinophils, basophils, mast cells, or dendritic cells. In another embodiment, the invention comprises compositions capable of decreasing immune cell function. In another embodiment, the compositions are capable of ablating immune cell function.

In another embodiment, the invention comprises compositions useful for treatment of diseases of the gastrointestinal tract. The scaffolds of the invention exhibit a high level of stability under low pH conditions. The stability at low pH suggests that the composition will be suitable for oral administration for a variety of gastrointestinal disorders, such as irritable bowel syndrome, gastroesophageal reflux, intestinal pseudo-obstructions, dumping syndrome, intractable nausea, peptic ulcer, appendicitis, ischemic colitis, ulcerative colitis, gastritis, *Helicobacter pylori* disease, Crohn's disease, Whipple's disease, celiac sprue, diverticulitis, diverticulosis, dysphagia, hiatus hernia, infections esophageal disorders, hiccups, rumination and others.

The invention further provides combinatorial compositions and methods of using such compositions in the prevention, treatment, reduction, or amelioration of disease or symptoms thereof. The Tn3 scaffolds of the invention may be combined with conventional therapies suitable for the prevention, treatment, reduction or amelioration of disease or symptoms thereof. Exemplary conventional therapies can be found in the Physician's Desk Reference (56th ed., 2002 and 57th ed., 2003). In some embodiments, Tn3 scaffolds of the invention may be combined with chemotherapy, radiation therapy, surgery, immunotherapy with a biologic (antibody or peptide), small molecules, or another therapy known in the art. In some embodiments, the combinatorial therapy is administered together. In other embodiments, the combinatorial therapy is administered separately.

The invention also provides methods of diagnosing diseases. The Tn3 scaffolds of the invention which bind a specific target associated with a disease may be implemented in a method used to diagnose said disease. In one embodiment, the Tn3 scaffolds of the invention are used in a method to diagnose a disease in a subject, said method comprising obtaining a sample from the subject, contacting the target with the Tn3 scaffold in said sample under conditions that allow the target:scaffold interaction to form, identifying the target:scaffold complex and thereby detecting the target in the sample. In other embodiments, the disease to be diagnosed is described herein.

The invention also provides methods of imaging specific targets. In one embodiment, Tn3 scaffolds of the invention conjugated to imaging agents such as green-fluorescent proteins, other fluorescent tags (Cy3®, Cy5®, Rhodamine and others), biotin, or radionuclides may be used in methods to image the presence, location, or progression of a specific target. In some embodiments, the method of imaging a target comprising a Tn3 scaffold of the invention is performed in vitro. In other embodiments, the method of imaging a target comprising a Tn3 scaffold of the invention is performed in vivo. In other embodiments, the method of imaging a target comprising a Tn3 scaffold of the invention is performed by MRI, PET scanning, X-ray, fluorescence detection or by other detection methods known in the art.

The invention also provides methods of monitoring disease progression, relapse, treatment, or amelioration using the scaffolds of the invention. In one embodiment, methods of monitoring disease progression, relapse, treatment, or amelioration is accomplished by the methods of imaging, diagnosing, or contacting a compound/target with a Tn3 scaffold of the invention as presented herein.

Pharmaceutical Dosing and Administration

To prepare pharmaceutical or sterile compositions including a Tn3 scaffold of the invention, a scaffold is mixed with a pharmaceutically acceptable carrier or excipient. For administration compositions are preferably pyrogen-free which are substantially free of endotoxins and/or related pyrogenic substances. Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present invention may also be administered via one or more routes of administration using one or more of a variety of methods known in the art. In certain embodiments, the Tn3 scaffolds of the invention can be formulated to ensure proper distribution in vivo.

EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

EXAMPLES

The invention is now described with reference to the following examples. These examples are illustrative only and the invention should in no way be construed as being limited to these examples but rather should be construed to encompass any and all variations which become evident as a result of the teachings provided herein.

Example 1

Construction of a 3 Loop Library on the Parent Tn3 Scaffold

A library was constructed based upon the parent Tn3 scaffold, described in International Patent Application Publ. No. WO 2009/058379, wherein it is designated "Tn3 SS4." The library contained randomized regions of the BC, DE and FG loops. This design incorporated characterized sequence and loop length diversity into the Tn3 library, consistent with patterns of diversity described for natural FnIII domains, three different lengths for the BC and FG loops, and used a "NHT" mixed codon scheme for introducing diversity into the library (H=A, T, C). This scheme generated 12 codons that coded for 12/20 amino acids (see TABLE 3), that is, each codon coded for a unique amino acid. Moreover, there were no stop or Cysteine (Cys) codons.

TABLE 3

| A | AAT = Asn | ATT = Ile | ACT = Thr |
| G | GAT = Asp | GTT = Val | GCT = Ala |
| C | CAT = His | CTT = Leu | CCT = Pro |
| T | TAT = Tyr | TTT = Phe | TCT = Ser |
|   | A | T | C |

The library diversity was generated using the degenerate oligonucleotides shown in TABLE 4.

TABLE 4

| Oligo | Loop | Sequence | SEQ ID NO |
|---|---|---|---|
| BC9 NHT | BC | ACCGCGCTGATTACCTGGNHTNHTSCGNHTGSTNHT NHTNHTGGCTGTGAACTGACCTATGGCATTAAA | 178 |
| BC11 NHT | BC | ACCGCGCTGATTACCTGGNHTNHTBSTNHTNHTNHT NHNTNHTNHTHTGGCTGTGAACTGACCTATGGCATT AAA | 179 |
| BC12 NHT | BC | ACCGCGCTGATTACCTGGNHTVMACCGNHTNHTNHT RRCRGCNHTVTTNHTGGCTGTGAACTGACCTATGGC ATTAAA | 180 |
| DE NHT | DE | CGATCGCACCACCATAGATCTGNHTNHTNHTNHTNH TNHTTATAGCATTGGTAACCTGAAACCG | 181 |
| FG9 NHT | FG | GAATATGAAGTGAGCCTGATTTGCNHTAMSNHTNHT GGTNHTNHTNHTKCGAAAGAAACCTTTACCACCGGT G | 182 |
| FG10 NHT | FG | GAATATGAAGTGAGCCTGATTTGCNHTAMSNHTNHT NHTNHTRGCNHTCCGGCGAAAGAAACCTTTACCACC GGTG | 183 |
| FG11 NHT | FG | GAATATGAAGTGAGCCTGATTTGCNHTAMSNHTNHT GGTNHTNHTAGCAACCCGGCGAAAGAAACCTTTACC ACCGGTG | 184 |

Nucleotide codes: N = G/A/T/C; H = A/T/C; R = A/G; S = G/C; B = T/C/G; V = A/C/G; M = A/C; K = G/T The library was assembled using the oligonucleotides shown in TABLE 5.

TABLE 5

| Oligo | Sequence | SEQ ID NO |
|---|---|---|
| BCX-DE bridge v2 | CAGATCTATGGTGGTGCGATCGCCCGGCACATCTT TAATGCCATAGGTCAGTTCACA | 185 |
| DE-FGX bridge v2 | GCAAATCAGGCTCACTTCATATTCGGTATCCGGTT TCAGGTTACCAATGCTAT | 186 |
| KpnI amp rev v2 | CGGGTCGGTTGGGGTACCGCCACCGGTGGTAAAGG TTTCTTT | 187 |
| KpnI reverse v2 | CGGGTCGGTTGGGGTA | 188 |
| BC library amp v2 | GGCCCAGCCGGCCATGGCCGCCATTGAAGTGAAAG ATGTGACCGATACCACCGCGCTGATTACCTGG | 189 |

A mix of the degenerate oligonucleotides (equimolar ratios of the oligonucleotides corresponding to the BC and FG loops, respectively), BCX-DE bridge v2, DE-FGX bridge v2, and KpnI amp rev v2, was assembled in a 20 cycle PCR reaction without an excess of external primers. This product was diluted and amplified in a regular PCR reaction using the primers BC library amp v2 and KpnI reverse v2. The resulting PCR product generated a complete Tn3 gene which was then digested with NcoI and KpnI and ligated into the phage display vector (described in WO 2009/058379). The DNA was transformed into *E. coli* by electroporation. The final diversity of the library was estimated to be about $7.9 \times 10^{10}$ members.

After electroporation, the library was incubated for 1 hour at 37° C. with shaking. M13K07 helper phage was added and after one hour the cells were diluted to a larger volume and grown at 37° C. with shaking overnight. The next day phage were removed and concentrated from the supernatant by precipitation with PEG 8000.

Example 2

Panning Libraries for Human CD40L-Specific Tn3 Scaffolds

Phage displayed Tn3 libraries containing $>10^{10}$ unique sequences were panned against CD40L. The diversity in these libraries was derived from sequence and length variability in the BC, DE and FG loops which are analogous to the three CDR loops within an antibody variable domain. Selection of lead Tn3 proteins was performed by panning of libraries on recombinant biotinylated human CD40L and a CD40L overexpressing CHO cell line. Alternate rounds of panning against these two reagents were used to ensure leads would recognize the recombinant extracellular domain as well as native, membrane-anchored CD40L.

Recombinant human CD40L (Human MEGA-CD40L™; Axxora) was biotinylated with EZ-LINK™ sulfo-NHS-biotin (PIERCE™, Rockford, Ill.) using a 5-fold molar excess of the biotinylation reagent. After incubation for 1 hour at room temperature, the sample was dialyzed in PBS overnight to remove unconjugated biotin. 10 μg biotinylated CD40L was immobilized on M280 streptavidin beads (DYNAL®, Carlsbad, Calif.), followed by blocking in PBS containing 10 mg/ml BSA for 2 hours. Input consisted of libraries developed as described in Example 1 or additionally, libraries developed using standard construction techniques, such as described in WO 2009/058379.

Phages were blocked in PBS containing 10 mg/ml BSA for 2 hours. The blocked input was added to blocked M280 streptavidin control beads (without target) and incubated on rocker for 2 hours at room temperature to deplete the library of binders to the beads. The depleted library was then added to the CD40L coated beads and incubated for 2 hours at room temperature on a rocking platform. After three washes with PBST (PBS+0.1% TWEEN®) to remove unbound phage, the beads were added to exponentially growing *E. coli* XL-1 Blue cells, which were subsequently co-infected with M13K07 helper phage in 60 ml 2×YT medium containing 50 μg/ml carbenicillin. After growing overnight at 37° C. with shaking, phage were harvested by PEG precipitation from the overnight culture media.

The second round of panning (Round 2) was performed on a CD40L overexpressing CHO cell line. The phage library was blocked in 3% BSA/PBS rocking at room temperature for 1 hour. Cells were detached with ACCUTASE™ (INVITROGEN™), washed 2× with 5 ml PBS, and $10^7$ cells were blocked in 1 ml 3% BSA/PBS rocking at room temperature for 30 minutes. The blocked cells were spun down at 500×g, 5 minutes, gently resuspended in the blocked phage library solution, and incubated 1 hour at room temperature. Unbound phage was removed by gently washing the cells 3 times in 1 ml 3% BSA/PBS and once in PBS, pelleting cells by centrifuging 500×g for 5 minutes in a microcentrifuge using a fresh Eppendorf tube for each wash. The cell pellet was added directly to exponentially growing *E. co/i* XL-1 Blue, which were then processed as described for Round 1.

Panning Round 3 was performed as described for Round 1, except bound phages were eluted by addition of 100 mM HCl followed by neutralization with 1M Tris-HCl, pH 8. Eluted, neutralized phage was used to infect *E. coli* XL1 Blue cells as described for Round 1.

Panning Round 4 was again carried out on cells as described for Round 2, except 5 washes in 3% BSA/PBS were conducted. Round 5 was done using 5 μg of biotinylated MEGA-CD40L™, but otherwise as described for Round 3.

After 5 rounds of panning, screening of resulting Tn3 variants as soluble protein was performed. Amplified and PEG precipitated phage stocks were used in a PCR to amplify a pool of fragments encompassing the encoded Tn3 sequences. This fragment pool was digested with NcoI+KpnI and cloned into the corresponding NcoI-KpnI sites of plasmid pSec-oppA(L25M)-Tn3 (see, for example, WO 2009/058379). Auto-inducing MAGICMEDIA® (INVITROGEN™) containing carbenicillin (100 μg/ml) in 96 well deep-well plates were inoculated with *E. coli* BL21 DE3 cells transformed with the pSec-oppA(L25M)-Tn3 derived constructs. Cultures were grown for 18 hours shaking at 37° C., and cells were separated from the media by centrifugation. The media containing secreted, soluble Tn3 variants was used directly in a screening assay for CD40L binding.

Ten sets of 96 clones were screened to identify Tn3 proteins that specifically bound to recombinant CD40L. Briefly, the screening assay utilized capture of soluble His-tagged Tn3 variants secreted into media through binding to an anti-His antibody immobilized in wells of microplates. After capture, media and excess protein were washed away and the interaction between captured Tn3 variants and CD40L was monitored by utilizing biotinylated Human MEGA-CD40L™ and measuring the remaining target (after washing the plate) by SA-HRP and conventional ELISA reagents.

In the capture step, the immobilized anti-His antibody was saturated with Tn3, and the molar amount of captured Tn3 in each well became virtually identical irrespectively of the expression levels of individual clones. This normalization of Tn3 levels resulted in assay levels proportional with the efficiency of target interaction and unaffected by potential differences in protein expression levels.

Positives from this assay were sequenced to identify 34 unique Tn3 sequences that bound recombinant CD40L. From the panel of unique CD40L-binding Tn3 sequences, a subset of 24 clones that had a robust assay signal and good expression levels judging by SDS-PAGE of the culture supernatants underwent re-expression and small scale purification.

Briefly, Superbroth media containing carbenicillin (100 μg/mL) with 1% glucose) was inoculated with *E. coli* BL21 DE3 cells transformed with the pSec-oppA(L25M)-Tn3 derived constructs. Cultures were grown at 37° C. to an optical density (O.D.) of 0.5-0.8 then induced with 0.2 mM IPTG. After shaking at 37° C. for 5 hours, cells were separated from the media by centrifugation. Purification of Tn3 scaffolds from the media was effected by batch purification using Ni-NTA Superflow (QIAGEN®), washing in 2×PBS with 20 mM imidazole, and elution with 2×PBS with 250 mM imidazole. Samples were dialyzed in PBS, and concentrations determined by UV absorbance at 280 nm according to Gill and von Hippel (Anal. Biochem. 182: 319, 1989).

Based on assay ranking and SEC behavior, expression of 8 leads was scaled up and purified to low endotoxin levels (<1 EU/mg) for testing in a functional cell assay.

Two Tn3 clones (designated 309 and 311) showed similar activity in biochemical and cell-based assays (FIGS. 6A, 6B, 6C), and were 3-5 fold more potent than the nearest rival clone.

Figure 6A:
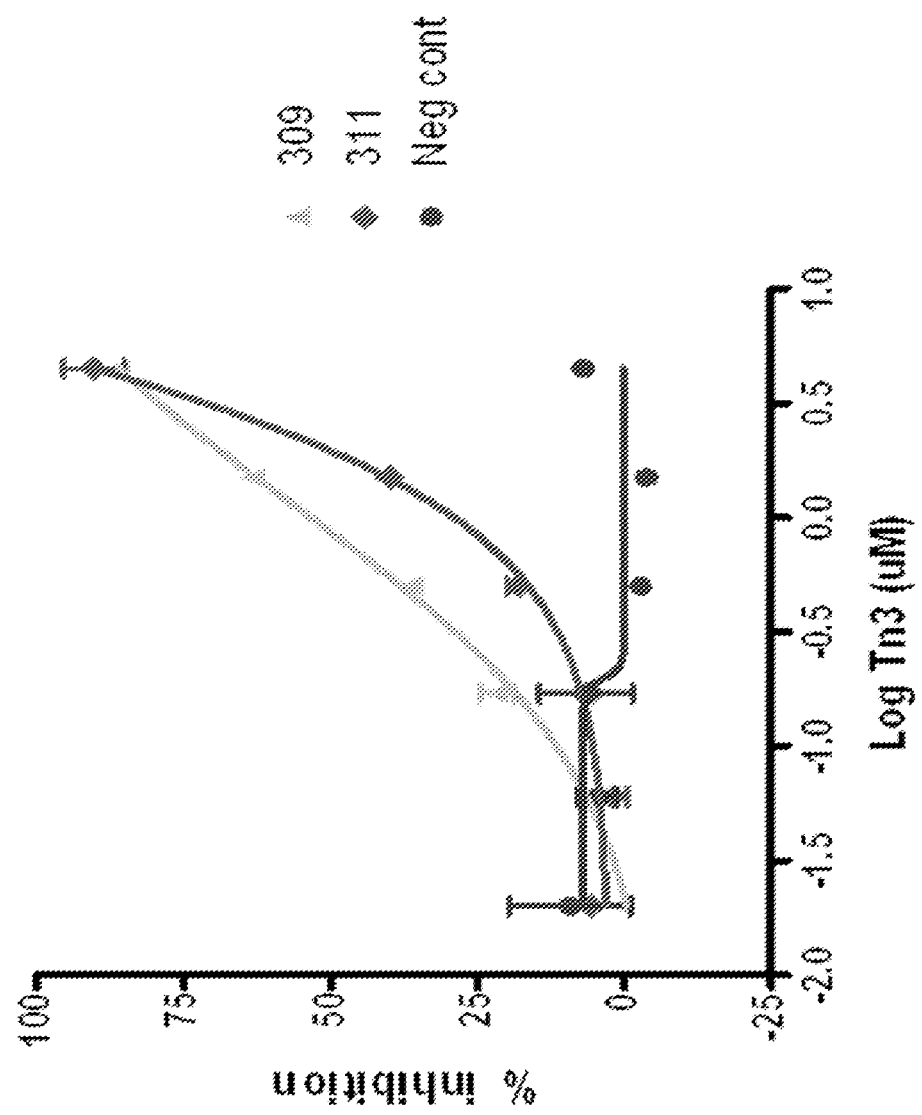
FIG. 6A shows the inhibitory effect of human CD40L-specific monovalent Tn3 monomer scaffolds 309 and 311 on human CD40L-induced CD86 expression on CD19 positive human PBMCs stimulated with Jurkat D1.1 cells.
Figure 6B:
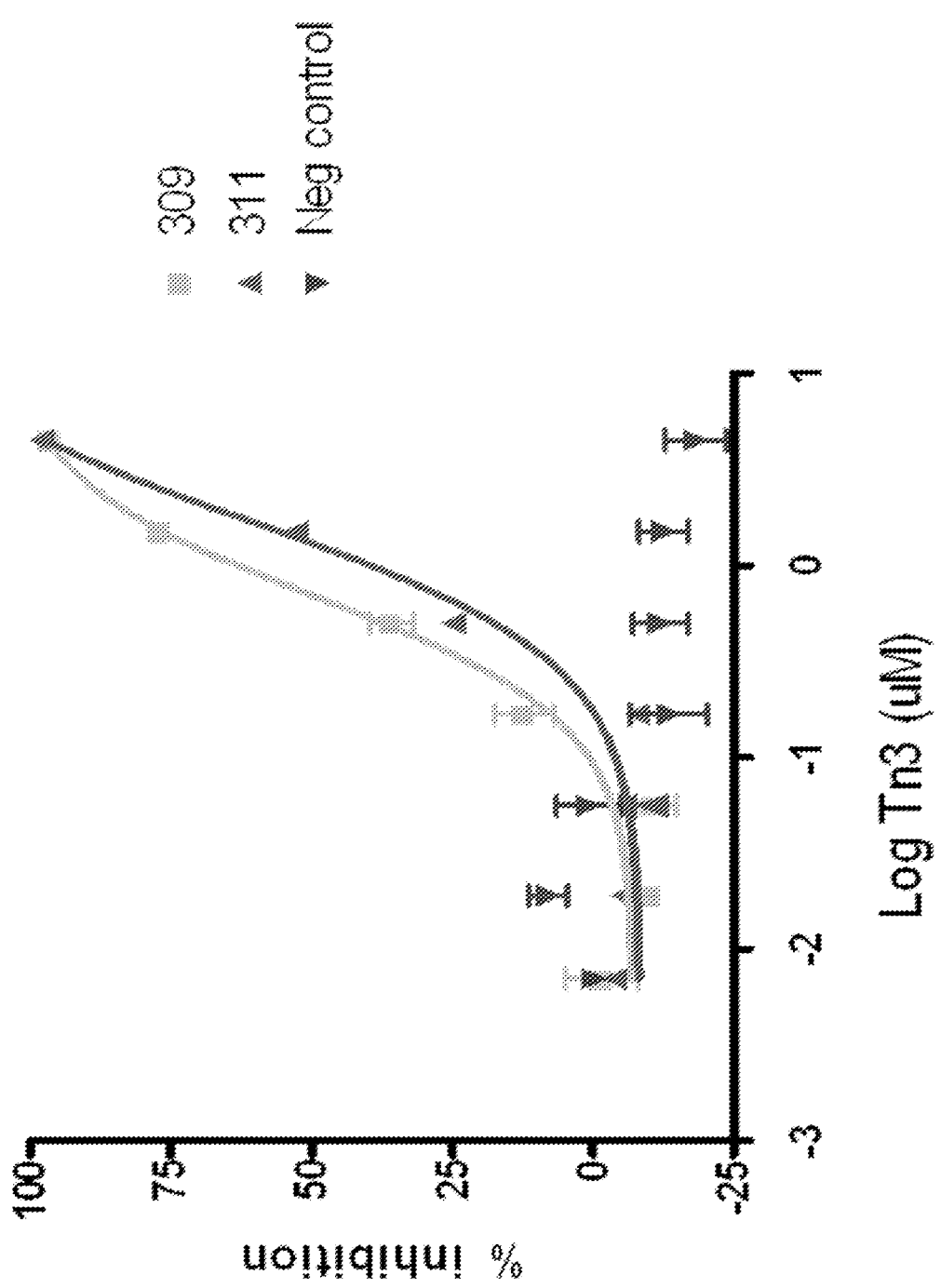
FIG. 6B shows the inhibitory effect of human CD40L-specific monovalent Tn3 monomer scaffolds 309 and 311 on human CD40L-stimulated B-cell proliferation.

Human CD40L-specific monovalent Tn3 scaffolds 309 and 311 inhibited total B cell number, plasma cell number and Ig class switching (FIGS. 6A, 6B and 6C). FIG. 6 A shows the inhibitory effect of 309 and 311 on HuCD40L-induced CD86 expression on CD19 positive human PBMCs stimulated with Jurkat D1.1 cells; FIG. 6B shows inhibition of HuCD40L stimulated B-cell proliferation by 309 and 311; and FIG. 6C C shows inhibition of plasma cell number in T/B cell co-cultures. 309 was also shown to bind activated primary T cells by FACS (data not shown). PBMCs were stimulated by recombinant human MEGA-CD40L™ (Axxora) or human CD40L expressing Jurkat cells (D1.1, ATCC®), and the percentage of CD19+/CD86+ cells was measured by FACS after 24 hours.

Figure 7A:
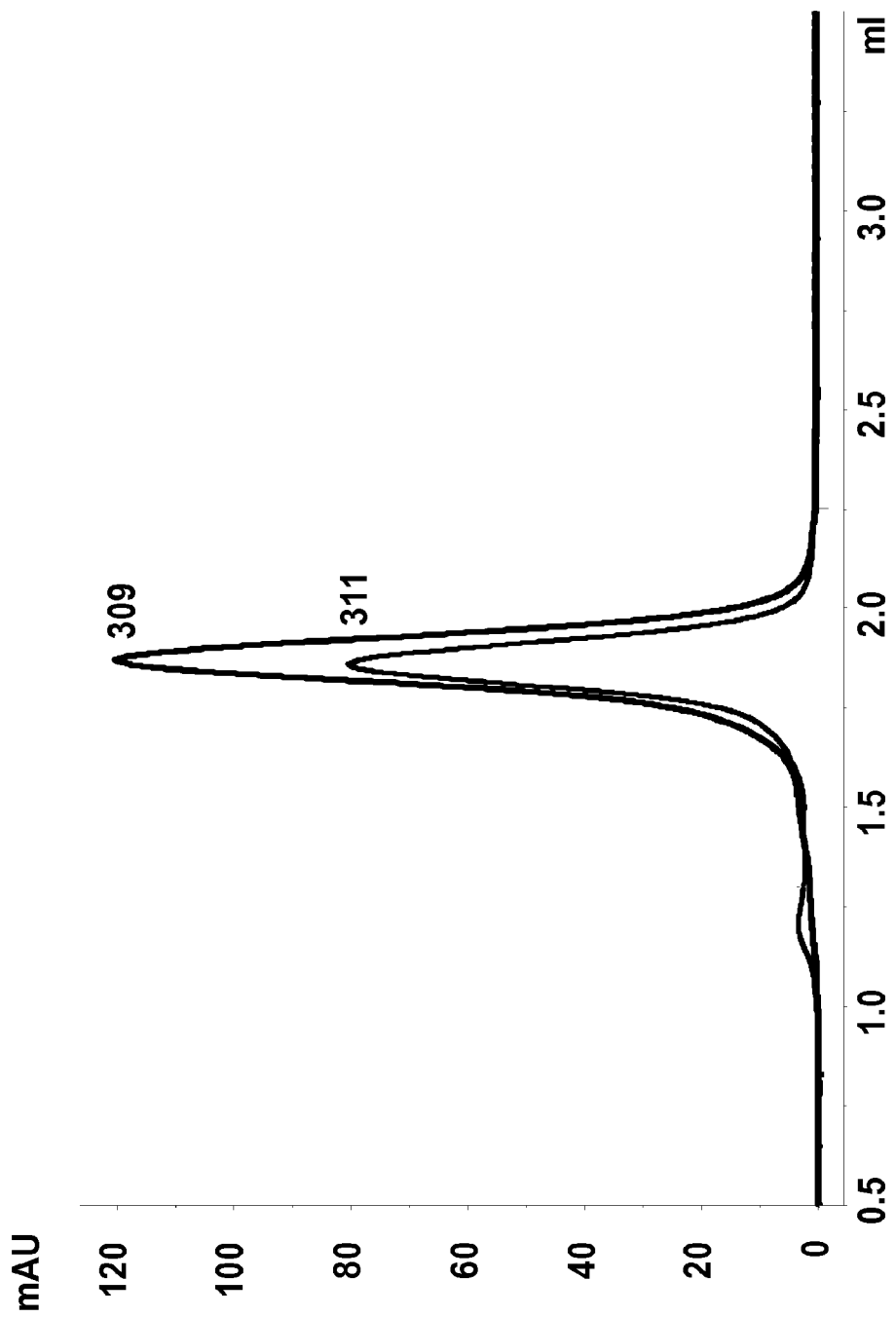
FIG. 7A shows that human CD40L-specific monovalent Tn3 scaffolds 309 and 311 have similar biophysical characteristics. Both scaffolds are monodispersed as measured by SEC.

The 309 and 311 lead clones were monodispersed and did not display any tendency to aggregate or form higher order oligomers in solution as determined by size exclusion chromatography (SEC) analysis of purified samples (FIG. 7A).

Figure 7B:
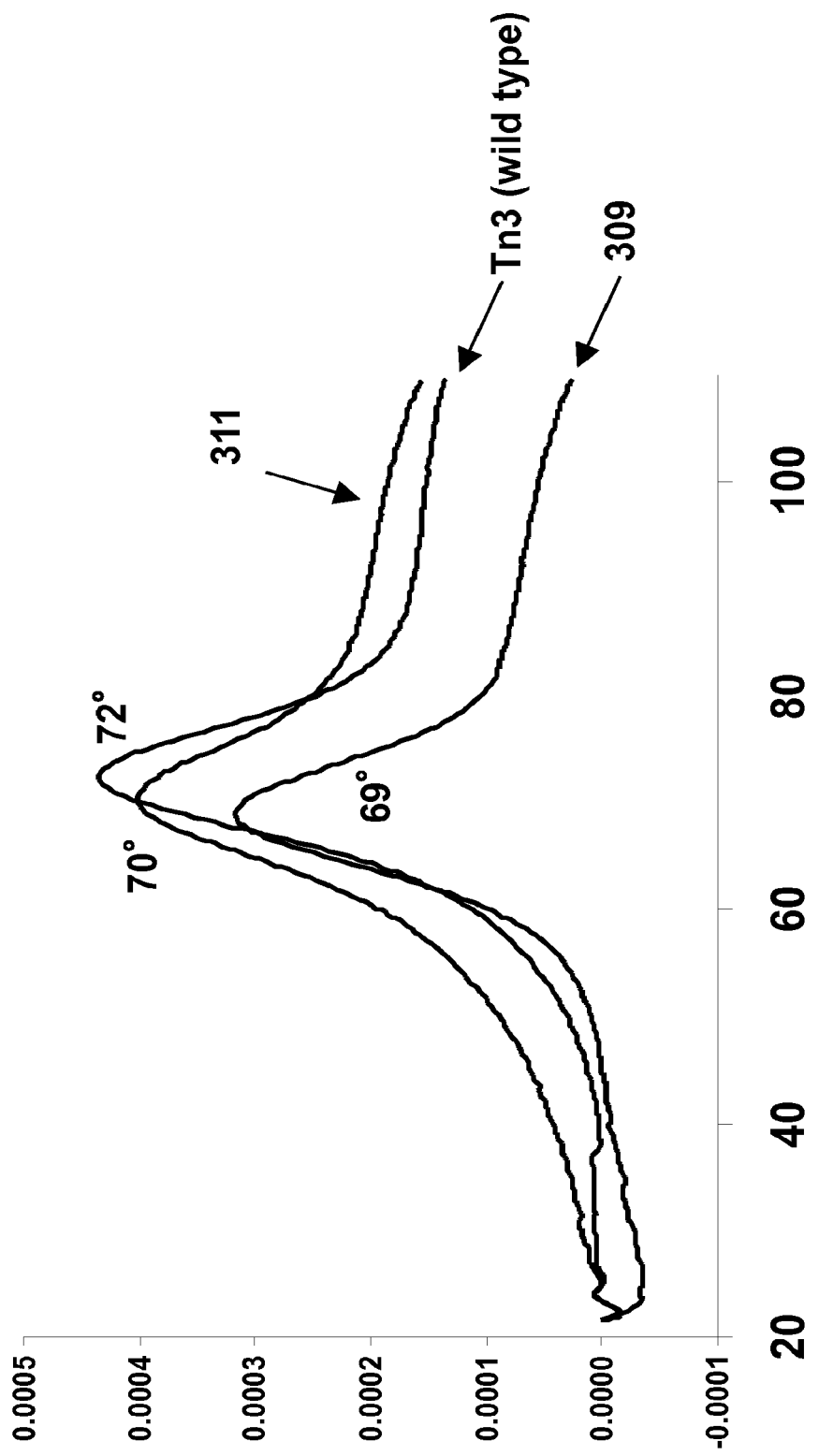
FIG. 7B shows that human CD40L-specific monovalent Tn3 scaffolds 309 and 311 have similar biophysical characteristics. Both scaffolds have similar thermostability as the parent Tn3 scaffold (designated Tn3(wild type) in the graph) as measured by differential scanning calorimetry (DSC).

The thermal stabilities of the 309 and 311 lead clones were determined by differential scanning calorimetry (DSC) using protein samples at 1 mg/mL in PBS pH 7.2 and compared to the thermal stability of the parental Tn3 protein (FIG. 7B). The 309 and 3011 lead clones had Tm's of 70±1° C. which was only slightly below the Tm of parent Tn3 (72° C.).

As no murine cross-reactive clones were identified a similar panning process as described above was carried out to identify the murine specific Tn3 designated M13. M13 also showed activity in a PBMC cell based assay (see FIG. 1A)

Example 3

CD40L-Specific Tn3 Scaffold Lead Optimization

Affinity optimization was used to increase the potency of the selected Tn3 leads. In general, one or more rounds of mutagenesis within the Tn3 loops contacting the target were conducted, with selection of improved variants from combinatorial phage display libraries.

3.1 Loop Swapping

In order to determine which of the 3 loops in the two leads were involved in interaction with CD40L, constructs were generated in which each single loop sequence was changed to the parent Tn3 loop sequence as found in human tenascin C. Activities of the mutated variants were compared to the original variants in a binding assay conducted as described for the screening assay described above (FIG. 10A). For both leads mutating the BC and DE loops resulted in a complete loss of binding to CD40L, whereas changing the FG loop to the parent Tn3 sequence had either no effect (for 309) or limited effect (311) on binding. Thus, the BC and DE loop appeared to contain the sequences mainly responsible for contacting CD40L, and were thus primarily selected for affinity optimization.

3.2 CD40L-Specific Tn3 Scaffold 309 Lead Optimization

As the loop swapping experiment indicated the 309 FG-loop sequence could be substituted with the parent Tn3 FG-loop sequence without substantial loss of binding potency, it was decided to use this construct (termed 309FGwt) as a backbone for affinity maturation. This would eliminate non-essential mutations deviating from the parent tenascin C sequence in order to reduce possible immunogenicity risk. It should be noted that the parent Tn3 FG-loop sequence contained an RGD motif which was later eliminated by a mutation in the final lead molecules. Three BC loop libraries and one DE-loop library were generated.

For the three BC loop libraries three rounds of PCR were done using the degenerated oligos BC9 PCR, BC 9-loop NNK and 309 BC-loop NNKdope (TABLE 6) together with the reverse primer Kpn1 amp rev v2 (TABLE 5) using a 309FGwt derived template in which the BC-loop codons had been replaced with stop codons. Subsequently PCR amplification of those fragments with the primers BC library amp v2 (TABLE 5) and KpnI reverse v2 gave the full length Tn3 library fragment.

For the DE-loop library a PCR amplification with DE PCR and KpnI amp reverse v2 on a 309FGwt derived template (in which the DE-loop codons had been replaced with stop codons) gave a fragment containing the randomized DE loop and wild type Tn3 FG-loop which was combined with a fragment encoding the Tn3 region upstream of the DE loop generated by PCR with BC library amp v2 and BCX-DE bridge v2 on a 309 template. The two fragments were joined in an overlap PCR with the external primers BC library amp v2 and KpnI reverse v2.

TABLE 6

DNA oligonucleotides used for 309FGwt LO library generation

| Oligo | Sequence | SEQ ID NO |
|---|---|---|
| BC9 PCR | 5'-ACCGCGCTGATTACCTGGTCT1213111GGCTGT GAACTGACCTATGGCATTAAAGATG | 190 |
| BC 9-loop NNK | 5'-ACCGCGCTGATTACCTGGNNKNNKSMGNNKGST NNKNNKNNKGGCTGTGAACTGACCTATGGCATTAAA-3' | 191 |
| 309 BC-loop NNKdope | 5'-ACCGCGCTGATTACCTGG76K45K45K77K44K 65K78T45K44KTGTGAACTGACCTATGGCATTAAA-3' | 192 |
| DE PCR | 5'-GATGTGCCGGGCGATCGCACCACCATAGATCTG 111111TATAGCATTGGTAACCTGAAACCGG-3' | 193 |
| Upstr BCloop Rev | CCAGGTAATCAGCGCGGTGGTAT | 194 |
| BC shuffle rev | CAGATCTATGGTGGTGCGATCGC | 195 |

TABLE 6-continued DNA oligonucleotides used for 309FGwt LO library generation

| Oligo | Sequence | SEQ ID NO |
|---|---|---|
| DE shuffle FWD | TGTGAACTGACCTATGGCATTAAAGATGT | 196 |

1 = Codons for all 19aa(-cys)
2 = Codons for Ala/Pro
3 = Codons for Ala/Gly;
4 = 70% G 10% A 10% C 10% T
5 = 10% G, 70% A, 10% C, 10% T
6 = 10% G, 10% A, 70% C, 10% T
7 = 10% G, 10% A, 10% C, 70% T
8 = 70% A 15% C 15% T
K = 50% G/50% T The NcoI-KpnI fragments were cloned into the phage display vector, and phage library generated as described in Example 1.

The four libraries were panned separately on Biotinylated Human MEGA-CD40L™ as described for the first round in Example 2, using 4 μg CD40L in Round 1 and 1 μg in Round 2. After amplification of phage output after Round 2, single-stranded DNA was isolated using a QIAGEN®Spin M13 kit (QIAGEN®, Valencia, Calif.), and the pools of BC-loop containing fragments from the BC loop libraries were amplified using BC lib amp v2 and BC shuffle rev, whereas the pool of DE-loop containing fragments was amplified from the DE-loop library using primers DE-shuffle FWD and KpnI reverse v2. The PCR fragments were gel-purified and assembled through their overlapping sequence using the external primers BC lib amp v2 and KpnI reverse v2. The resulting PCR fragment was used to generate a library in the phage vector as previously described. This library was panned for a total of 5 rounds on biotinylated Human MEGA-CD40L™ as described in Example 2, except the libraries were initially contacted with a target at a concentration of 50 nM, 20 nM, 20 nM, and 10 nM (in a total volume of 50 μl) for Rounds 1 through 4 for 2 hours prior to incubation with blocked M280 streptavidin magnetic beads for 10 minutes followed by washing.

Outputs were pool cloned into the NcoI-KpnI sites of plasmid pSec-oppA(L25M)-Tn3 pSec, and sixteen 96 well plates were screened for CD40L binding using soluble protein in the screening assay described above. The 270 highest scoring clones were cherry-picked, re-assayed and sequenced. Ten clones were chosen for further characterization based on binding assay and sequence analysis. This included assessment of potency in the PBMC assay, $K_d$ determination for binding to CD40L in a biosensor assay, thermodynamic stability determined by differential scanning calorimetry, and tendency to aggregate or form higher order oligomers in solution by size exclusion chromatography analysis. Results are summarized in TABLE 7. Sequences of the 309 and 309FGwt clones aligned with the ten optimized clones (designated 340, 341, 342, 343, 344, 345, 346, 347, 348 and 349) are shown in FIGS. 11A and 11B.

Affinity matured variants showed 1-3 logs higher potency than the 309 clone, retained high stability as measured by DSC, and most were monodispersed as measured by SEC.

TABLE 7

| Variant | PBMC IC50 (nM) | Kd (nM) | SEC Profile | Tm, DSC (° C.) |
|---|---|---|---|---|
| 309 | 226 | 191 | OK | 72 |
| 309FGwt | 760 | nd | OK | 71 |
| 340 | 0.7 | 2.2 | OK | 77 |
| 341 | 0.7 | nd | OK(?) | 71 |
| 342 | 0.7 | 1.4 | OK | 73 |
| 343 | 0.6 | 2.0 | OK | 69 (?) |
| 344 | 1.3 | nd | OK | (65 + 78.5) |
| 345 | 37.3 | 39 | OK | 72 |
| 346 | 9.0 | 14.9 | OK | 71 |
| 347 | 11.0 | 10.7 | OK | 70 |
| 348 | 1.0 | 1.8 | ? | nd |
| 349 | 38.2 | 21 | OK(?) | nd |

Figure 10A:
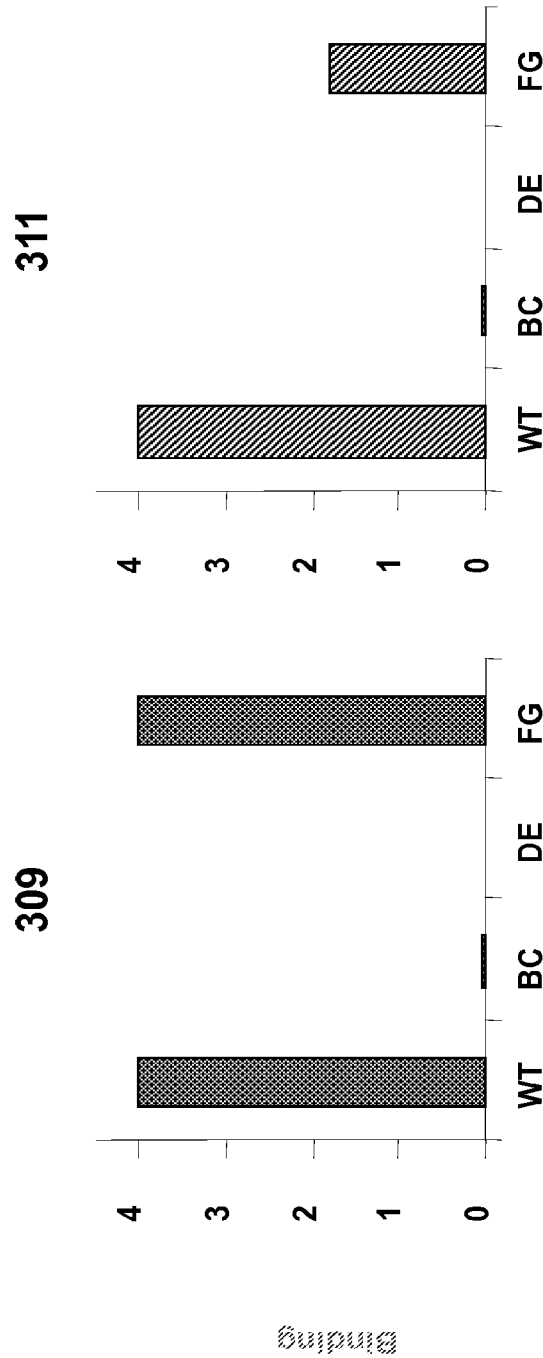
FIG. 10A shows the effect of mutating loop sequences of 309 (left panel) and 311 (right panel) on CD40L binding. Binding indicates signal strength in the binding assay. WT is the variant with the original lead sequence (parent Tn3 sequence), whereas BC, DE and FG denotes variants in which the BC, DE, or FG loop sequence has been changed to the parent Tn3 sequence as present in human Tenascin C.
Figure 10B:
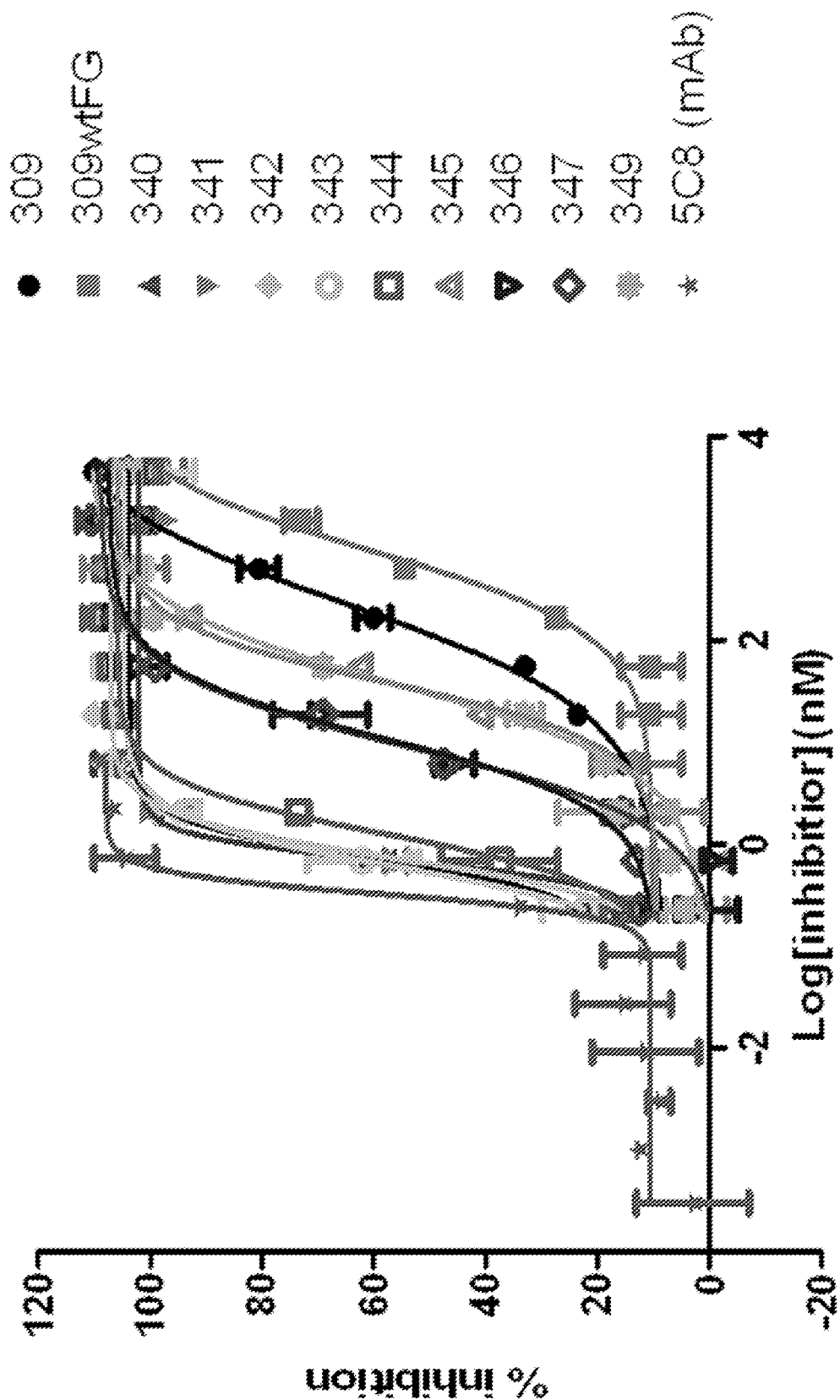
FIG. 10B shows inhibition profiles of a panel of affinity optimized scaffolds as measured by the human CD40L-induced CD86 expression on CD19 positive human PBMCs stimulated with Jurkat D1.1 cells. Human CD40L-specific Tn3 clone 309 monomers were affinity optimized. Affinity optimized monomers are designated as clone 340 to clone 349. The clone 309wtFG construct had the entire FG loop replaced with the FG loop of the parent Tn3 scaffold. The 5c8 anti-CD40L monoclonal antibody was also assayed.

PBMC assays were performed by stimulating PBMCs with human CD40L-expressing Jurkat cells (D1.1, ATCC®), and the percentage of CD19+/CD86+ cells was measured by FACS after 24 hours. This assay was used to test and rank the panel of leading Tn3 scaffolds to emerge from prioritization based on biochemical criteria. Results of the PBMC assays are shown in FIG. 10B, and summarized in TABLE 7.

Affinity measurements were performed on the PROTEON™ XPR36 protein interaction array system (Bio-Rad, Hercules, Calif.) with GLC sensor chip at 25° C. PROTEON™ phosphate buffered saline with 0.005% TWEEN® 20, pH 7.4 (PBS/TWEEN®) was used as running buffer. Human MEGA-CD40L™ was immobilized on the chip at a surface density of approximately 2300 RU. Two-fold dilutions of the Tn3 variants (340, 342, 343, 345, 346, 347, 348, and 349) were prepared in PBS/TWEEN®/0.5 mg/ml BSA, pH 7.4 (from 150 to 4.7 nM). Samples of each concentration were injected into the six analyte channels at a flow rate of 30 μl/min. for 300 seconds. The $K_d$ was determined by using the equilibrium analysis setting within the PROTEON™ software. Results are shown in TABLE 7.

The ten TCD40L-specific Tn3 variants were analyzed for stability by DSC. Briefly, DSC measurements were conducted on a VP-Capillary DSC (MicroCal). Proteins were exchanged into PBS (pH 7.2) through extensive dialysis, and adjusted to a concentration of 0.25-0.5 mg/ml for DSC analysis. Samples were scanned from 20-95° C. at a scan rate of 90° C./hour, with no repeat scan. The results are shown in TABLE 7.

Up to a 300-fold improvement in $IC_{50}$ over 309, and over 1000-fold improvement over the 309FGwt backbone used for lead optimization library generation was obtained for the best clones. Seven clones had $K_d$'s in the single digit nM range.

3.3 CD40L-Specific Tn3 Scaffold 311 Lead Optimization

Prior to conducting the loop usage experiment mentioned previously (see FIG. 10A)

Figure 10C:
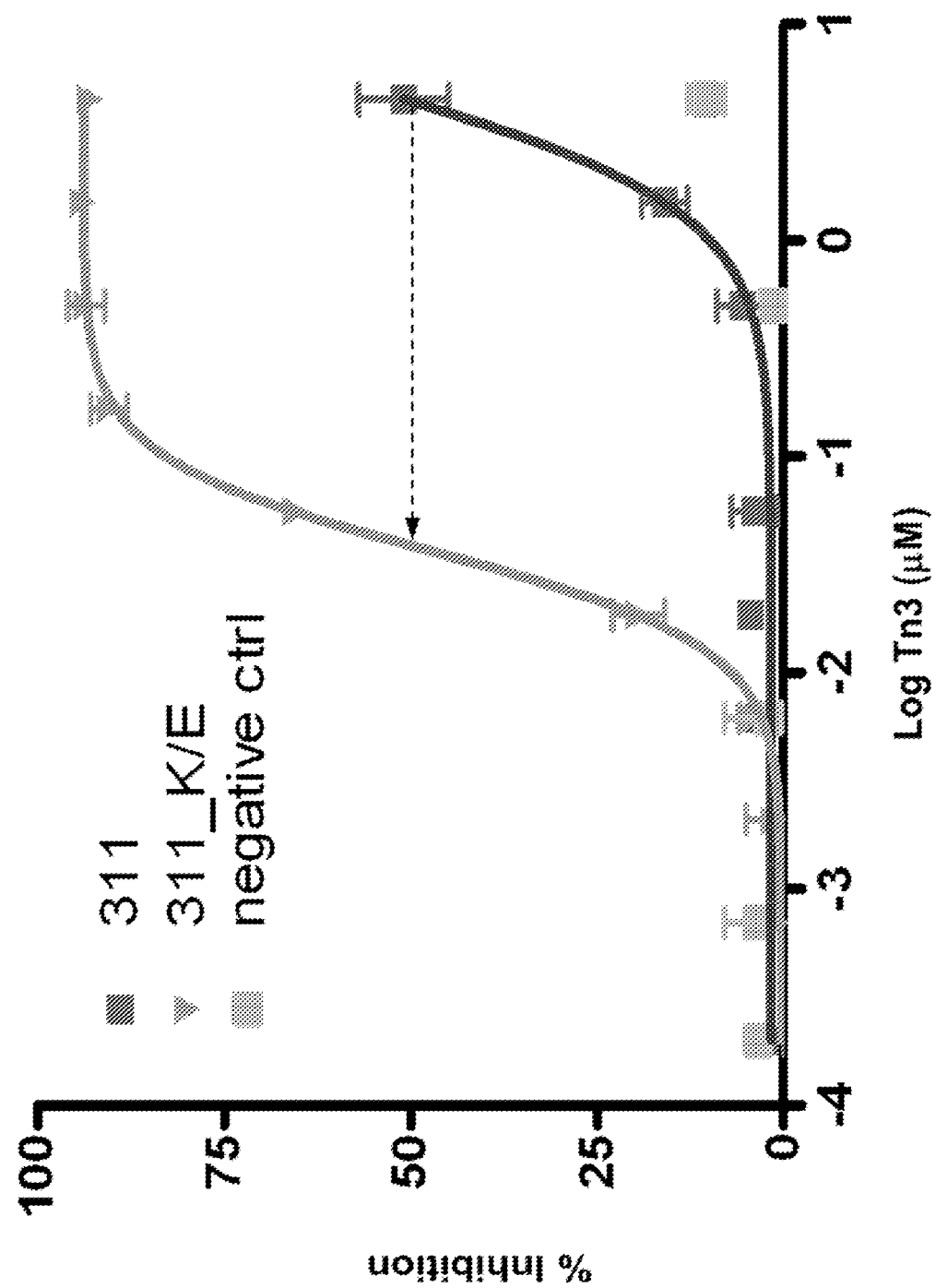
FIG. 10C shows inhibition profiles as measured by the human CD40L-induced CD86 expression on CD19 positive human PBMCs stimulated with Jurkat D1.1 cells. The profile of human CD40L-specific Tn3 311 monomer, its K4E variant, and a negative control are shown.
Figure 10D:
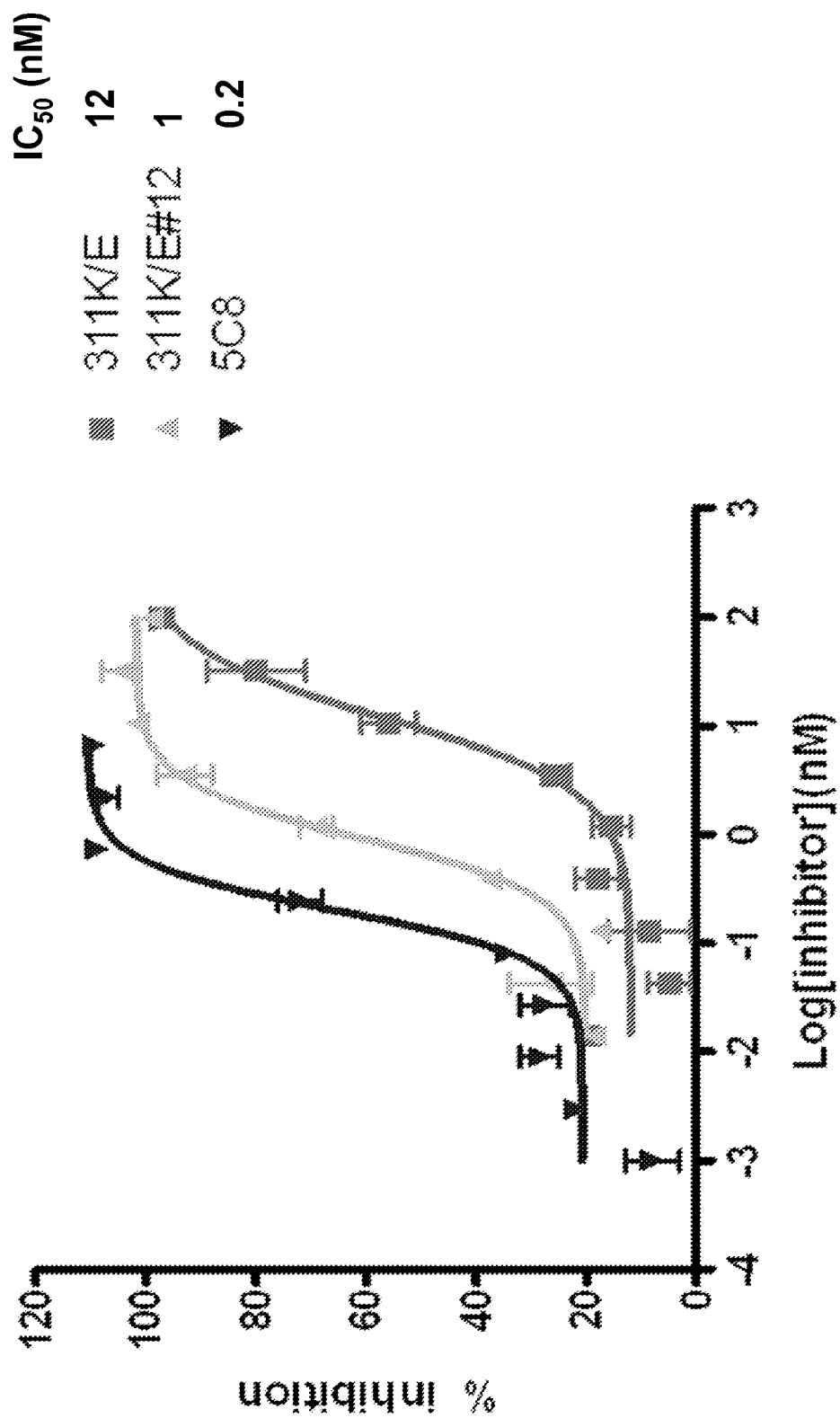
FIG. 10D shows inhibition profiles as measured by the human CD40L-induced CD86 expression on CD19 positive human PBMCs stimulated with Jurkat D1.1 cells. The profile of human CD40L-specific Tn3 311K4E monomer, the affinity optimized 311K4E_12 monomer, and the 5c8 anti-CD40L monoclonal antibody are shown. $IC_{50}$'s for the two constructs and the antibody are also presented.

An initial attempt at a lead optimization library focused on introducing diversity in the FG-loop of 311, generating and screening the resulting phage display library. Screening was conducted after 4 rounds of panning on Biotinylated human MEGA-CD40L™ as previously described, and it was found that a majority of the positive hits contained a fortuitous mutation of residue K4 to E in the N-terminal constant region of Tn3, upstream of the BC-loop. No obvious consensus among the FG-loop sequences of positive hits was detected. Introducing the single K4E mutation into 311 resulted in an approximately 100-fold increase in potency (from approximately 4 μM to 36 nM) in the PBMC assay (see FIG. 10C).

As the loop swap experiment indicated that the BC and DE loop sequences were required for binding to CD40L, these loops were then targeted in the 311K4E backbone for further affinity maturation. Two separate libraries were generated. One library targeted the BC-loop with a strategy where each residue had a 50% chance of being wild type 311 sequence, and approximately 50% chance of being one of the other 11 NHT encoded residues. The other library completely randomized the 6-residue DE-loop.

For the BC-loop library, the oligonucleotides BC11-311Gly and BC11-311NHT (TABLE 8) were used in PCR reactions with the reverse primer KpnI amp rev v2 (TABLE 5) on a 311 derived template in which the BC-loop codons had been replaced with stop codons to generate fragments including BC, DE and FG loops. Finally, amplification of a 1:1 mixture of these fragments with the primers BC library amp K4E and KpnI amp rev v2 gave the full length Tn3 library fragment.

The DE-loop library was generated as the 309FGwt DE-loop library described above, except a 311 derived template was used in the PCR reactions and the BC library amp K4E primer was used in the final PCR amplification.

TABLE 8

Oligos employed for 311K4E lead optimization library generation.

| Oligo | Sequence | SEQ ID |
|---|---|---|
| BC11-311Gly | 5'-ACCGCGCTGATTACCTGG26T25TV1T46T46T45T45T25T37T35TGGCTGTGAACTGACCTATGGCATTAAA-3' | 197 |
| BC11-311NHT | 5'-ACCGCGCTGATTACCTGG26T25TV1T46T46T45T45T25T37T35TNHTTGTGAACTGACCTATGGCATTAAA-3' | 198 |
| BC library amp K4E | 5'-GGCCCAGCCGGCCATGGCCGCCATTGAAGTGGAAGATGTGACCGATACCACCGCGCTGATTACCTGG-3' | 199 |
| BC11-311Gly | 5'-ACCGCGCTGATTACCTGG26T25TV1T46T46T45T45T25T37T35TGGCTGTGAACTGACCTATGGCATTAAA-3' | 197 |
| BC11-311NHT | 5'-ACCGCGCTGATTACCTGG26T25TV1T46T46T45T45T25T37T35TNHTTGTGAACTGACCTATGGCATTAAA-3' | 198 |
| BC library amp K4E | 5'-GGCCCAGCCGGCCATGGCCGCCATTGAAGTGGAAGATGTGACCGATACCACCGCGCTGATTACCTGG-3' | 199 |

1 = 70% G, 10% A, 10% C, 10% T
2 = 10% G, 70% A, 10% C, 10% T
3 = 10% G, 10% A, 70% C, 10% T
4 = 10% G, 10% A, 10% C, 70% T
5 = 70% A, 15% C, 15% T
6 = 15% A, 70% C, 15% T
7 = 15% A, 15% C, 70% T
V = 33% A, 33% C, 33% G
H = 33% A, 33% C, 33% T

The full length library fragments were digested with NeoI and KpnI, cloned into the phage display vector, and phage libraries generated as described in Example 1.

The two libraries were panned separately on Biotinylated human MEGA-CD40L™ as described in Example 1, using 10 □g of protein in Round 1, 5 □g in Round 2, and 5 □g in Round 3. After amplification of phage output after Round 3, single stranded DNA was isolated using a QIAGEN® kit (QIAGEN®, Valencia, Calif.), and the two libraries were shuffled as described for the 309FGwt libraries. The shuffled library was panned for a total of 5 rounds on biotinylated human MEGA-CD40L™ as described above for the 309FGwt shuffled library using 100 nM, 20 nM, 4 nM, 1 nM and 1 nM of target for Rounds 1 through 5.

Figure 12A:
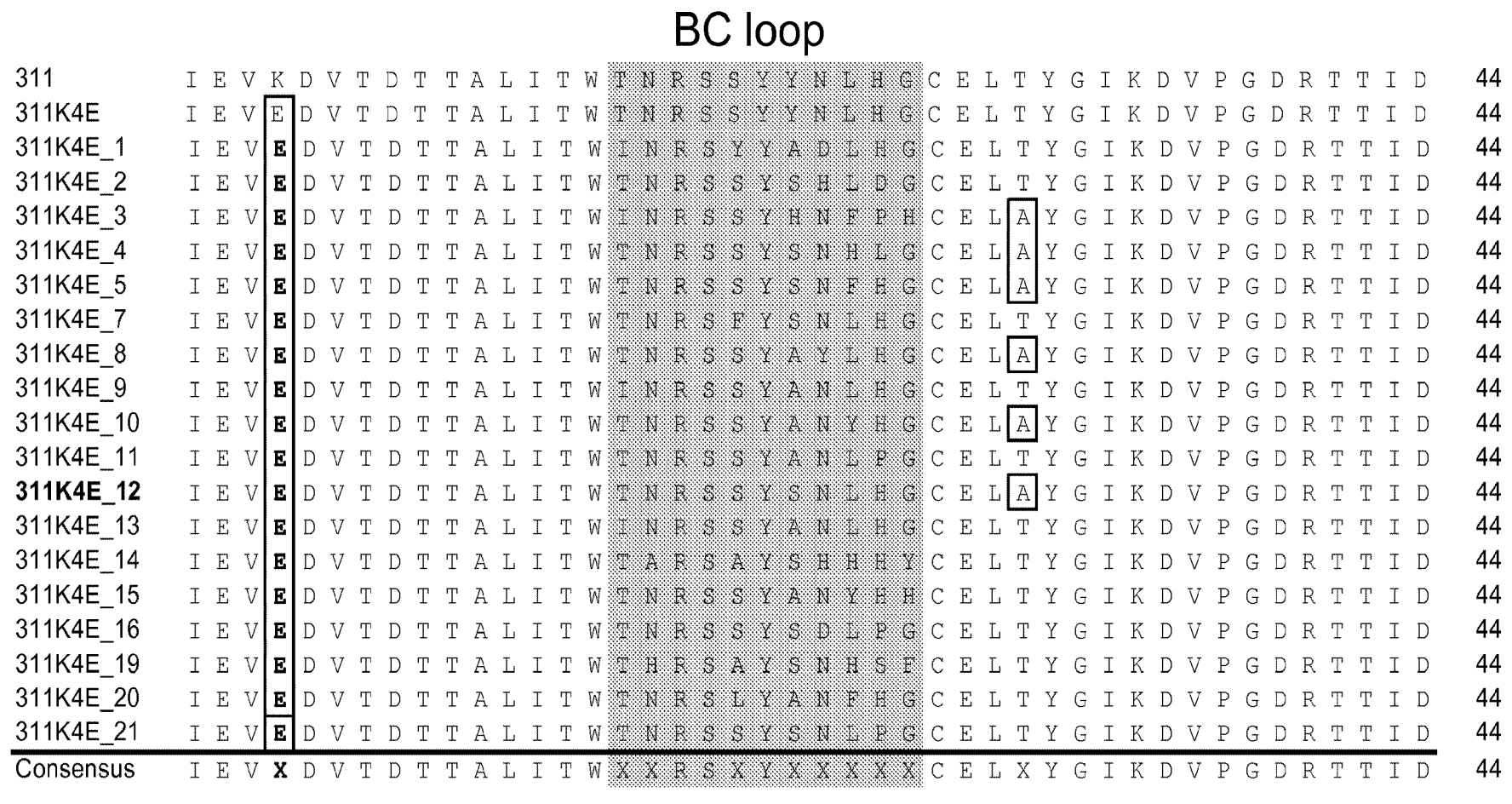
Figure 12B:
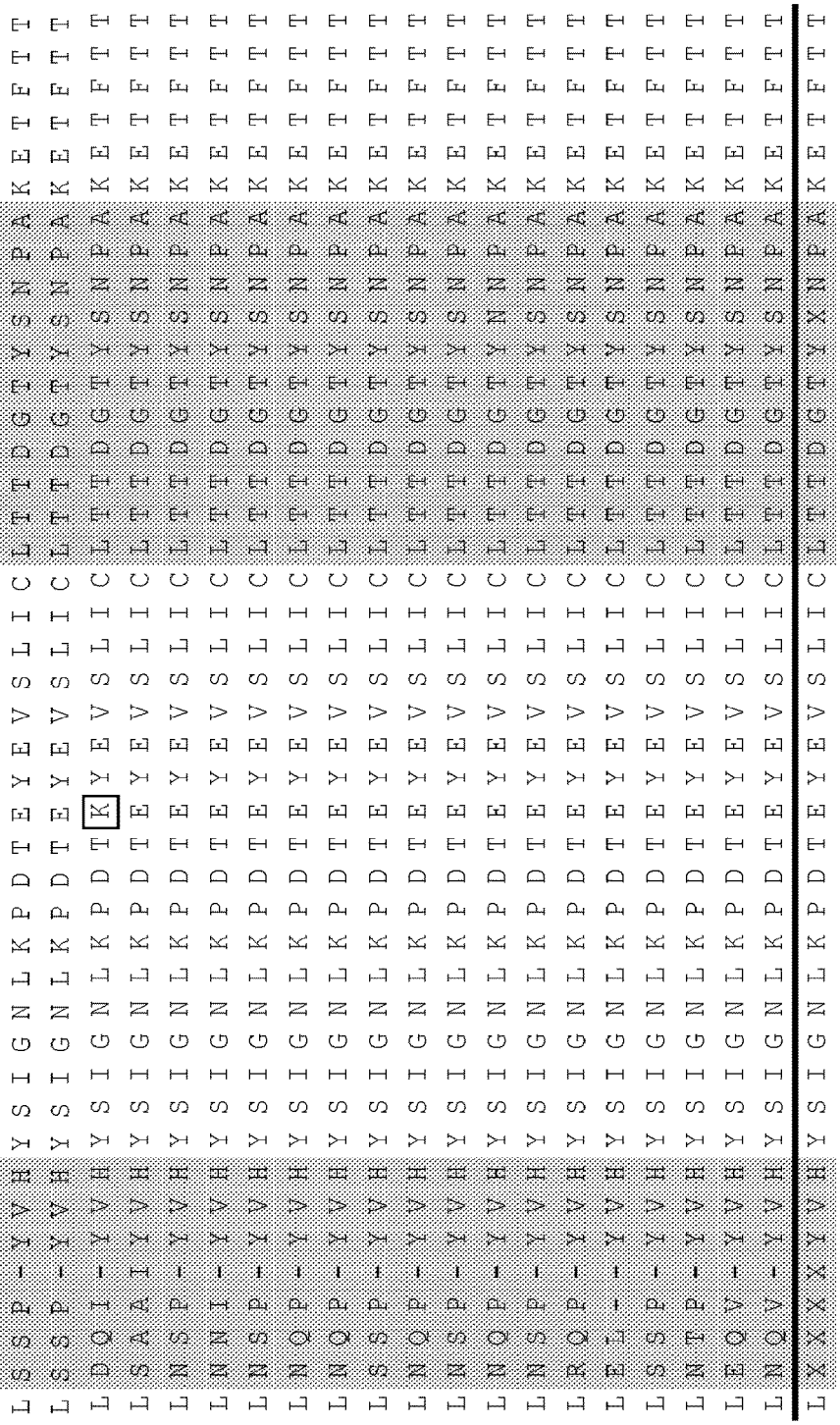
Figure 13:
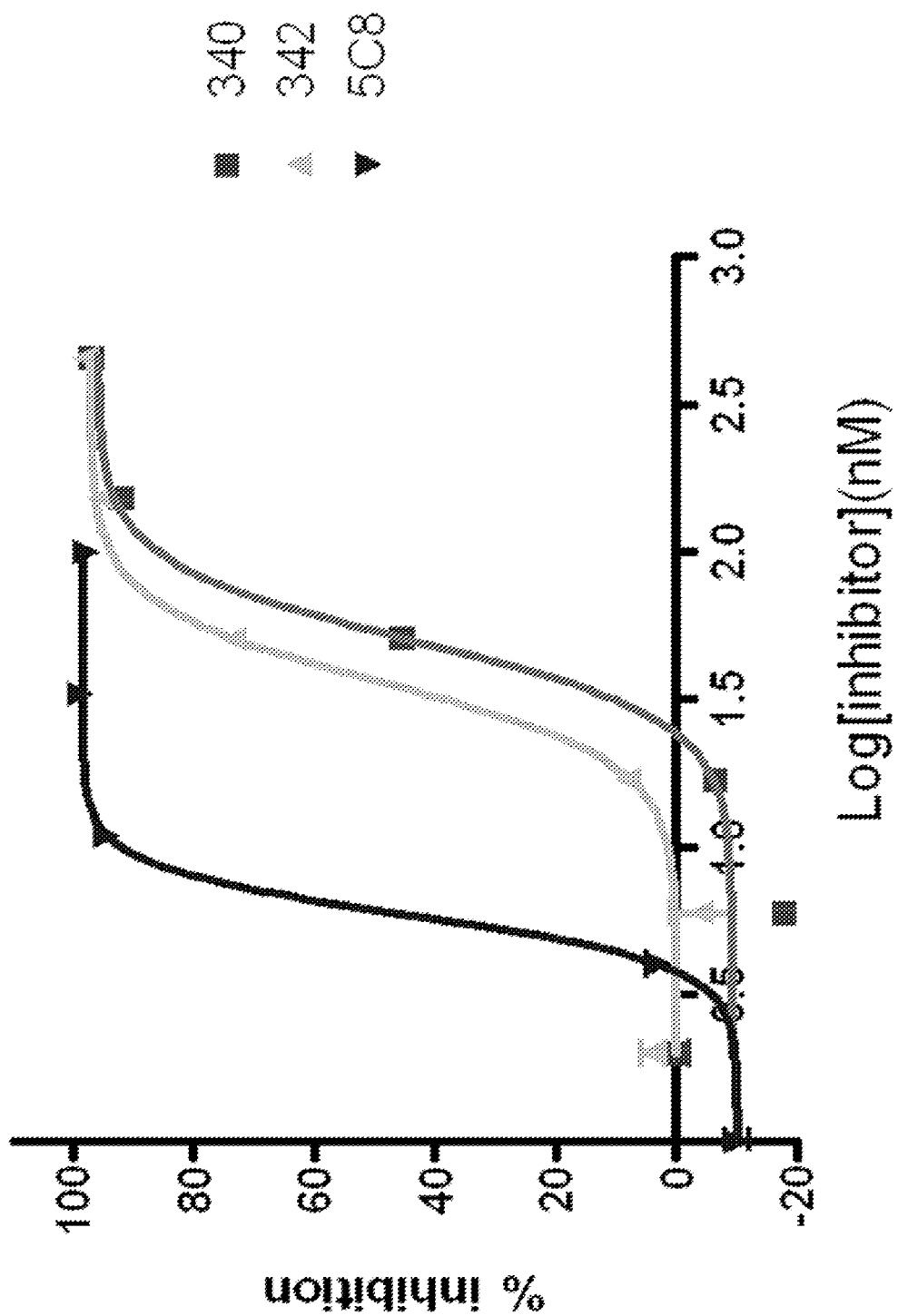
FIG. 13 shows a human NfkB inhibition assay that uses HEK293 cells expressing human CD40 receptor and containing an NfkB-Luciferase reporter construct. Addition of human CD40L results in signaling (measured by luciferase activity) that can be inhibited by CD40L binding molecules. The CD40L-specific Tn3 scaffolds 340 and 342, as well as the 5c8 anti-CD40L monoclonal antibody were assayed.
Figure 14:
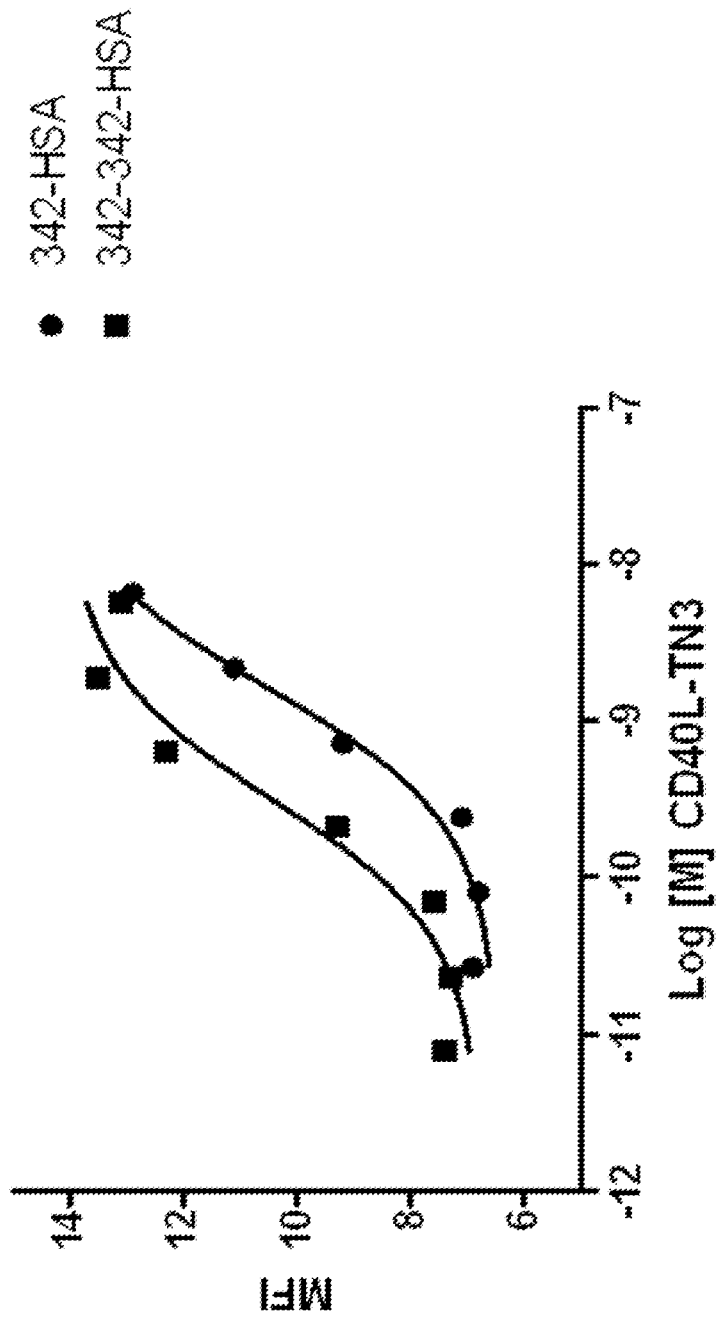
FIG. 14 shows binding of human CD40L-specific Tn3 scaffolds to 24 h anti-CD3/28 activated human CD4+ T Cells. A monovalent 342 scaffold fused to HSA (designated 342-HSA) and a bivalent 342 scaffold fused to HSA (designated 342-342-HSA) were assayed.
Figure 15:
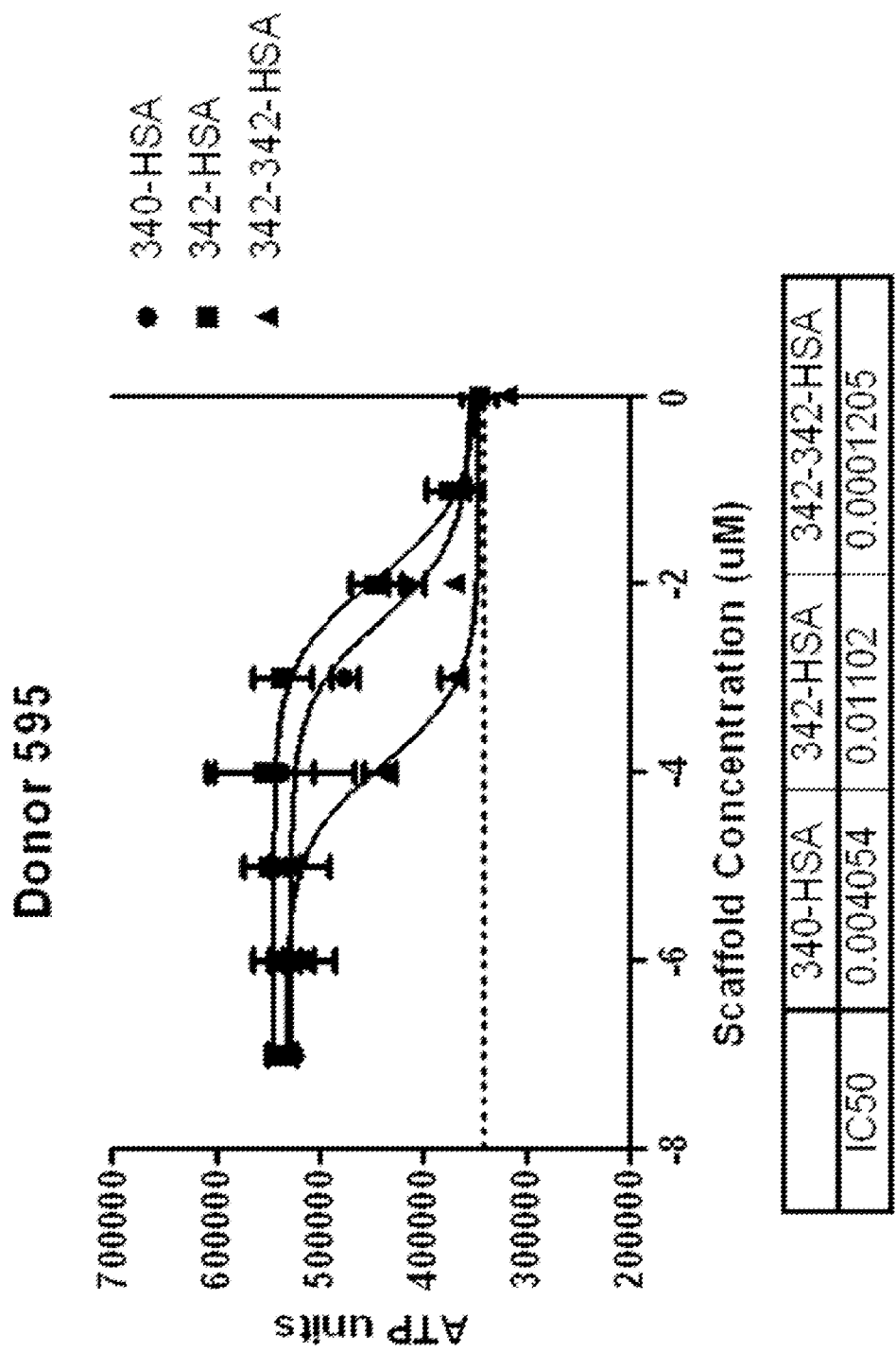
FIG. 15 shows inhibition of primary human T/B cell proliferation at day 3. A monovalent 340 scaffold fused to HSA (340-HSA), a monovalent 342 scaffold fused to HSA (342-HSA), and a bivalent 342 scaffold fused to HSA (342-342-HSA) were assayed. $IC_{50}$ values for each construct are shown.

Outputs were pool cloned into the soluble secretion vector as previously described, and five 96-well plates were screened for CD40L binding using the soluble protein screening assay described previously. Positive hits were identified relative to the signal obtained with the 311K4E backbone variant. The 18 highest scoring unique clones, designated 311K4E_1, 311K4E_2, 311K4E_3, 311K4E_4311K4E_5, 311K4E_7, 311K4E_8, 311K4E_9, 311K4E_10, 311K4E_11, 311K4E_12, 311K4E_13, 311K4E_14, 311K4E_15, 311K4E_16, 311K4E_19, 311K4E_20 and 311K4E_21 (sequences shown in FIG. 12A and FIG. 12B) were assayed as crude unpurified proteins for off-rate ranking. Off-rate estimates of unpurified Tn3 scaffolds were performed on the PROTEON™ XPR36 protein interaction array system (BIO-RAD®, Hercules, Calif.) in a biosensor assay with CD40L immobilized on a chip. Human MEGA-CD40L™ was immobilized on a GLC chip BIO-RAD®) and all variants diluted to an estimated concentration of 80 nM, injected at a flow rate of 30 µl/min for 300 seconds with the dissociation time set to 1200 seconds. PBS, 0.005% TWEEN®20, 3 mM EDTA, pH7.4 was used as running buffer. Off-rates were ranked by visual inspection of the sensorgrams. A subset of four variants which displayed the slowest off-rates, 311K4E_3, 311K4E_11, 311K4E_12 and 311K4E_15, was purified, and $K_d$ values were determined to be between 1.1 and 6.4 nM (TABLE 9).

TABLE 9

$K_d$ of 311K4E and 4 affinity purified variants binding to human CD40L.

| 311 Variant | $K_d$ (nM) |
|---|---|
| 311K4E | 18 |
| 311K4E_12 | 1.1 |
| 311K4E_11 | 6.3 |
| 311K4E_15 | 1.6 |
| 311K4E_3 | 6.4 |

As indicated in FIG. 10D, the decreased $K_d$ (from 18 nM to 1 nM) of 311K4E_12 corresponded to a 12-fold increase in potency in the PBMC assay relative to the 311K4E backbone.

In conclusion, the lead optimization campaigns of initial hits 309 and 311 from the naïve libraries lead to single-digit nM binders of CD40L.

A similar optimization campaign was performed on the murine-specific M13 molecule (data not shown). The resulting optimized murine CD40L-specific molecule (designated M31) showed an approximately 20-fold increase in potency in the PBMC assay over the parent molecule (FIG. 1A).

Example 4

Expression and Purification of Untagged CD40L-Specific Tn3-HSA Fusions

Tn3 constructs fused to HSA as outlined in FIGS. 2A and 9A were expressed in mammalian 293F cell line by transient transfection. Tn3-HSA fusion expression constructs were generated based on an in-house generated mammalian expression vector. To increase product homogeneity, a mutant form of HSA (designated HSA C34S) was employed in which the unpaired, partially exposed cysteine 34 had been mutated to serine (Zhao et al., 2009, Eur. J. Pharm. Biopharm. 72: 405-11).

Figure 9B:
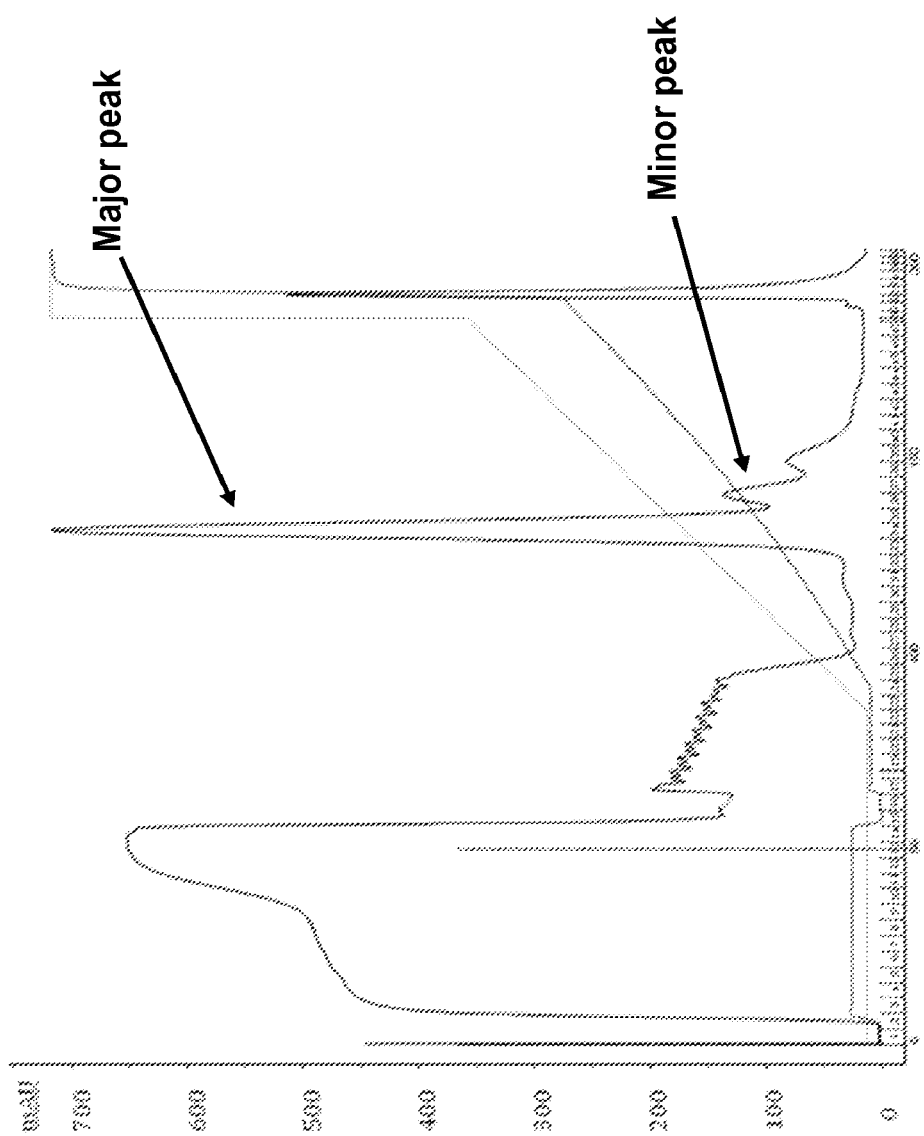
FIG. 9B shows a test purification from 293F cells over an IEX column. The shoulder fraction (<10% of the major peak) contains O-glycosylated protein linked to serine residues present in the linkers.

The fusion protein could be purified in a one-step purification by ion exchange chromatography (IEX). An example of elution of 309-309-HSA from a Q-HP column (GE HealthCare) by a salt gradient is shown in FIG. 9B. In addition to the main peak, minor later eluting peaks were seen (constituting less than 10% of the total peak area). Mass spectrometry analysis indicated these minor side peaks were enriched for O-glycosylated 309-309-HSA species. Fractions containing the main peak were pooled and used for subsequent activity assays.

For larger scale purifications, the IEX step mentioned above was preceded by capturing the Tn3-HSA fusions from the culture supernatant by affinity chromatography using HSA affinity matrixes, e.g., HI-TRAP® Blue HP (GE HealthCare). After washing, HSA fusion protein could be eluted with an Octenoic Acid containing buffer. Eluate was loaded onto the Q-HP column after 3-fold dilution in phosphate buffer.

Analysis of the minor peak(s) revealed the presence of O-linked carbohydrate moieties. The O-glycan were proposed to be a heterogeneous mix of carbohydrates derived from a previously reported O-xylosylated core structure (Wakabayashi et al., 1999, J. Biol. Chem. 274:5436-5442) shown below:

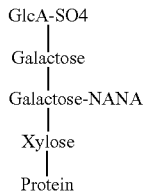

The predominate site of the attachment was determined to be in the GGGGS (SEQ ID NO: 147) linker between the Tn3 domains. The glycan was also found to be present to a lesser extent in the GGGGS (SEQ ID NO:147) linker found between the Tn3 and HSA. The levels of O-glycan were therefore higher in the bivalent constructs as compared to the monovalent constructs and were higher in material produced in HEK cells as compared to CHO cells. The levels also varied between the different Tn3 constructs. Thus, the level of O-glycan may be reduced through careful host cell section, for example use of CHO cells or other cells found to produce material with lower levels of O-glycan. In addition, material containing the O-glycan can be removed via purification methods to yield a more homogenous product lacking the O-glycan. Alternatively, the linker may be modified to remove the primary site(s) of O-glycan attachment, for example by mutating the Ser residue to a Gly. The linkers in several constructs were reengineered to have one or more GGGGG (SEQ ID NO: 148) linker. No O-glycans of any type were detected in material having the GGGGG (SEQ ID NO:148) linker(s) and no difference in activity was seen (data not shown).

Example 5

Extension of Serum Half-Life of CD40L-Specific Tn3 Scaffolds

Fusion to serum albumin was explored as a strategy to extend the serum half-life of CD40L-specific Tn3 scaffolds. In order to determine the pharmacokinetic (PK) properties of murine CD40L specific Tn3-MSA fusions a mouse PK assay was conducted. MSA fusions were chosen for studies of surrogate molecules over the corresponding HSA fusions since mouse FcRn binds HSA considerably weaker than it binds MSA, resulting in decreased recycling from endosomes and consequently increased turnover (Andersen et al. J. Biol. Chem. 285, 4826-4836, 2010).

Figure 3A:
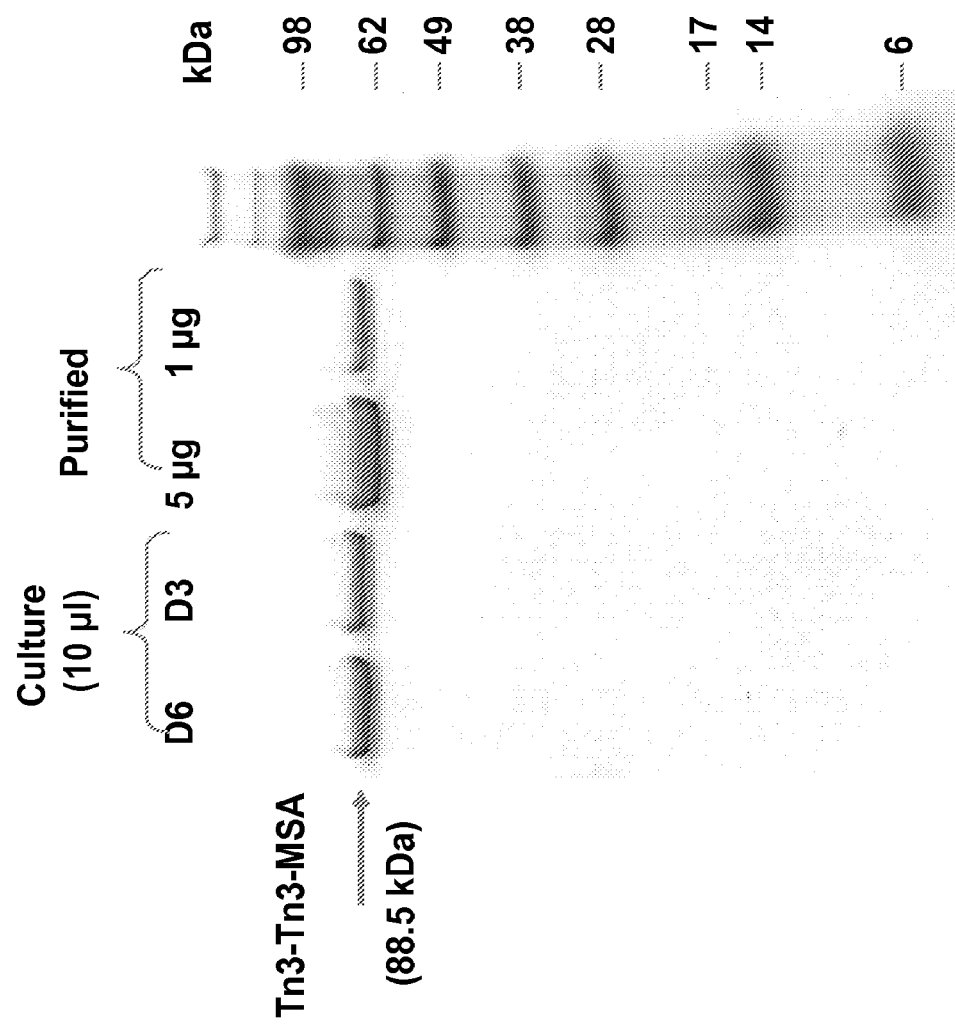
FIG. 3A shows high expression levels of murine CD40L-specific tandem bivalent Tn3 scaffold fused to mouse serum albumin (MSA) in HEK 293 cells. These constructs have 1 ($G_4$S) repeat in the linker between the Tn3 scaffold units and 3 ($G_4$S) repeats in the linker between the Tn3 scaffold and MSA. In addition, the construct contains a N49Q mutation into each of the M13 and M31 scaffolds to remove a potential N-linked glycosylation site. 10 μl culture supernatant taken 3 or 6 days after transfection were run on an SDS-PAGE gel along with known quantities of the purified protein. Expression level was estimated to 200 mg/l 6 days post transfection. Purification was carried out by IMAC through a C-terminal His-tag.

HEK 293 cells were used for expression of mouse CD40L-specific tandem bivalent Tn3 scaffold fused to MSA. High levels of expression were observed (FIG. 3A). These constructs had a ($G_4S$) linker between the Tn3 scaffold units and 3 ($G_4S$) repeats in the linker between the scaffold and MSA. In addition, a N49Q mutation was introduced into each of the M13 and M31 scaffolds to remove a potential N-linked glycosylation site. This mutation did not affect the potency of these scaffolds (data not shown). Expression level was estimated to 200 mg/L 6 days post transfection. Purification was carried out by IMAC through a C-terminal His-tag. The yield of purified protein was estimated to be 125 mg/L culture supernatant.

Figure 3B:
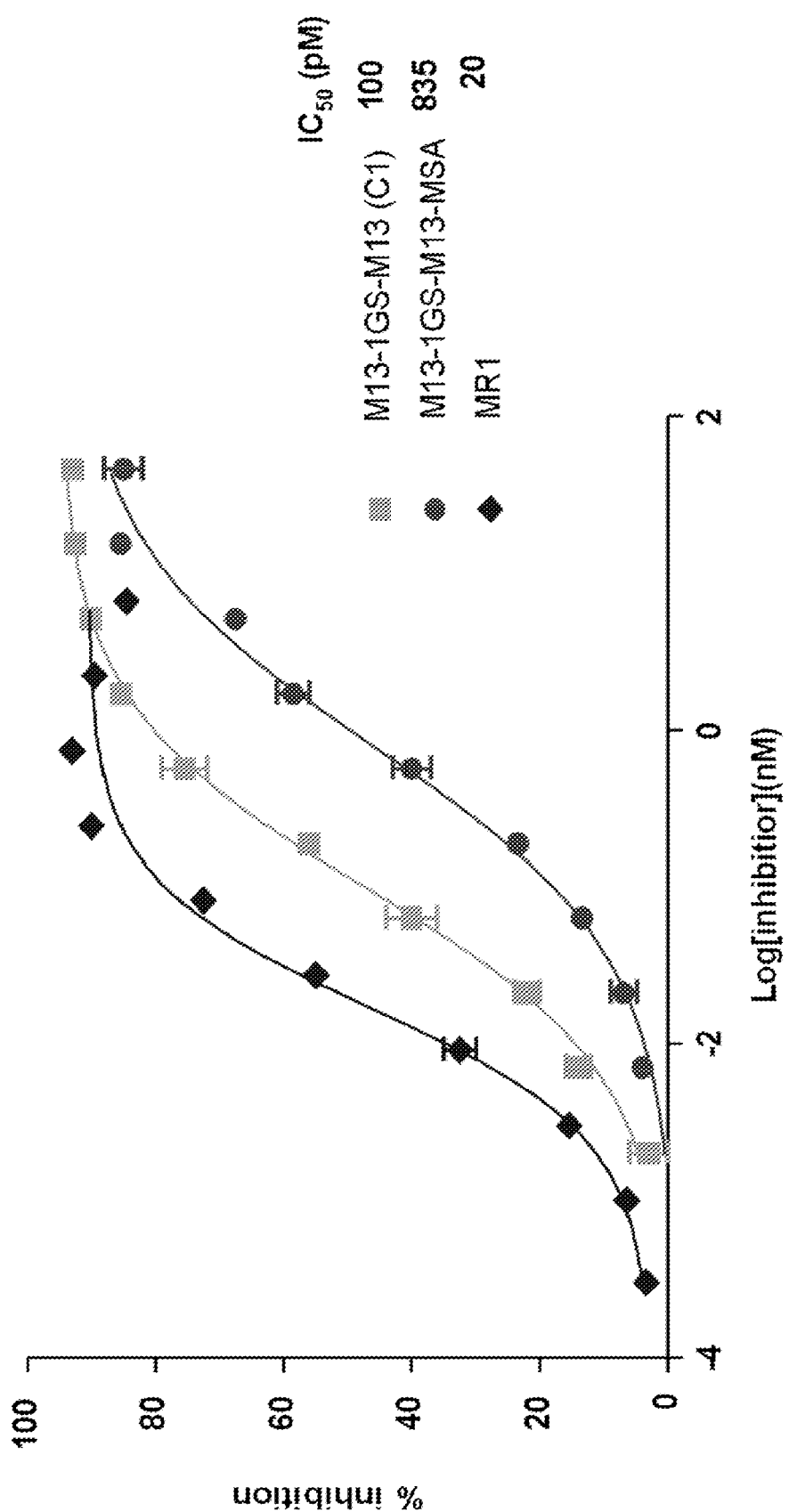
FIG. 3B shows inhibition of murine CD40L (MuCD40L)-induced CD86 expression measured using a D10G4.1/ PBMC cell assay. A CD40L-specific tandem bivalent Tn3 scaffold (M13-1GS-M13), the same construct fused to mouse serum albumin (MSA) (M13-1GS-M13-MSA), and the MR1 anti-murine CD40L monoclonal antibody were assayed. $IC_{50}$ values are provided for all constructs.
Figure 3C:
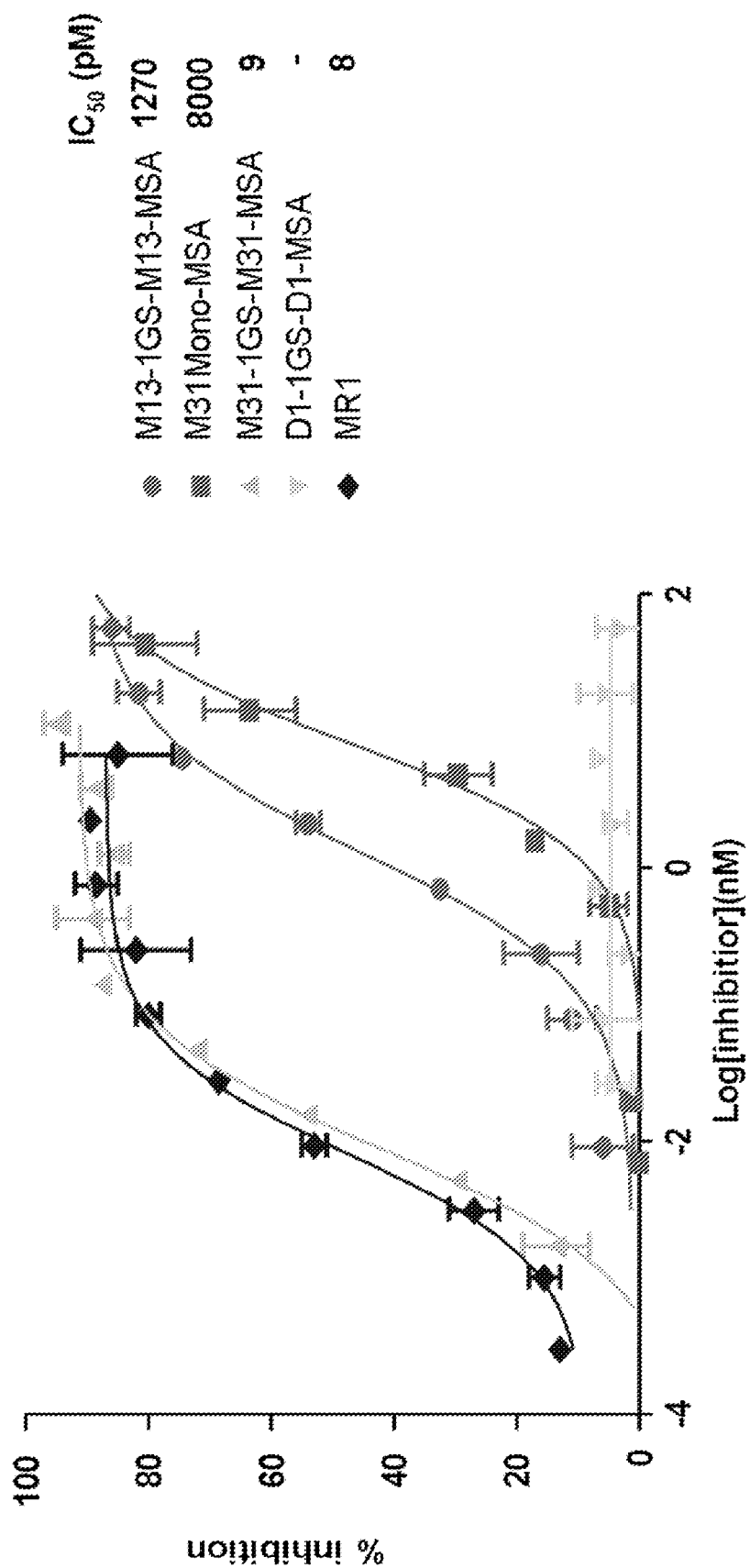
FIG. 3C shows inhibition of murine CD40L (MuCD40L)-induced CD86 expression measured using a D10G4.1/ PBMC cell assay. A CD40L-specific tandem bivalent Tn3 scaffold (M13-1GS-M13) fused to mouse serum albumin (MSA) (M13-1GS-M13-MSA), an affinity matured variant of the M13 scaffold conjugated to MSA (M31Mono-MSA), a tandem bivalent scaffold comprising the M31 affinity optimized variant conjugated to MSA (M31-1GS-M31-MSA), a negative control tandem bivalent scaffold that does not bind murine CD40L (D1-1GS-D1-MSA), and the MR1 monoclonal antibody were assayed. $IC_{50}$ values are provided.

When MSA was fused to bivalent M13 scaffolds, an 8-fold decrease in potency compared to the M13 dimeric scaffold without MSA was observed (FIG. 3B). A bivalent scaffold comprising affinity matured M31 fused to MSA was 140 times more potent than the corresponding bivalent M13 scaffold fused to MSA, approximately 900 times more potent than the monovalent M31 MSA fusion, and had a potency comparable to the MR1 anti murine CD40L monoclonal antibody (FIG. 3C).

To determine the PK properties of CD40L-specific Tn3-MSA fusions a mouse PK analysis was carried out. Protein constructs were administered intravenously at 10 mg/kg in 5-7 week old female CD-1 mice. Each mouse was bled 150 µl at various time points and serum concentration of Tn3-HSA fusion determined by an ELISA assay. Briefly, NUNC® MAXISORP™ plates were coated with anti-FLAG® M2 antibody (Agilent), blocked in 4% milk in PBS+0.1% TWEEN® (PBST) and incubated with murine MEGA-CD40L™ (Axxora). The MEGA-CD40L™ was immobilized through its FLAG® tag. Serum samples and protein standards were diluted in 4% milk PBST and added after washing plate in PBST. After incubation the plate was washed in PBST and rabbit anti-TN3 polyclonal antibody (COVANCE®) was used to detect the Tn3-HSA fusion constructs using Goat anti-rabbit HRP-conjugated antibody (Jackson ImmunoResearch) in a standard ELISA protocol. Concentrations in serum samples were determined based on linear regression of standard curves generated by assays of dilution of the same Tn3-MSA fusion construct. Concentrations were determined as an average for 3 different mice.

Figure 4A:
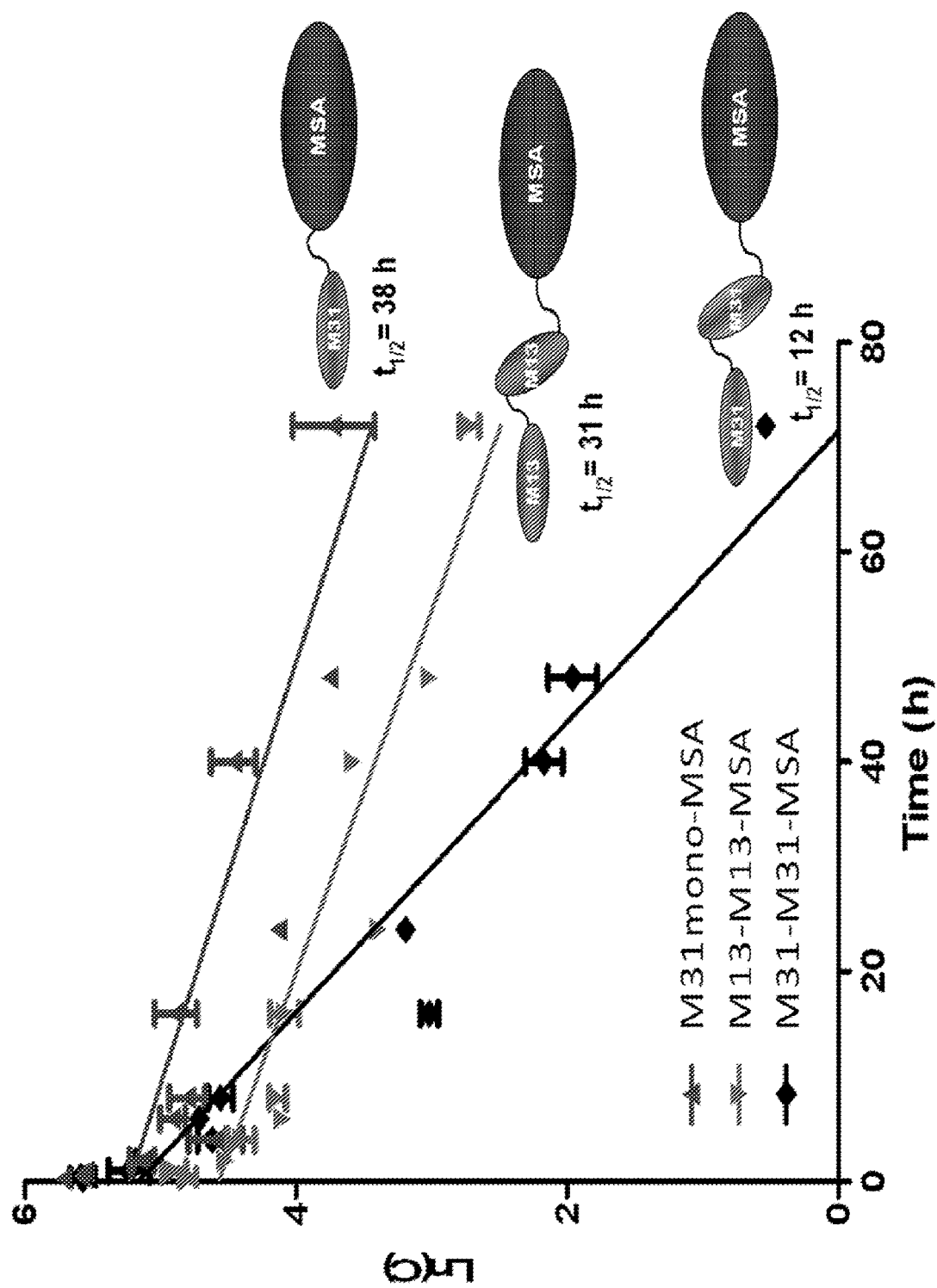
FIG. 4A shows the pharmacokinetics of several murine CD40L specific constructs in mouse as determined by ELISA. The plasma half-life ($t_{1/2}$) values for each construct are indicated.

As seen in FIG. 4A, M31-MSA and M13-M13-MSA had half-lives of 38 and 31 hours, respectively, whereas the M31-M31-HSA construct had a half-life of 12 hours. In comparison, the M13-M13 tandem construct by itself (not fused to MSA) displayed a half-life of 30 minutes (not shown).

Figure 9C:
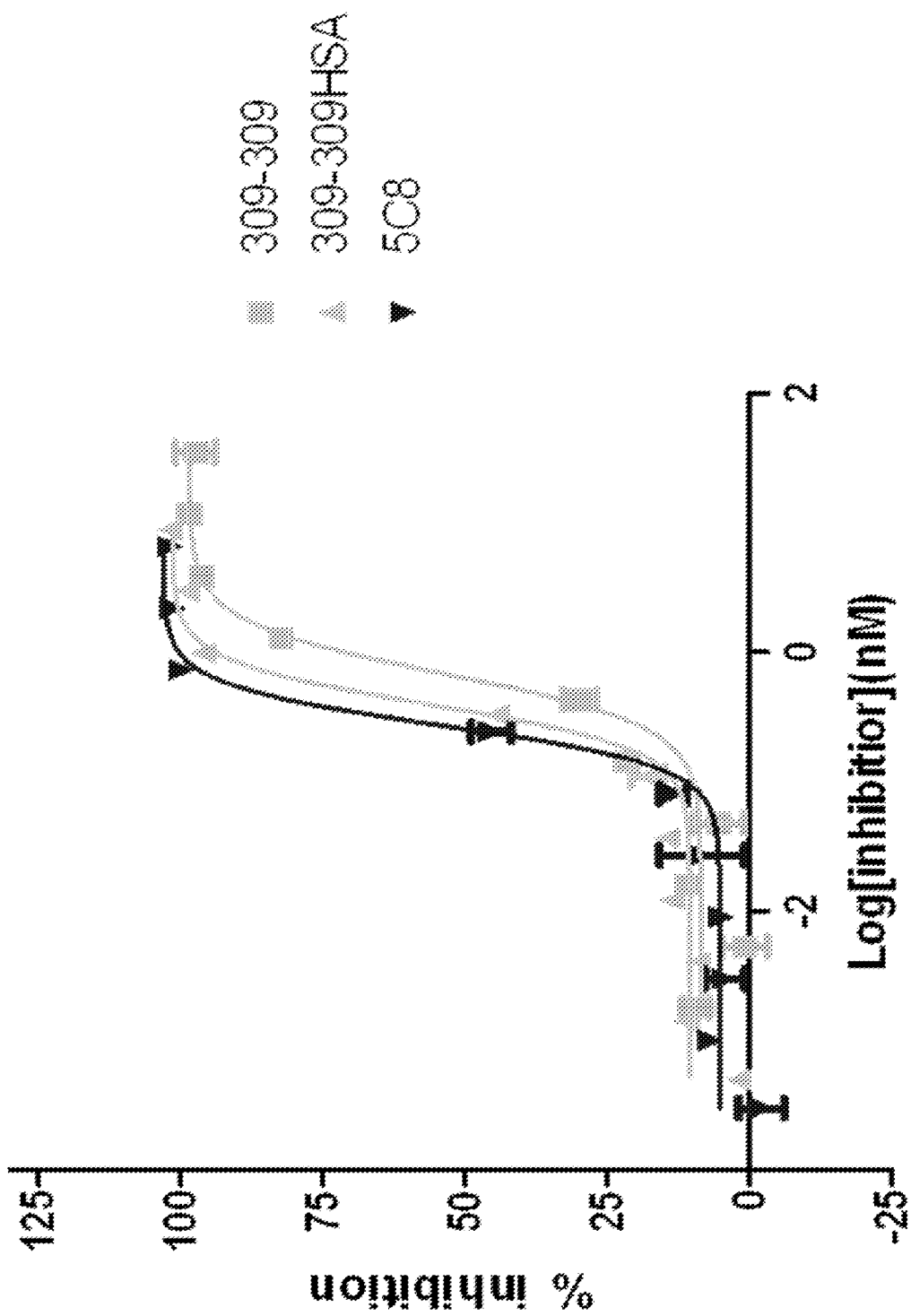
FIG. 9C shows inhibition in the human CD40L-induced CD86 expression on CD19 positive human PBMCs stimulated with Jurkat D1.1 cells. A bivalent (309) human CD40L-specific Tn3 scaffold, the same scaffold fused to HSA, and Biogen's 5c8 anti-human CD40L monoclonal antibody were assayed.

In contrast to the observations in mouse scaffolds, when HSA was fused to human CD40L specific scaffolds there was no significant decrease in potency. FIG. 9C shows that there was no significant decrease in potency by fusing a human CD40L-specific bivalent Tn3 scaffold comprising two 309 monomer to HSA as measured in PMBC assays.

Figure 4B:
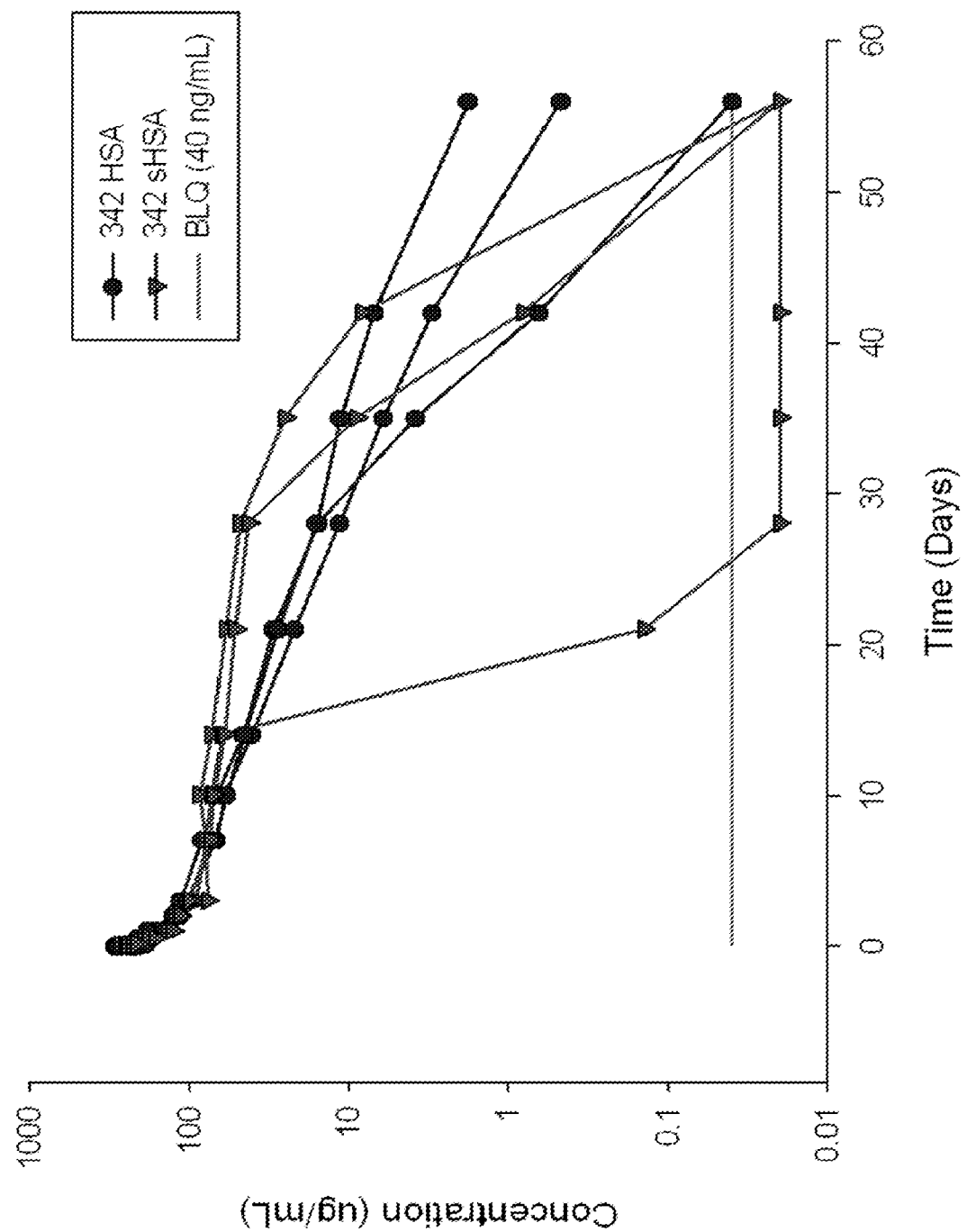
FIG. 4B shows the pharmacokinetics of the human CD40L specific 342-HSA and a 342-HSA variant comprising the substitution of Leu at position 463 with Asn (L463N) and the substitution of Lys at position 524 with Leu (K524L) in Cynomolgus monkey as determined by ELISA.

The PK properties of the human CD40L-specific 342-HSA monomer construct were compared to those of a 342-HSA variant comprising two substitutions (L463N and K524L) to enhance serum half-life in Cynomolgus monkey following a single intravenous injection. Protein constructs were administered via slow bolus injection at 10 mg/kg to male Cynomolgus monkeys weighing 2-5 kg. 1 mL of blood/animal/time point was collected from a peripheral vessel at predose, 5 minutes and 30 minutes post dose; 2, 12, 24, and 48 hours post dose; and on Days 4, 8, 11, 15, 22, 29, 36, 43 and 57. Serum concentration of Tn3-HSA fusion determined by an ELISA assay. Briefly, NUNC® MAXISORP™ plates were coated with anti-FLAG® M2 antibody (Agilent), blocked in 4% milk in PBS+0.1% TWEEN® (PBST) and incubated with human MEGA-CD40L™ (Axxora). The MEGA-CD40L™ was immobilized through its FLAG®tag. Serum samples and protein standards were diluted in 4% milk PBST and added after washing plate in PBST. After incubation the plate was washed in PBST and rabbit anti-TN3 polyclonal antibody (COVANCE®) was used to detect the Tn3-HSA fusion constructs using Goat anti-rabbit HRP-conjugated antibody (Jackson ImmunoResearch) in a standard ELISA protocol. Concentrations in serum samples were determined based on linear regression of standard curves generated by assays of dilution of the same Tn3-HSA fusion construct. Concentrations are plotted in FIG. 4B. The half-life of the 342-HSA construct was about 7 days, while the 342-HSA L463N/K524L variant construct showed an increased half-life of 13-17 days during the initial linear phase (FIG. 4B). After 30 days, the serum concentrations of the 342-HSA L463N/K524L variant construct dropped off more rapidly as compared to the wild type HSA construct. These observations may indicate some immunogenicity of this construct in monkeys.

Example 6

Characterization of CD40L-Specific Tn3 Scaffolds 6.1 Experimental Methods 6.1.1 PBMC stimulation assay: Blood was obtained from healthy donors according to MedImmune safety guidelines. PBMCs were isolated via CPT tubes (spin 1500 g for 20 minutes) and $1 \times 10^6$ PBMCs (per condition) were stimulated by recombinant human MEGA-CD40L™ (Axxora) or human CD40L expressing Jurkat cells (D1.1, ATCC®). The percentage of CD19+/CD86+ cells was measured by FACS after 24 hours stimulation. This assay was used to test and rank the panel of leading Tn3 scaffolds to emerge from prioritization based on biochemical criteria. The assay can also be performed with a murine CD40L-expressing cell line (D10.G4) or murine MEGA-CD40L™ (Axxora ALX522120) in place of the human cell or recombinant protein stimulation as murine ligand cross reacts with human receptor.

6.1.2 MurineCD40R/NFκB assay: NFκB reporter NIH3T3 cells (Panomics NFκB reporter system and in-house mCD40R transfection) were stimulated with murine MEGA-CD40L™ (Axxora, cat. ALX522120) recombinant protein or CD40L over-expressing D10.G4 cells (ATCC®) for 24 hours with or without Tn3 scaffolds. BRIGHT-GLOW™ (Promega E2610) was added according to manufacturer's directions. The readout was luminescence (700) via the NFκB reporter activation performed on an ENVISION® system (PERKINELMER®).

6.1.3 Human CD40R/NFκB assay: Reporter HEK293 cells (Panomics and in-house) were stimulated with MEGA-CD40L™ (Axxora ALX522110) recombinant protein or CD40L overexpressing D1.1 Jurkat subclone cells (ATCC®) for 24 hours with or without Tn3 scaffolds. BRIGHT-GLOW™ (Promega E2610) was added according to manufacturer's directions. The readout was luminescence (700) via the NFκB reporter activation performed on an ENVISION® system (PERKINELMER®).

6.1.4 Dual cell assay: Primary T/B cells were isolated from various donors. Anti-CD3 stimulated, mitomycin C treated human CD4+ T cells ($1 \times 10^5$) were cultured with purified human B cells ($5 \times 10^4$). Readouts were as follows: Day 2: Activation markers (FACS), Day 5: B cell proliferation (ATP metabolite, CELL-TITER GLO™, INVITROGEN™), Day 7: plasma cell differentiation (FACS) Day 7: Ig production (ELISAs, R&D Systems).

6.1.5 Platelet aggregation assays: Adenosine diphosphate (ADP) was from Chrono-Log (Havertown, Pa., USA). All other products were at least reagent grade. Blood samples were collected from healthy volunteers in 12.9 mM sodium citrate and centrifuged at 150×g for 15 minutes to obtain PRP (platelet rich plasma). After separation of PRP, tubes were centrifuged again at 1,200×g for 15 minutes to obtain PPP (platelet poor plasma). Platelets were washed using the method described by Mustard et al. (Br. J. Haematol. 22:193-204, 1972), and re-suspended in Tyrode's solution containing $CaCl_2$ 2 mM, $MgCl_2$ 1 mM, 0.1% dextrose, 0.35% bovine serum albumin, 0.05 U/mL apyrase, pH 7.35. Platelet aggregation was studied using a light transmission aggregometer (Chrono-Log 700-4DR, Chrono-Log Corporation, Havertown, Pa., USA) and recorded for 10 min after stimulation of platelets with the indicated platelet agonists as described. Tn3 scaffolds were pre-incubated with the soluble CD40L (sCD40L) to form immunocomplexes prior to addition.

6.1.6 Immunization assays: Sheep Red Blood Cells (SRBC) were purchased from Colorado Serum (Denver, Colo.) and diluted 10-fold in HBSS medium immediately before use. Mice were immunized with 0.2 ml of diluted SRBC on day 0. Primary Germinal center (GC) response in challenged mice was assayed 14 days after immunization via FACS (GC B cells, non-GC B-cells, and all T cell subsets). Tn3 scaffolds and controls were administered on days 9-13 in 24 hour increments as indicated.

6.1.7 KLH-specific T cell dependent antibody response (TDAR) assays: Cynomolgus Monkeys (*Macaca fascicularis*) of Chinese origin and weighing 3.1-4.6 kg, (COVANCE® Research Products, Alice Tex.) were dosed intravenously (saphenous or cephalic vein) once weekly with the indicated dose (0.5, 5, 40 mg/kg) of inhibitor (342-monomer-Tn3-HSA and 342-342 bivalent-Tn3-HSA or control/vehicle. KLH (Lot No. MD158678A, Supplier PIERCE™ Biotechnologies, Rockford, Ill.) was reconstituted with the appropriate amount of sterile water for injection (Supplier Midwest Veterinary Supply, Norristown, Pa.) under sterile conditions. Vials were swirled to mix and then pooled together into a sterile vial. 1 mL of KLH solution (10 mg/mL) was administered subcutaneously on each animal's back, to the left of the midline on two occasions (Day 1 and Day 29), within 1 hour of the end of the test or control article administration. Blood samples for further analysis were obtained from all animals at the following time points: pretest, Days 4, 6, 8, 11, 15, 22, 25, 32, 34, 36, 39, 43, 46, 50 and 57. Samples collected on Days 8, 15 and 22 were taken prior to dosing. Evaluation of KLH-specific IgM and IgG antibody titers were done at days 8, 11 and 15. The titers of KLH-specific IgM and IgG antibodies at day 15 are shown in FIGS. 5G and 5H, respectively. The cutpoint titration method utilized an ELISA format to detect anti-KLH antibodies in monkey serum. The samples were incubated with KLH, which was immobilized on an ELISA plate. After incubation, the plates were washed, and the bound antibodies were detected with Goat anti-Monkey IgG-HRP or IgM-HRP and then visualized with tetramethylbenzidine (TMB).

For all experiments utilizing animals currently acceptable practices of good animal husbandry were followed e.g., Guide for the Care and Use of Laboratory Animals; National Academy Press, 2011. Huntingdon Life Sciences, East Millstone, N.J. is fully accredited by the Association for Assessment and Accreditation of Laboratory Animal Care International (AAALAC). Animals were monitored by the technical staff for any conditions requiring possible veterinary care and treated as necessary.

6.2 CD40L Specific Tn3 Scaffolds Functionally Neutralize CD40: CD40 Interactions.

CD40L-expressing T cells engage CD40-expressing B cells resulting in the activation of NFκB signaling pathway (Zangani, 2009). Thus, an NFκB-luciferase reporter cell line was used to determine if the anti-CD40L-Tn3 molecules could inhibit signaling downstream of CD40 engagement. HEK293 cells expressing human CD40L and the reporter were stimulated with either human or murine MEGA-CD40L™ at $EC_{90}$ (Effective Concentration that results in 90% inhibition; i.e., 1.5 μg/ml for human MEGA-CD40L™, and 3 μg/ml for murine MEGA-CD40L$^{T}$M)

The human-specific 342 molecule inhibited human CD40L-induced NFκB activity with an $IC_{50}$ of 1.5 nM (FIG. 13). The murine-specific M31 molecule, neutralized murine CD40L-induced NFxB activity with an $IC_{50}$=1.6 nM (FIG. 1B). The positive control anti-CD40L monoclonal antibodies 5c8 (anti human CD40L) and MR1 (anti murine CD40L) both performed about 10-fold better than the monomeric Tn3 scaffolds with $IC_{50}$'s of 0.200 nM+/−SD (lowest threshold of the assay). This could be in part due to the bivalent nature of the monoclonal antibodies contributing to the avidity of the interaction with their respective CD40L's.

6.3 Dimeric CD40L Specific Tn3 Scaffolds Exhibit Improved Binding.

Experimental data indicates that the binding of a CD40L-specific Tn3 bivalent scaffold was improved over that of a CD40L-specific Tn3 monomer scaffold. The binding of the CD40L-specific Tn3 bivalent scaffold to CD40L improved the action on the target, in some cases by approximately 3 logs over that of a CD40L specific Tn3 monomer scaffold in vitro, as shown in FIG. 2C and FIG. 2D (murine), and FIG. 8A and FIG. 8B (human).

FIG. 2C shows the competitive inhibition of murine CD40L binding to murine CD40 receptor immobilized on a biosensor chip by murine CD40L-specific monovalent (M13) or bivalent tandem scaffolds. M13 monomers were linked with varying length peptide linkers comprising one (1GS), three (3GS), five (5GS) or seven (7GS) "GGGGS" (SEQ ID NO: 147) repeats. The $IC_{50}$ of the M13-1GS-M13 scaffold was 29 nM, whereas the $IC_{50}$ of the monomer M13 scaffold was 71 nM. The $IC_{50}$ of divalent M13 scaffolds with longer linkers were dramatically lower (5-6 nM).

FIG. 2D shows the inhibitory effect of murine CD40L-specific monovalent (M13) or bivalent tandem scaffolds on murine CD40L-induced CD86 expression on B cells. The bivalent scaffolds were approximately 3 logs more potent than the monovalent scaffolds.

FIGS. 8A and 8B show that human CD40L-specific Tn3 scaffolds 309 and 311 displayed enhanced potency in a bivalent tandem format. The bivalent 311 scaffolds (FIG. 8A) and the bivalent 309 scaffolds (FIG. 8B) showed approximately a 7-fold and a 500-1000-fold improvement, respectively, in inhibition of human CD40L-induced expression on CD19 positive human PBMCs stimulated with Jurkat D1.1 cells. The bivalent 309 scaffolds were comparable in potency to Biogen's 5c8 anti human CD40L monoclonal antibody.

Solubility, stability and ease of purification was not disrupted with the addition of varying length peptide linkers comprising one (1GS), three (3GS), five (5GS) or seven (7GS) "GGGGS" (SEQ ID NO: 147) repeats (see FIG. 2B).

6.4 CD40L Specific Tn3 Scaffolds Binding and Function.

In addition to the biochemical binding described above, it was important to verify that these novel Tn3 scaffolds were able to bind endogenous CD40L expressed on primary T cells following activation. T cells were isolated from multiple donors and activated as described. After 24 hours, CD40L expression was upregulated as determined by staining with 5c8 (human-specific) monoclonal antibody and MR1 (murine-specific) monoclonal antibody (data not shown). The CD40L specific Tn3 scaffold molecules were able to detect comparable levels of CD40L expression as the monoclonal antibodies confirming that these molecules can bind native protein.

One of the functional consequences of the CD40L:CD40 interaction is the up regulation of co-stimulatory molecules on B cells (Yellin et al., J. Exp. Med. 6:1857-1864, 1995). The CD40L-directed Tn3 molecules were tested for their ability to prevent this. Cell lines endogenously expressing human or murine CD40L (D1.1 Jurkat subclone or D10.G4 respectively) were used to stimulate peripheral blood mononuclear cells (PBMC). Once stimulated, the activation of B cells was assessed by measuring the percentage of CD86 up regulation by CD19+ B cells via flow cytometry. In this assay, the positive control monoclonal antibodies were able to inhibit the CD19+ percentage of cells with CD86 expression with ICsos of 0.170 nM (5c8) and 0.230 nM (MR1). The human-specific optimized Tn3, 342 was able to antagonize CD86 up regulation with $IC_{50}$ values=0.700 nM (n=5 donors) (see FIG. 10B and TABLE 7).

The murine-specific optimized Tn3 M31 had and $IC_{50}$ of 1.5 nM. These similar results were observed when MEGA-CD40L™ recombinant protein was used to stimulate PBMCs. The experimental data demonstrated that both molecules, whether murine or human specific, cannot only inhibit the main signaling pathway within a cell (NFκB), but also one of its most important functional roles: T-B cell interactions. This inhibitory action can counteract CD40L's contribution in many auto immune diseases and conditions.

6.5 Anti-CD40L Tn3's Inhibit B Cell Proliferation and Plasma Cell Differentiation Following T/B Co-Culture.

Interactions of CD40L on T cells with CD40-expressing B cells are a fundamental aspect of T cell help which facilitates the development of adaptive immune responses (Banchereau, 1994; Oxenius, 1996, van Kooten & Banchereau, 1997). To model this, the anti-hCD40L Tn3-HSA fusions of 340, 342 and 342-342 dimer were evaluated in primary cell co-cultures of T cells and B cells where anti-CD3 stimulated, mitomycin C treated human CD4+ T cells were cultured with purified human B cells. The ability of the B cells to proliferate at day four to differentiate into plasma cells (PC) by day seven and switch their antibody class of production were measured (PC and antibody data not shown) (FIG. 15) (Ettinger, 2007). The CD40L-specific Tn3 scaffold 342-342-HSA was able to reduce T cell induced proliferation by at least 50% as compared to the cell proliferation of B-cells in the absence of scaffolds, or in the presence of a non-specific control scaffold. Proliferation is a pre-cursor, signal one, to plasma cell differentiation, upon CD40L:CD40 ligation. Inhibition of plasma cell differentiation and antibody class switching (data not shown) were also observed.

6.6 In Vivo Disruption of the CD40:CD40L Axis.

The central role of CD40L:CD40R interactions in T-dependent immune responses have been well characterized (Noelle, 1992; Renshaw, 1994, Wykes, 2003). The murine CD40L-specific Tn3 scaffold M31 (M31-MSA and M31-M31-MSA) was used to evaluate the effects of these novel molecules in a T-dependent immunization model by immunizing mice (intravenously) at day zero with Sheep Red Blood Cells (SRBC).

On days 9-13, mice were injected intraperitoneally daily with the indicated dose of inhibitor and at day 14 splenic and lymph node GC B cells were quantitated. Daily dosing was required given the short $T_{1/2}$ of this molecule in vivo, 31 hours (FIG. 4). It is well established that CD40L controls humoral responses such as the generation of germinal centers in anatomical sites such as the spleen and lymph nodes from previous findings (Jacob, 1991). Here, the disruption of the CD40L:CD40 axis contribution to that formation was observed in a dose dependent manner with M31-MSA versus naïve or our non-specific control, D1-MSA, as shown by the percentage of GC B cells.

Figure 5A:
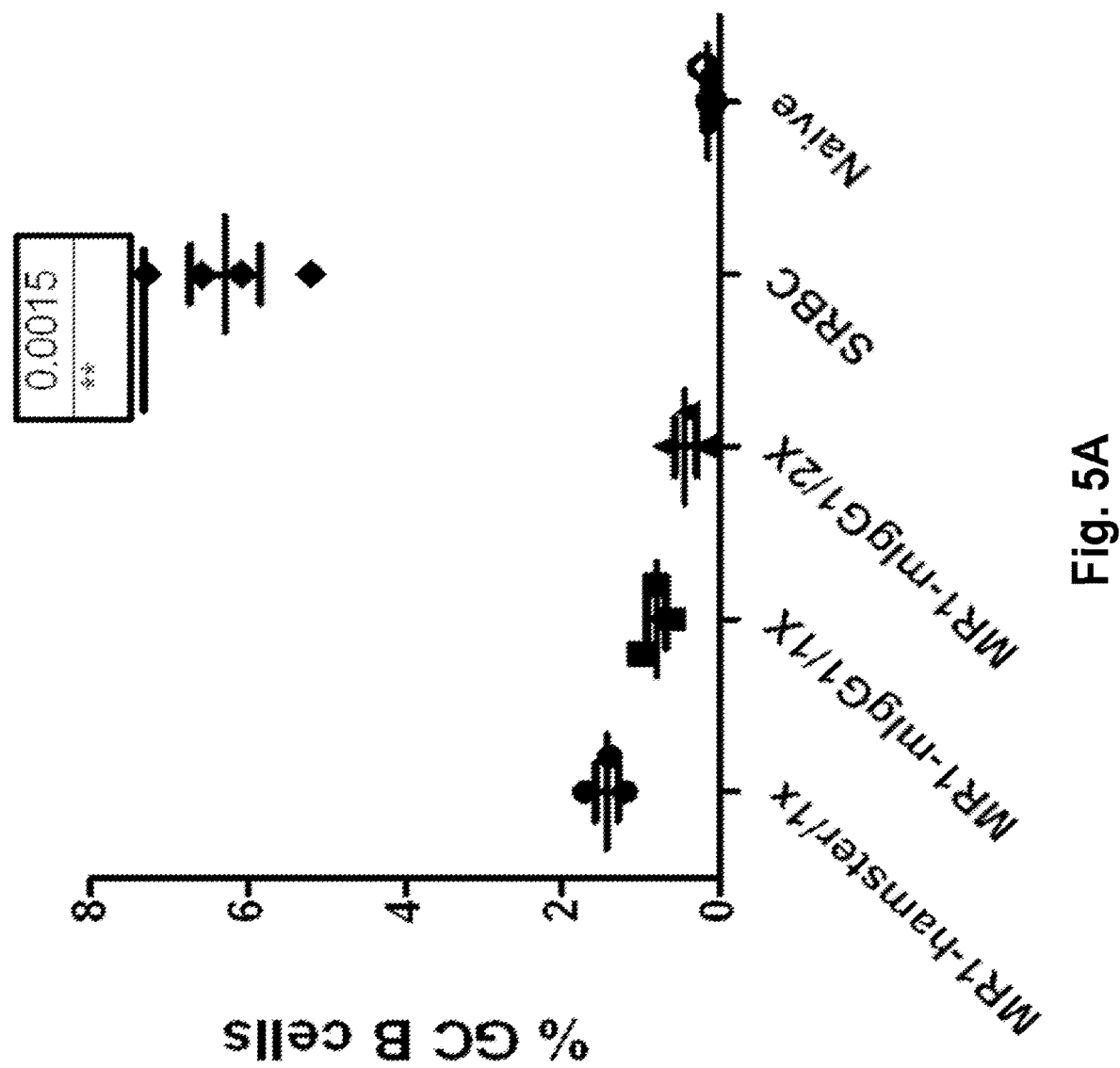
FIG. 5A shows B cell maturation in the germinal centers (GC) from a sheep red blood cell (SRBC) immunization assay. The MR1 monoclonal anti-murine CD40L antibody was assayed.
Figure 5B:
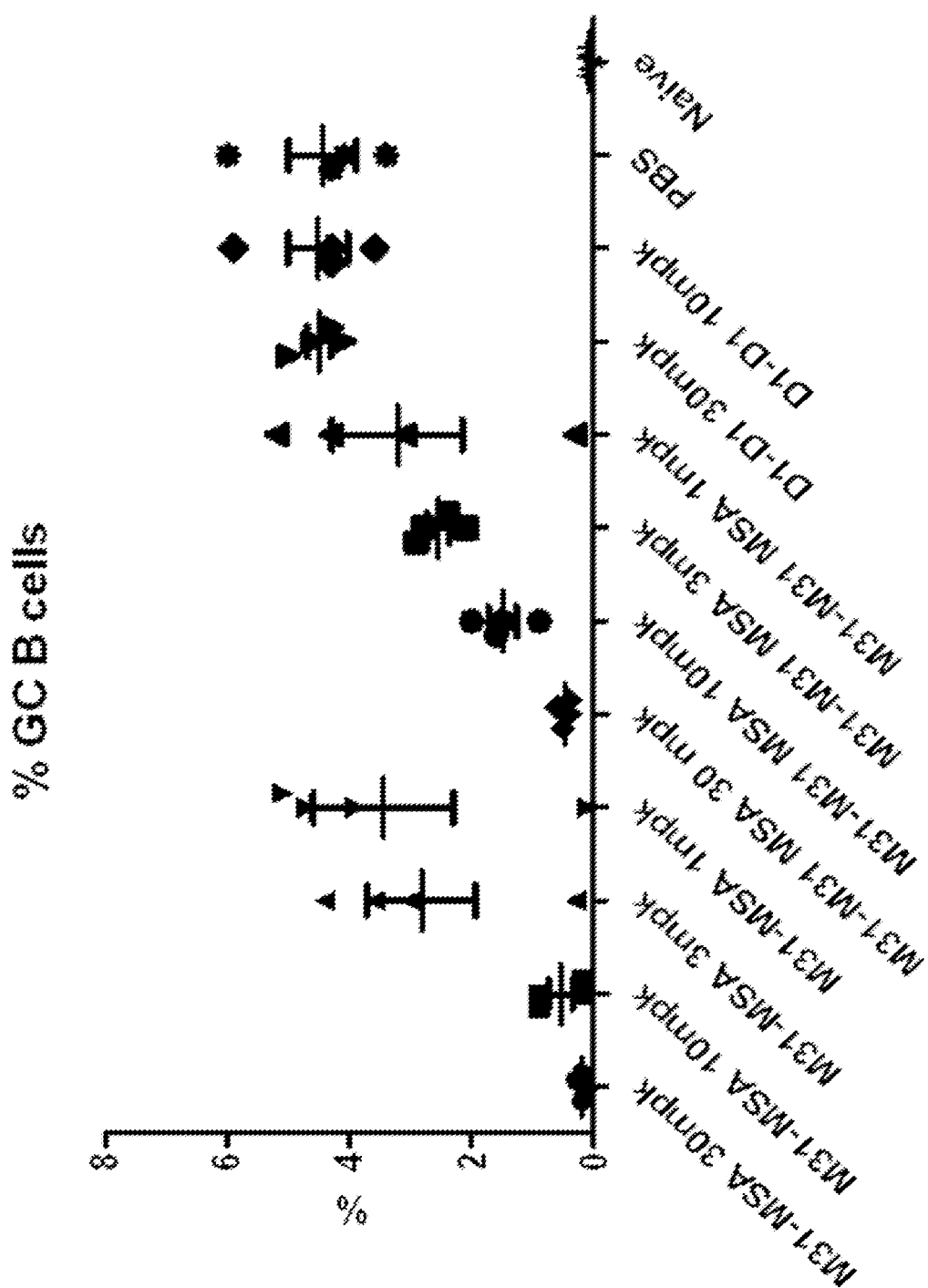
FIG. 5B shows B cell maturation in the germinal centers (GC) from a sheep red blood cell (SRBC) immunization assay. M31-derived monovalent and bivalent constructs fused to MSA were assayed. The D1-D1 bivalent construct conjugated to MSA was used a negative control.
Figure 5C:
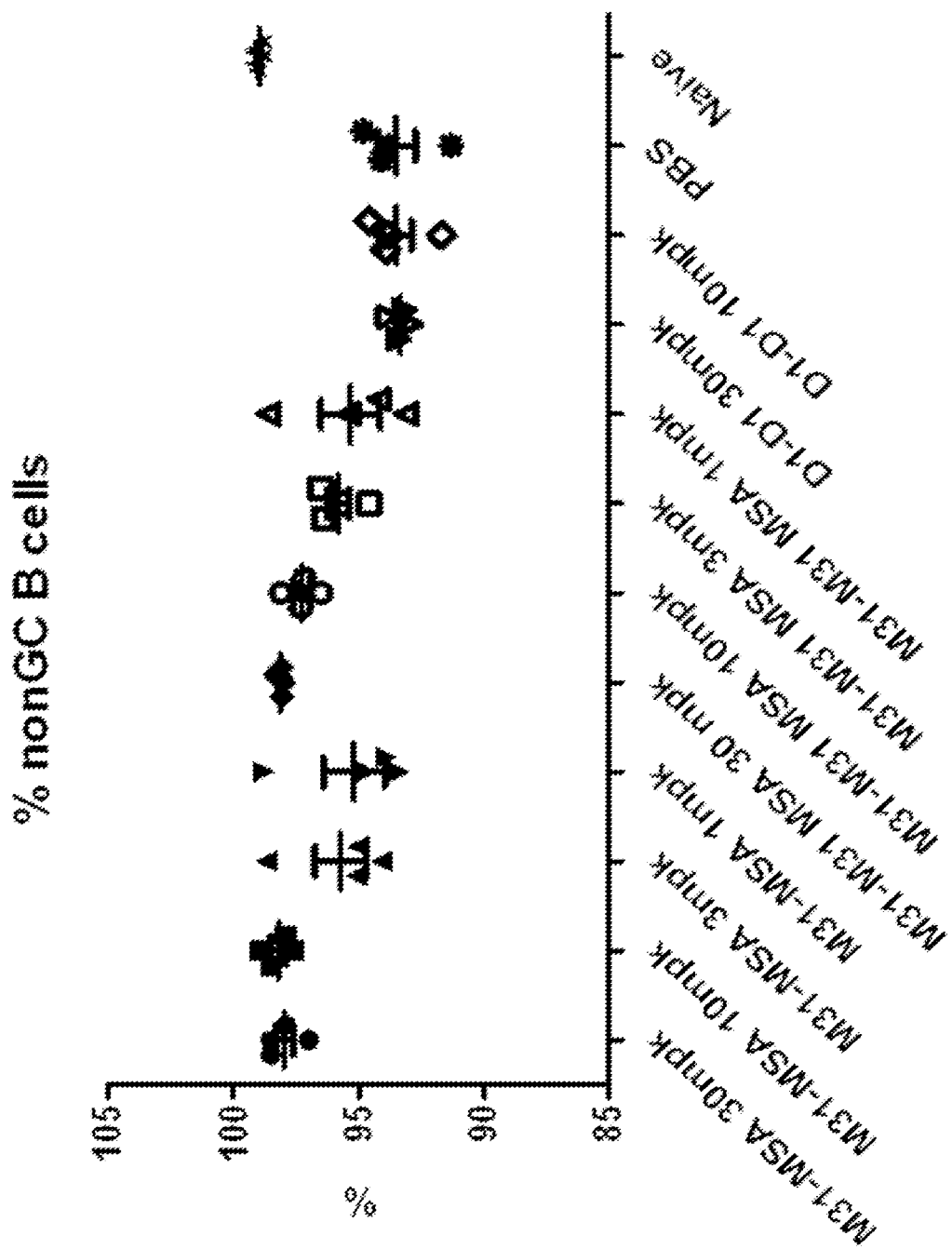
FIG. 5C shows B cell maturation in periphery (nonGC) from a sheep red blood cell (SRBC) immunization assay. M31-derived monovalent and bivalent constructs fused to MSA were assayed. The D1-D1 bivalent construct conjugated to MSA was used a negative control.
Figure 5D:
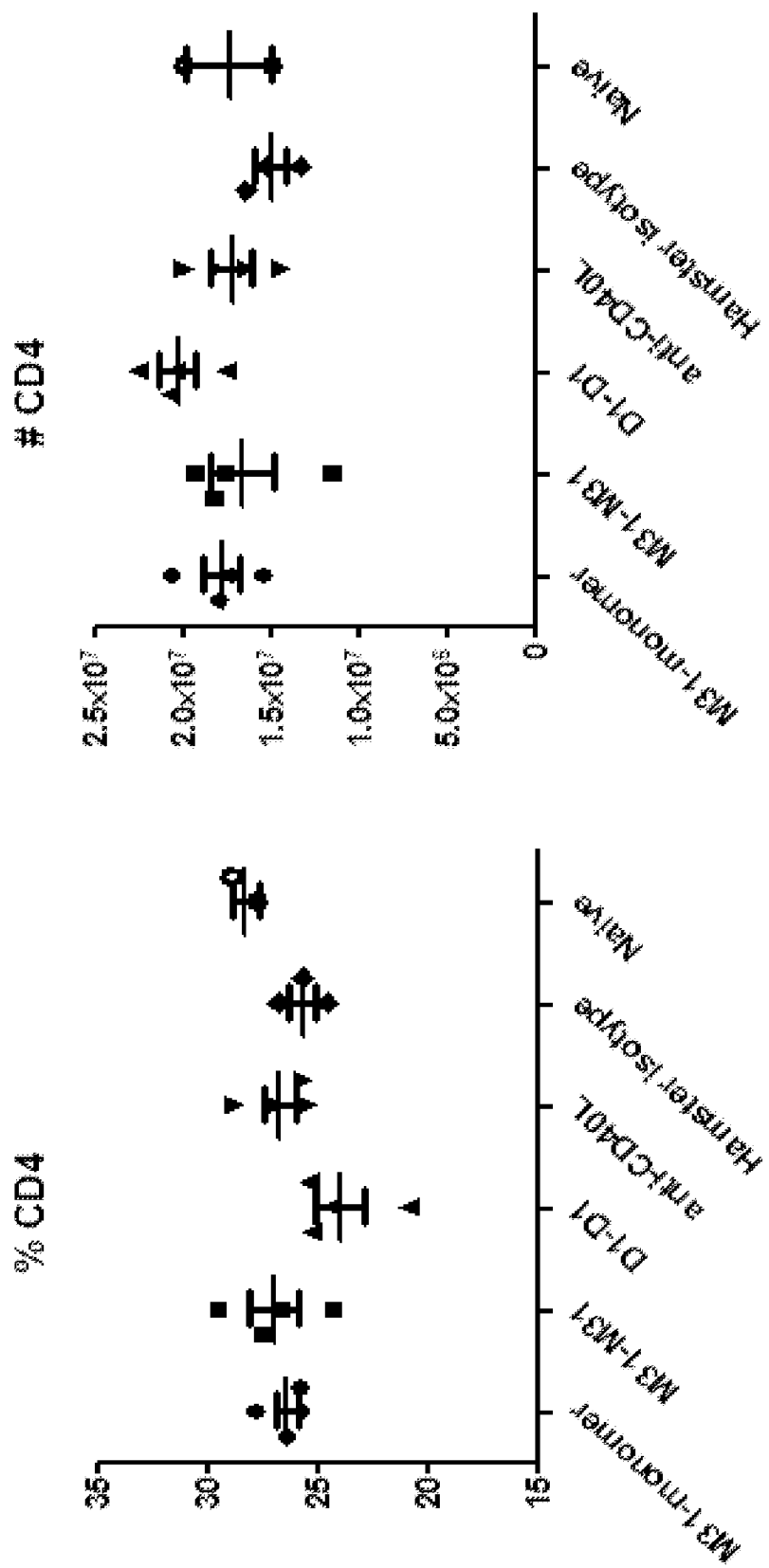
FIG. 5D shows the percentage (% CD4) and number (#CD4) of CD4 positive cells from a sheep red blood cell (SRBC) immunization assay. M31-derived monovalent and bivalent constructs fused to MSA, and the MR1 anti-CD40L monoclonal antibodies were assayed. The D1-D1 bivalent construct conjugated to MSA was used a negative control.
Figure 5E:
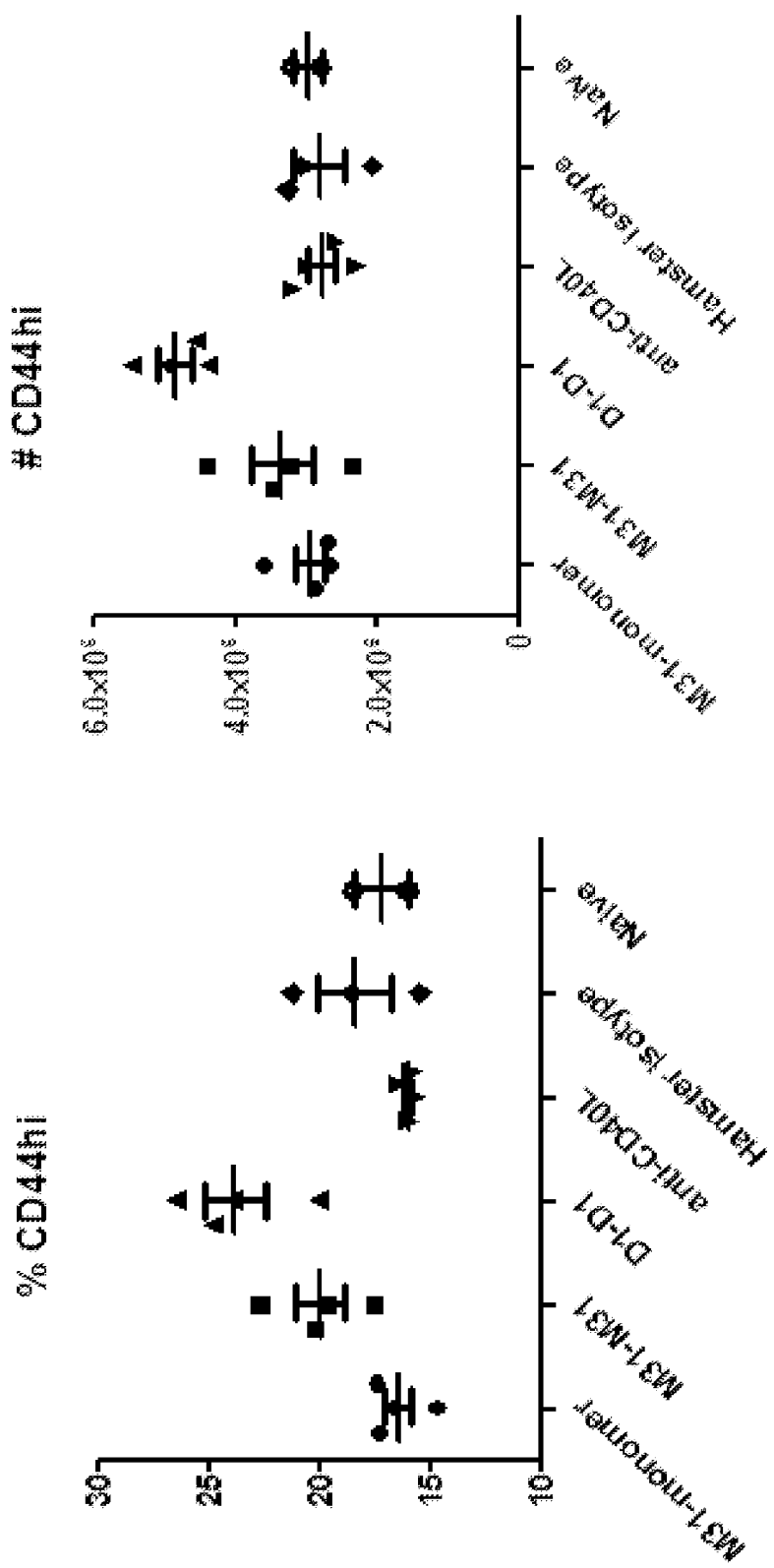
FIG. 5E shows the percentage (% CD44hi) and number (#CD44hi) of CD44hi positive cells from a sheep red blood cell (SRBC) immunization assay. M31-derived monovalent and bivalent constructs fused to MSA and the MR1 anti-CD40L monoclonal antibodies were assayed. The D1-D1 bivalent construct conjugated to MSA was used a negative control
Figure 5F:
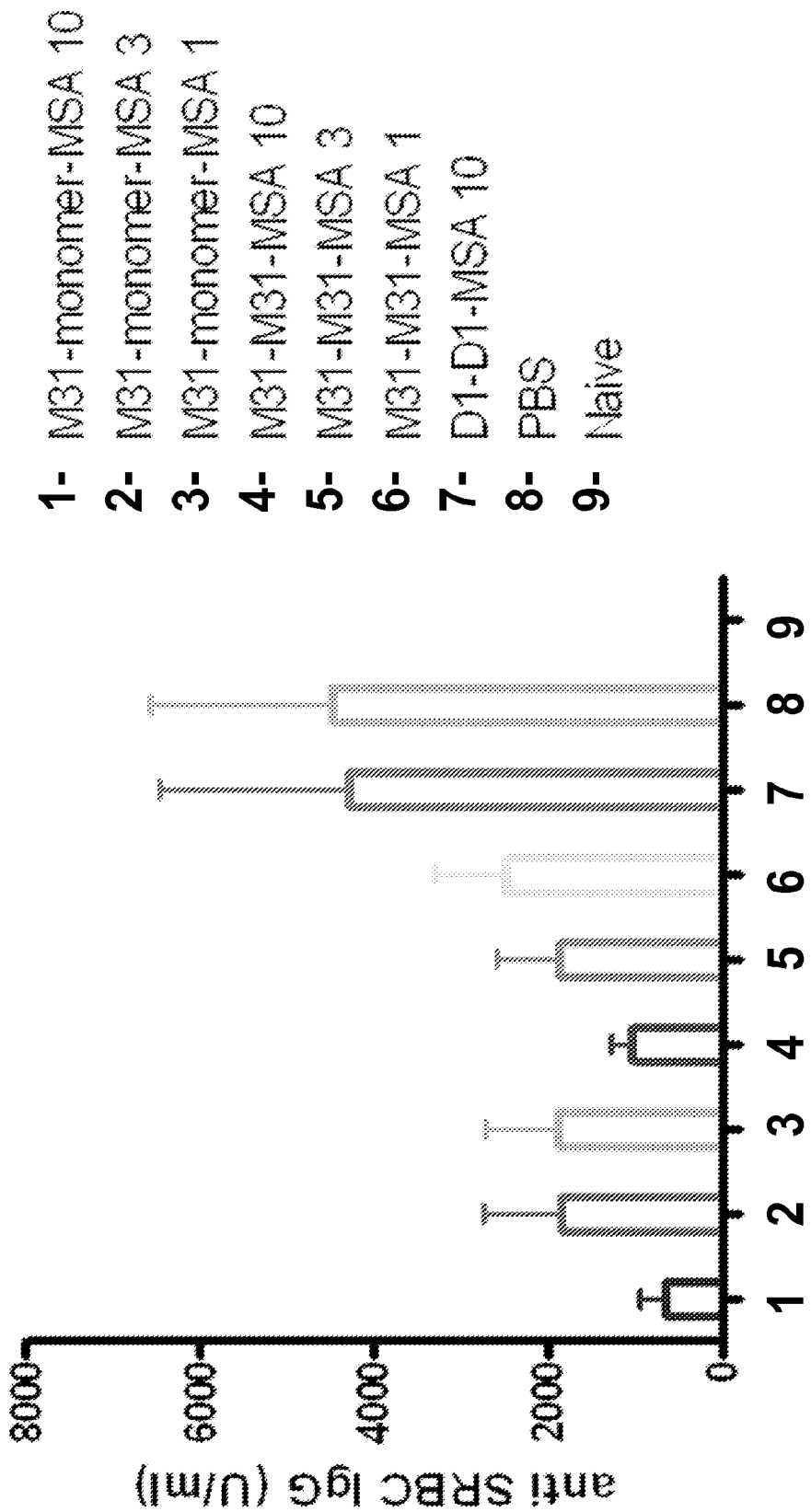
FIG. 5F shows the amount of anti-SRBC IgG from a sheep red blood cell (SRBC) immunization assay. M31-derived monovalent and bivalent constructs fused to MSA assayed. The D1-D1 bivalent construct conjugated to MSA was used a negative control.
Figure 5G:
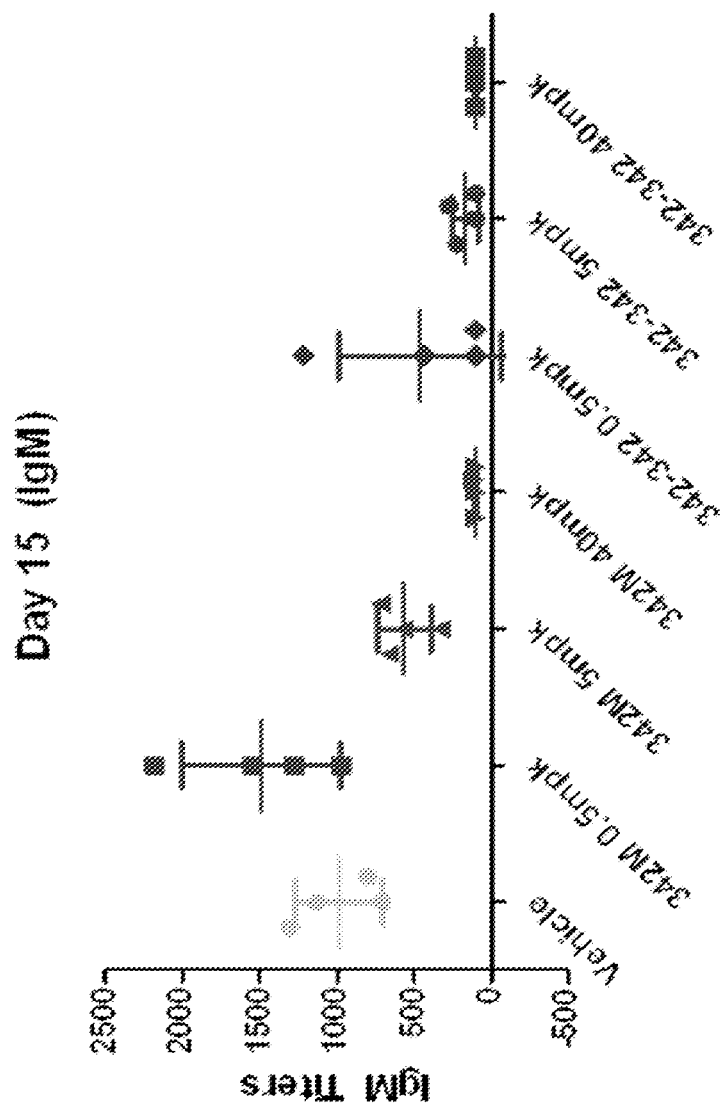
FIG. 5G shows the anti-KLH IgM titers from a KLH-specific T cell dependent antibody response (TDAR) model. 342-derived monovalent and bivalent constructs fused to HSA were assayed.
Figure 5H:
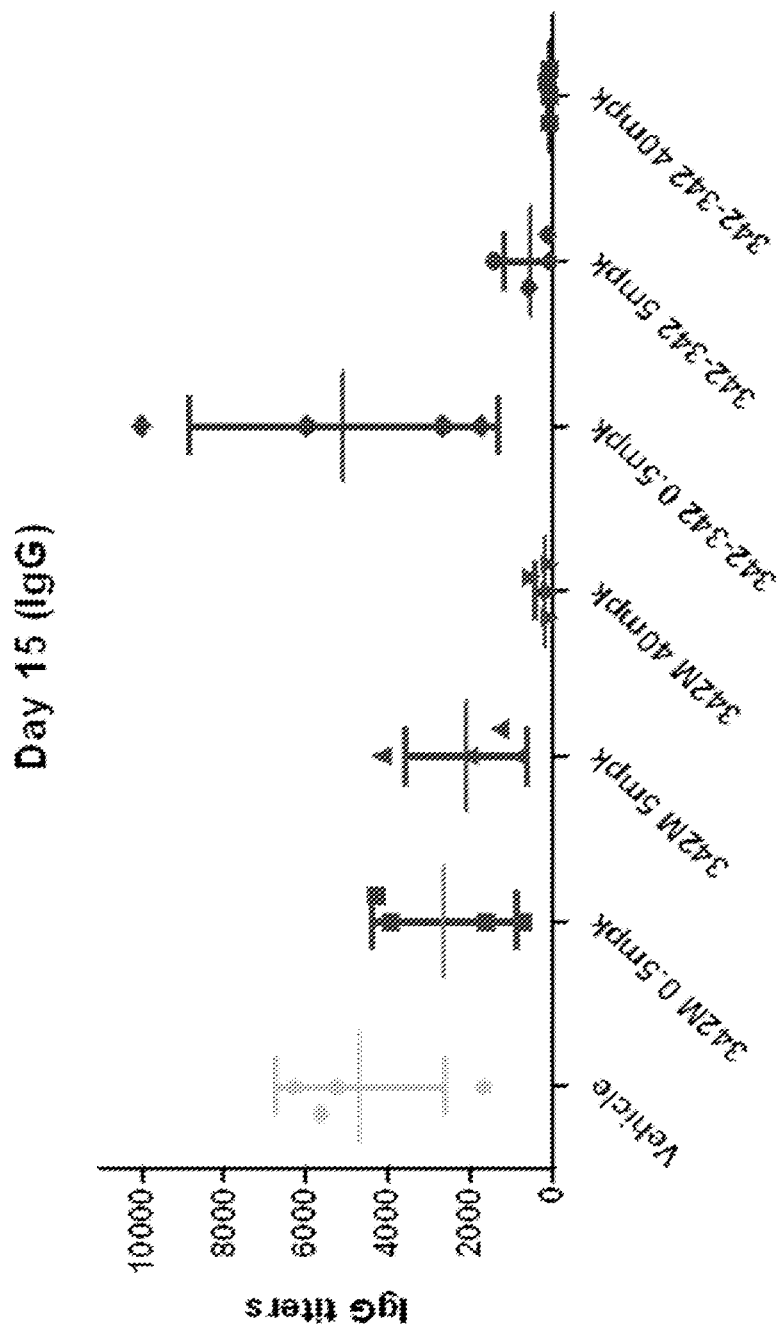
FIG. 5H shows the anti-KLH IgG titers from a KLH-specific T cell dependent antibody response (TDAR) model. 342-derived monovalent and bivalent constructs fused to HSA were assayed.

Even at 10 mg/kg M31-MSA was able to abolish the percent of GC B cells (FIG. 5B) as well as the MR1 monoclonal antibody (FIG. 5A). Other sub-populations of cells appeared normal including specific T-cell populations assuring that the results observed were not due to T cell depletion (FIG. 5C, FIG. 5D, FIG. 5E). In addition, the results from the anti-SRBC Ig ELISA data mirrored those of the germinal center B cell data (FIG. 5F). Taken together, these data indicated that the murine-specific Tn3 scaffold M31-MSA can abrogate reactions driven via CD40 signaling.

Similarly, the human CD40L-specific Tn3 scaffold 342 (342-HSA and 342-342-HSA) was used to evaluate the effects of these novel molecules in KLH-specific T cell dependent antibody response (TDAR) model in Cynomolgus Monkeys. Here, the disruption of the CD40L:CD40 axis results in suppression of antibody generation to the KLH antigen in a dose dependent manner. As shown in FIGS. 5G and 5H the 342-bivalent construct suppressed the levels of IgM and IgG antibodies at 0.5 mg/kg (mpk) and nearly complete suppression was seen at 5 mg/kg. The 342-monomer construct also suppressed the levels of IgM and IgG but at higher concentrations with nearly complete suppression seen at 40 mg/kg. These data indicated that the human-specific Tn3 scaffold constructs 342-HSA and 342-342-HSA can both abrogate reactions driven via CD40 signaling.

6.7 Human CD40L-Specific Tn3 Scaffolds do not Induce Platelet Aggregation.

Human clinical trials with anti-CD40L monoclonal antibodies were halted when thromboembolisms occurred in several patients (Davidson et al. *Arth Rheu*, 43:S271). Subsequent pre-clinical analyses suggested this to be an on-target class effect of anti-CD40L monoclonal antibodies. Thus it was important to test the human CD40L-specific Tn3 scaffolds in platelet aggregation assays.

Figure 16A:
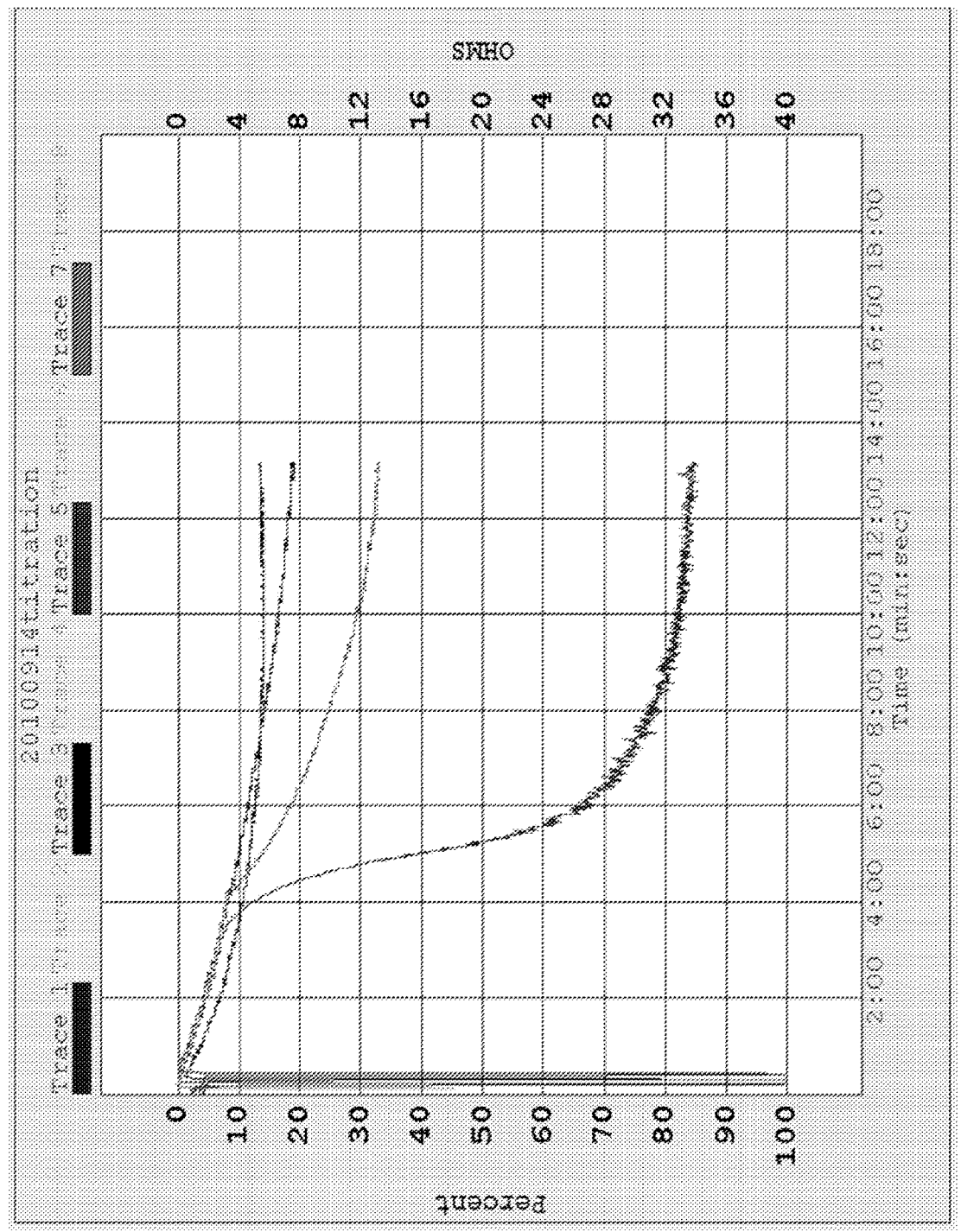
FIG. 16A shows an aggregation assay on washed platelets. The graph shows a representative ADP induced aggregation positive control for a donor (Top three traces respectively) ADP: 0.5 µM, 1 µM, and 2 µM) along with the immune complex (IC) of 5c8 monoclonal antibody (600 nM) and soluble human CD40L (200 nM).
Figure 16B:
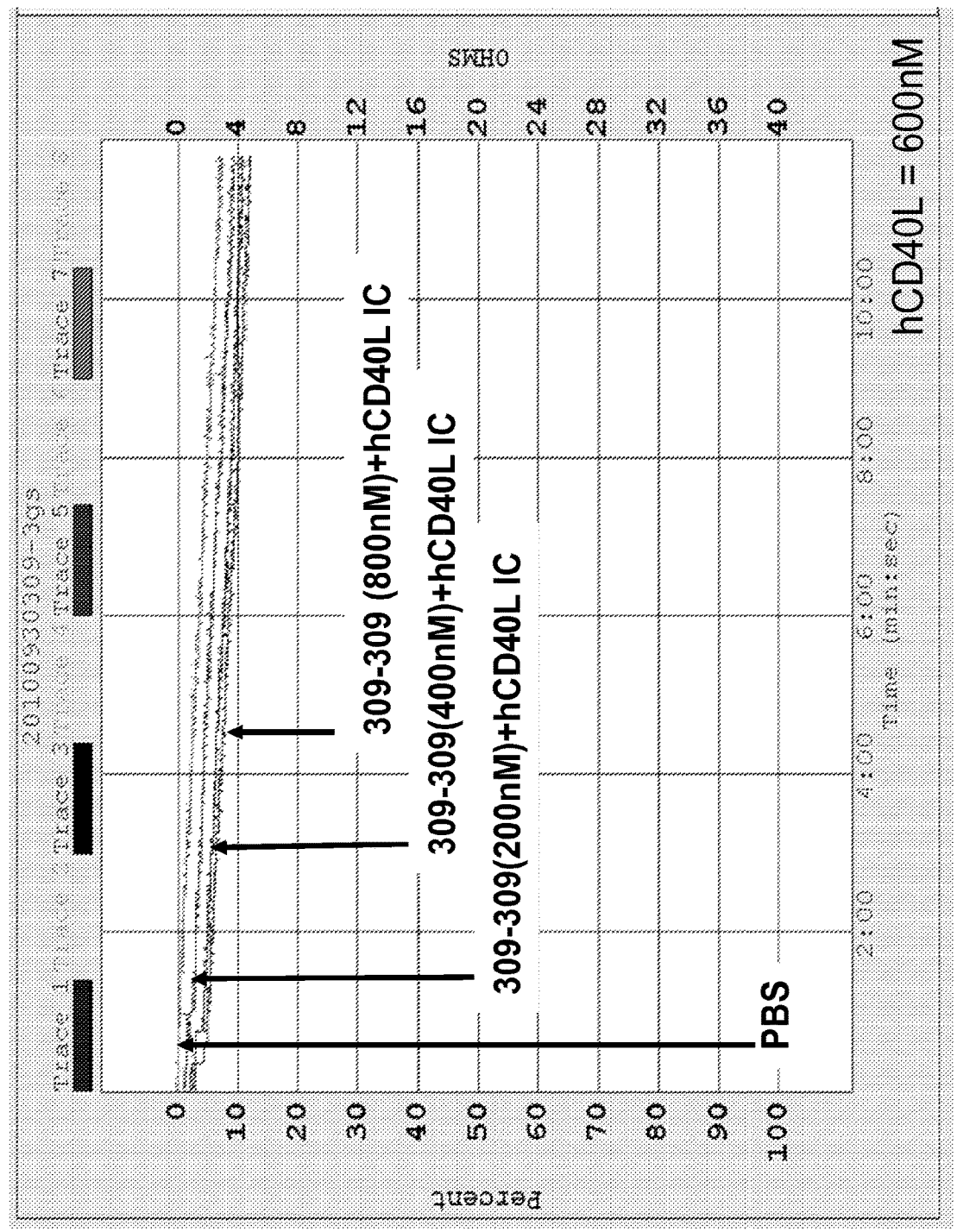
FIG. 16B shows an aggregation assay on washed platelets. The graph shows lack of aggregation when preformed immuno complexes of 309-309 bivalent scaffolds (not fused to HSA) and soluble human CD40L were used. The concentration of human CD40L (soluble form) was kept constant at 600 nM and the concentration of the scaffold constructs was varied from 200 nM to 800 nM.

When a ratio of three molecules of physiological CD40L to one molecule of the anti-CD40L monoclonal antibody was used, pro-aggregator effects were observed in citrated Platelet Rich Plasma (PRP), washed platelets, and whole blood (FIG. 16A). These effects were mediated by monoclonal antibody Fc domain dependent interactions subsequent to CD40L binding (data not shown). In the absence of the Fc domain fusion, no aggregation was observed. No aggregation was observed in multiple donors with any of the human CD40L specific Tn3 scaffolds either as dimers or as HSA fusion proteins (FIG. 16B and FIG. 16C).

Figure 8A:
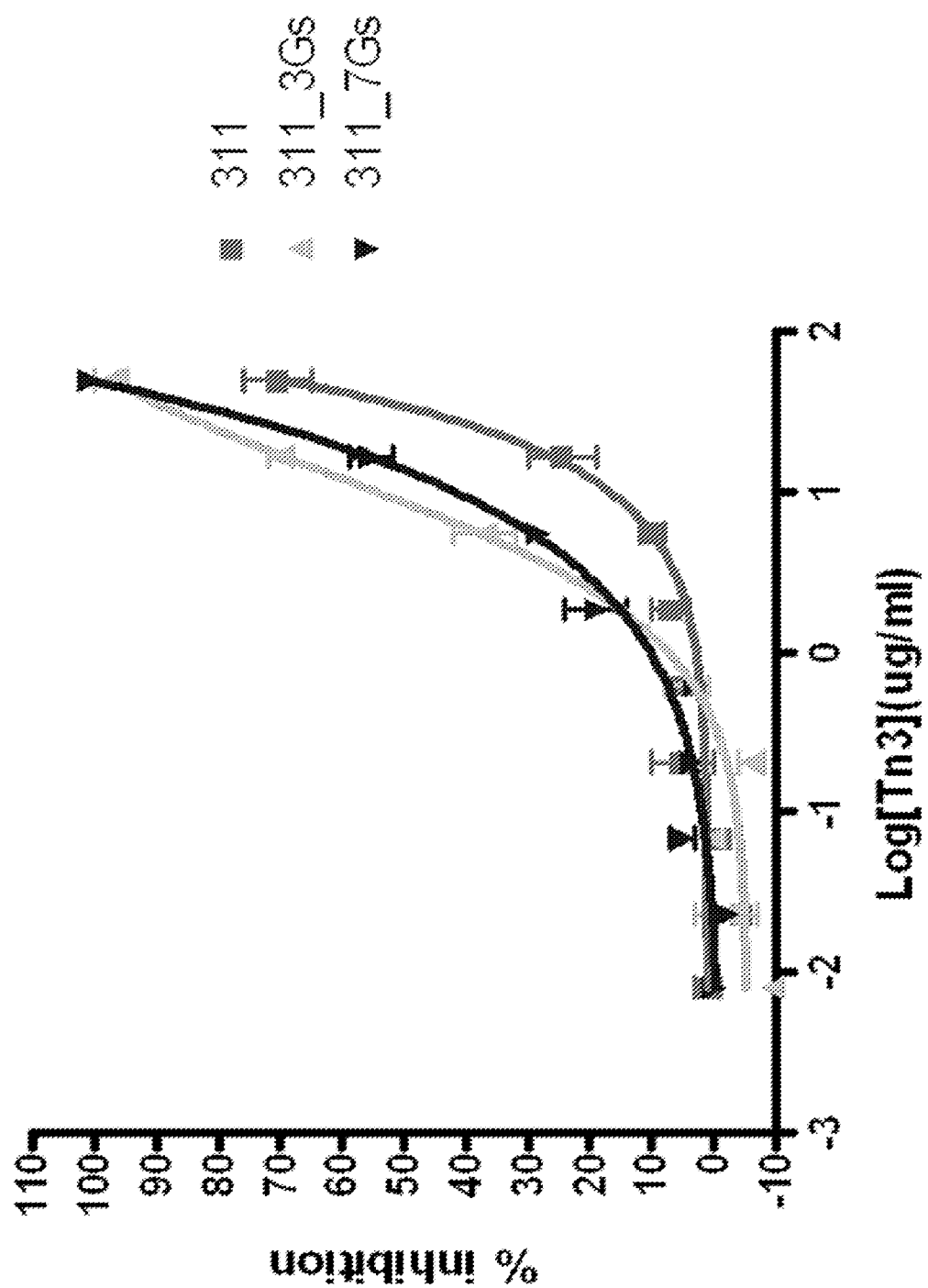
FIG. 8A shows inhibition of human CD40L-induced CD86 expression on CD19 positive human PBMCs stimulated with Jurkat D1.1 cells. Monovalent (311) and bivalent (311_3GS and 311_7GS) human CD40L-specific Tn3 scaffolds were assayed. $IC_{50}$ values for each construct are shown.
Figure 8B:
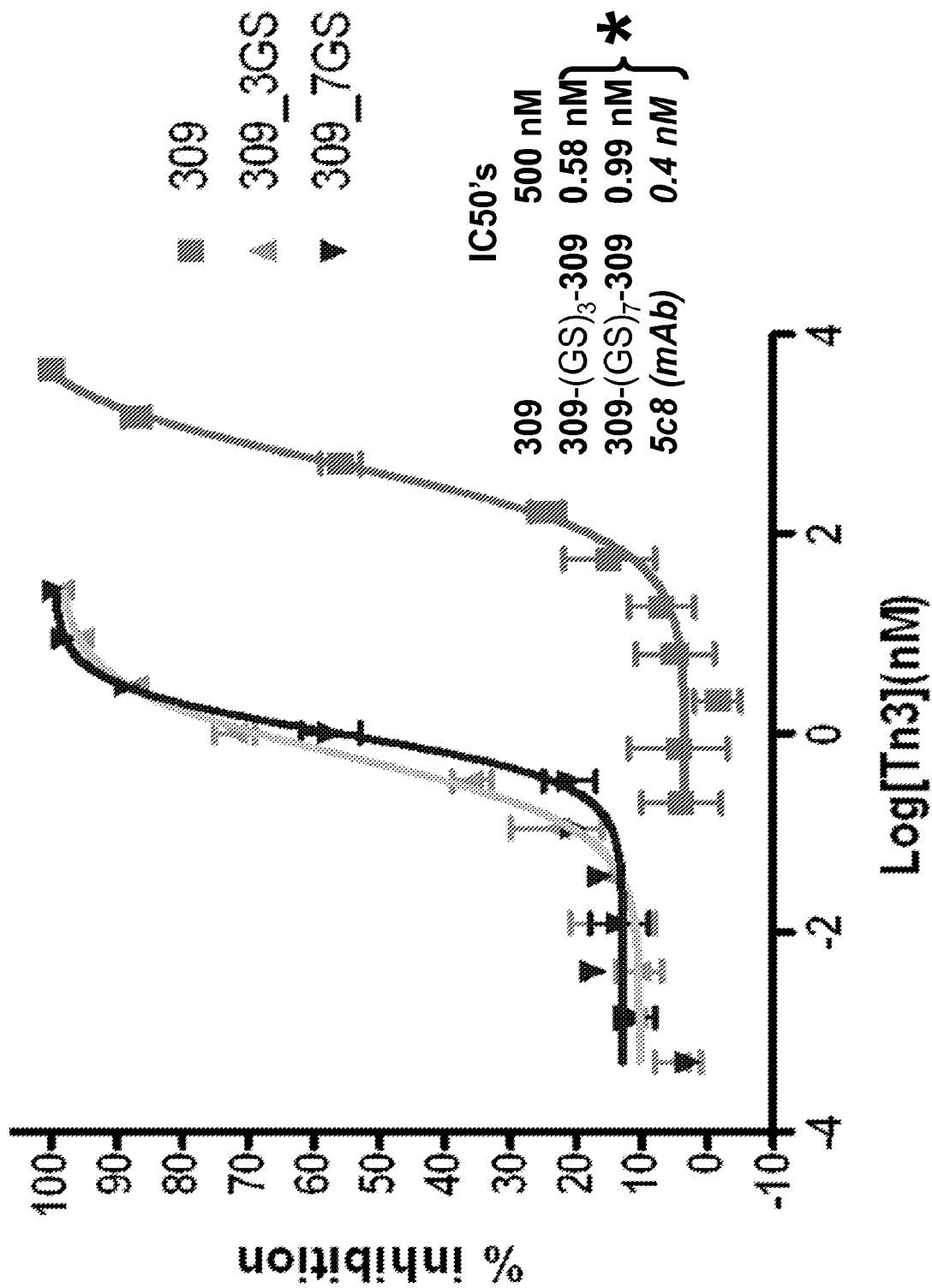
FIG. 8B shows inhibition of human CD40L-induced CD86 expression on CD19 positive human PBMCs stimulated with Jurkat D1.1 cells. Monovalent (309) and bivalent (309_3GS and 309_7GS) human CD40L-specific Tn3 scaffolds were assayed, as well as Biogen's 5c8 anti-human CD40L monoclonal antibody. $IC_{50}$ values for each construct and the antibody are shown.
Figure 16C:
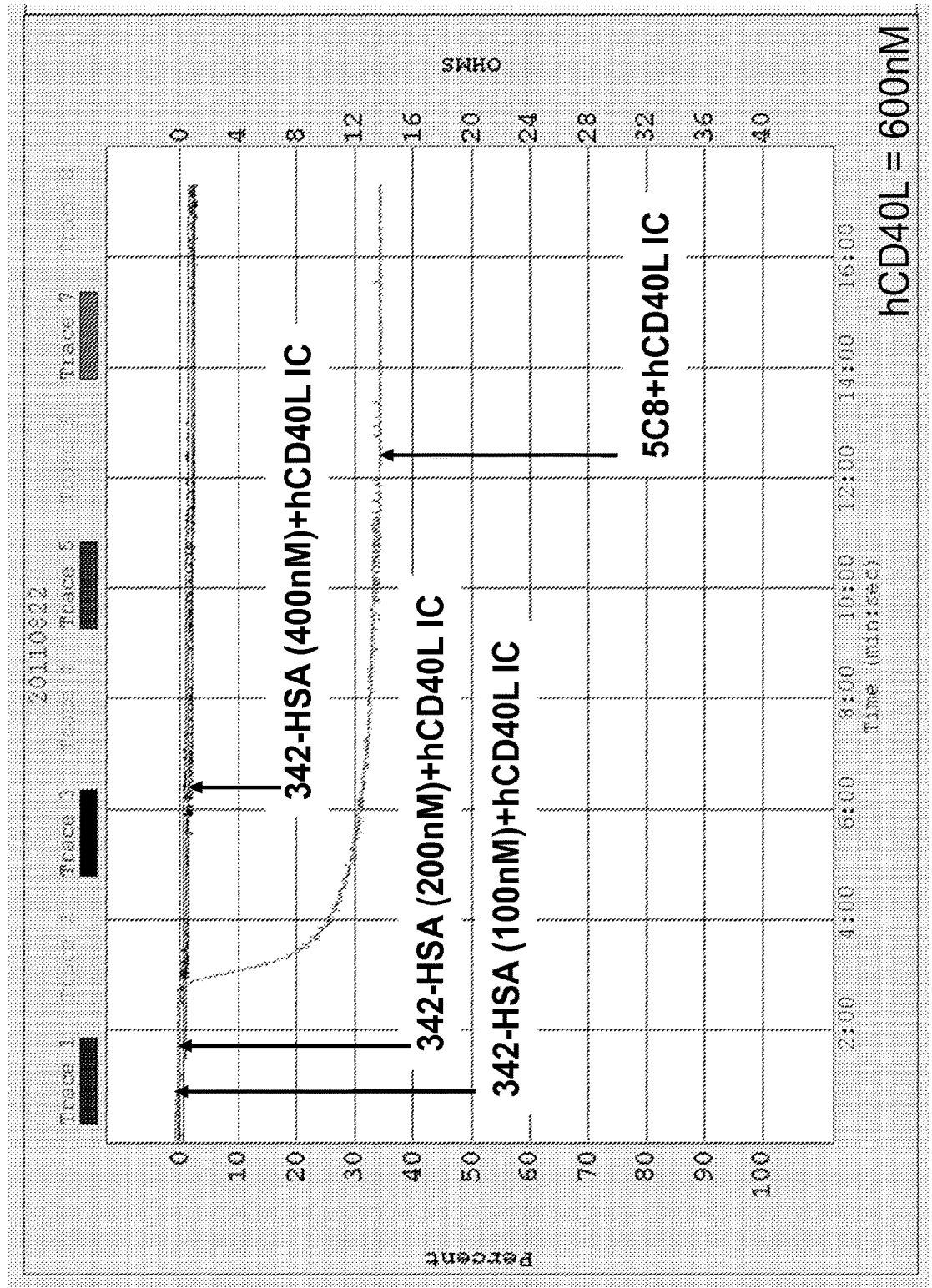
FIG. 16C an aggregation assay on washed platelets. The graph shows lack of aggregation when preformed immuno complexes of 342 monovalent scaffolds fused to HSA and soluble human CD40L were used. The concentration of human CD40L (soluble form) was kept constant at 600 nM and the concentration of the scaffold constructs was varied from 100 nM to 400 nM. The graph also shows rapid aggregation induced by the immune complex of Biogen 5c8 monoclonal antibody and soluble human CD40L.

Deleterious side-effects as observed in the clinical trials were observed by creating a soluble CD40L/anti-CD40L monoclonal antibody immunocomplex in the presence of platelets (FIG. 16A and 5C8 trace on FIG. 16C). Another example of this can be seen in the histology of the transgenic human FcγRIIa murine study (Francis et al., 2010). Upon administration of soluble CD40L/monoclonal antibody immune complexes, an abundance of thrombi was seen within the lung tissue within minutes after administration. However, when duplicated with anti-CD40L Tn3 scaffolds, normal histology was present in the lung in accordance with the control samples (data not shown).

Example 7

Fibronectin Type III Domains Engineered to Bind CD40L: Cloning, Expression, Purification, Crystallization and Preliminary X-Ray Diffraction Analysis of Two Complexes Recombinant human soluble CD40L was co-crystallized with two CD40L-specific Tn3 monomer scaffolds, 309 and 311K4E-12, both isolated as CD40L binders from phage display libraries. The crystals diffracted to 3.1 and 2.9 Å respectively. In addition, recombinant human soluble CD40L was co-crystalized with the optimized Tn3 monomer 342 alone and with both the 342 monomer and the 311K4E_12 monomer. The crystals for these structures diffracted to 2.8 and 1.9 Å respectively. The corresponding crystal structures help to understand the interaction between Tn3 scaffolds and CD40L and can be used to design higher affinity CD40L binders and tandem constructs binding multiple epitopes.

7.1 Expression and Purification of Tn3 Molecules and Human Soluble CD40L

To produce tagless Tn3 molecules for crystallization, the proteins were expressed in *E. coli* using an in-house IPTG-inducible vector designed to secrete recombinantly expressed proteins into the periplasmic space. This vector has a Ptac promoter, OppA signal peptide mutant L25/M (MTNITKRSLVAAGVLAALMAGNVAMA) (SEQ ID NO: 210), a C-terminal 8×His-tag in addition to a thrombin cleavage site. The Tn3 sequences were subcloned between signal peptide and thrombin cleavage site.

Expressed secreted His-tagged proteins were purified using Ni-NTA resin according to the manufacturer's instructions (QIAGEN®, Valencia, Calif., USA) and then cleaved by thrombin followed by Ni-NTA affinity purification again to remove the uncut intact protein and the cut His-tagged fragment. This purification step was followed by ion-exchange step using HI-TRAP® Q columns (GE Healthcare, Piscataway, N.J., USA) performed on Äkta Purifier (GE Healthcare, Piscataway, N.J., USA). The purified tagless Tn3 proteins show greater than 95% purity and homogeneity based on SDS-PAGE and SEC results.

Human soluble CD40L (113-261, UNIPROT: P29965) gene was synthesized by GENEART™ with an N-terminal 6×His-tag and was cloned into an in house mammalian expression vector under the control of the cytomegalovirus major immediate early (hCMVie) promoter (Boshart et al., Cell 41: 521-530, 1985). The CD40L gene was cloned in frame with a CD33 signal peptide. The EBNA and Ori P genes in the vector were used to increase protein expression. The CD40L gene also incorporated a SV40 poly-A sequence to allow proper processing of its mRNA 3'-end. The construct was transiently transfected into 293F suspension cells (human embryonic kidney cells [HEK] grown in 293 FREE-STYLE™ Medium and using 293FECTIN™, INVITROGEN™, Carlsbad, Calif., USA). Cells were grown using standard protocol and media was harvested after 4 and 8 days. The soluble CD40L protein was then purified using Ni-NTA resin followed by an ion-exchange step using HI-TRAP® SP FF column (GE Healthcare, Piscataway, N.J., USA) and dialysis against 50 mM Tris pH 7.5, 50 mM NaCl.

Figure 19:
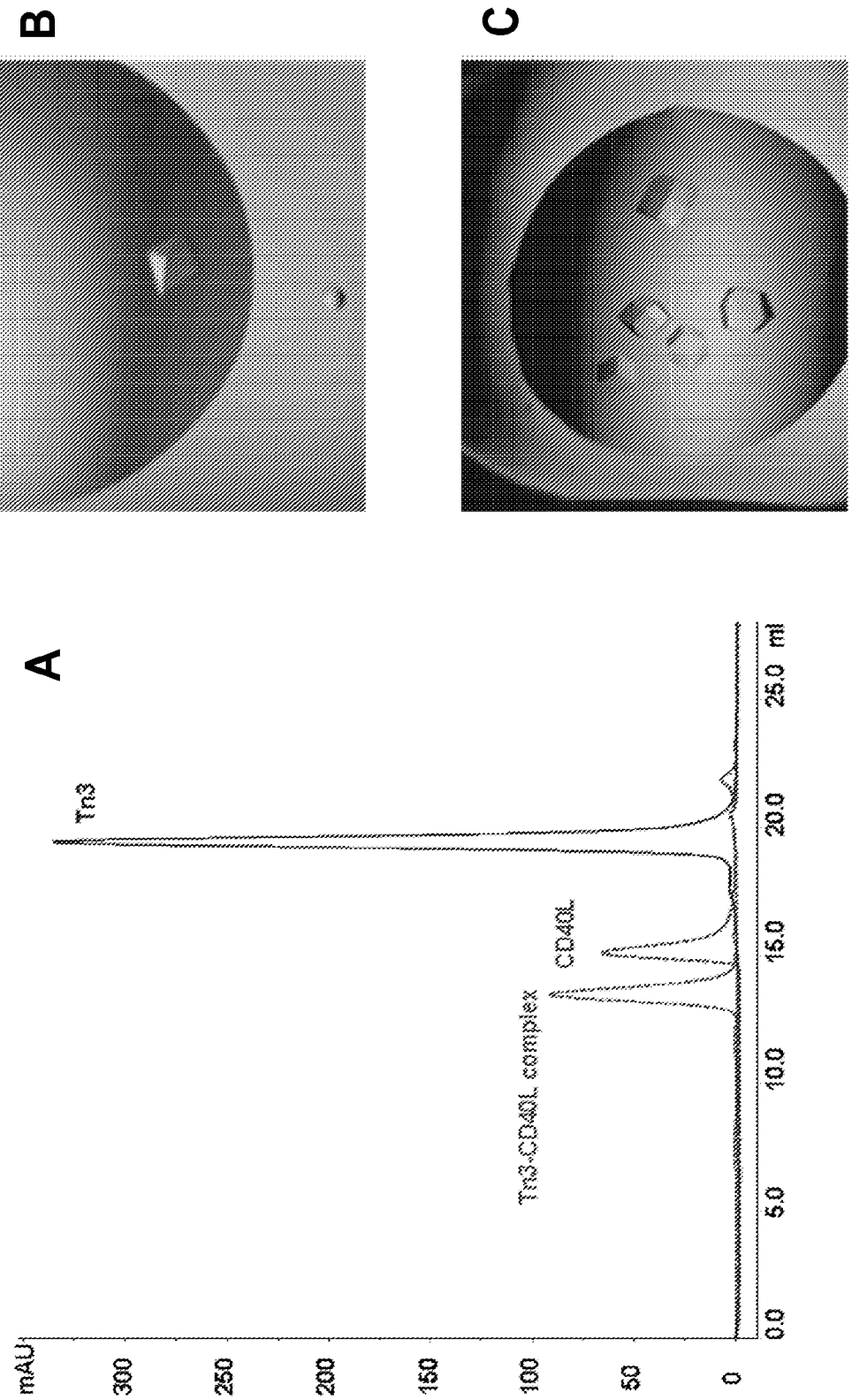
FIG. 19. Panel A shows an exemplary chromatogram of the elution of Tn3 scaffold (309 or 311K4E_12), CD40L and the complex between them off the size exclusion SUPERDEX® 200 10/300 GL column. Panel B shows crystals of the 309-CD40L complex. The crystal shown grew to dimensions up to 0.15×0.15×0.1 mm. Panel C shows crystals of the 311K4E_12-CD40L complex.

To prepare complexes the Tn3 molecule, either 309 or 311K4E_12 or 342, was mixed with CD40L in a 1.1:1 ratio, concentrated using VIVASPIN® concentrators (30,000 Da cut-off; GE Healthcare, Piscataway, N.J., USA) to approximately 10 mg/ml and subjected to size-exclusion chromatography (SEC) using SUPERDEX® 200 10/300 GL column (GE Healthcare, Piscataway, N.J., USA) pre-equilibrated with 50 mM Tris-HCl, pH 7.5, 100 mM NaCl, 0.02% NaN3 (FIG. 19, panel A). After the separation step the complex was concentrated to 18 mg/ml and subjected to crystallization. The 342-311K4E_12-CD40L complex was prepared essentially as described above using a 1.1:1.1:1 ratio of the three components.

7.2 Crystallization Screening and Optimization

Sitting drop crystallization experiments were set up in 96-well Intelli-plates (Art Robbins Instruments, Sunnyvale, Calif., USA) using a Phoenix crystallization robot (Art Robbins Instruments, Sunnyvale, Calif., USA) by mixing 300 nL volumes of well solution and protein complex solution in the drop compartment and letting it equilibrate against 50 μL of well solution. Commercial crystallization screens from Hampton Research (Aliso Viejo, Calif., USA), Emerald BioSystems (Bainbridge Island, Wash., USA) and Molecular Dimensions (Apopka, Fla., USA) were used.

Crystallization of the 309-CD40L, 342-CD40L and 342-311K4E_12-CD40L complexes each required an optimization step which included additional screening using Additive Screen HT (Hampton Research, Aliso Viejo, Calif., USA). In the optimization step the well solution of the 96-well plate was filled with 80% of successful solution from the initial screening and 20% of respective additive. The drop was made of 300 nL of protein solution and 300 nL of the new well solution after thorough mixing of the latter. The diffraction quality crystals were harvested directly from 96-well plate. For cryo-preservation the crystal was transferred into three consecutive solutions of mother liquor with increasing glycerol concentrations.

The diffraction quality 311-CD40L crystals grew at the initial screen out of solution that did not require addition of cryo agent.

7.3 X-Ray Diffraction and Data Collection

X-ray diffraction patterns for the 309-CD40L complex were collected from single crystal at the Beamline 5.0.3 of the Advanced Light Source in Lawrence Berkeley National Laboratory (University of California, Berkeley) equipped with ADSC Q315R CCD X-Ray detector (Area Detector Systems Corporation, Poway, Calif., USA). 360 consecutive images with oscillation range of 0.5° were collected at crystal-to-detector distance of 300 mm and an exposure time of 0.8 seconds.

X-ray diffraction patterns for the 311K4E_12-CD40L, 342-CD40L and 342-311K4E_12-CD40L complexes were collected from single crystals at the Beamline 31-ID-D of the Advanced Photon Source in Argonne National Laboratory (University of Chicago, Chicago, Ill.) equipped with a Rayonix 225 HE detector (Rayonix LLC, Evanston, Ill., USA). 180 consecutive images with oscillation range of 1° were collected at crystal-to-detector distance of 300 mm and an exposure time of 0.8 seconds.

Reduction and scaling for all data sets were performed using HKL2000 suite (Otwinowski & Minor, Methods in Enzymology, 276:307-326. 1997).

7.4 Results and Discussion

The most reproducible crystallization condition of the 309-CD40L complex appeared to be B5 (0.2 M NaNO$_3$, 20% PEG3350) in Peg/Ion Screen (Hampton Research). Further optimization with Additive Screen yielded diffraction quality crystal from the A1 condition (0.1M BaCl2.2H2O). The crystal shown in FIG. 19, panel B was harvested from a 96-well plate, and cooled in liquid Nitrogen after transfer to the mother liquor solution supplemented with 20% Glycerol.

Space group symmetry: The crystal belonged to orthorhombic space group P212121 with cell parameters a=85.69 Å, b=90.64 Å, c=95.56 Å and diffracted to 3.1 Å. The asymmetric unit is expected to contain a trimer of CD40L and three 309 molecules with VM value about 2.3 Å3/Da.

For the 311K4E_12-CD40L crystallization the Cryo I & II screen (Emerald BioStructures) yielded number of conditions which required neither optimization nor cryo preservation. A single crystal (FIG. 19, panel C) from condition F7 (40% PEG 600, 0.1M CH3COONa, 0.2M MgCl2) was used for data collection.

Space group symmetry: The crystal belonged to cubic space group P213 with cell parameter 97.62 Å and diffracted to 2.6 Å. The asymmetric unit contains one CD40L and one 311K4E_12 molecule with VM value about 2.9 Å3/Da.

342-CD40L space group symmetry: The crystal belonged to space group P321 with cell parameters a=93.53 Å, b=93.53 Å, c=66.69 Å, resolution 2.8 Å. The asymmetric unit contains one CD40L monomer and one 342 monomer.

342-311K4E_12-CD40L space group symmetry: The crystal belonged to space group P21 with cell parameters a=80.32 Å, b=143.48 Å, c=111.27 Å, 3=98.22°, resolution 1.9 Å. The asymmetric unit contains two CD40 trimers, six 342 monomers, and six 311K4E-12 monomers.

Data statistics for all the structures are shown in TABLE 10.

TABLE 10

| X-Ray data collection statistics. | | |
|---|---|---|
|  | 309-CD40L | 311K4E-12 |
| Wavelength, Å | 0.9793 | 0.9793 |
| Resolution, Å | 50.0-3.05 (3.16-3.05)$^a$ | 50.0-2.94 |
| Space group | P2$_1$2$_1$2$_1$ | P2$_1$3 |
| Cell parameters, Å | a = 85.69, b = 90.64, c = 95.56 | a = 97.62 |
| Total reflections | 94,024 | 128,140 |
| Unique reflections | 14,555 | 6720 |
| Average redundancy | 6.5 (6.4)$^a$ | 19.2 (19.7) |
| Completeness, % | 100.0 (100.0)$^a$ | 99.4 (100.0) |
| R$_{sym}$ | 0.097 (0.443)$^a$ | 0.114 (0.785) |
| Mean I/σ (I) | 17.2 (4.6)$^a$ | 20.1 (2.4) |
|  | 342-CD40L | 342-311K4E_12-CD40L |
| Wavelength, Å | 0.9793 | 0.9793 |
| Resolution, Å | 50.0-2.8 (2.83-2.82)$^a$ | 144.5-1.9 (1.96-1.95)$^a$ |
| Space group | P321 | P2$_1$ |
| Cell parameters, Å | a = 93.53, b = 93.53, c = 66.69 | a = 80.32, b = 143.48, c = 111.27, β = 98.22° |
| Total reflections | 66,038 (549)$^a$ | 733,814 (1806)$^a$ |
| Unique reflections | 8,406 (88)$^a$ | 179,232 (1806)$^a$ |

TABLE 10-continued

X-Ray data collection statistics.

| Average redundancy | 7.9 (6.2)[a] | 4.1 (4.2)[a] |
|---|---|---|
| Completeness, % | 99.9 (100.0)[a] | 99.7 (99.6)[a] |
| $R_{sym}$ | 0.19 (0.79)[a] | 0.06 (0.57)[a] |
| Mean I/σ (I) | 8.1 (1.4)[a] | 14.5 (3.0)[a] |

[a]Values in parentheses correspond to the highest resolution shell

Figure 17A:
FIG. 17A shows a ribbon representation of the crystal structure of soluble CD40L in a complex with the CD40L-specific Tn3 309 monomer scaffold. CD40L forms a trimer (polypeptides A, B and C). Each 309 scaffold (polypeptides D, E and F, circled) makes contact with two CD40L polypeptides. The specific contacts between each 309 scaffold and the first and second CD40L polypeptides are listed. This is a "top-down" view of the structure.

CD40L formed a trimer (polypeptides A, B, and C in FIG. 17A). Each 309 Tn3 scaffold (polypeptides D, E, and F in FIG. 17A) made contact with two CD40L polypeptides. The crystal structure revealed that there are six specific contacts between each 309 scaffold and the first and second CD40L polypeptides. Aspartic acid 17 in the BC makes contact with threonine 251 in the first CD40L. Glutamic acid 18 in the BC loop makes contact with arginine 203 in the first CD40L and with isoleucine 204 in the second CD40L. Serine 47 in the DE loop makes contact with histidine 249 in the first CD40L. Tryptophan 49 in the DE loop makes contact with valine 247 in the first CD40L. Aspartic acid 70 in the FG loop makes contact with serine 185 in the second CD40L (see FIG. 17A). CD40L amino acid residues contacting the 311 scaffold are also shown in FIG. 18A.

Figure 17B:
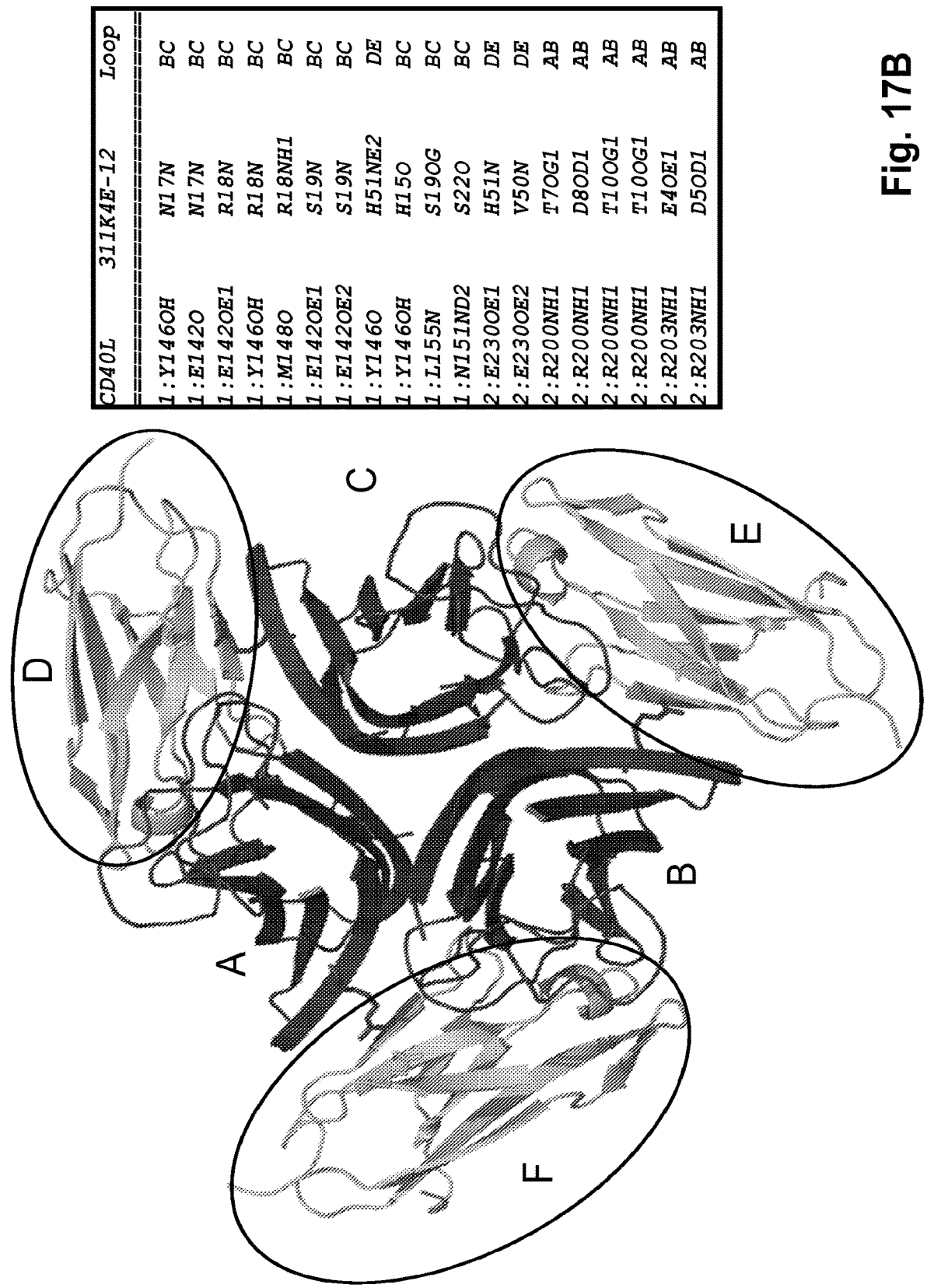
FIG. 17B shows a ribbon representation of the crystal structure of soluble CD40L in a complex with the CD40L-specific Tn3 311K4E_12 monomer scaffold. CD40L forms a trimer (polypeptides A, B and C). Each 311K4E_12 monomer scaffold (polypeptides D, E and F, circled) makes contact with two CD40L polypeptides. The specific contacts between each 311K4E_12 monomer scaffold and the first and second CD40L polypeptides are listed. This is a "top-down" view of the structure.

An in the case of 309, each 311K4E_12 monomer scaffold (polypeptides A, B, and C in FIG. 17B) makes contact with two CD40L polypeptides. The crystal structure revealed that there are 19 specific contacts between each 311K4E_12 scaffold and the first and second CD40L polypeptides. Asparagine 17 in the BC loop makes contacts with tyrosine 146 and glutamic acid 142 in the first CD40L. Arginine 18 in the BC loop makes contact with glutamic acid 142, tyrosine 146, and methionine 148 in the first CD40L. Serine 19 in the BC loop makes contact with glutamic acid 142 and leucine 155 in the first CD40L. Serine 22 in the BC loop makes contact with asparagine 151 in the first CD40L. Histidine 15 in the BC loop makes contact with tyrosine 146 in the first CD40L. Histidine 51 in the DE loop makes contact with tyrosine 146 in the first CD40L and with glutamic acid 230 in the second CD40L. Valine 50 in the DE loop makes contact with glutamic acid 230 in the second CD40L. The N-terminal region of the 311K4E_12 monomer scaffold is connected to the second CD40L. Arginine 200 in the second CD40L makes contact with threonine 7, aspartic acid 8, and threonine 10 in the N-terminal region of 311K4E_12. Arginine 203 in the second CD40L makes contact with glutamic acid 4 and aspartic acid 5. CD40L amino acid residues contacting the 309 scaffold are also shown in FIG. 18B.

Figure 17C:
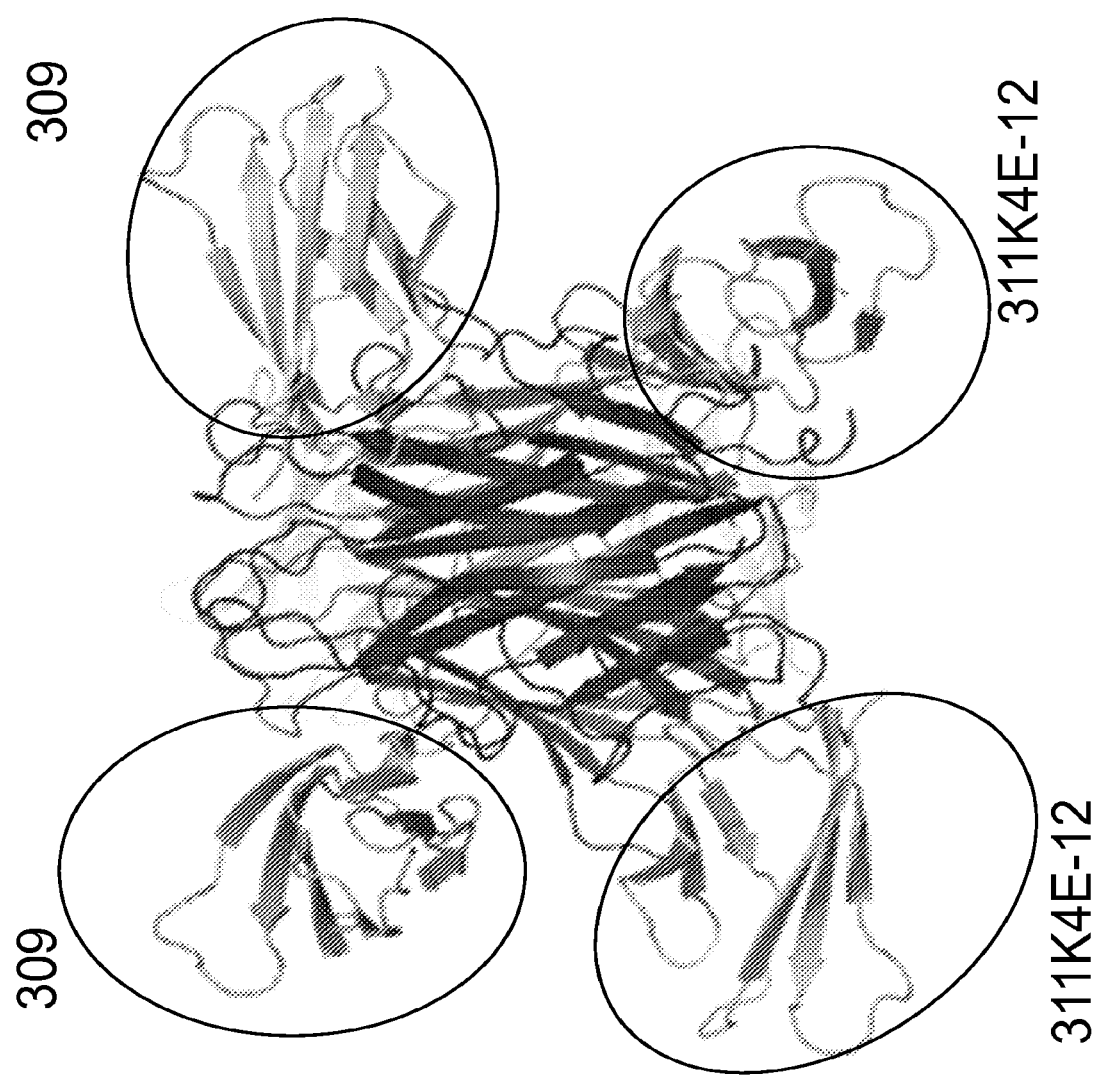
FIG. 17C shows a ribbon representation illustrating that the 311K4E_12 and 309 scaffolds (circled) bind to different epitopes located in different parts of the CD40L trimer complex. Both scaffolds bind in the same groove that would interact with the CD40 receptor. This is a "side" view of the structure.
Figure 17D:
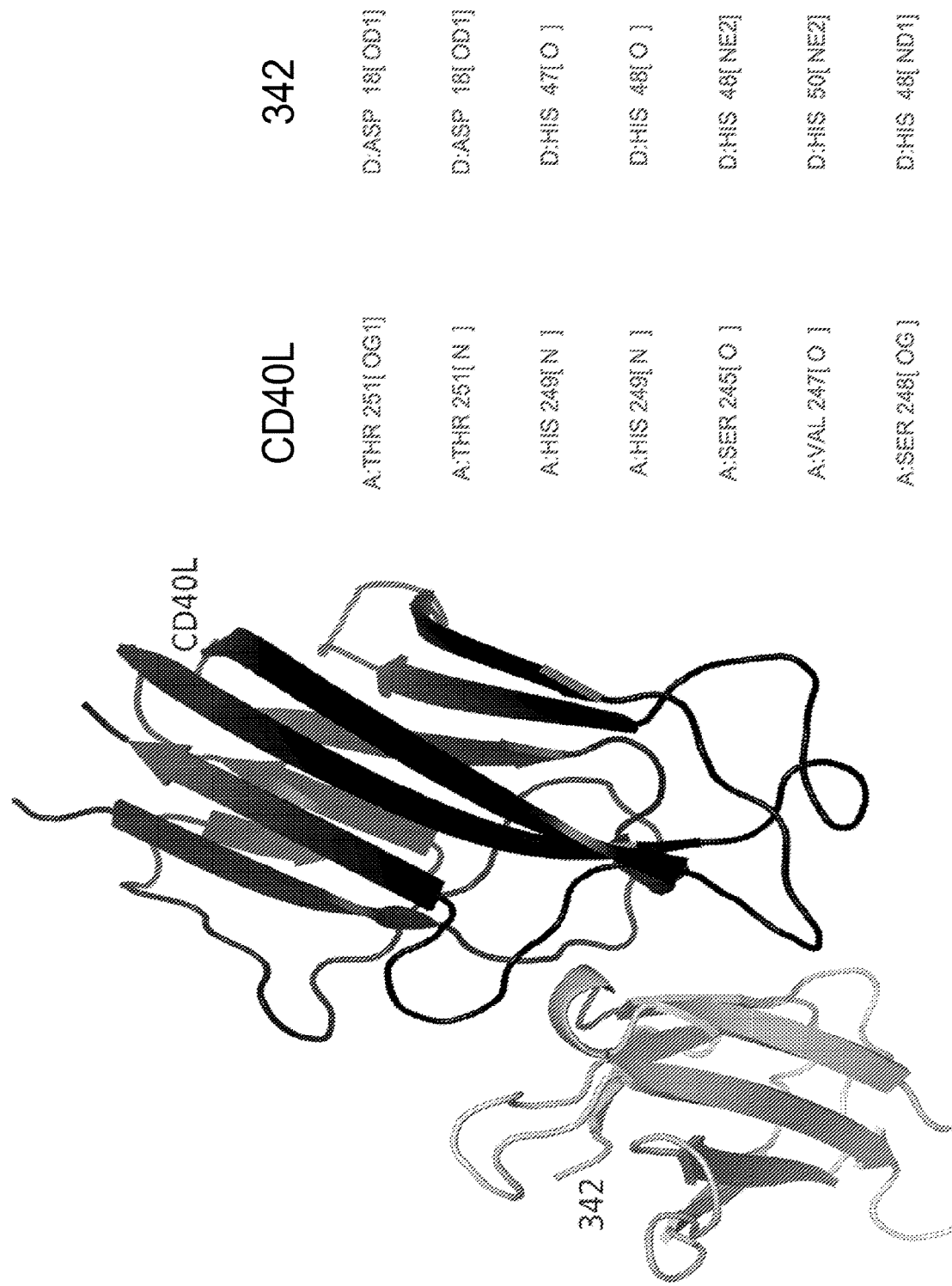
FIG. 17D shows a ribbon representation of the crystal structure of soluble CD40L in a complex with the CD40L-specific Tn3 342 monomer scaffold. Only one CD40L and one 342 monomer scaffold are shown. The specific contacts between the 342 monomer scaffold and the first CD40L polypeptides are listed.
Figure 17E:
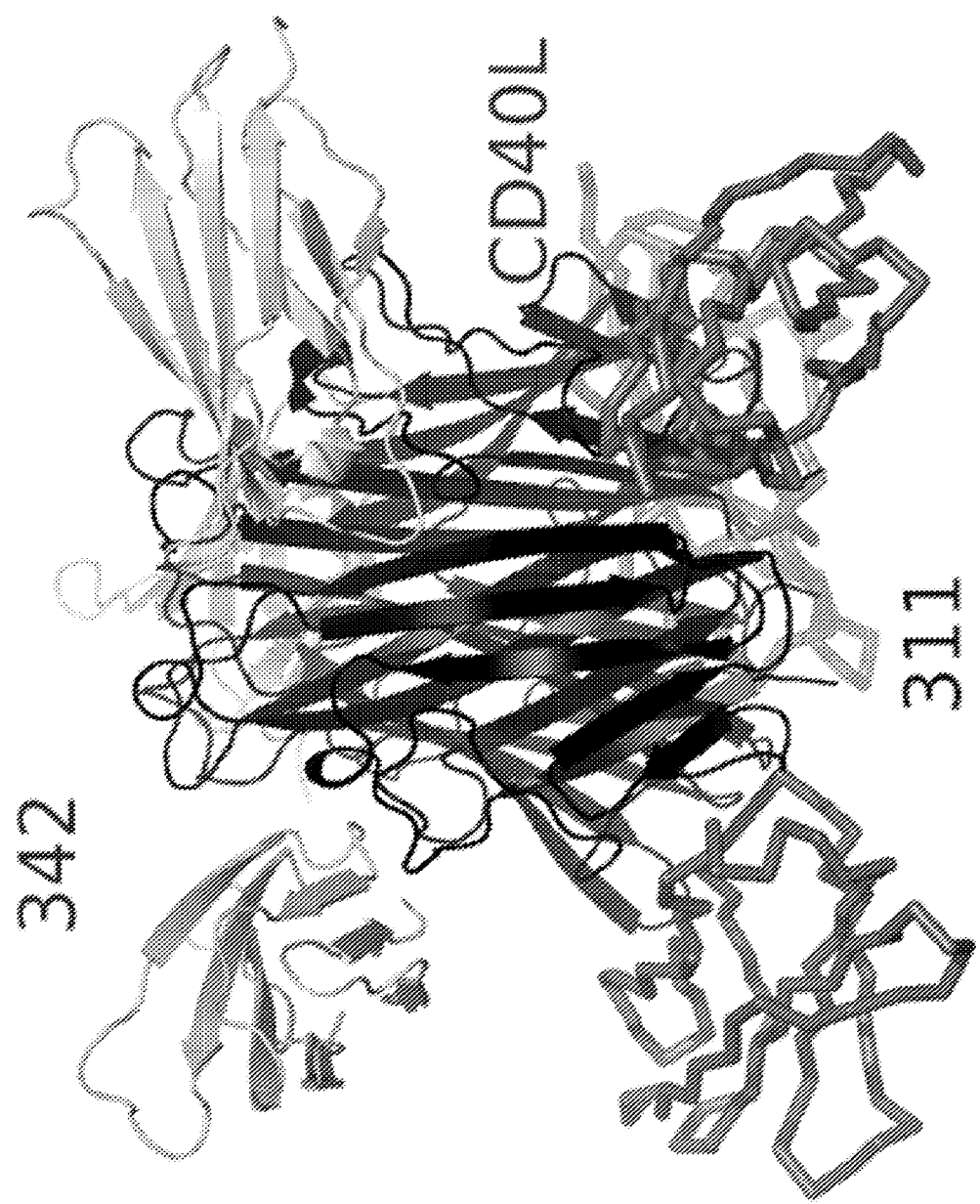
FIG. 17E shows a ribbon representation illustrating that the 342 and 311K4E_12 scaffolds can bind simultaneously to different epitopes located in different parts of the CD40L trimer complex. Both scaffolds bind in the same groove that would interact with the CD40 receptor. This is a "side" view of the structure.

The crystal structures of CD40L in complexes with 309 and 311K4E_12 showed that the 311K4E_12 and 309 monomer scaffolds bind to different epitopes located in different parts of the CD40L trimer complex (FIG. 17C). The structures showed that both scaffolds bind in the same groove that would interact with the CD40 receptor.

The crystal structure of a 342 with CD40L is provided in FIG. 20 and shows that while 342 binds on the same part of CD40L specific changes in the contact residues are seen as compared to the parental 309 clone. Specifically, in 342 aspartate 18 in the BC loop makes contact with threonine 251 of CD40L and histidine 47 of the DE loop makes contact with histidine 249 of CD40L, histidine 48 of the DE loop makes contact with histidine 249, serine 245 and serine 248 of CD40L, and histidine 50 of the DE loop makes contact with valine 247 of CD40L.

The crystal structure of a 342 and 311K4E_12 with CD40L demonstrates that both scaffolds can bind simultaneously to their respective epitopes which are located in different parts of the CD40L trimer complex (FIG. 21). The contacts for each of the separate scaffolds (as described above) are maintained.

The examples shown above illustrate various aspects of the invention and practice of the methods of the invention. These examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

```
SEQUENCES
CD40L sp|P29965|CD40L_HUMAN - Membrane form
Cytoplasmic domain = 1-20
Signal anchor type II membrane protein region = 21-46
Soluble form = 113-261
                                              SEQ ID NO: 1
MIETYNQTSPRSAATGLPISMKIFMYLLTVFLITQMIGSALFAVYLHRRLDKIEDERNLH

EDFVFMKTIQRCNTGERSLSLLNCEEIKSQFEGFVKDIMLNKEETKKENSFEMQKGDQNP

QIAAHVISEASSKTTSVLQWAEKGYYTMSNNLVTLENGKQLTVKRQGLYYIYAQVTFCSN

REASSQAPFIASLCLKSPGRFERILLRAANTHSSAKPCGQQSIHLGGVFELQPGASVFVN

VTDPSQVSHGTGFTSFGLLKL

CD40L-Soluble form, corresponds also to the co-crystallized
construct
                                              SEQ ID NO: 2
MQKGDQNPQIAAHVISEASSKTTSVLQWAEKGYYTMSNNLVTLENGKQLTVKRQGLYYIY

AQVTFCSNREASSQAPFIASLCLKSPGRFERILLRAANTHSSAKPCGQQSIHLGGVFELQ

PGASVFVNVTDPSQVSHGTGFTSFGLLKL
```

-continued

Tn3 (with unmodified loops)
SEQ ID No: 3
IEVKDVTDTTALITWFKPLAEIDGCELTYGIKDVPGDRTTIDLTEDENQYSIGNLKPDTE

YEVSLICRRGDMSSNPAKETFTT

3rd FnIII of tenascin C, AB loop (Tn3)
SEQ ID NO: 4
KDVTDTT

3rd FnIII of tenascin C, BC loop (Tn3)
SEQ ID NO: 5
FKPLAEIDG

3rd FnIII of tenascin C, CD loop (Tn3)
SEQ ID NO: 6
KDVPGDR

3rd FnIII of tenascin C, DE loop (Tn3)
SEQ ID NO: 7
TEDENQ

3rd FnIII of tenascin C, EF loop (Tn3)
SEQ ID NO: 8
GNLKPDTE

3rd FnIII of tenascin C, FG loop (Tn3); also in 309FGwt,
340, 341, 342, 343, 344, 345, 346, 347, 348, and 349 clones
SEQ ID NO: 9
RRGDMSSNPA 3rd FnIII of tenascin C, beta strand A (Tn3)
SEQ ID NO: 10
RLDAPSQIEV 3rd FnIII of tenascin C, beta strand A (Tn3) N-terminal
truncation
SEQ ID NO: 11
IEV 3rd FnIII of tenascin C, beta strand B (Tn3)
SEQ ID NO: 12
ALITW 3rd FnIII of tenascin C, beta strand C (Tn3 variant)
SEQ ID NO: 13
CELAYGI 3rd FnIII of tenascin C, beta strand C (Tn3)
SEQ ID NO: 14
CELTYGI 3rd FnIII of tenascin C, beta strand D (Tn3)
SEQ ID NO: 15
TTIDL 3rd FnIII of tenascin C, beta strand E (Tn3)
SEQ ID NO: 16
YSI 3rd FnIII of tenascin C, beta strand F (Tn3)
SEQ ID NO: 17
YEVSLIC 3rd FnIII of tenascin C, beta strand G (Tn3)
SEQ ID NO: 18
KETFTT Clone 309 - Parental clone isolated from naiive Tn3 library
SEQ ID NO: 19
AIEVKDVTDTTALITWSDEFGHYDGCELTYGIKDVPGDRTTIDLWWHSAWYSIGNLKPDT

EYEVSLICYTDQEAGNPAKETFTTGGGTLGHHHHHHHH

Clone 309 - Parental clone isolated from naiive Tn3 library
(w/o N-term A, and C-term linker and His8 tag)
SEQ ID NO: 20
IEVKDVTDTTALITWSDEFGHYDGCELTYGIKDVPGDRTTIDLWWHSAWYSIGNLKPDTE

YEVSLICYTDQEAGNPAKETFTT

-continued

Clone 309FGwt - Parental clone with "humanized" FG loop
SEQ ID NO: 21
AIEVKDVTDTTALITWSDEFGHYDGCELTYGIKDVPGDRTTIDLWWHSAWYSIGNLKPDT

EYEVSLICRRGDMSSNPAKETFTTGGGTLGHHHHHHHH

Clone 309FGwt - Parental clone with "humanized" FG loop
(w/o N-term A, and C-term linker and His8 tag)
SEQ ID NO: 22
IEVKDVTDTTALITWSDEFGHYDGCELTYGIKDVPGDRTTIDLWWHSAWYSIGNLKPDTE

YEVSLICRRGDMSSNPAKETFTT

Clone 340 - Affinity Mature variant
SEQ ID NO: 23
AIEVKDVTDTTALITWSDDFDNYEWCELTYGIKDVPGDRTTIDLWYHMAWYSIGNLKPDT

EYEVSLICRRGDMSSNPAKETFTTGGGTLGHHHHHHHH

Clone 340 - Affinity Mature variant (w/o N-term A, and
C-term linker and His8 tag)
SEQ ID NO: 24
IEVKDVTDTTALITWSDDFDNYEWCELTYGIKDVPGDRTTIDLWYHMAWYSIGNLKPDTE

YEVSLICRRGDMSSNPAKETFTT

Clone 341 - Affinity Mature variant
SEQ ID NO: 25
AIEVKDVTDTTALITWSDDFADYVWCELTYGIKDVPGDRTTIDLWWHSAWYSIGNLKPDT

EYEVSLICRRGDMSSNPAKETFTTGGGTLGHHHHHHHH

Clone 341 - Affinity Mature variant (w/o N-term A, and
C-term linker and His8 tag)
SEQ ID NO: 26
IEVKDVTDTTALITWSDDFADYVWCELTYGIKDVPGDRTTIDLWWHSAWYSIGNLKPDTE

YEVSLICRRGDMSSNPAKETFTT

Clone 342 - Affinity Mature variant (w/WT FG loop)
SEQ ID NO: 27
AIEVKDVTDTTALITWSDDFGEYVWCELTYGIKDVPGDRTTIDLWYHHAHYSIGNLKPDT

EYEVSLICRRGDMSSNPAKETFTTGGGTLGHHHHHHHH

Clone 342 - Affinity Mature variant (w/WT FG loop;
w/o N-term A, and C-term linker and His8 tag)
SEQ ID NO: 28
IEVKDVTDTTALITWSDDFGEYVWCELTYGIKDVPGDRTTIDLWYHHAHYSIGNLKPDTE

YEVSLICRRGDMSSNPAKETFTT

Clone 343 - Affinity Mature variant
SEQ ID NO: 29
AIEVKDVTDTTALITWLDDWGSYHVCELTYGIKDVPGDRTTIDLWYHQAWYSIGNLKPDT

EYEVSLICRRGDMSSNPAKETFTTGGGTLGHHHHHHHH

Clone 343 - Affinity Mature variant (w/o N-term A, and
C-term linker and His8 tag)
SEQ ID NO: 30
IEVKDVTDTTALITWLDDWGSYHVCELTYGIKDVPGDRTTIDLWYHQAWYSIGNLKPDTE

YEVSLICRRGDMSSNPAKETFTT

Clone 344 - Affinity Mature variant
SEQ ID NO: 31
AIEVKDVTDTTALITWSDEVGDYVVCELTYGIKDVPGDRTTIDLWYHMAWYSIGNLKPDT

EYEVSLICRRGDMSSNPAKETFTTGGGTLGHHHHHHHH

Clone 344 - Affinity Mature variant (w/o N-term A, and
C-term linker and His8 tag)
SEQ ID NO: 32
IEVKDVTDTTALITWSDEVGDYVVCELTYGIKDVPGDRTTIDLWYHMAWYSIGNLKPDTE

YEVSLICRRGDMSSNPAKETFTT

-continued

Clone 345 - Affinity Mature variant
SEQ ID NO: 33
AIEVKDVTDTTALITWSDDFAEYVGCELTYGIKDVPGDRTTIDLWWHSAWYSIGNLKPDT

EYEVSLICRRGDMSSNPAKETFTTGGGTLGHHHHHHHH

Clone 345 - Affinity Mature variant (w/o N-term A, and
C-term linker and His8 tag)
SEQ ID NO: 34
IEVKDVTDTTALITWSDDFAEYVGCELTYGIKDVPGDRTTIDLWWHSAWYSIGNLKPDTE

YEVSLICRRGDMSSNPAKETFTT

Clone 346 - Affinity Mature variant
SEQ ID NO: 35
AIEVKDVTDTTALITWSDDFEEYVVCELTYGIKDVPGDRTTIDLWWHSAWYSIGNLKPDT

EYEVSLICRRGDMSSNPAKETFTTGGGTLGHHHHHHHH

Clone 346 - Affinity Mature variant (w/o N-term A, and
C-term linker and His8 tag)
SEQ ID NO: 36
IEVKDVTDTTALITWSDDFEEYVVCELTYGIKDVPGDRTTIDLWWHSAWYSIGNLKPDTE

YEVSLICRRGDMSSNPAKETFTT

Clone 347 - Affinity Mature variant
SEQ ID NO: 37
AIEVKDVTDTTALITWSDEVGQYVGCELTYGIKDVPGDRTTIDLWYHMAWYSIGNLKPDT

EYEVSLICRRGDMSSNPAKETFTTGGGTLGHHHHHHHH

Clone 347 - Affinity Mature variant (w/o N-term A, and
C-term linker and His8 tag)
SEQ ID NO: 38
IEVKDVTDTTALITWSDEVGQYVGCELTYGIKDVPGDRTTIDLWYHMAWYSIGNLKPDTE

YEVSLICRRGDMSSNPAKETFTT

Clone 348 - Affinity Mature variant
SEQ ID NO: 39
AIEVKDVTDTTALITWSDDIGLYVWCELTYGIKDVPGDRTTIDLWFHQAWYSIGNLKPDT

EYEVSLICRRGDMSSNPAKETFTTGGGTLGHHHHHHHH

Clone 348 - Affinity Mature variant (w/o N-term A, and
C-term linker and His8 tag)
SEQ ID NO: 40
IEVKDVTDTTALITWSDDIGLYVWCELTYGIKDVPGDRTTIDLWFHQAWYSIGNLKPDTE

YEVSLICRRGDMSSNPAKETFTT

Clone 349 - Affinity Mature variant
SEQ ID NO: 41
AIEVKDVTDTTALITWSDEHAEFIGCELTYGIKDVPGDRTTIDLWWHSAWYSIGNLKPDT

EYEVSLICRRGDMSSNPAKETFTTGGGTLGHHHHHHHH

Clone 349 - Affinity Mature variant (w/o N-term A, and
C-term linker and His8 tag)
SEQ ID NO: 42
IEVKDVTDTTALITWSDEHAEFIGCELTYGIKDVPGDRTTIDLWWHSAWYSIGNLKPDTE

YEVSLICRRGDMSSNPAKETFTT

Clone 311 - Parental clone isolated from naiive Tn3 library
SEQ ID NO: 43
AIEVKDVTDTTALITWTNRSSYYNLHGCELTYGIKDVPGDRTTIDLSSPYVHYSIGNLKP

DTEYEVSLICLTTDGTYSNPAKETFTTGGGTLGHHHHHHHH

Clone 311 - Parental clone isolated from naiive Tn3 library
(w/o N-term A, and C-term linker and His8 tag)
SEQ ID NO: 44
IEVKDVTDTTALITWTNRSSYYNLHGCELTYGIKDVPGDRTTIDLSSPYVHYSIGNLKPD

TEYEVSLICLTTDGTYSNPAKETFTT

Clone 311K4E - Variant from first round of affinity
maturation
SEQ ID NO: 45
AIEVEDVTDTTALITWTNRSSYYNLHGCELTYGIKDVPGDRTTIDLSSPYVHYSIGNLKP

DTEYEVSLICLTTDGTYSNPAKETFTTGGGTLGHHHHHHHH

Clone 311K4E - Variant from first round of affinity
maturation (w/o N-term A, and C-term linker and His8 tag)
SEQ ID NO: 46
IEVEDVTDTTALITWTNRSSYYNLHGCELTYGIKDVPGDRTTIDLSSPYVHYSIGNLKPD

TEYEVSLICLTTDGTYSNPAKETFTT

Clone 311K4E_1 - Clone Variant from second round of
affinity maturation
SEQ ID NO: 47
AIEVEDVTDTTALITWINRSYYADLHGCELTYGIKDVPGDRTTIDLDQIYVHYSIGNLKP

DTKYEVSLICLTTDGTYSNPAKETFTTGGGTLGHHHHHHHH

Clone 311K4E_1 - Clone Variant from second round of
affinity maturation (w/o N-term A, and C-term linker and
His8 tag)
SEQ ID NO: 48
IEVEDVTDTTALITWINRSYYADLHGCELTYGIKDVPGDRTTIDLDQIYVHYSIGNLKPD

TKYEVSLICLTTDGTYSNPAKETFTT

Clone 311K4E_2 - Clone Variant from second round of
affinity maturation
SEQ ID NO: 49
AIEVEDVTDTTALITWTNRSSYSHLDGCELTYGIKDVPGDRTTIDLSAAIYVHYSIGNLK

PDTEYEVSLICLTTDGTYSNPAKETFTTGGGTLGHHHHHHHH

Clone 311K4E_2 - Clone Variant from second round of
affinity maturation (w/o N-term A, and C-term linker
and His8 tag)
SEQ ID NO: 50
IEVEDVTDTTALITWTNRSSYSHLDGCELTYGIKDVPGDRTTIDLSAAIYVHYSIGNLKP

DTEYEVSLICLTTDGTYSNPAKETFTT

Clone 311K4E_3 - Clone Variant from second round of
affinity maturation
SEQ ID NO: 51
AIEVEDVTDTTALITWINRSSYHNFPHCELAYGIKDVPGDRTTIDLNSPYVHYSIGNLKP

DTEYEVSLICLTTDGTYSNPAKETFTTGGGTLGHHHHHHHH

Clone 311K4E_3 - Clone Variant from second round of
affinity maturation (w/o N-term A, and C-term linker
and His8 tag)
SEQ ID NO: 52
IEVEDVTDTTALITWINRSSYHNFPHCELAYGIKDVPGDRTTIDLNSPYVHYSIGNLKPD

TEYEVSLICLTTDGTYSNPAKETFTT

Clone 311K4E_4 - Clone Variant from second round of
affinity maturation
SEQ ID NO: 53
AIEVEDVTDTTALITWTNRSSYSNHLGCELAYGIKDVPGDRTTIDLNNIYVHYSIGNLKP

DTEYEVSLICLTTDGTYSNPAKETFTTGGGTLGHHHHHHHH

Clone 311K4E_4 - Clone Variant from second round of
affinity maturation (w/o N-term A, and C-term linker
and His8 tag)
SEQ ID NO: 54
IEVEDVTDTTALITWTNRSSYSNHLGCELAYGIKDVPGDRTTIDLNNIYVHYSIGNLKPD

TEYEVSLICLTTDGTYSNPAKETFTT

Clone 311K4E_5 - Clone Variant from second round of
affinity maturation
SEQ ID NO: 55
AIEVEDVTDTTALITWTNRSSYSNFHGCELAYGIKDVPGDRTTIDLNSPYVHYSIGNLKP

DTEYEVSLICLTTDGTYSNPAKETFTTGGGTLGHHHHHHHH

-continued

Clone 311K4E_5 - Clone Variant from second round of
affinity maturation (w/o N-term A, and C-term linker and
His8 tag)
SEQ ID NO: 56
IEVEDVTDTTALITWTNRSSYSNFHGCELAYGIKDVPGDRTTIDLNSPYVHYSIGNLKPD

TEYEVSLICLTTDGTYSNPAKETFTT

Clone 311K4E_7 - Clone Variant from second round of
affinity maturation
SEQ ID NO: 57
AIEVEDVTDTTALITWTNRSFYSNLHGCELTYGIKDVPGDRTTIDLNQPYVHYSIGNLKP

DTEYEVSLICLTTDGTYSNPAKETFTTGGGTLGHHHHHHHH

Clone 311K4E_7 - Clone Variant from second round of
affinity maturation (w/o N-term A, and C-term linker and
His8 tag)
SEQ ID NO: 58
IEVEDVTDTTALITWTNRSFYSNLHGCELTYGIKDVPGDRTTIDLNQPYVHYSIGNLKPD

TEYEVSLICLTTDGTYSNPAKETFTT

Clone 311K4E_8 - Clone Variant from second round of
affinity maturation
SEQ ID NO: 59
AIEVEDVTDTTALITWTNRSSYAYLHGCELAYGIKDVPGDRTTIDLNQPYVHYSIGNLKP

DTEYEVSLICLTTDGTYSNPAKETFTTGGGTLGHHHHHHHH

Clone 311K4E_8 - Clone Variant from second round of
affinity maturation (w/o N-term A, and C-term linker and
His8 tag)
SEQ ID NO: 60
IEVEDVTDTTALITWTNRSSYAYLHGCELAYGIKDVPGDRTTIDLNQPYVHYSIGNLKPD

TEYEVSLICLTTDGTYSNPAKETFTT

Clone 311K4E_9 - Clone Variant from second round of
affinity maturation
SEQ ID NO: 61
AIEVEDVTDTTALITWINRSSYANLHGCELTYGIKDVPGDRTTIDLSSPYVHYSIGNLKP

DTEYEVSLICLTTDGTYSNPAKETFTTGGGTLGHHHHHHHH

Clone 311K4E_9 - Clone Variant from second round of
affinity maturation (w/o N-term A, and C-term linker and
His8 tag)
SEQ ID NO: 62
IEVEDVTDTTALITWINRSSYANLHGCELTYGIKDVPGDRTTIDLSSPYVHYSIGNLKPD

TEYEVSLICLTTDGTYSNPAKETFTT

Clone 311K4E_10 - Clone Variant from second round of
affinity maturation
SEQ ID NO: 63
AIEVEDVTDTTALITWTNRSSYANYHGCELAYGIKDVPGDRTTIDLNQPYVHYSIGNLKP

DTEYEVSLICLTTDGTYSNPAKETFTTGGGTLGHHHHHHHH

Clone 311K4E_10 - Clone Variant from second round of
affinity maturation (w/o N-term A, and C-term linker and
His8 tag)
SEQ ID NO: 64
IEVEDVTDTTALITWTNRSSYANYHGCELAYGIKDVPGDRTTIDLNQPYVHYSIGNLKPD

TEYEVSLICLTTDGTYSNPAKETFTT

Clone 311K4E_11 - Clone Variant from second round of
affinity maturation
SEQ ID NO: 65
AIEVEDVTDTTALITWTNRSSYANLPGCELTYGIKDVPGDRTTIDLNSPYVHYSIGNLKP

DTEYEVSLICLTTDGTYSNPAKETFTTGGGTLGHHHHHHHH

Clone 311K4E_11 - Clone Variant from second round of
affinity maturation (w/o N-term A, and C-term linker and
His8 tag)
SEQ ID NO: 66
IEVEDVTDTTALITWTNRSSYANLPGCELTYGIKDVPGDRTTIDLNSPYVHYSIGNLKPD

TEYEVSLICLTTDGTYSNPAKETFTT

Clone 311K4E_12 - Clone Variant from second round of
affinity maturation
SEQ ID NO: 67
AIEVEDVTDTTALITWTNRSSYSNLHGCELAYGIKDVPGDRTTIDLNQPYVHYSIGNLKP

DTEYEVSLICLTTDGTYNNPAKETFTTGGGTLGHHHHHHHH

Clone 311K4E_12 - Clone Variant from second round of
affinity maturation (w/o N-term A, and C-term linker and
His8 tag)
SEQ ID NO: 68
IEVEDVTDTTALITWTNRSSYSNLHGCELAYGIKDVPGDRTTIDLNQPYVHYSIGNLKPD

TEYEVSLICLTTDGTYNNPAKETFTT

Clone 311K4E_13 - Clone Variant from second round of
affinity maturation
SEQ ID NO: 69
AIEVEDVTDTTALITWINRSSYANLHGCELTYGIKDVPGDRTTIDLNSPYVHYSIGNLKP

DTEYEVSLICLTTDGTYSNPAKETFTTGGGTLGHHHHHHHH

Clone 311K4E_13 - Clone Variant from second round of
affinity maturation (w/o N-term A, and C-term linker and
His8 tag)
SEQ ID NO: 70
IEVEDVTDTTALITWINRSSYANLHGCELTYGIKDVPGDRTTIDLNSPYVHYSIGNLKPD

TEYEVSLICLTTDGTYSNPAKETFTT

Clone 311K4E_14 - Clone Variant from second round of
affinity maturation
SEQ ID NO: 71
AIEVEDVTDTTALITWTARSAYSHHHYCELTYGIKDVPGDRTTIDLRQPYVHYSIGNLKP

DTEYEVSLICLTTDGTYSNPAKETFTTGGGTLGHHHHHHHH

Clone 311K4E_14 - Clone Variant from second round of
affinity maturation (w/o N-term A, and C-term linker and
His8 tag)
SEQ ID NO: 72
IEVEDVTDTTALITWTARSAYSHHHYCELTYGIKDVPGDRTTIDLRQPYVHYSIGNLKPD

TEYEVSLICLTTDGTYSNPAKETFTT

Clone 311K4E_15 - Clone Variant from second round of
affinity maturation
SEQ ID NO: 73
AIEVEDVTDTTALITWTNRSSYANYHHCELTYGIKDVPGDRTTIDLELYVHYSIGNLKPD

TEYEVSLICLTTDGTYSNPAKETFTTGGGTLGHHHHHHHH

Clone 311K4E_15 - Clone Variant from second round of
affinity maturation (w/o N-term A, and C-term linker and
His8 tag)
SEQ ID NO: 74
IEVEDVTDTTALITWTNRSSYANYHHCELTYGIKDVPGDRTTIDLELYVHYSIGNLKPDT

EYEVSLICLTTDGTYSNPAKETFTT

Clone 311K4E_16 - Clone Variant from second round of
affinity maturation
SEQ ID NO: 75
AIEVEDVTDTTALITWTNRSSYSDLPGCELTYGIKDVPGDRTTIDLSSPYVHYSIGNLKP

DTEYEVSLICLTTDGTYSNPAKETFTTGGGTLGHHHHHHHH

-continued

Clone 311K4E_16 - Clone Variant from second round of
affinity maturation (w/o N-term A, and C-term linker and
His8 tag)
SEQ ID NO: 76
IEVEDVTDTTALITWTNRSSYSDLPGCELTYGIKDVPGDRTTIDLSSPYVHYSIGNLKPD

TEYEVSLICLTTDGTYSNPAKETFTT

Clone 311K4E_19 - Clone Variant from second round of
affinity maturation
SEQ ID NO: 77
AIEVEDVTDTTALITWTHRSAYSNHSFCELTYGIKDVPGDRTTIDLNTPYVHYSIGNLKP

DTEYEVSLICLTTDGTYSNPAKETFTTGGGTLGHHHHHHHH

Clone 311K4E_19 - Clone Variant from second round of
affinity maturation (w/o N-term A, and C-term linker and
His8 tag)
SEQ ID NO: 78
IEVEDVTDTTALITWTHRSAYSNHSFCELTYGIKDVPGDRTTIDLNTPYVHYSIGNLKPD

TEYEVSLICLTTDGTYSNPAKETFTT

Clone 311K4E_20 - Clone Variant from second round of
affinity maturation
SEQ ID NO: 79
AIEVEDVTDTTALITWTNRSLYANFHGCELTYGIKDVPGDRTTIDLEQVYVHYSIGNLKP

DTEYEVSLICLTTDGTYSNPAKETFTTGGGTLGHHHHHHHH

Clone 311K4E_20 - Clone Variant from second round of
affinity maturation (w/o N-term A, and C-term linker and
His8 tag)
SEQ ID NO: 80
IEVEDVTDTTALITWTNRSLYANFHGCELTYGIKDVPGDRTTIDLEQVYVHYSIGNLKPD

TEYEVSLICLTTDGTYSNPAKETFTT

Clone 311K4E_21 - Clone Variant from second round of
affinity maturation
SEQ ID NO: 81
AIEVEDVTDTTALITWTNRSSYSNLPGCELTYGIKDVPGDRTTIDLNQVYVHYSIGNLKP

DTEYEVSLICLTTDGTYSNPAKETFTTGGGTLGHHHHHHHH

Clone 311K4E_21 - Clone Variant from second round of
affinity maturation (w/o N-term A, and C-term linker and
His8 tag)
SEQ ID NO: 82
IEVEDVTDTTALITWTNRSSYSNLPGCELTYGIKDVPGDRTTIDLNQVYVHYSIGNLKPD

TEYEVSLICLTTDGTYSNPAKETFTT

Clone 309 and 309FGwt - BC Loop
SEQ ID NO: 83
SDEFGHYDG

Clone 340 - BC Loop
SEQ ID NO: 84
SDDFDNYEW

Clone 341 - BC Loop
SEQ ID NO: 85
SDDFADYVW

Clone 342 - BC Loop
SEQ ID NO: 86
SDDFGEYVW

Clone 343 - BC Loop
SEQ ID NO: 87
LDDWGSYHV

Clone 344 - BC Loop
SEQ ID NO: 88
SDEVGDYVV

Clone 345 - BC Loop
SEQ ID NO: 89
SDDFAEYVG

-continued

```
Clone 346 - BC Loop
                                         SEQ ID NO: 90
SDDFEEYVV Clone 347 - BC Loop
                                         SEQ ID NO: 91
SDEVGQYVG Clone 348 - BC Loop
                                         SEQ ID NO: 92
SDDIGLYVW Clone 349 - BC Loop
                                         SEQ ID NO: 93
SDEHAEFIG Clone 309, 309FGwt, 341, 345, 346, 349 - DE Loop
                                         SEQ ID NO: 94
WWHSAW Clone 340, 344, 347 - DE Loop
                                         SEQ ID NO: 95
WYHMAW Clone 342 - DE Loop
                                         SEQ ID NO: 96
WYHHAH Clone 343 - DE Loop
                                         SEQ ID NO: 97
WYHQAW Clone 348 - DE Loop
                                         SEQ ID NO: 98
WFHQAW Clone 309 - FG Loop
                                         SEQ ID NO: 99
YTDQEAGNPA Clone 311, 311K4E - BC Loop
                                         SEQ ID NO: 100
TNRSSYYNLHG Clone 311K4E_1 - BC Loop
                                         SEQ ID NO: 101
INRSYYADLHG Clone 311K4E_2 - BC Loop
                                         SEQ ID NO: 102
TNRSSYSHLDG Clone 311K4E_3 - BC Loop
                                         SEQ ID NO: 103
INRSSYHNFPH Clone 311K4E_4 - BC Loop
                                         SEQ ID NO: 104
TNRSSYSNHLG Clone 311K4E_5 - BC Loop
                                         SEQ ID NO: 105
TNRSSYSNFHG Clone 311K4E_7 - BC Loop
                                         SEQ ID NO: 106
TNRSFYSNLHG Clone 311K4E_8 - BC Loop
                                         SEQ ID NO: 107
TNRSSYAYLHG Clone 311K4E_9, 311K4E_13 - BC Loop
                                         SEQ ID NO: 108
INRSSYANLHG Clone 311K4E_10 - BC Loop
                                         SEQ ID NO: 109
TNRSSYANYHG
```

```
Clone 311K4E_11 - BC Loop
                                               SEQ ID NO: 110
TNRSSYANLPG Clone 311K4E_12 - BC Loop
                                               SEQ ID NO: 111
TNRSSYSNLHG Clone 311K4E_14 - BC Loop
                                               SEQ ID NO: 112
TARSAYSHHHY Clone 311K4E_15 - BC Loop
                                               SEQ ID NO: 113
TNRSSYANYHH Clone 311K4E_16 - BC Loop
                                               SEQ ID NO: 114
TNRSSYSDLPG Clone 311K4E_19 - BC Loop
                                               SEQ ID NO: 115
THRSAYSNHSF Clone 311K4E_20 - BC Loop
                                               SEQ ID NO: 116
TNRSLYANFHG Clone 311K4E_21 - BC Loop
                                               SEQ ID NO: 117
TNRSSYSNLPG Clone 311, 311K4E, 311K4E_9, 311K4E_16 - DE Loop
                                               SEQ ID NO: 118
SSPYVH Clone 311K4E_1 - DE Loop
                                               SEQ ID NO: 119
DQIYVH Clone 311K4E_2 - DE Loop
                                               SEQ ID NO: 120
SAAIYVH Clone 311K4E_3, 311K4E_5, 311K4E_11, 311K4E_13 - DE Loop
                                               SEQ ID NO: 121
NSPYVH Clone 311K4E_4 - DE Loop
                                               SEQ ID NO: 122
NNIYVH Clone 311K4E_7, 311K4E_8, 311K4E_10, 311K4E_12 - DE Loop
                                               SEQ ID NO: 123
NQPYVH Clone 311K4E_14 - DE Loop
                                               SEQ ID NO: 124
RQPYVH Clone 311K4E_15 - DE Loop
                                               SEQ ID NO: 125
ELYVH Clone 311K4E_19 - DE Loop
                                               SEQ ID NO: 126
NTPYVH Clone 311K4E_20 - DE Loop
                                               SEQ ID NO: 127
EQVYVH Clone 311K4E_21 - DE Loop
                                               SEQ ID NO: 128
NQVYVH
```

-continued

```
Clone 311, 311K4E, 311K4E_1, 311K4E_2, 311K4E_3, 311K4E_4,
311K4E_5, 311K4E_7, 311K4E_8, 311K4E_9, 311K4E_10,
311K4E_11, 311K4E_13, 311K4E_14, 311K4E_15, 311K4E_16,
311K4E_19, 311K4E_20, 311K4E_21 - FG Loop
                                                  SEQ ID NO: 129
LTTDGTYSNPA Clone 311K4E_12 - FG Loop
                                                  SEQ ID NO: 130
LTTDGTYNNPA 2G5 Linker - (Gly4Ser)2
                                                  SEQ ID NO: 131
GGGGSGGGGS 3G5 Linker - (Gly4Ser)3
                                                  SEQ ID NO: 132
GGGGSGGGGSGGGGS HSA C345 mutant
Cys->Ser mutation location is underlined
                                                  SEQ ID NO: 133
DAHKSEVAHRFKDLGEENFKALVLIAFAQYLQQSPFEDHVKLVNEVTEFAKTCVADESAE

NCDKSLHTLFGDKLCTVATLRETYGEMADCCAKQEPERNECFLQHKDDNPNLPRLVRPEV

DVMCTAFHDNEETFLKKYLYEIARRHPYFYAPELLFFAKRYKAAFTECCQAADKAACLLP

KLDELRDEGKASSAKQRLKCASLQKFGERAFKAWAVARLSQRFPKAEFAEVSKLVTDLTK

VHTECCHGDLLECADDRADLAKYICENQDSISSKLKECCEKPLLEKSHCIAEVENDEMPA

DLPSLAADFVESKDVCKNYAEAKDVFLGMFLYEYARRHPDYSVVLLLRLAKTYETTLEKC

CAAADPHECYAKVFDEFKPLVEEPQNLIKQNCELFEQLGEYKFQNALLVRYTKKVPQVST

PTLVEVSRNLGKVGSKCCKHPEAKRMPCAEDYLSVVLNQLCVLHEKTPVSDRVTKCCTES

LVNRRPCFSALEVDETYVPKEFNAETFTFHADICTLSEKERQIKKQTALVELVKHKPKAT

KEQLKAVMDDFAAFVEKCCKADDKETCFAEEGKKLVAASQAALGL 342-2GS-HSAC34S - Monovalent Construct
HSAC34S is underlined
                                                  SEQ ID NO: 134
SQIEVKDVTDTTALITWSDDFGEYVWCELTYGIKDVPGDRTTIDLWYHHAHYSIGNLKPD

TEYEVSLICRSGDMSSNPAKETFTTGGGGSGGGGSDAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL 342-3GS-342-2GS-HSAC34S Bivalent Construct
HSA is underlined
                                                  SEQ ID NO: 135
SQIEVKDVTDTTALITWSDDFGEYVWCELTYGIKDVPGDRTTIDLWYHHAHYSIGNLKPD

TEYEVSLICRSGDMSSNPAKETFTTGGGGSGGGGSGGGGSRLDAPSQIEVKDVTDTTALI

TWSDDFGEYVWCELTYGIKDVPGDRTTIDLWYHHAHYSIGNLKPDTEYEVSLICRSGDMS

SNPAKETFTTGGGGSGGGGSDAHKSEVAHRFKDLGEENFKALVLIAFAQYLQQSPFEDHV
```

KLVNEVTEFAKTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFYAPELLFFAKR

YKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCE

KPLLEKSHCIAEVENDEMPADLPSLAADFVESKDVCKNYAEAKDVFLGMFLYEYARRHPD

YSVVLLLRLAKTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAEDYLSVVLNQL

CVLHEKTPVSDRVTKCCTESLVNRRPCFSALEVDETYVPKEFNAETFTFHADICTLSEKE

RQIKKQTALVELVKHKPKATKEQLKAVMDDFAAFVEKCCKADDKETCFAEEGKKLVAASQ

AALGL 311 clone family AB loop N-term E variant
                                            SEQ ID NO: 136
EDVTDTT 311 clone family EF loop C-term K variant
                                            SEQ ID NO: 137
GNLKPDTK HSA human full-length
                                            SEQ ID NO: 138
DAHKSEVAHRFKDLGEENFKALVLIAFAQYLQQCPFEDHVKLVNEVTEFAKTCVADESAE

NCDKSLHTLFGDKLCTVATLRETYGEMADCCAKQEPERNECFLQHKDDNPNLPRLVRPEV

DVMCTAFHDNEETFLKKYLYEIARRHPYFYAPELLFFAKRYKAAFTECCQAADKAACLLP

KLDELRDEGKASSAKQRLKCASLQKFGERAFKAWAVARLSQRFPKAEFAEVSKLVTDLTK

VHTECCHGDLLECADDRADLAKYICENQDSISSKLKECCEKPLLEKSHCIAEVENDEMPA

DLPSLAADFVESKDVCKNYAEAKDVFLGMFLYEYARRHPDYSVVLLLRLAKTYETTLEKC

CAAADPHECYAKVFDEFKPLVEEPQNLIKQNCELFEQLGEYKFQNALLVRYTKKVPQVST

PTLVEVSRNLGKVGSKCCKHPEAKRMPCAEDYLSVVLNQLCVLHEKTPVSDRVTKCCTES

LVNRRPCFSALEVDETYVPKEFNAETFTFHADICTLSEKERQIKKQTALVELVKHKPKAT

KEQLKAVMDDFAAFVEKCCKADDKETCFAEEGKKLVAASQAALGL

309 FG loop variant (RR->RS mutant); may be present in 342
constructs
                                            SEQ ID NO: 139
RSGDMSSNPA 2GX Linker - (Gly4X)2; X = Ala, Gly, Leu, Ile, Val
                                            SEQ ID NO: 140
GGGGXGGGGX 3GX Linker - (Gly4X)3; X = Ala, Gly, Leu, Ile, Val
                                            SEQ ID NO: 141
GGGGXGGGGXGGGGX G10 Linker - (Gly4Gly)2
                                            SEQ ID NO: 142
GGGGGGGGGG G15 Linker - (Gly4Gly)3
                                            SEQ ID NO: 143
GGGGGGGGGGGGGGG 342-G10-HSAC34S - Monovalent construct 2 - all Gly linkers
HSA is underlined
                                            SEQ ID NO: 144
SQIEVKDVTDTTALITWSDDFGEYVWCELTYGIKDVPGDRTTIDLWYHHAHYSIGNLKPD

TEYEVSLICRSGDMSSNPAKETFTTGGGGGGGGGGDAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK
FGERAFKAWAVARLSQRFPKAEFAEVSKLVTDLTKVHTECCHGDLLECADDRADLAKYIC
ENQDSISSKLKECCEKPLLEKSHCIAEVENDEMPADLPSLAADFVESKDVCKNYAEAKDV
FLGMFLYEYARRHPDYSVVLLLRLAKTYETTLEKCCAAADPHECYAKVFDEFKPLVEEPQ
NLIKQNCELFEQLGEYKFQNALLVRYTKKVPQVSTPTLVEVSRNLGKVGSKCCKHPEAKR
MPCAEDYLSVVLNQLCVLHEKTPVSDRVTKCCTESLVNRRPCFSALEVDETYVPKEFNAE
TFTFHADICTLSEKERQIKKQTALVELVKHKPKATKEQLKAVMDDFAAFVEKCCKADDKE
TCFAEEGKKLVAASQAALGL

342-G15-342-G10-HSAC34S Bivalent construct 2 - all Gly
linkers
HSA is underlined
                                           SEQ ID NO: 145
SQIEVKDVTDTTALITWSDDFGEYVWCELTYGIKDVPGDRTTIDLWYHHAHYSIGNLKPD
TEYEVSLICRSGDMSSNPAKETFTTGGGGGGGGGGGGGGGRLDAPSQIEVKDVTDTTALI
TWSDDFGEYVWCELTYGIKDVPGDRTTIDLWYHHAHYSIGNLKPDTEYEVSLICRSGDMS
SNPAKETFTTGGGGGGGGGGDAHKSEVAHRFKDLGEENFKALVLIAFAQYLQQSPFEDHV
KLVNEVTEFAKTCVADESAENCDKSLHTLFGDKLCTVATLRETYGEMADCCAKQEPERNE
CFLQHKDDNPNLPRLVRPEVDVMCTAFHDNEETFLKKYLYEIARRHPYFYAPELLFFAKR
YKAAFTECCQAADKAACLLPKLDELRDEGKASSAKQRLKCASLQKFGERAFKAWAVARLS
QRFPKAEFAEVSKLVTDLTKVHTECCHGDLLECADDRADLAKYICENQDSISSKLKECCE
KPLLEKSHCIAEVENDEMPADLPSLAADFVESKDVCKNYAEAKDVFLGMFLYEYARRHPD
YSVVLLLRLAKTYETTLEKCCAAADPHECYAKVFDEFKPLVEEPQNLIKQNCELFEQLGE
YKFQNALLVRYTKKVPQVSTPTLVEVSRNLGKVGSKCCKHPEAKRMPCAEDYLSVVLNQL
CVLHEKTPVSDRVTKCCTESLVNRRPCFSALEVDETYVPKEFNAETFTFHADICTLSEKE
RQIKKQTALVELVKHKPKATKEQLKAVMDDFAAFVEKCCKADDKETCFAEEGKKLVAASQ
AALGL Clone 342 - Affinity Mature variant (w/FG loop variant
RR->RS underlined)
                                           SEQ ID NO: 146
IEVKDVTDTTALITWSDDFGEYVWCELTYGIKDVPGDRTTIDLWYHHAHYSIGNLKPDTE
YEVSLICRSGDMSSNPAKETFTT Gly-Ser linker module, $(G_4S)_n$ where n = 1-7; the $(G_4S)_n$
module wherein n = 1 is shown
                                           SEQ ID NO: 147
GGGGS Gly linker module $(G_5)_n$ where n = 1-7; the $(G_5)_n$ module
wherein n = 1 is shown
                                           SEQ ID NO: 148
GGGGG Gly-Ala linker module, $(G_4A)_n$ where n = 1-7; the $(G_4A)_n$
module wherein n = 1 is shown
                                           SEQ ID NO: 149
GGGGA Poly-Histidine Tag ($H_8$) - An optional component of the
Tn3 scaffolds useful for purification maybe combined
with additional linker residues.
                                           SEQ ID NO: 150
HHHHHHHH Linker-Poly-Histidine Tag - An optional component of the
Tn3 scaffolds useful for purification
                                           SEQ ID NO: 151
GGGGSHHHHHHHH Mature MSA wild type
SEQ ID NO: 152
EAHKSEIAHRYNDLGEQHFKGLVLIAFSQYLQKCSYDEHAKLVQEVTDFAKTCVADESAA
NCDKSLHTLFGDKLCAIPNLRENYGELADCCTKQEPERNECFLQHKDDNPSLPPFERPEA
EAMCTSFKENPTTFMGHYLHEVARRHPYFYAPELLYYAEQYNEILTQCCAEADKESCLTP
KLDGVKEKALVSSVRQRMKCSSMQKFGERAFKAWAVARLSQTFPNADFAEITKLATDLTK
VNKECCHGDLLECADDRAELAKYMCENQATISSKLQTCCDKPLLKKAHCLSEVEHDTMPA
DLPAIAADFVEDQEVCKNYAEAKDVFLGTFLYEYSRRHPDYSVSLLLRLAKKYEATLEKC
CAEANPPACYGTVLAEFQPLVEEPKNLVKTNCDLYEKLGEYGFQNAILVRYTQKAPQVST
PTLVEAARNLGRVGTKCCTLPEDQRLPCVEDYLSAILNRVCLLHEKTPVSEHVTKCCSGS
LVERRPCFSALTVDETYVPKEFKAETFTFHSDICTLPEKEKQIKKQTALAELVKHKPKAT
AEQLKTVMDDFAQFLDTCCKAADKDTCFSTEGPNLVTRCKDALA Mature MSA-C34S/C579S Cys mutant; mutated residues
underlined

SEQ ID NO: 153

EAHKSEIAHRYNDLGEQHFKGLVLIAFSQYLQKSSYDEHAKLVQEVTDFAKTCVADESAA

NCDKSLHTLFGDKLCAIPNLRENYGELADCCTKQEPERNECFLQHKDDNPSLPPFERPEA

EAMCTSFKENPTTFMGHYLHEVARRHPYFYAPELLYYAEQYNEILTQCCAEADKESCLTP

KLDGVKEKALVSSVRQRMKCSSMQKFGERAFKAWAVARLSQTFPNADFAEITKLATDLTK

VNKECCHGDLLECADDRAELAKYMCENQATISSKLQTCCDKPLLKKAHCLSEVEHDTMPA

DLPAIAADFVEDQEVCKNYAEAKDVFLGTFLYEYSRRHPDYSVSLLLRLAKKYEATLEKC

CAEANPPACYGTVLAEFQPLVEEPKNLVKTNCDLYEKLGEYGFQNAILVRYTQKAPQVST

PTLVEAARNLGRVGTKCCTLPEDQRLPCVEDYLSAILNRVCLLHEKTPVSEHVTKCCSGS

LVERRPCFSALTVDETYVPKEFKAETFTFHSDICTLPEKEKQIKKQTALAELVKHKPKAT

AEQLKTVMDDFAQFLDTCCKAADKDTCFSTEGPNLVTRSKDALA

Clone M13; BC, DE, FG loops are underlined

SEQ ID NO: 154

IEVKDVTDTTALITWHDAFGYDFGCELTYGIKDVPGDRTTIDLPDHFHNYSIGNLKPDT

EYEVSLICANDHGFDSNPAKETFTT

Clone M13N49Q; N49Q mutation underlined

SEQ ID NO: 155

IEVKDVTDTTALITWHDAFGYDFGCELTYGIKDVPGDRTTIDLPDHFHQYSIGNLKPDT

EYEVSLICANDHGFDSNPAKETFTT

M13N49Q-1GS-M13N49Q bivalent Construct; N49Q mutation underlined

SEQ ID NO: 156

SQIEVKDVTDTTALITWHDAFGYDFGCELTYGIKDVPGDRTTIDLPDHFHQYSIGNLKPD

TEYEVSLICANDHGFDSNPAKETFTTGGGGSRLDAPSQIEVKDVTDTTALITWHDAFGY

DFGCELTYGIKDVPGDRTTIDLPDHFHQYSIGNLKPDTEYEVSLICANDHGFDSNPAKET

FTT

M13N49Q-3GS-MSA-C34S/C5795S monovalent construct; mutations underlined

SEQ ID NO: 157

SQIEVKDVTDTTALITWHDAFGYDFGCELTYGIKDVPGDRTTIDLPDHFHQYSIGNLKPD

TEYEVSLICANDHGFDSNPAKETFTTGGGGSGGGGSGGGGSEAHKSEIAHRYNDLGEQHF

KGLVLIAFSQYLQKSSYDEHAKLVQEVTDFAKTCVADESAANCDKSLHTLFGDKLCAIPN

LRENYGELADCCTKQEPERNECFLQHKDDNPSLPPFERPEAEAMCTSFKENPTTFMGHYL

HEVARRHPYFYAPELLYYAEQYNEILTQCCAEADKESCLTPKLDGVKEKALVSSVRQRMK

-continued

CSSMQKFGERAFKAWAVARLSQTFPNADFAEITKLATDLTKVNKECCHGDLLECADDRAE

LAKYMCENQATISSKLQTCCDKPLLKKAHCLSEVEHDTMPADLPAIAADFVEDQEVCKNY

AEAKDVFLGTFLYEYSRRHPDYSVSLLLRLAKKYEATLEKCCAEANPPACYGTVLAEFQP

LVEEPKNLVKTNCDLYEKLGEYGFQNAILVRYTQKAPQVSTPTLVEAARNLGRVGTKCCT

LPEDQRLPCVEDYLSAILNRVCLLHEKTPVSEHVTKCCSGSLVERRPCFSALTVDETYVP

KEFKAETFTFHSDICTLPEKEKQIKKQTALAELVKHKPKATAEQLKTVMDDFAQFLDTCC

KAADKDTCFSTEGPNLVTR<u>S</u>KDALA

M13N49Q-1GS-M13N49Q-3GS-MSA-C34S/C579S bivalent construct;
mutations underlined
SEQ ID NO: 158
SQIEVKDVTDTTALITWHDAFGYDFGCELTYGIKDVPGDRTTIDLPDHFH<u>Q</u>YSIGNLKPD

TEYEVSLICANDHGFDSNPAKETFTTTGGGGSRLDAPSQIEVKDVTDTTALITWHDAFGY

DFGCELTYGIKDVPGDRTTIDLPDHFH<u>Q</u>YSIGNLKPDTEYEVSLICANDHGFDSNPAKET

FTTGGGGSGGGGSGGGGSEAHKSEIAHRYNDLGEQHFKGLVLIAFSQYLQK<u>S</u>SYDEHAKL

VQEVTDFAKTCVADESAANCDKSLHTLFGDKLCAIPNLRENYGELADCCTKQEPERNECF

LQHKDDNPSLPPFERPEAEAMCTSFKENPTTFMGHYLHEVARRHPYFYAPELLYYAEQYN

EILTQCCAEADKESCLTPKLDGVKEKALVSSVRQRMKCSSMQKFGERAFKAWAVARLSQT

FPNADFAEITKLATDLTKVNKECCHGDLLECADDRAELAKYMCENQATISSKLQTCCDKP

LLKKAHCLSEVEHDTMPADLPAIAADFVEDQEVCKNYAEAKDVFLGTFLYEYSRRHPDYS

VSLLLRLAKKYEATLEKCCAEANPPACYGTVLAEFQPLVEEPKNLVKTNCDLYEKLGEYG

FQNAILVRYTQKAPQVSTPTLVEAARNLGRVGTKCCTLPEDQRLPCVEDYLSAILNRVCL

LHEKTPVSEHVTKCCSGSLVERRPCFSALTVDETYVPKEFKAETFTFHSDICTLPEKEKQ

IKKQTALAELVKHKPKATAEQLKTVMDDFAQFLDTCCKAADKDTCFSTEGPNLVTR<u>S</u>KDA

LA

Clone M31; BC, DE, FG loops are underlined
SEQ ID NO: 159
IEVKDVTDTTALITW<u>HDPSGYDFW</u>CELTYGIKDVPGDRTTIDL<u>PDHFHN</u>YSIGNLKPDTE YEVSLIC<u>ANDHGFDSYPA</u>KETFTT Clone M31N49Q; N49Q mutation underlined
SEQ ID NO: 160
IEVKDVTDTTALITWHDPSGYDFWCELTYGIKDVPGDRTTIDLPDHFH<u>Q</u>YSIGNLKPDTE

YEVSLICANDHGFDSYPAKETFTT

M31N49Q-1GS-M31N49Q bivalent construct; N49Q mutation
underlined
SEQ ID NO: 161
SQIEVKDVTDTTALITWHDPSGYDFWCELTYGIKDVPGDRTTIDLPDHFH<u>Q</u>YSIGNLKPD

TEYEVSLICANDHGFDSYPAKETFTTTGGGGSRLDAPSQIEVKDVTDTTALITWHDPSGY

DFWCELTYGIKDVPGDRTTIDLPDHFH<u>Q</u>YSIGNLKPDTEYEVSLICANDHGFDSYPAKET

FTT

M31N49Q-3GS-MSA-C34S/C579S monovalent construct; mutations
underlined
SEQ ID NO: 162
SQIEVKDVTDTTALITWHDPSGYDFWCELTYGIKDVPGDRTTIDLPDHFH<u>Q</u>YSIGNLKPD

TEYEVSLICANDHGFDSYPAKETFTTGGGGSGGGGSGGGGSEAHKSEIAHRYNDLGEQHF

KGLVLIAFSQYLQK<u>S</u>SYDEHAKLVQEVTDFAKTCVADESAANCDKSLHTLFGDKLCAIPN

LRENYGELADCCTKQEPERNECFLQHKDDNPSLPPFERPEAEAMCTSFKENPTTFMGHYL

HEVARRHPYFYAPELLYYAEQYNEILTQCCAEADKESCLTPKLDGVKEKALVSSVRQRMK

-continued

CSSMQKFGERAFKAWAVARLSQTFPNADFAEITKLATDLTKVNKECCHGDLLECADDRAE

LAKYMCENQATISSKLQTCCDKPLLKKAHCLSEVEHDTMPADLPAIAADFVEDQEVCKNY

AEAKDVFLGTFLYEYSRRHPDYSVSLLLRLAKKYEATLEKCCAEANPPACYGTVLAEFQP

LVEEPKNLVKTNCDLYEKLGEYGFQNAILVRYTQKAPQVSTPTLVEAARNLGRVGTKCCT

LPEDQRLPCVEDYLSAILNRVCLLHEKTPVSEHVTKCCSGSLVERRPCFSALTVDETYVP

KEFKAETFTFHSDICTLPEKEKQIKKQTALAELVKHKPKATAEQLKTVMDDFAQFLDTCC

KAADKDTCFSTEGPNLVTRSKDALA

M31N49Q-1GS-M31N49Q-3GS-MSA-C34S/C579S bivalent construct; mutations underlined

SEQ ID NO: 163

SQIEVKDVTDTTALITWHDPSGYDFWCELTYGIKDVPGDRTTIDLPDHFHQYSIGNLKPD

TEYEVSLICANDHGFDSYPAKETFTTTGGGGSRLDAPSQIEVKDVTDTTALITWHDPSGY

DFWCELTYGIKDVPGDRTTIDLPDHFHQYSIGNLKPDTEYEVSLICANDHGFDSYPAKET

FTTGGGGSGGGGSGGGGSEAHKSEIAHRYNDLGEQHFKGLVLIAFSQYLQKSSYDEHAKL

VQEVTDFAKTCVADESAANCDKSLHTLFGDKLCAIPNLRENYGELADCCTKQEPERNECF

LQHKDDNPSLPPFERPEAEAMCTSFKENPTTFMGHYLHEVARRHPYFYAPELLYYAEQYN

EILTQCCAEADKESCLTPKLDGVKEKALVSSVRQRMKCSSMQKFGERAFKAWAVARLSQT

FPNADFAEITKLATDLTKVNKECCHGDLLECADDRAELAKYMCENQATISSKLQTCCDKP

LLKKAHCLSEVEHDTMPADLPAIAADFVEDQEVCKNYAEAKDVFLGTFLYEYSRRHPDYS

VSLLLRLAKKYEATLEKCCAEANPPACYGTVLAEFQPLVEEPKNLVKTNCDLYEKLGEYG

FQNAILVRYTQKAPQVSTPTLVEAARNLGRVGTKCCTLPEDQRLPCVEDYLSAILNRVCL

LHEKTPVSEHVTKCCSGSLVERRPCFSALTVDETYVPKEFKAETFTFHSDICTLPEKEKQ

IKKQTALAELVKHKPKATAEQLKTVMDDFAQFLDTCCKAADKDTCFSTEGPNLVTRSKDA

LA

Clone D1 - Negative control Tn3

SEQ ID NO: 164

IEVKDVTDTTALITWSPGERIWMFTGCELTYGIKDVPGDRTTIDLTEDENQYSIGNLKPD

TEYEVSLICPNYERISNPAKETFTTT

D1-1GS-D1-3G-MSA-C34S/C579S bivalent construct; mutations underlined

SEQ ID NO: 165

SQIEVKDVTDTTALITWSPGERIWMFTGCELTYGIKDVPGDRTTIDLTEDENQYSIGNLK

PDTEYEVSLICPNYERISNPAKETFTTTGGGGSRLDAPSQIEVKDVTDTTALITWSPGER

IWMFTGCELTYGIKDVPGDRTTIDLTEDENQYSIGNLKPDTEYEVSLICPNYERISNPAK

ETFTTGGGGSGGGGSGGGGSEAHKSEIAHRYNDLGEQHFKGLVLIAFSQYLQKSSYDEHA

KLVQEVTDFAKTCVADESAANCDKSLHTLFGDKLCAIPNLRENYGELADCCTKQEPERNE

CFLQHKDDNPSLPPFERPEAEAMCTSFKENPTTFMGHYLHEVARRHPYFYAPELLYYAEQ

YNEILTQCCAEADKESCLTPKLDGVKEKALVSSVRQRMKCSSMQKFGERAFKAWAVARLS

QTFPNADFAEITKLATDLTKVNKECCHGDLLECADDRAELAKYMCENQATISSKLQTCCD

KPLLKKAHCLSEVEHDTMPADLPAIAADFVEDQEVCKNYAEAKDVFLGTFLYEYSRRHPD

YSVSLLLRLAKKYEATLEKCCAEANPPACYGTVLAEFQPLVEEPKNLVKTNCDLYEKLGE

YGFQNAILVRYTQKAPQVSTPTLVEAARNLGRVGTKCCTLPEDQRLPCVEDYLSAILNRV

CLLHEKTPVSEHVTKCCSGSLVERRPCFSALTVDETYVPKEFKAETFTFHSDICTLPEKE

KQIKKQTALAELVKHKPKATAEQLKTVMDDFAQFLDTCCKAADKDTCFSTEGPNLVTR<u>S</u>K

DALA

Clone 342 RDG to SDG mutant; mutation underlined
SEQ ID NO: 166
IEVKDVTDTTALITWSDDFGEYVWCELTYGIKDVPGDRTTIDLWYHHAHYSIGNLKPDTE YEVSLICR<u>S</u>GDMSSNPAKETFTT 309FGwt consensus
All strands are parent Tn3 strands; beta strand C is CELTYGI
variant (SEQ ID NO: 14); AB, CD, EF loop are parent Tn3
loops X1 = Ser or Leu X2 = Asp or Glu X3 = His, Ile, Val, Phe or Trp X4 = Ala, Gly, Glu or Asp X5 = Glu, Leu, Gln, Ser, Asp or Asn X6 = Phe or Tyr X7 = Ile, Val, His, Glu or Asp X8 = Gly, Trp or Val X9 = Trp, Phe or Tyr X10 = Ser, Gln, Met or His X11 = Trp or His X12 = Arg or Ser

SEQ ID NO: 167
IEVKDVTDTTALITWX1DX2X3X4X5X6X7X8CELTYGIKDVPGDRTTIDLWX9HX10

AX11YSIGNLKPDTEYEVSLICRX12GDMSSNPAKETFTT

309FGwt consensus, BC loop
X1 = Ser or Leu

X2 = Asp or Glu

X3 = His, Ile, Val, Phe or Trp

X4 = Ala, Gly, Glu or Asp

X5 = Glu, Leu, Gln, Ser, Asp or Asn

X6 = Phe or Tyr

X7 = Ile, Val, His, Glu or Asp

X8 = Gly, Trp or Val

SEQ ID NO: 168
X1DX2X3X4X5X6X7X8

309FGwt consensus, DE loop
X9 = Trp, Phe or Tyr

X10 = Ser, Gln, Met or His

X11 = Trp or His

SEQ ID NO: 169
WX9HX10AX11

309FGwt consensus, FG loop
X12 = Arg or Ser

SEQ ID NO: 170
RX12GDMSSNPA 311 consensus; all strands are parent Tn3 strands; two beta strand C variants (SEQ ID NO: 13 and 14); CD loop is parent Tn3 loop X1 = Lys or Glu X2 = Thr or Ile X3 = Asn or Ala X4 = Ser, Leu, Ala, Phe or Tyr X5 = Tyr, Ala, Gly, Val, Ile or Ser (BC/N-term contact)

X6 = Tyr, Ser, Ala or His

X7 = Asn, Asp, His or Tyr

X8 = Leu, Phe, His or Tyr

X9 = His, Pro, Ser, Leu or Asp

X10 = Gly, Phe, His or Tyr

X11 = Ala or Thr

X12 = Ser, Asn, Glu, Arg or Asp

X13 = Ser, Gln, Thr, Asn or Ala

X14 = Pro, Val, -, Ile or Ala (- no amino acid)

X15 = - or Ile (- no amino acid)

X16 = Glu or Lys

X17 = Ser or Asn

SEQ ID NO: 171
IEVX1DVTDTTALITWX2X3RSX4X5X6X7X8X9X10CELX11YGIKDVPGDRTTIDL
X12X13X14X15YVHYSIGNLKPDTX16YEVSLICLTTDGTYX17NPAKETFTT 311 consensus; beta strand C in 311 family clones
X11 = Ala or Thr

SEQ ID NO: 172
CELX11YGI 311 consensus; AB loop
X1 = Lys or Glu

SEQ ID NO: 173
X1DVTDTT 311 consensus; BC loop

X2 = Thr or Ile

X3 = Asn or Ala

X4 = Ser, Leu, Ala, Phe or Tyr

X5 = Tyr, Ala, Gly, Val, Ile or Ser (BC/N-term contact)

X6 = Tyr, Ser, Ala or His

X7 = Asn, Asp, His or Tyr

X8 = Leu, Phe, His or Tyr

X9 = His, Pro, Ser, Leu or Asp

X10 = Gly, Phe, His or Tyr

SEQ ID NO: 174
X2X3RSX4X5X6X7X8X9X10

```
311 consensus; DE loop

X12 = Ser, Asn, Glu, Arg or Asp

X13 = Ser, Gln, Thr, Asn or Ala

X14 = Pro, Val, -, Ile or Ala (- no amino acid)

X15 = - or Ile (- no amino acid)

SEQ ID NO: 175
X12X13X14X15YVH 311 consensus; EF loop
X16 = Glu or Lys

SEQ ID NO: 176
GNLKPDTX16

311 consensus; FG loop
X17 = Ser or Asn

SEQ ID NO: 177
LTTDGTYX17NPA

BC9 NHT oligo; loop BC
Nucleotide codes: N = G/A/T/C; H = A/T/C; R = A/G; S = G/C;
B = T/C/G; V = A/C/G; M = A/C; K = G/T
                                                      SEQ ID NO: 178
ACCGCGCTGATTACCTGGNHTNHTSCGNHTGSTNHTNHTNHTGGCTGTGAACTGACCTAT

GGCATTAAA

BC11 NHT oligo; loop BC
Nucleotide codes: N = G/A/T/C; H = A/T/C; R = A/G; S = G/C;
B = T/C/G; V = A/C/G; M = A/C; K = G/T
                                                      SEQ ID NO: 179
ACCGCGCTGATTACCTGGNHTNHTBSTNHTNHTNHTNHTNHTNHTNHTGGCTGTGAACTG

ACCTATGGCATTAAA

BC12 NHT oligo; loop BC
Nucleotide codes: N = G/A/T/C; H = A/T/C; R = A/G; S = G/C;
B = T/C/G; V = A/C/G; M = A/C; K = G/T
                                                      SEQ ID NO: 180
ACCGCGCTGATTACCTGGNHTVMACCGNHTNHTNHTRRCRGCNHTVTTNHTGGCTGTGAA

CTGACCTATGGCATTAAA

DE NHT oligo; DE loop
Nucleotide codes: N = G/A/T/C; H = A/T/C; R = A/G; S = G/C;
B = T/C/G; V = A/C/G; M = A/C; K = G/T
                                                      SEQ ID NO: 181
CGATCGCACCACCATAGATCTGNHTNHTNHTNHTNHTNHTTATAGCATTGGTAACCTGAA

ACCG

FG9 NHT oligo; FG loop
Nucleotide codes: N = G/A/T/C; H = A/T/C; R = A/G; S = G/C;
B = T/C/G; V = A/C/G; M = A/C; K = G/T
                                                      SEQ ID NO: 182
GAATATGAAGTGAGCCTGATTTGCNHTAMSNHTNHTGGTNHTNHTNHTKCGAAAGAAACC

TTTACCACCGGTG

FG10 NHT oligo; FG loop
Nucleotide codes: N = G/A/T/C; H = A/T/C; R = A/G; S = G/C;
B = T/C/G; V = A/C/G; M = A/C; K = G/T
                                                      SEQ ID NO: 183
GAATATGAAGTGAGCCTGATTTGCNHTAMSNHTNHTNHTNHTRGCNHTCCGGCGAAAGAA

ACCTTTACCACCGGTG

FG11 NHT oligo; FG loop
Nucleotide codes: N = G/A/T/C; H = A/T/C; R = A/G; S = G/C;
B = T/C/G; V = A/C/G; M = A/C; K = G/T
                                                      SEQ ID NO: 184
GAATATGAAGTGAGCCTGATTTGCNHTAMSNHTNHTGGTNHTNHTAGCAACCCGGCGAAA

GAAACCTTTACCACCGGTG
```

-continued

BCX-DE bridge v2 oligo
SEQ ID NO: 185
CAGATCTATGGTGGTGCGATCGCCCGGCACATCTTTAATGCCATAGGTCAGTTCACA DE-FGX bridge v2 oligo
SEQ ID NO: 186
GCAAATCAGGCTCACTTCATATTCGGTATCCGGTTTCAGGTTACCAATGCTAT KpnI amp rev v2 oligo
SEQ ID NO: 187
CGGGTCGGTTGGGGTACCGCCACCGGTGGTAAAGGTTTCTTT KpnI reverse v2 oligo
SEQ ID NO: 188
CGGGTCGGTTGGGGTA BC library amp v2 oligo
SEQ ID NO: 189
GGCCCAGCCGGCCATGGCCGCCATTGAAGTGAAAGATGTGACCGATACCACCGCGCTGAT
TACCTGG BC9 PCR oligo
Nucleotide codes: 1 = codons for all 19 aa(-cys); 2 = codons
for Ala/Pro 50/50; 3 = codons for Ala/Gly
SEQ ID NO: 190
ACCGCGCTGATTACCTGGTCT1213111GGCTGTGAACTGACCTATGGCATTAAAGATG BC 9-loop NNK oligo
Nucleotide codes: K = 50% G/50% T
SEQ ID NO: 191
ACCGCGCTGATTACCTGGNNKNNKSMGNNKGSTNNKNNKNNKGGCTGTGAACTGACCTA
TGGCATTAAA 309 BC-loop NNKdope oligo
Nucleotide codes: 4 = 70% G 10% A 10% C 10% T; 5 = 10% G,
70% A, 10% C, 10% T; 6 = 10% G, 10% A, 70% C, 10% T; 7 =
10% G, 10% A, 10% C, 70% T; 8 = 70% A 15% C 15% T; and
K = 50% G/50% T
SEQ ID NO: 192
ACCGCGCTGATTACCTGG76K45K45K77K44K65K78T45K44KTGTGAACTGACCTA
TGGCATTAAA DE PCR oligo
Nucleotide codes: 1 = codons for all 19 aa(-cys)
SEQ ID NO: 193
GATGTGCCGGGCGATCGCACCACCATAGATCTG111111TATAGCATTGGTAACCTGAAA
CCGG Upstr BCloop Rev oligo
SEQ ID NO: 194
CCAGGTAATCAGCGCGGTGGTAT BC shuffle rev oligo
SEQ ID NO: 195
CAGATCTATGGTGGTGCGATCGC DE shuffle FWD oligo
SEQ ID NO: 196
TGTGAACTGACCTATGGCATTAAAGATGT BC11-311Gly oligo
Nucleotide codes: 1 = 70% G, 10% A, 10% C, 10% T; 2 = 10%
G, 70% A, 10% C, 10% T; 3 = 10% G, 10% A, 70% C, 10% T;
4 = 10% G, 10% A, 10% C, 70% T; 5 = 70% A, 15% C, 15% T;
6 = 15% A, 70% C, 15% T; 7 = 15% A, 15% C, 70% T; V = 33%
A, 33% C, 33% G.
SEQ ID NO: 197
ACCGCGCTGATTACCTGG26T25TV1T46T46T45T45T25T37T35TGGCTGTGAACTG
ACCTATGGCATTAAA BC11-311NHT oligo
Nucleotide codes: 1 = 70% G, 10% A, 10% C, 10% T; 2 = 10%
G, 70% A, 10% C, 10% T; 3 = 10% G, 10% A, 70% C, 10% T;
4 = 10% G, 10% A, 10% C, 70% T; 5 = 70% A, 15% C, 15% T;
6 = 15% A, 70% C, 15% T; 7 = 15% A, 15% C, 70% T; V = 33%
A, 33% C, 33% G; and H = 33% A, 33% C, 33% T

SEQ ID NO: 198

ACCGCGCTGATTACCTGG26T25TV1T46T46T45T45T25T37T35TNHTTGTGAACTG

ACCTATGGCATTAAA

BC library amp K4E oligo

SEQ ID NO: 199

GGCCCAGCCGGCCATGGCCGCCATTGAAGTGGAAGATGTGACCGATACCACCGCGCTGAT

TACCTGG

Extended half-life HSA variant(C34S, L463N, K524L);
mutations are underlined

SEQ ID NO: 200

DAHKSEVAHRFKDLGEENFKALVLIAFAQYLQQSPFEDHVKLVNEVTEFAKTCVADESAE

NCDKSLHTLFGDKLCTVATLRETYGEMADCCAKQEPERNECFLQHKDDNPNLPRLVRPEV

DVMCTAFHDNEETFLKKYLYEIARRHPYFYAPELLFFAKRYKAAFTECCQAADKAACLLP

KLDELRDEGKASSAKQRLKCASLQKFGERAFKAWAVARLSQRFPKAEFAEVSKLVTDLTK

VHTECCHGDLLECADDRADLAKYICENQDSISSKLKECCEKPLLEKSHCIAEVENDEMPA

DLPSLAADFVESKDVCKNYAEAKDVFLGMFLYEYARRHPDYSVVLLLRLAKTYETTLEKC

CAAADPHECYAKVFDEFKPLVEEPQNLIKQNCELFEQLGEYKFQNALLVRYTKKVPQVST

PTLVEVSRNLGKVGSKCCKHPEAKRMPCAEDYLSVVLNQLCVNHEKTPVSDRVTKCCTES

LVNRRPCFSALEVDETYVPKEFNAETFTFHADICTLSEKERQILKQTALVELVKHKPKAT

KEQLKAVMDDFAAFVEKCCKADDKETCFAEEGKKLVAASQAALGL

311K4E_12-I variant monovalent construct (comprises GS
linker and C34S HSA); linker and mutated serine are
underlined

SEQ ID NO: 201

SQIEVEDVTDTTALITWTNRSSYSNLHGCELAYGIKDVPGDRTTIDLNQPYVHYSIGNLK

PDTEYEVSLICLTTDGTYNNPAKETFTTGGGGSGGGGSDAHKSEVAHRFKDLGEENFKAL

VLIAFAQYLQQSPFEDHVKLVNEVTEFAKTCVADESAENCDKSLHTLFGDKLCTVATLRE

TYGEMADCCAKQEPERNECFLQHKDDNPNLPRLVRPEVDVMCTAFHDNEETFLKKYLYEI

ARRHPYFYAPELLFFAKRYKAAFTECCQAADKAACLLPKLDELRDEGKASSAKQRLKCAS

LQKFGERAFKAWAVARLSQRFPKAEFAEVSKLVTDLTKVHTECCHGDLLECADDRADLAK

YICENQDSISSKLKECCEKPLLEKSHCIAEVENDEMPADLPSLAADFVESKDVCKNYAEA

KDVFLGMFLYEYARRHPDYSVVLLLRLAKTYETTLEKCCAAADPHECYAKVFDEFKPLVE

EPQNLIKQNCELFEQLGEYKFQNALLVRYTKKVPQVSTPTLVEVSRNLGKVGSKCCKHPE

AKRMPCAEDYLSVVLNQLCVLHEKTPVSDRVTKCCTESLVNRRPCFSALEVDETYVPKEF

NAETFTFHADICTLSEKERQIKKQTALVELVKHKPKATKEQLKAVMDDFAAFVEKCCKAD

DKETCFAEEGKKLVAASQAALGL

311K4E_12-I variant monovalent construct (comprises beta
strand C CELTYG variant, all G linker, and C34S HSA);
linker and mutated serine are underlined

SEQ ID NO: 202

SQIEVEDVTDTTALITWTNRSSYSNLHGCELTYGIKDVPGDRTTIDLNQPYVHYSIGNLK

PDTEYEVSLICLTTDGTYNNPAKETFTTGGGGGGGGGGDAHKSEVAHRFKDLGEENFKAL

VLIAFAQYLQQSPFEDHVKLVNEVTEFAKTCVADESAENCDKSLHTLFGDKLCTVATLRE

TYGEMADCCAKQEPERNECFLQHKDDNPNLPRLVRPEVDVMCTAFHDNEETFLKKYLYEI

```
                                           -continued
ARRHPYFYAPELLFFAKRYKAAFTECCQAADKAACLLPKLDELRDEGKASSAKQRLKCAS

LQKFGERAFKAWAVARLSQRFPKAEFAEVSKLVTDLTKVHTECCHGDLLECADDRADLAK

YICENQDSISSKLKECCEKPLLEKSHCIAEVENDEMPADLPSLAADFVESKDVCKNYAEA

KDVFLGMFLYEYARRHPDYSVVLLLRLAKTYETTLEKCCAAADPHECYAKVFDEFKPLVE

EPQNLIKQNCELFEQLGEYKFQNALLVRYTKKVPQVSTPTLVEVSRNLGKVGSKCCKHPE

AKRMPCAEDYLSVVLNQLCVLHEKTPVSDRVTKCCTESLVNRRPCFSALEVDETYVPKEF

NAETFTFHADICTLSEKERQIKKQTALVELVKHKPKATKEQLKAVMDDFAAFVEKCCKAD

DKETCFAEEGKKLVAASQAALGL

311K4E_12-I variant bivalent construct (comprises GS
linkers and C34S HSA); linkers and mutated serine are
underlined
                                           SEQ ID NO: 203
SQIEVEDVTDTTALITWTNRSSYSNLHGCELAYGIKDVPGDRTTIDLNQPYVHYSIGNLK

PDTEYEVSLICLTTDGTYNNPAKETFTTGGGGSGGGGSGGGGSRLDAPSQIEVEDVTDTT

ALITWTNRSSYSNLHGCELAYGIKDVPGDRTTIDLNQPYVHYSIGNLKPDTEYEVSLICL

TTDGTYNNPAKETFTTGGGGSGGGGSDAHKSEVAHRFKDLGEENFKALVLIAFAQYLQQS

PFEDHVKLVNEVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIARRHPYFYAPEL

LFFAKRYKAAFTECCQAADKAACLLPKLDELRDEGKASSAKQRLKCASLQKFGERAFKAW

AVARLSQRFPKAEFAEVSKLVTDLTKVHTECCHGDLLECADDRADLAKYICENQDSISSK

LKECCEKPLLEKSHCIAEVENDEMPADLPSLAADFVESKDVCKNYAEAKDVFLGMFLYEY

ARRHPDYSVVLLLRLAKTYETTLEKCCAAADPHECYAKVFDEFKPLVEEPQNLIKQNCEL

FEQLGEYKFQNALLVRYTKKVPQVSTPTLVEVSRNLGKVGSKCCKHPEAKRMPCAEDYLS

VVLNQLCVLHEKTPVSDRVTKCCTESLVNRRPCFSALEVDETYVPKEFNAETFTFHADIC

TLSEKERQIKKQTALVELVKHKPKATKEQLKAVMDDFAAFVEKCCKADDKETCFAEEGKK

LVAASQAALGL

311K4E_12-I variant bivalent construct (comprises all G
linkers and S34 HSA); linkers and mutated serine are
underlined
                                           SEQ ID NO: 204
SQIEVEDVTDTTALITWTNRSSYSNLHGCELTYGIKDVPGDRTTIDLNQPYVHYSIGNLK

PDTEYEVSLICLTTDGTYNNPAKETFTTGGGGGGGGGGGGGGGGRLDAPSQIEVEDVTDTT

ALITWTNRSSYSNLHGCELAYGIKDVPGDRTTIDLNQPYVHYSIGNLKPDTEYEVSLICL

TTDGTYNNPAKETFTTGGGGGGGGGGDAHKSEVAHRFKDLGEENFKALVLIAFAQYLQQS

PFEDHVKLVNEVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIARRHPYFYAPEL

LFFAKRYKAAFTECCQAADKAACLLPKLDELRDEGKASSAKQRLKCASLQKFGERAFKAW

AVARLSQRFPKAEFAEVSKLVTDLTKVHTECCHGDLLECADDRADLAKYICENQDSISSK

LKECCEKPLLEKSHCIAEVENDEMPADLPSLAADFVESKDVCKNYAEAKDVFLGMFLYEY

ARRHPDYSVVLLLRLAKTYETTLEKCCAAADPHECYAKVFDEFKPLVEEPQNLIKQNCEL

FEQLGEYKFQNALLVRYTKKVPQVSTPTLVEVSRNLGKVGSKCCKHPEAKRMPCAEDYLS

VVLNQLCVLHEKTPVSDRVTKCCTESLVNRRPCFSALEVDETYVPKEFNAETFTFHADIC

TLSEKERQIKKQTALVELVKHKPKATKEQLKAVMDDFAAFVEKCCKADDKETCFAEEGKK

LVAASQAALGL
```

-continued 309-3GS-309 bivalent construct

SEQ ID NO: 205
SQIEVKDVTDTTALITWSDEFGHYDGCELTYGIKDVPGDRTTIDLWWHSAWYSIGNLKPD

TEYEVSLICYTDQEAGNPAKETFTTGGGGSGGGGSGGGGSRLDAPSQIEVKDVTDTTALI

TWSDEFGHYDGCELTYGIKDVPGDRTTIDLWWHSAWYSIGNLKPDTEYEVSLICYTDQEA

GNPAKETFTT 309-2GS-HSAC34S monovalent construct

SEQ ID NO: 206
SQIEVKDVTDTTALITWSDEFGHYDGCELTYGIKDVPGDRTTIDLWWHSAWYSIGNLKPD

TEYEVSLICYTDQEAGNPAKETFTTGGGGSGGGGSDAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL

SEQ ID NO: 207
309-3GS-309-2GS-HSAC34S bivalent construct
SQIEVKDVTDTTALITWSDEFGHYDGCELTYGIKDVPGDRTTIDLWWHSAWYSIGNLKPD

TEYEVSLICYTDQEAGNPAKETFTTGGGGSGGGGSGGGGSRLDAPSQIEVKDVTDTTALI

TWSDEFGHYDGCELTYGIKDVPGDRTTIDLWWHSAWYSIGNLKPDTEYEVSLICYTDQEA

GNPAKETFTTGGGGSGGGGSDAHKSEVAHRFKDLGEENFKALVLIAFAQYLQQSPFEDHV

KLVNEVTEFAKTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFYAPELLFFAKR

YKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCE

KPLLEKSHCIAEVENDEMPADLPSLAADFVESKDVCKNYAEAKDVFLGMFLYEYARRHPD

YSVVLLLRLAKTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAEDYLSVVLNQL

CVLHEKTPVSDRVTKCCTESLVNRRPCFSALEVDETYVPKEFNAETFTFHADICTLSEKE

RQIKKQTALVELVKHKPKATKEQLKAVMDDFAAFVEKCCKADDKETCFAEEGKKLVAASQ

AALGL 342-3GS-342 bivalent construct

SEQ ID NO: 208
SQIEVKDVTDTTALITWSDDFGEYVWCELTYGIKDVPGDRTTIDLWYHHAHYSIGNLKPD

TEYEVSLICRSGDMSSNPAKETFTTGGGGSGGGGSGGGGSRLDAPSQIEVKDVTDTTALI

TWSDDFGEYVWCELTYGIKDVPGDRTTIDLWYHHAHYSIGNLKPDTEYEVSLICRSGDMS

SNPAKETFTT

Gly-Ser linker module, (G₄X)ₙ where X = G, S, A, L, I, or V
and n = 1-7; the (G₄X)ₙ module wherein n = 1 is shown
                                                                SEQ ID NO: 209
GGGGX OppA signal peptide mutant L25/M                                SEQ ID NO: 210

MTNITKRSLVAAGVLAALMAGNVAMA

---

The invention claimed is:

1. An isolated nucleic acid molecule encoding a Tn3 scaffold comprising a CD40L-specific monomer subunit, wherein the CD40L-specific monomer subunit comprises seven beta strands designated A, B, C, D, E, F, and G, and six loop regions designated AB, BC, CD, DE, EF, and FG, wherein:

(a) the AB loop comprises the amino acid sequence of SEQ ID NO:4;

(b) the BC loop comprises the amino acid sequence of one of SEQ ID NOs:83, 84, 85, 86, 87, 88, 89, 90, 91, 92, 93 or 168 at the BC loop;

(c) the CD loop comprises the amino acid sequence of SEQ ID NO:6;

(d) the DE loop comprises the amino acid sequence of one of SEQ ID NOs:94, 95, 96, 97, 98, or 169;

(e) the EF loop comprises the amino acid sequence of SEQ ID NO: 8; and (f) the FG loop comprises the amino acid sequence of one of SEQ ID NOs:9, 99, 139 or 170.

2. The isolated nucleic acid of claim 1, wherein the Tn3 scaffold comprises two CD40L-specific monomer subunits connected in tandem by a peptide linker.

3. The isolated nucleic acid of claim 2, wherein the Tn3 scaffold binds CD40L and prevents binding of CD40L to CD40 and/or disrupts CD40-mediated signaling.

4. The isolated nucleic acid of claim 1, wherein:

(a) the BC loop comprises the amino acid sequence of SEQ ID NO:83, the DE loop comprises the amino acid sequence of SEQ ID NO:94, and the FG loop comprises the amino acid sequence of SEQ ID NO:9 or 139; or (b) the BC loop comprises the amino acid sequence of SEQ ID NO:83, the DE loop comprises the amino acid sequence of SEQ ID NO:94, and the FG loop comprises the amino acid sequence of SEQ ID NO:99; or (c) the BC loop comprises the amino acid sequence of SEQ ID NO:84, the DE loop comprises the amino acid sequence of SEQ ID NO:95, and the FG loop comprises the amino acid sequence of SEQ ID NO:9 or 139; or (d) the BC loop comprises the amino acid sequence of SEQ ID NO:85, the DE loop comprises the amino acid sequence of SEQ ID NO:94, and the FG loop comprises the amino acid sequence of SEQ ID NO:9 or 139; or (e) the BC loop comprises the amino acid sequence of SEQ ID NO:86, the DE loop comprises the amino acid sequence of SEQ ID NO:96, and the FG loop comprises the amino acid sequence of SEQ ID NO:9 or 139; or (f) the BC loop comprises the amino acid sequence of SEQ ID NO:87, the DE loop comprises the amino acid sequence of SEQ ID NO:97, and the FG loop comprises the amino acid sequence of SEQ ID NO:9 or 139; or (g) the BC loop comprises the amino acid sequence of SEQ ID NO:88, the DE loop comprises the amino acid sequence of SEQ ID NO:95, and the FG loop comprises the amino acid sequence of SEQ ID NO:9 or 139; or (h) the BC loop comprises the amino acid sequence of SEQ ID NO:89, the DE loop comprises the amino acid sequence of SEQ ID NO:94, and the FG loop comprises the amino acid sequence of SEQ ID NO:9 or 139; or (i) the BC loop comprises the amino acid sequence of SEQ ID NO:90, the DE loop comprises the amino acid sequence of SEQ ID NO:94, and the FG loop comprises the amino acid sequence of SEQ ID NO:9 or 139; or (j) the BC loop comprises the amino acid sequence of SEQ ID NO:91, the DE loop comprises the amino acid sequence of SEQ ID NO:95, and the FG loop comprises the amino acid sequence of SEQ ID NO:9 or 139; or (k) the BC loop comprises the amino acid sequence of SEQ ID NO:92, the DE loop comprises the amino acid sequence of SEQ ID NO:98, and the FG loop comprises the amino acid sequence of SEQ ID NO:9 or 139; or (l) the BC loop comprises the amino acid sequence of SEQ ID NO:93, the DE loop comprises the amino acid sequence of SEQ ID NO:94, and the FG loop comprises the amino acid sequence of SEQ ID NO:9 or 139.

5. The isolated nucleic acid molecule of claim 1, wherein:

(a) the A beta strand consists of the amino acid sequence of SEQ ID NO: 11;

(b) the B beta strand consists of the amino acid sequence of SEQ ID NO: 12;

(c) the C beta strand consists of the amino acid sequence of SEQ ID NO: 13 or 14;

(d) the D beta strand consists of the amino acid sequence of SEQ ID NO: 15;

(e) the E beta strand consists of the amino acid sequence of SEQ ID NO: 16;

(f) the F beta strand consists of the amino acid sequence of SEQ ID NO: 17; and (g) the G beta strand consists of the amino acid sequence of SEQ ID NO: 18.

6. The isolated nucleic acid molecule of claim 1, wherein the Tn3 scaffold comprises the amino acid sequence of one of SEQ ID NOs: 134, 135, 144, 145, 166, 205, 206, 207 or 208.

7. The isolated nucleic acid molecule of claim 2, wherein the peptide linker comprises amino acid sequence $(G_mX)_n$, wherein:

(a) X is Serine, Alanine, Glycine, Leucine, Isoleucine or Valine;

(b) m and n are integers;

(c) m is 1, 2, 3 or 4; and (d) n is 1, 2, 3, 4, 5, 6 or 7.

8. The isolated nucleic acid molecule of claim 7, wherein the peptide linker comprises the amino acid sequence of SEQ ID NO: 131, SEQ ID NO: 132, SEQ ID NO: 142, or SEQ ID NO: 143.

9. An isolated nucleic acid molecule encoding a Tn3 scaffold fusion protein, wherein the fusion protein comprises a Tn3 scaffold protein and a heterologous moiety, wherein:

the Tn3 scaffold protein comprises a CD40L-specific monomer subunit, wherein the CD40L-specific monomer subunit comprises seven beta strands designated A, B, C, D, E, F, and G, and six loop regions designated AB, BC, CD, DE, EF, and FG, wherein the AB loop comprises SEQ ID NO; 4; the BC loop comprises the amino acid sequence as shown in one of SEQ ID NOs: 83, 84, 85, 86, 87, 88, 89, 90, 91, 92, 93 or 168; the CD loop comprises the amino acid sequence as shown in SEQ ID NO: 6; the DE loop comprises the amino acid sequence as shown in one of SEQ ID NOs: 94, 95, 96, 97, 98, or 169; the EF loop comprises the amino acid sequence as shown in SEQ ID NO:8; and the FG loop comprises the amino acid sequence as shown in one of SEQ ID NOs: 9, 99, 139, or 170, and wherein the encoded Tn3 scaffold specifically binds to CD40L; and wherein the heterologous moiety is biotin, an albumin, a human serum albumin (HSA), an HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, or a cytokine.

10. The isolated nucleic acid molecule of claim 9, wherein the heterologous moiety is HSA.

11. The isolated nucleic acid molecule of claim 10, wherein the HSA comprises the amino acid sequence of one of SEQ ID NOs: 133 or 138.

12. The isolated nucleic acid molecule of claim 9, wherein the A beta strand consists of the amino acid sequence of SEQ ID NO:11, the B beta strand consists of the amino acid sequence of SEQ ID NO:12, the C beta strand consists of the amino acid sequence of SEQ ID NO:13 or 14, the D beta strand consists of the amino acid sequence of SEQ ID NO:15, the E beta strand consists of the amino acid sequence of SEQ ID NO:16, the F beta strand consists of the amino acid sequence of SEQ ID NO:17, and the G beta strand consists of the amino acid sequence of SEQ ID NO:18.

13. The isolated nucleic acid molecule of claim 9, wherein the Tn3 scaffold comprises two CD40L-specific monomer subunits connected in tandem by a peptide linker.

14. The isolated nucleic acid molecule of claim 13, wherein each of the two CD40L-specific monomer subunits comprise the amino acid sequence of one of SEQ ID NOs: 20, 22, 24, 26, 28, 30, 32, 34, 36, 40, 42, or 146.

15. The isolated nucleic acid molecule of claim 14, wherein the heterologous moiety is HSA or the HSA FcRn binding portion.

16. The isolated nucleic acid molecule of claim 15, wherein the Tn3 scaffold fusion protein comprises the amino acid sequence as shown in SEQ ID NO:135 or 145.

17. An expression vector comprising the nucleic acid of claim 1.

18. A host cell comprising the expression vector of claim 17.

19. A method of producing a Tn3 scaffold comprising: culturing the host cell of claim 18 under conditions in which the Tn3 scaffold encoded by the nucleic acid molecule is expressed.

20. The isolated nucleic acid molecule of claim 4, wherein the BC loop comprises the amino acid sequence of SEQ ID NO:86, the DE loop comprises the amino acid sequence of SEQ ID NO:96, and the FG loop comprises the amino acid sequence of SEQ ID NO: 139.

21. The isolated nucleic acid molecule of claim 14, wherein each of the two CD40L-specific monomer subunits comprise the amino acid sequence of SEQ ID NO:146.

22. The isolated nucleic acid molecule of claim 16, wherein the Tn3 scaffold fusion protein comprises the amino acid sequence as shown in SEQ ID NO:145.

* * * * *

SEQUENCE LISTING

<160> NUMBER OF SEQ ID NOS: 210

<210> SEQ ID NO 1
<211> LENGTH: 261
<212> TYPE: PRT
<213> ORGANISM: Homo sapiens

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 2
<211> LENGTH: 149
<212> TYPE: PRT
<213> ORGANISM: Homo sapiens

<400> SEQUENCE: 2

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145

<210> SEQ ID NO 3
<211> LENGTH: 83
<212> TYPE: PRT
<213> ORGANISM: Artificial Sequence
<220> FEATURE:
<223> OTHER INFORMATION: synthetic construct

<400> SEQUENCE: 3

Ile Glu Val Lys Asp Val Thr Asp Thr Thr Ala Leu Ile Thr Trp Phe
1               5                   10                  15

Lys Pro Leu Ala Glu Ile Asp Gly Cys Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Lys Asp Val Thr Asp Thr Thr
1               5

<210> SEQ ID NO 5
<211> LENGTH: 9
<212> TYPE: PRT
<213> ORGANISM: Artificial Sequence
<220> FEATURE:

```
<223> OTHER INFORMATION: synthetic construct

<400> SEQUENCE: 5

Phe Lys Pro Leu Ala Glu Ile Asp Gly
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic construct

<400> SEQUENCE: 6

Lys Asp Val Pro Gly Asp Arg
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic construct

<400> SEQUENCE: 7

Thr Glu Asp Glu Asn Gln
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic construct

<400> SEQUENCE: 8

Gly Asn Leu Lys Pro Asp Thr Glu
1               5

<210> SEQ ID NO 9
<211> LENGTH: 10
<212> TYPE: PRT
<213> ORGANISM: Artificial Sequence
<220> FEATURE:
<223> OTHER INFORMATION: synthetic construct

<400> SEQUENCE: 9

Arg Arg Gly Asp Met Ser Ser Asn Pro Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic construct

<400> SEQUENCE: 10

Arg Leu Asp Ala Pro Ser Gln Ile Glu Val
1               5                   10

<210> SEQ ID NO 11
<211> LENGTH: 3
<212> TYPE: PRT
<213> ORGANISM: Artificial Sequence
<220> FEATURE:
<223> OTHER INFORMATION: synthetic construct
```

```
<400> SEQUENCE: 11

Ile Glu Val
1

<210> SEQ ID NO 12
<211> LENGTH: 5
<212> TYPE: PRT
<213> ORGANISM: Artificial Sequence
<220> FEATURE:
<223> OTHER INFORMATION: synthetic construct

<400> SEQUENCE: 12

Ala Leu Ile Thr Trp
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic construct

<400> SEQUENCE: 13

Cys Glu Leu Ala Tyr Gly Ile
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic construct

<400> SEQUENCE: 14

Cys Glu Leu Thr Tyr Gly Ile
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic construct

<400> SEQUENCE: 15

Thr Thr Ile Asp Leu
1               5

<210> SEQ ID NO 16
<211> LENGTH: 3
<212> TYPE: PRT
<213> ORGANISM: Artificial Sequence
<220> FEATURE:
<223> OTHER INFORMATION: synthetic construct

<400> SEQUENCE: 16

Tyr Ser Ile
1

<210> SEQ ID NO 17
<211> LENGTH: 7
<212> TYPE: PRT
<213> ORGANISM: Artificial Sequence
<220> FEATURE:
<223> OTHER INFORMATION: synthetic construct
```

```
<400> SEQUENCE: 17

Tyr Glu Val Ser Leu Ile Cys
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic construct

<400> SEQUENCE: 18

Lys Glu Thr Phe Thr Thr
1               5

<210> SEQ ID NO 19
<211> LENGTH: 98
<212> TYPE: PRT
<213> ORGANISM: Artificial Sequence
<220> FEATURE:
<223> OTHER INFORMATION: synthetic construct

<400> SEQUENCE: 19

Ala Ile Glu Val Lys Asp Val Thr Asp Thr Thr Ala Leu Ile Thr Trp
1               5                   10                  15

Ser Asp Glu Phe Gly His Tyr Asp Gly Cys Glu Leu Thr Tyr Gly Ile
                20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
        50                  55                  60

Ser Leu Ile Cys Tyr Thr Asp Gln Glu Ala Gly Asn Pro Ala Lys Glu
65                  70                  75                  80

Thr Phe Thr Thr Gly Gly Gly Thr Leu Gly His His His His His
                    85                  90                  95

His His

<210> SEQ ID NO 20
<211> LENGTH: 83
<212> TYPE: PRT
<213> ORGANISM: Artificial Sequence
<220> FEATURE:
<223> OTHER INFORMATION: synthetic construct

<400> SEQUENCE: 20

Ile Glu Val Lys Asp Val Thr Asp Thr Thr Ala Leu Ile Thr Trp Ser
1               5                   10                  15

Asp Glu Phe Gly His Tyr Asp Gly Cys Glu Leu Thr Tyr Gly Ile Lys
                20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
        50                  55                  60

Leu Ile Cys Tyr Thr Asp Gln Glu Ala Gly Asn Pro Ala Lys Glu Thr
65                  70                  75                  80

Phe Thr Thr

<210> SEQ ID NO 21
<211> LENGTH: 98
<212> TYPE: PRT
```

```
<213> ORGANISM: Artificial Sequence
<220> FEATURE:
<223> OTHER INFORMATION: synthetic construct

<400> SEQUENCE: 21

Ala Ile Glu Val Lys Asp Val Thr Asp Thr Thr Ala Leu Ile Thr Trp
1               5                   10                  15

Ser Asp Glu Phe Gly His Tyr Asp Gly Cys Glu Leu Thr Tyr Gly Ile
            20                  25                  30

Lys Asp Val Pro Gly Asp Arg Thr Thr Ile Asp Leu Trp Trp His Ser
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
                85                  90                  95

His His

<210> SEQ ID NO 22
<211> LENGTH: 83
<212> TYPE: PRT
<213> ORGANISM: Artificial Sequence
<220> FEATURE:
<223> OTHER INFORMATION: synthetic construct

<400> SEQUENCE: 22

Ile Glu Val Lys Asp Val Thr Asp Thr Thr Ala Leu Ile Thr Trp Ser
1               5                   10                  15

Asp Glu Phe Gly His Tyr Asp Gly Cys Glu Leu Thr Tyr Gly Ile Lys
            20                  25                  30

Asp Val Pro Gly Asp Arg Thr Thr Ile Asp Leu Trp Trp His Ser Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 23
<211> LENGTH: 98
<212> TYPE: PRT
<213> ORGANISM: Artificial Sequence
<220> FEATURE:
<223> OTHER INFORMATION: synthetic construct

<400> SEQUENCE: 23

Ala Ile Glu Val Lys Asp Val Thr Asp Thr Thr Ala Leu Ile Thr Trp
1               5                   10                  15

Ser Asp Asp Phe Asp Asn Tyr Glu Trp Cys Glu Leu Thr Tyr Gly Ile
            20                  25                  30

Lys Asp Val Pro Gly Asp Arg Thr Thr Ile Asp Leu Trp Tyr His Met
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
```

His His

<210> SEQ ID NO 24
<211> LENGTH: 83
<212> TYPE: PRT
<213> ORGANISM: Artificial Sequence
<220> FEATURE:
<223> OTHER INFORMATION: synthetic construct

<400> SEQUENCE: 24

```
Ile Glu Val Lys Asp Val Thr Asp Thr Thr Ala Leu Ile Thr Trp Ser
1               5                   10                  15
Asp Asp Phe Asp Asn Tyr Glu Trp Cys Glu Leu Thr Tyr Gly Ile Lys
            20                  25                  30
Asp Val Pro Gly Asp Arg Thr Thr Ile Asp Leu Trp Tyr His Met Ala
        35                  40                  45
Trp Tyr Ser Ile Gly Asn Leu Lys Pro Asp Thr Glu Tyr Glu Val Ser
    50                  55                  60
Leu Ile Cys Arg Arg Gly Asp Met Ser Ser Asn Pro Ala Lys Glu Thr
65                  70                  75                  80
Phe Thr Thr
```

<210> SEQ ID NO 25
<211> LENGTH: 98
<212> TYPE: PRT
<213> ORGANISM: Artificial Sequence
<220> FEATURE:
<223> OTHER INFORMATION: synthetic construct

<400> SEQUENCE: 25

```
Ala Ile Glu Val Lys Asp Val Thr Asp Thr Thr Ala Leu Ile Thr Trp
1               5                   10                  15
Ser Asp Asp Phe Ala Asp Tyr Val Trp Cys Glu Leu Thr Tyr Gly Ile
            20                  25                  30
Lys Asp Val Pro Gly Asp Arg Thr Thr Ile Asp Leu Trp Trp His Ser
        35                  40                  45
Ala Trp Tyr Ser Ile Gly Asn Leu Lys Pro Asp Thr Glu Tyr Glu Val
    50                  55                  60
Ser Leu Ile Cys Arg Arg Gly Asp Met Ser Ser Asn Pro Ala Lys Glu
65                  70                  75                  80
Thr Phe Thr Thr Gly Gly Gly Thr Leu Gly His His His His His His
                85                  90                  95
His His
```

<210> SEQ ID NO 26
<211> LENGTH: 83
<212> TYPE: PRT
<213> ORGANISM: Artificial Sequence
<220> FEATURE:
<223> OTHER INFORMATION: synthetic construct

<400> SEQUENCE: 26

```
Ile Glu Val Lys Asp Val Thr Asp Thr Thr Ala Leu Ile Thr Trp Ser
1               5                   10                  15
Asp Asp Phe Ala Asp Tyr Val Trp Cys Glu Leu Thr Tyr Gly Ile Lys
            20                  25                  30
Asp Val Pro Gly Asp Arg Thr Thr Ile Asp Leu Trp Trp His Ser Ala
        35                  40                  45
```

-continued

Trp Tyr Ser Ile Gly Asn Leu Lys Pro Asp Thr Glu Tyr Glu Val Ser
 50                  55                  60

Leu Ile Cys Arg Arg Gly Asp Met Ser Ser Asn Pro Ala Lys Glu Thr
 65                  70                  75                  80

Phe Thr Thr

<210> SEQ ID NO 27
<211> LENGTH: 98
<212> TYPE: PRT
<213> ORGANISM: Artificial Sequence
<220> FEATURE:
<223> OTHER INFORMATION: synthetic construct

<400> SEQUENCE: 27

Ala Ile Glu Val Lys Asp Val Thr Asp Thr Thr Ala Leu Ile Thr Trp
 1               5                  10                  15

Ser Asp Asp Phe Gly Glu Tyr Val Trp Cys Glu Leu Thr Tyr Gly Ile
                 20                  25                  30

Lys Asp Val Pro Gly Asp Arg Thr Thr Ile Asp Leu Trp Tyr His His
             35                  40                  45

Ala His Tyr Ser Ile Gly Asn Leu Lys Pro Asp Thr Glu Tyr Glu Val
         50                  55                  60

Ser Leu Ile Cys Arg Arg Gly Asp Met Ser Ser Asn Pro Ala Lys Glu
 65                  70                  75                  80

Thr Phe Thr Thr Gly Gly Gly Thr Leu Gly His His His His His His
                 85                  90                  95

His His

<210> SEQ ID NO 28
<211> LENGTH: 83
<212> TYPE: PRT
<213> ORGANISM: Artificial Sequence
<220> FEATURE:
<223> OTHER INFORMATION: synthetic construct

<400> SEQUENCE: 28

Ile Glu Val Lys Asp Val Thr Asp Thr Thr Ala Leu Ile Thr Trp Ser
 1               5                  10                  15

Asp Asp Phe Gly Glu Tyr Val Trp Cys Glu Leu Thr Tyr Gly Ile Lys
                 20                  25                  30

Asp Val Pro Gly Asp Arg Thr Thr Ile Asp Leu Trp Tyr His His Ala
             35                  40                  45

His Tyr Ser Ile Gly Asn Leu Lys Pro Asp Thr Glu Tyr Glu Val Ser
         50                  55                  60

Leu Ile Cys Arg Arg Gly Asp Met Ser Ser Asn Pro Ala Lys Glu Thr
 65                  70                  75                  80

Phe Thr Thr

<210> SEQ ID NO 29
<211> LENGTH: 98
<212> TYPE: PRT
<213> ORGANISM: Artificial Sequence
<220> FEATURE:
<223> OTHER INFORMATION: synthetic construct

<400> SEQUENCE: 29

Ala Ile Glu Val Lys Asp Val Thr Asp Thr Thr Ala Leu Ile Thr Trp
 1               5                  10                  15

Leu Asp Asp Trp Gly Ser Tyr His Val Cys Glu Leu Thr Tyr Gly Ile
            20                  25                  30

Lys Asp Val Pro Gly Asp Arg Thr Thr Ile Asp Leu Trp Tyr His Gln
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 30
<211> LENGTH: 83
<212> TYPE: PRT
<213> ORGANISM: Artificial Sequence
<220> FEATURE:
<223> OTHER INFORMATION: synthetic construct

<400> SEQUENCE: 30

Ile Glu Val Lys Asp Val Thr Asp Thr Thr Ala Leu Ile Thr Trp Leu
1               5                   10                  15

Asp Asp Trp Gly Ser Tyr His Val Cys Glu Leu Thr Tyr Gly Ile Lys
            20                  25                  30

Asp Val Pro Gly Asp Arg Thr Thr Ile Asp Leu Trp Tyr His Gln Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 31
<211> LENGTH: 98
<212> TYPE: PRT
<213> ORGANISM: Artificial Sequence
<220> FEATURE:
<223> OTHER INFORMATION: synthetic construct

<400> SEQUENCE: 31

Ala Ile Glu Val Lys Asp Val Thr Asp Thr Thr Ala Leu Ile Thr Trp
1               5                   10                  15

Ser Asp Glu Val Gly Asp Tyr Val Val Cys Glu Leu Thr Tyr Gly Ile
            20                  25                  30

Lys Asp Val Pro Gly Asp Arg Thr Thr Ile Asp Leu Trp Tyr His Met
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 32
<211> LENGTH: 83
<212> TYPE: PRT
<213> ORGANISM: Artificial Sequence
<220> FEATURE:
<223> OTHER INFORMATION: synthetic construct

<400> SEQUENCE: 32

```
Ile Glu Val Lys Asp Val Thr Asp Thr Thr Ala Leu Ile Thr Trp Ser
1               5                   10                  15

Asp Glu Val Gly Asp Tyr Val Val Cys Glu Leu Thr Tyr Gly Ile Lys
            20                  25                  30

Asp Val Pro Gly Asp Arg Thr Thr Ile Asp Leu Trp Tyr His Met Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 33
<211> LENGTH: 98
<212> TYPE: PRT
<213> ORGANISM: Artificial Sequence
<220> FEATURE:
<223> OTHER INFORMATION: synthetic construct

<400> SEQUENCE: 33

```
Ala Ile Glu Val Lys Asp Val Thr Asp Thr Thr Ala Leu Ile Thr Trp
1               5                   10                  15

Ser Asp Asp Phe Ala Glu Tyr Val Gly Cys Glu Leu Thr Tyr Gly Ile
            20                  25                  30

Lys Asp Val Pro Gly Asp Arg Thr Thr Ile Asp Leu Trp Trp His Ser
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His
```

<210> SEQ ID NO 34
<211> LENGTH: 83
<212> TYPE: PRT
<213> ORGANISM: Artificial Sequence
<220> FEATURE:
<223> OTHER INFORMATION: synthetic construct

<400> SEQUENCE: 34

```
Ile Glu Val Lys Asp Val Thr Asp Thr Thr Ala Leu Ile Thr Trp Ser
1               5                   10                  15

Asp Asp Phe Ala Glu Tyr Val Gly Cys Glu Leu Thr Tyr Gly Ile Lys
            20                  25                  30

Asp Val Pro Gly Asp Arg Thr Thr Ile Asp Leu Trp Trp His Ser Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 35
<211> LENGTH: 98
<212> TYPE: PRT
<213> ORGANISM: Artificial Sequence
<220> FEATURE:
<223> OTHER INFORMATION: synthetic construct

<400> SEQUENCE: 35

```
Ala Ile Glu Val Lys Asp Val Thr Asp Thr Thr Ala Leu Ile Thr Trp
1               5                   10                  15

Ser Asp Asp Phe Glu Glu Tyr Val Val Cys Glu Leu Thr Tyr Gly Ile
                20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
                85                  90                  95

His His
```

<210> SEQ ID NO 36
<211> LENGTH: 83
<212> TYPE: PRT
<213> ORGANISM: Artificial Sequence
<220> FEATURE:
<223> OTHER INFORMATION: synthetic construct

<400> SEQUENCE: 36

```
Ile Glu Val Lys Asp Val Thr Asp Thr Thr Ala Leu Ile Thr Trp Ser
1               5                   10                  15

Asp Asp Phe Glu Glu Tyr Val Val Cys Glu Leu Thr Tyr Gly Ile Lys
                20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 37
<211> LENGTH: 98
<212> TYPE: PRT
<213> ORGANISM: Artificial Sequence
<220> FEATURE:
<223> OTHER INFORMATION: synthetic construct

<400> SEQUENCE: 37

```
Ala Ile Glu Val Lys Asp Val Thr Asp Thr Thr Ala Leu Ile Thr Trp
1               5                   10                  15

Ser Asp Glu Val Gly Gln Tyr Val Gly Cys Glu Leu Thr Tyr Gly Ile
                20                  25                  30

Lys Asp Val Pro Gly Asp Arg Thr Thr Ile Asp Leu Trp Tyr His Met
            35                  40                  45

Ala Trp Tyr Ser Ile Gly Asn Leu Lys Pro Asp Thr Glu Tyr Glu Val
        50                  55                  60
```

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 38
<211> LENGTH: 83
<212> TYPE: PRT
<213> ORGANISM: Artificial Sequence
<220> FEATURE:
<223> OTHER INFORMATION: synthetic construct

<400> SEQUENCE: 38

Ile Glu Val Lys Asp Val Thr Asp Thr Thr Ala Leu Ile Thr Trp Ser
1               5                   10                  15

Asp Glu Val Gly Gln Tyr Val Gly Cys Glu Leu Thr Tyr Gly Ile Lys
                20                  25                  30

Asp Val Pro Gly Asp Arg Thr Thr Ile Asp Leu Trp Tyr His Met Ala
            35                  40                  45

Trp Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr

<210> SEQ ID NO 39
<211> LENGTH: 98
<212> TYPE: PRT
<213> ORGANISM: Artificial Sequence
<220> FEATURE:
<223> OTHER INFORMATION: synthetic construct

<400> SEQUENCE: 39

Ala Ile Glu Val Lys Asp Val Thr Asp Thr Thr Ala Leu Ile Thr Trp
1               5                   10                  15

Ser Asp Asp Ile Gly Leu Tyr Val Trp Cys Glu Leu Thr Tyr Gly Ile
                20                  25                  30

Lys Asp Val Pro Gly Asp Arg Thr Thr Ile Asp Leu Trp Phe His Gln
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 40
<211> LENGTH: 83
<212> TYPE: PRT
<213> ORGANISM: Artificial Sequence
<220> FEATURE:
<223> OTHER INFORMATION: synthetic construct

<400> SEQUENCE: 40

Ile Glu Val Lys Asp Val Thr Asp Thr Thr Ala Leu Ile Thr Trp Ser
1               5                   10                  15

Asp Asp Ile Gly Leu Tyr Val Trp Cys Glu Leu Thr Tyr Gly Ile Lys

```
                    20                  25                  30
Asp Val Pro Gly Asp Arg Thr Thr Ile Asp Leu Trp Phe His Gln Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 41
<211> LENGTH: 98
<212> TYPE: PRT
<213> ORGANISM: Artificial Sequence
<220> FEATURE:
<223> OTHER INFORMATION: synthetic construct

<400> SEQUENCE: 41

Ala Ile Glu Val Lys Asp Val Thr Asp Thr Thr Ala Leu Ile Thr Trp
1               5                   10                  15

Ser Asp Glu His Ala Glu Phe Ile Gly Cys Glu Leu Thr Tyr Gly Ile
            20                  25                  30

Lys Asp Val Pro Gly Asp Arg Thr Thr Ile Asp Leu Trp Trp His Ser
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
                85                  90                  95

His His

<210> SEQ ID NO 42
<211> LENGTH: 83
<212> TYPE: PRT
<213> ORGANISM: Artificial Sequence
<220> FEATURE:
<223> OTHER INFORMATION: synthetic construct

<400> SEQUENCE: 42

Ile Glu Val Lys Asp Val Thr Asp Thr Thr Ala Leu Ile Thr Trp Ser
1               5                   10                  15

Asp Glu His Ala Glu Phe Ile Gly Cys Glu Leu Thr Tyr Gly Ile Lys
            20                  25                  30

Asp Val Pro Gly Asp Arg Thr Thr Ile Asp Leu Trp Trp His Ser Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 43
<211> LENGTH: 101
<212> TYPE: PRT
<213> ORGANISM: Artificial Sequence
<220> FEATURE:
<223> OTHER INFORMATION: synthetic construct

<400> SEQUENCE: 43
```

```
Ala Ile Glu Val Lys Asp Val Thr Asp Thr Thr Ala Leu Ile Thr Trp
1               5                   10                  15

Thr Asn Arg Ser Ser Tyr Tyr Asn Leu His Gly Cys Glu Leu Thr Tyr
            20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100
```

<210> SEQ ID NO 44
<211> LENGTH: 86
<212> TYPE: PRT
<213> ORGANISM: Artificial Sequence
<220> FEATURE:
<223> OTHER INFORMATION: synthetic construct

<400> SEQUENCE: 44

```
Ile Glu Val Lys Asp Val Thr Asp Thr Thr Ala Leu Ile Thr Trp Thr
1               5                   10                  15

Asn Arg Ser Ser Tyr Tyr Asn Leu His Gly Cys Glu Leu Thr Tyr Gly
            20                  25                  30

Ile Lys Asp Val Pro Gly Asp Arg Thr Thr Ile Asp Leu Ser Ser Pro
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Thr Tyr Ser Asn Pro Ala
65                  70                  75                  80

Lys Glu Thr Phe Thr Thr
                85
```

<210> SEQ ID NO 45
<211> LENGTH: 101
<212> TYPE: PRT
<213> ORGANISM: Artificial Sequence
<220> FEATURE:
<223> OTHER INFORMATION: synthetic construct

<400> SEQUENCE: 45

```
Ala Ile Glu Val Glu Asp Val Thr Asp Thr Thr Ala Leu Ile Thr Trp
1               5                   10                  15

Thr Asn Arg Ser Ser Tyr Tyr Asn Leu His Gly Cys Glu Leu Thr Tyr
            20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
```

<210> SEQ ID NO 46
<211> LENGTH: 86
<212> TYPE: PRT
<213> ORGANISM: Artificial Sequence
<220> FEATURE:
<223> OTHER INFORMATION: synthetic construct

<400> SEQUENCE: 46

```
Ile Glu Val Glu Asp Val Thr Asp Thr Thr Ala Leu Ile Thr Trp Thr
1               5                   10                  15
Asn Arg Ser Ser Tyr Tyr Asn Leu His Gly Cys Glu Leu Thr Tyr Gly
            20                  25                  30
Ile Lys Asp Val Pro Gly Asp Arg Thr Thr Ile Asp Leu Ser Ser Pro
        35                  40                  45
Tyr Val His Tyr Ser Ile Gly Asn Leu Lys Pro Asp Thr Glu Tyr Glu
    50                  55                  60
Val Ser Leu Ile Cys Leu Thr Thr Asp Gly Thr Tyr Ser Asn Pro Ala
65                  70                  75                  80
Lys Glu Thr Phe Thr Thr
                85
```

<210> SEQ ID NO 47
<211> LENGTH: 101
<212> TYPE: PRT
<213> ORGANISM: Artificial Sequence
<220> FEATURE:
<223> OTHER INFORMATION: synthetic construct

<400> SEQUENCE: 47

```
Ala Ile Glu Val Glu Asp Val Thr Asp Thr Thr Ala Leu Ile Thr Trp
1               5                   10                  15
Ile Asn Arg Ser Tyr Tyr Ala Asp Leu His Gly Cys Glu Leu Thr Tyr
            20                  25                  30
Gly Ile Lys Asp Val Pro Gly Asp Arg Thr Thr Ile Asp Leu Asp Gln
        35                  40                  45
Ile Tyr Val His Tyr Ser Ile Gly Asn Leu Lys Pro Asp Thr Lys Tyr
    50                  55                  60
Glu Val Ser Leu Ile Cys Leu Thr Thr Asp Gly Thr Tyr Ser Asn Pro
65                  70                  75                  80
Ala Lys Glu Thr Phe Thr Thr Gly Gly Gly Thr Leu Gly His His His
                85                  90                  95
His His His His His
            100
```

<210> SEQ ID NO 48
<211> LENGTH: 86
<212> TYPE: PRT
<213> ORGANISM: Artificial Sequence
<220> FEATURE:
<223> OTHER INFORMATION: synthetic construct

<400> SEQUENCE: 48

```
Ile Glu Val Glu Asp Val Thr Asp Thr Thr Ala Leu Ile Thr Trp Ile
1               5                   10                  15
Asn Arg Ser Tyr Tyr Ala Asp Leu His Gly Cys Glu Leu Thr Tyr Gly
            20                  25                  30
Ile Lys Asp Val Pro Gly Asp Arg Thr Thr Ile Asp Leu Asp Gln Ile
        35                  40                  45
```

Tyr Val His Tyr Ser Ile Gly Asn Leu Lys Pro Asp Thr Lys Tyr Glu
            50                  55                  60

Val Ser Leu Ile Cys Leu Thr Thr Asp Gly Thr Tyr Ser Asn Pro Ala
 65                  70                  75                  80

Lys Glu Thr Phe Thr Thr
                 85

<210> SEQ ID NO 49
<211> LENGTH: 102
<212> TYPE: PRT
<213> ORGANISM: Artificial Sequence
<220> FEATURE:
<223> OTHER INFORMATION: synthetic construct

<400> SEQUENCE: 49

Ala Ile Glu Val Glu Asp Val Thr Asp Thr Thr Ala Leu Ile Thr Trp
 1               5                  10                  15

Thr Asn Arg Ser Ser Tyr Ser His Leu Asp Gly Cys Glu Leu Thr Tyr
                20                  25                  30

Gly Ile Lys Asp Val Pro Gly Asp Arg Thr Thr Ile Asp Leu Ser Ala
             35                  40                  45

Ala Ile Tyr Val His Tyr Ser Ile Gly Asn Leu Lys Pro Asp Thr Glu
         50                  55                  60

Tyr Glu Val Ser Leu Ile Cys Leu Thr Thr Asp Gly Thr Tyr Ser Asn
 65                  70                  75                  80

Pro Ala Lys Glu Thr Phe Thr Thr Gly Gly Gly Thr Leu Gly His His
                 85                  90                  95

His His His His His His
            100

<210> SEQ ID NO 50
<211> LENGTH: 87
<212> TYPE: PRT
<213> ORGANISM: Artificial Sequence
<220> FEATURE:
<223> OTHER INFORMATION: synthetic construct

<400> SEQUENCE: 50

Ile Glu Val Glu Asp Val Thr Asp Thr Thr Ala Leu Ile Thr Trp Thr
 1               5                  10                  15

Asn Arg Ser Ser Tyr Ser His Leu Asp Gly Cys Glu Leu Thr Tyr Gly
                20                  25                  30

Ile Lys Asp Val Pro Gly Asp Arg Thr Thr Ile Asp Leu Ser Ala Ala
             35                  40                  45

Ile Tyr Val His Tyr Ser Ile Gly Asn Leu Lys Pro Asp Thr Glu Tyr
         50                  55                  60

Glu Val Ser Leu Ile Cys Leu Thr Thr Asp Gly Thr Tyr Ser Asn Pro
 65                  70                  75                  80

Ala Lys Glu Thr Phe Thr Thr
                 85

<210> SEQ ID NO 51
<211> LENGTH: 101
<212> TYPE: PRT
<213> ORGANISM: Artificial Sequence
<220> FEATURE:
<223> OTHER INFORMATION: synthetic construct

<400> SEQUENCE: 51

Ala Ile Glu Val Glu Asp Val Thr Asp Thr Thr Ala Leu Ile Thr Trp
1               5                   10                  15

Ile Asn Arg Ser Ser Tyr His Asn Phe Pro His Cys Glu Leu Ala Tyr
            20                  25                  30

Gly Ile Lys Asp Val Pro Gly Asp Arg Thr Thr Ile Asp Leu Asn Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 52
<211> LENGTH: 86
<212> TYPE: PRT
<213> ORGANISM: Artificial Sequence
<220> FEATURE:
<223> OTHER INFORMATION: synthetic construct

<400> SEQUENCE: 52

Ile Glu Val Glu Asp Val Thr Asp Thr Thr Ala Leu Ile Thr Trp Ile
1               5                   10                  15

Asn Arg Ser Ser Tyr His Asn Phe Pro His Cys Glu Leu Ala Tyr Gly
            20                  25                  30

Ile Lys Asp Val Pro Gly Asp Arg Thr Thr Ile Asp Leu Asn Ser Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 53
<211> LENGTH: 101
<212> TYPE: PRT
<213> ORGANISM: Artificial Sequence
<220> FEATURE:
<223> OTHER INFORMATION: synthetic construct

<400> SEQUENCE: 53

Ala Ile Glu Val Glu Asp Val Thr Asp Thr Thr Ala Leu Ile Thr Trp
1               5                   10                  15

Thr Asn Arg Ser Ser Tyr Ser Asn His Leu Gly Cys Glu Leu Ala Tyr
            20                  25                  30

Gly Ile Lys Asp Val Pro Gly Asp Arg Thr Thr Ile Asp Leu Asn Asn
            35                  40                  45

Ile Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 54
<211> LENGTH: 86
<212> TYPE: PRT
<213> ORGANISM: Artificial Sequence
<220> FEATURE:
<223> OTHER INFORMATION: synthetic construct

<400> SEQUENCE: 54

Ile Glu Val Glu Asp Val Thr Asp Thr Thr Ala Leu Ile Thr Trp Thr
1               5                   10                  15

Asn Arg Ser Ser Tyr Ser Asn His Leu Gly Cys Glu Leu Ala Tyr Gly
            20                  25                  30

Ile Lys Asp Val Pro Gly Asp Arg Thr Thr Ile Asp Leu Asn Asn Ile
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 55
<211> LENGTH: 101
<212> TYPE: PRT
<213> ORGANISM: Artificial Sequence
<220> FEATURE:
<223> OTHER INFORMATION: synthetic construct

<400> SEQUENCE: 55

Ala Ile Glu Val Glu Asp Val Thr Asp Thr Thr Ala Leu Ile Thr Trp
1               5                   10                  15

Thr Asn Arg Ser Ser Tyr Ser Asn Phe His Gly Cys Glu Leu Ala Tyr
            20                  25                  30

Gly Ile Lys Asp Val Pro Gly Asp Arg Thr Thr Ile Asp Leu Asn Ser
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 56
<211> LENGTH: 86
<212> TYPE: PRT
<213> ORGANISM: Artificial Sequence
<220> FEATURE:
<223> OTHER INFORMATION: synthetic construct

<400> SEQUENCE: 56

Ile Glu Val Glu Asp Val Thr Asp Thr Thr Ala Leu Ile Thr Trp Thr
1               5                   10                  15

Asn Arg Ser Ser Tyr Ser Asn Phe His Gly Cys Glu Leu Ala Tyr Gly
            20                  25                  30

Ile Lys Asp Val Pro Gly Asp Arg Thr Thr Ile Asp Leu Asn Ser Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
 65                  70                  75                  80

Lys Glu Thr Phe Thr Thr
                 85

<210> SEQ ID NO 57
<211> LENGTH: 101
<212> TYPE: PRT
<213> ORGANISM: Artificial Sequence
<220> FEATURE:
<223> OTHER INFORMATION: synthetic construct

<400> SEQUENCE: 57

Ala Ile Glu Val Glu Asp Val Thr Asp Thr Thr Ala Leu Ile Thr Trp
 1               5                  10                  15

Thr Asn Arg Ser Phe Tyr Ser Asn Leu His Gly Cys Glu Leu Thr Tyr
                20                  25                  30

Gly Ile Lys Asp Val Pro Gly Asp Arg Thr Thr Ile Asp Leu Asn Gln
             35                  40                  45

Pro Tyr Val His Tyr Ser Ile Gly Asn Leu Lys Pro Asp Thr Glu Tyr
         50                  55                  60

Glu Val Ser Leu Ile Cys Leu Thr Thr Asp Gly Thr Tyr Ser Asn Pro
 65                  70                  75                  80

Ala Lys Glu Thr Phe Thr Thr Gly Gly Gly Thr Leu Gly His His
                 85                  90                  95

His His His His His
            100

<210> SEQ ID NO 58
<211> LENGTH: 86
<212> TYPE: PRT
<213> ORGANISM: Artificial Sequence
<220> FEATURE:
<223> OTHER INFORMATION: synthetic construct

<400> SEQUENCE: 58

Ile Glu Val Glu Asp Val Thr Asp Thr Thr Ala Leu Ile Thr Trp Thr
 1               5                  10                  15

Asn Arg Ser Phe Tyr Ser Asn Leu His Gly Cys Glu Leu Thr Tyr Gly
                20                  25                  30

Ile Lys Asp Val Pro Gly Asp Arg Thr Thr Ile Asp Leu Asn Gln Pro
             35                  40                  45

Tyr Val His Tyr Ser Ile Gly Asn Leu Lys Pro Asp Thr Glu Tyr Glu
         50                  55                  60

Val Ser Leu Ile Cys Leu Thr Thr Asp Gly Thr Tyr Ser Asn Pro Ala
 65                  70                  75                  80

Lys Glu Thr Phe Thr Thr
                 85

<210> SEQ ID NO 59
<211> LENGTH: 101
<212> TYPE: PRT
<213> ORGANISM: Artificial Sequence
<220> FEATURE:
<223> OTHER INFORMATION: synthetic construct

<400> SEQUENCE: 59

Ala Ile Glu Val Glu Asp Val Thr Asp Thr Thr Ala Leu Ile Thr Trp

-continued

```
               1               5                  10                 15
           Thr Asn Arg Ser Ser Tyr Ala Tyr Leu His Gly Cys Glu Leu Ala Tyr
                           20                 25                 30

Gly Ile Lys Asp Val Pro Gly Asp Arg Thr Thr Ile Asp Leu Asn Gln
                           35                 40                 45

Pro Tyr Val His Tyr Ser Ile Gly Asn Leu Lys Pro Asp Thr Glu Tyr
                       50                 55                 60

Glu Val Ser Leu Ile Cys Leu Thr Thr Asp Gly Thr Tyr Ser Asn Pro
            65                 70                 75                 80

Ala Lys Glu Thr Phe Thr Thr Gly Gly Gly Thr Leu Gly His His His
                           85                 90                 95

His His His His His
                          100
```

<210> SEQ ID NO 60
<211> LENGTH: 86
<212> TYPE: PRT
<213> ORGANISM: Artificial Sequence
<220> FEATURE:
<223> OTHER INFORMATION: synthetic construct

<400> SEQUENCE: 60

```
           Ile Glu Val Glu Asp Val Thr Asp Thr Thr Ala Leu Ile Thr Trp Thr
            1               5                  10                 15

Asn Arg Ser Ser Tyr Ala Tyr Leu His Gly Cys Glu Leu Ala Tyr Gly
                           20                 25                 30

Ile Lys Asp Val Pro Gly Asp Arg Thr Thr Ile Asp Leu Asn Gln Pro
                           35                 40                 45

Tyr Val His Tyr Ser Ile Gly Asn Leu Lys Pro Asp Thr Glu Tyr Glu
                       50                 55                 60

Val Ser Leu Ile Cys Leu Thr Thr Asp Gly Thr Tyr Ser Asn Pro Ala
            65                 70                 75                 80

Lys Glu Thr Phe Thr Thr
                           85
```

<210> SEQ ID NO 61
<211> LENGTH: 101
<212> TYPE: PRT
<213> ORGANISM: Artificial Sequence
<220> FEATURE:
<223> OTHER INFORMATION: synthetic construct

<400> SEQUENCE: 61

```
           Ala Ile Glu Val Glu Asp Val Thr Asp Thr Thr Ala Leu Ile Thr Trp
            1               5                  10                 15

Ile Asn Arg Ser Ser Tyr Ala Asn Leu His Gly Cys Glu Leu Thr Tyr
                           20                 25                 30

Gly Ile Lys Asp Val Pro Gly Asp Arg Thr Thr Ile Asp Leu Ser Ser
                           35                 40                 45

Pro Tyr Val His Tyr Ser Ile Gly Asn Leu Lys Pro Asp Thr Glu Tyr
                       50                 55                 60

Glu Val Ser Leu Ile Cys Leu Thr Thr Asp Gly Thr Tyr Ser Asn Pro
            65                 70                 75                 80

Ala Lys Glu Thr Phe Thr Thr Gly Gly Gly Thr Leu Gly His His His
                           85                 90                 95

His His His His His
                          100
```

<210> SEQ ID NO 62
<211> LENGTH: 86
<212> TYPE: PRT
<213> ORGANISM: Artificial Sequence
<220> FEATURE:
<223> OTHER INFORMATION: synthetic construct

<400> SEQUENCE: 62

```
Ile Glu Val Glu Asp Val Thr Asp Thr Thr Ala Leu Ile Thr Trp Ile
1               5                   10                  15
Asn Arg Ser Ser Tyr Ala Asn Leu His Gly Cys Glu Leu Thr Tyr Gly
            20                  25                  30
Ile Lys Asp Val Pro Gly Asp Arg Thr Thr Ile Asp Leu Ser Ser Pro
        35                  40                  45
Tyr Val His Tyr Ser Ile Gly Asn Leu Lys Pro Asp Thr Glu Tyr Glu
    50                  55                  60
Val Ser Leu Ile Cys Leu Thr Thr Asp Gly Thr Tyr Ser Asn Pro Ala
65                  70                  75                  80
Lys Glu Thr Phe Thr Thr
                85
```

<210> SEQ ID NO 63
<211> LENGTH: 101
<212> TYPE: PRT
<213> ORGANISM: Artificial Sequence
<220> FEATURE:
<223> OTHER INFORMATION: synthetic construct

<400> SEQUENCE: 63

```
Ala Ile Glu Val Glu Asp Val Thr Asp Thr Thr Ala Leu Ile Thr Trp
1               5                   10                  15
Thr Asn Arg Ser Ser Tyr Ala Asn Tyr His Gly Cys Glu Leu Ala Tyr
            20                  25                  30
Gly Ile Lys Asp Val Pro Gly Asp Arg Thr Thr Ile Asp Leu Asn Gln
        35                  40                  45
Pro Tyr Val His Tyr Ser Ile Gly Asn Leu Lys Pro Asp Thr Glu Tyr
    50                  55                  60
Glu Val Ser Leu Ile Cys Leu Thr Thr Asp Gly Thr Tyr Ser Asn Pro
65                  70                  75                  80
Ala Lys Glu Thr Phe Thr Thr Gly Gly Gly Thr Leu Gly His His His
                85                  90                  95
His His His His His
            100
```

<210> SEQ ID NO 64
<211> LENGTH: 86
<212> TYPE: PRT
<213> ORGANISM: Artificial Sequence
<220> FEATURE:
<223> OTHER INFORMATION: synthetic construct

<400> SEQUENCE: 64

```
Ile Glu Val Glu Asp Val Thr Asp Thr Thr Ala Leu Ile Thr Trp Thr
1               5                   10                  15
Asn Arg Ser Ser Tyr Ala Asn Tyr His Gly Cys Glu Leu Ala Tyr Gly
            20                  25                  30
Ile Lys Asp Val Pro Gly Asp Arg Thr Thr Ile Asp Leu Asn Gln Pro
        35                  40                  45
Tyr Val His Tyr Ser Ile Gly Asn Leu Lys Pro Asp Thr Glu Tyr Glu
```

```
Val Ser Leu Ile Cys Leu Thr Thr Asp Gly Thr Tyr Ser Asn Pro Ala
 65                  70                  75                  80

Lys Glu Thr Phe Thr Thr
                 85

<210> SEQ ID NO 65
<211> LENGTH: 101
<212> TYPE: PRT
<213> ORGANISM: Artificial Sequence
<220> FEATURE:
<223> OTHER INFORMATION: synthetic construct

<400> SEQUENCE: 65

Ala Ile Glu Val Glu Asp Val Thr Asp Thr Thr Ala Leu Ile Thr Trp
 1               5                  10                  15

Thr Asn Arg Ser Ser Tyr Ala Asn Leu Pro Gly Cys Glu Leu Thr Tyr
             20                  25                  30

Gly Ile Lys Asp Val Pro Gly Asp Arg Thr Thr Ile Asp Leu Asn Ser
         35                  40                  45

Pro Tyr Val His Tyr Ser Ile Gly Asn Leu Lys Pro Asp Thr Glu Tyr
     50                  55                  60

Glu Val Ser Leu Ile Cys Leu Thr Thr Asp Gly Thr Tyr Ser Asn Pro
 65                  70                  75                  80

Ala Lys Glu Thr Phe Thr Thr Gly Gly Gly Thr Leu Gly His His His
                 85                  90                  95

His His His His
        100

<210> SEQ ID NO 66
<211> LENGTH: 86
<212> TYPE: PRT
<213> ORGANISM: Artificial Sequence
<220> FEATURE:
<223> OTHER INFORMATION: synthetic construct

<400> SEQUENCE: 66

Ile Glu Val Glu Asp Val Thr Asp Thr Thr Ala Leu Ile Thr Trp Thr
 1               5                  10                  15

Asn Arg Ser Ser Tyr Ala Asn Leu Pro Gly Cys Glu Leu Thr Tyr Gly
             20                  25                  30

Ile Lys Asp Val Pro Gly Asp Arg Thr Thr Ile Asp Leu Asn Ser Pro
         35                  40                  45

Tyr Val His Tyr Ser Ile Gly Asn Leu Lys Pro Asp Thr Glu Tyr Glu
     50                  55                  60

Val Ser Leu Ile Cys Leu Thr Thr Asp Gly Thr Tyr Ser Asn Pro Ala
 65                  70                  75                  80

Lys Glu Thr Phe Thr Thr
                 85

<210> SEQ ID NO 67
<211> LENGTH: 101
<212> TYPE: PRT
<213> ORGANISM: Artificial Sequence
<220> FEATURE:
<223> OTHER INFORMATION: synthetic construct

<400> SEQUENCE: 67

Ala Ile Glu Val Glu Asp Val Thr Asp Thr Thr Ala Leu Ile Thr Trp
 1               5                  10                  15
```

```
Thr Asn Arg Ser Ser Tyr Ser Asn Leu His Gly Cys Glu Leu Ala Tyr
            20                  25                  30

Gly Ile Lys Asp Val Pro Gly Asp Arg Thr Thr Ile Asp Leu Asn Gln
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Asn Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 68
<211> LENGTH: 86
<212> TYPE: PRT
<213> ORGANISM: Artificial Sequence
<220> FEATURE:
<223> OTHER INFORMATION: synthetic construct

<400> SEQUENCE: 68

Ile Glu Val Glu Asp Val Thr Asp Thr Thr Ala Leu Ile Thr Trp Thr
1               5                   10                  15

Asn Arg Ser Ser Tyr Ser Asn Leu His Gly Cys Glu Leu Ala Tyr Gly
            20                  25                  30

Ile Lys Asp Val Pro Gly Asp Arg Thr Thr Ile Asp Leu Asn Gln Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Asn Asn Pro Ala
65                  70                  75                  80

Lys Glu Thr Phe Thr Thr
                85

<210> SEQ ID NO 69
<211> LENGTH: 101
<212> TYPE: PRT
<213> ORGANISM: Artificial Sequence
<220> FEATURE:
<223> OTHER INFORMATION: synthetic construct

<400> SEQUENCE: 69

Ala Ile Glu Val Glu Asp Val Thr Asp Thr Thr Ala Leu Ile Thr Trp
1               5                   10                  15

Ile Asn Arg Ser Ser Tyr Ala Asn Leu His Gly Cys Glu Leu Thr Tyr
            20                  25                  30

Gly Ile Lys Asp Val Pro Gly Asp Arg Thr Thr Ile Asp Leu Asn Ser
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100
```

```
<210> SEQ ID NO 70
<211> LENGTH: 86
<212> TYPE: PRT
<213> ORGANISM: Artificial Sequence
<220> FEATURE:
<223> OTHER INFORMATION: synthetic construct

<400> SEQUENCE: 70

Ile Glu Val Glu Asp Val Thr Asp Thr Thr Ala Leu Ile Thr Trp Ile
1               5                   10                  15

Asn Arg Ser Ser Tyr Ala Asn Leu His Gly Cys Glu Leu Thr Tyr Gly
            20                  25                  30

Ile Lys Asp Val Pro Gly Asp Arg Thr Thr Ile Asp Leu Asn Ser Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 71
<211> LENGTH: 101
<212> TYPE: PRT
<213> ORGANISM: Artificial Sequence
<220> FEATURE:
<223> OTHER INFORMATION: synthetic construct

<400> SEQUENCE: 71

Ala Ile Glu Val Glu Asp Val Thr Asp Thr Thr Ala Leu Ile Thr Trp
1               5                   10                  15

Thr Ala Arg Ser Ala Tyr Ser His His His Tyr Cys Glu Leu Thr Tyr
            20                  25                  30

Gly Ile Lys Asp Val Pro Gly Asp Arg Thr Thr Ile Asp Leu Arg Gln
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 72
<211> LENGTH: 86
<212> TYPE: PRT
<213> ORGANISM: Artificial Sequence
<220> FEATURE:
<223> OTHER INFORMATION: synthetic construct

<400> SEQUENCE: 72

Ile Glu Val Glu Asp Val Thr Asp Thr Thr Ala Leu Ile Thr Trp Thr
1               5                   10                  15

Ala Arg Ser Ala Tyr Ser His His Tyr Cys Glu Leu Thr Tyr Gly
            20                  25                  30

Ile Lys Asp Val Pro Gly Asp Arg Thr Thr Ile Asp Leu Arg Gln Pro
        35                  40                  45

Tyr Val His Tyr Ser Ile Gly Asn Leu Lys Pro Asp Thr Glu Tyr Glu
    50                  55                  60
```

```
Val Ser Leu Ile Cys Leu Thr Thr Asp Gly Thr Tyr Ser Asn Pro Ala
 65                  70                  75                  80

Lys Glu Thr Phe Thr Thr
                85
```

<210> SEQ ID NO 73
<211> LENGTH: 100
<212> TYPE: PRT
<213> ORGANISM: Artificial Sequence
<220> FEATURE:
<223> OTHER INFORMATION: synthetic construct

<400> SEQUENCE: 73

```
Ala Ile Glu Val Glu Asp Val Thr Asp Thr Thr Ala Leu Ile Thr Trp
  1               5                  10                  15

Thr Asn Arg Ser Ser Tyr Ala Asn Tyr His His Cys Glu Leu Thr Tyr
                 20                  25                  30

Gly Ile Lys Asp Val Pro Gly Asp Arg Thr Thr Ile Asp Leu Glu Leu
             35                  40                  45

Tyr Val His Tyr Ser Ile Gly Asn Leu Lys Pro Asp Thr Glu Tyr Glu
 50                  55                  60

Val Ser Leu Ile Cys Leu Thr Thr Asp Gly Thr Tyr Ser Asn Pro Ala
 65                  70                  75                  80

Lys Glu Thr Phe Thr Thr Gly Gly Gly Thr Leu Gly His His His His
                 85                  90                  95

His His His His
            100
```

<210> SEQ ID NO 74
<211> LENGTH: 85
<212> TYPE: PRT
<213> ORGANISM: Artificial Sequence
<220> FEATURE:
<223> OTHER INFORMATION: synthetic construct

<400> SEQUENCE: 74

```
Ile Glu Val Glu Asp Val Thr Asp Thr Thr Ala Leu Ile Thr Trp Thr
  1               5                  10                  15

Asn Arg Ser Ser Tyr Ala Asn Tyr His His Cys Glu Leu Thr Tyr Gly
                 20                  25                  30

Ile Lys Asp Val Pro Gly Asp Arg Thr Thr Ile Asp Leu Glu Leu Tyr
             35                  40                  45

Val His Tyr Ser Ile Gly Asn Leu Lys Pro Asp Thr Glu Tyr Glu Val
 50                  55                  60

Ser Leu Ile Cys Leu Thr Thr Asp Gly Thr Tyr Ser Asn Pro Ala Lys
 65                  70                  75                  80

Glu Thr Phe Thr Thr
                85
```

<210> SEQ ID NO 75
<211> LENGTH: 101
<212> TYPE: PRT
<213> ORGANISM: Artificial Sequence
<220> FEATURE:
<223> OTHER INFORMATION: synthetic construct

<400> SEQUENCE: 75

```
Ala Ile Glu Val Glu Asp Val Thr Asp Thr Thr Ala Leu Ile Thr Trp
  1               5                  10                  15
```

```
Thr Asn Arg Ser Ser Tyr Ser Asp Leu Pro Gly Cys Glu Leu Thr Tyr
            20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
 50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
            85                  90                  95

His His His His His
            100

<210> SEQ ID NO 76
<211> LENGTH: 86
<212> TYPE: PRT
<213> ORGANISM: Artificial Sequence
<220> FEATURE:
<223> OTHER INFORMATION: synthetic construct

<400> SEQUENCE: 76

Ile Glu Val Glu Asp Val Thr Asp Thr Thr Ala Leu Ile Thr Trp Thr
1               5                   10                  15

Asn Arg Ser Ser Tyr Ser Asp Leu Pro Gly Cys Glu Leu Thr Tyr Gly
            20                  25                  30

Ile Lys Asp Val Pro Gly Asp Arg Thr Thr Ile Asp Leu Ser Ser Pro
            35                  40                  45

Tyr Val His Tyr Ser Ile Gly Asn Leu Lys Pro Asp Thr Glu Tyr Glu
 50                  55                  60

Val Ser Leu Ile Cys Leu Thr Thr Asp Gly Thr Tyr Ser Asn Pro Ala
65                  70                  75                  80

Lys Glu Thr Phe Thr Thr
            85

<210> SEQ ID NO 77
<211> LENGTH: 101
<212> TYPE: PRT
<213> ORGANISM: Artificial Sequence
<220> FEATURE:
<223> OTHER INFORMATION: synthetic construct

<400> SEQUENCE: 77

Ala Ile Glu Val Glu Asp Val Thr Asp Thr Thr Ala Leu Ile Thr Trp
1               5                   10                  15

Thr His Arg Ser Ala Tyr Ser Asn His Ser Phe Cys Glu Leu Thr Tyr
            20                  25                  30

Gly Ile Lys Asp Val Pro Gly Asp Arg Thr Thr Ile Asp Leu Asn Thr
            35                  40                  45

Pro Tyr Val His Tyr Ser Ile Gly Asn Leu Lys Pro Asp Thr Glu Tyr
 50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
            85                  90                  95

His His His His His
            100

<210> SEQ ID NO 78
```

```
<211> LENGTH: 86
<212> TYPE: PRT
<213> ORGANISM: Artificial Sequence
<220> FEATURE:
<223> OTHER INFORMATION: synthetic construct

<400> SEQUENCE: 78

Ile Glu Val Glu Asp Val Thr Asp Thr Thr Ala Leu Ile Thr Trp Thr
1               5                   10                  15

His Arg Ser Ala Tyr Ser Asn His Ser Phe Cys Glu Leu Thr Tyr Gly
            20                  25                  30

Ile Lys Asp Val Pro Gly Asp Arg Thr Thr Ile Asp Leu Asn Thr Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 79
<211> LENGTH: 101
<212> TYPE: PRT
<213> ORGANISM: Artificial Sequence
<220> FEATURE:
<223> OTHER INFORMATION: synthetic construct

<400> SEQUENCE: 79

Ala Ile Glu Val Glu Asp Val Thr Asp Thr Thr Ala Leu Ile Thr Trp
1               5                   10                  15

Thr Asn Arg Ser Leu Tyr Ala Asn Phe His Gly Cys Glu Leu Thr Tyr
            20                  25                  30

Gly Ile Lys Asp Val Pro Gly Asp Arg Thr Thr Ile Asp Leu Glu Gln
        35                  40                  45

Val Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 80
<211> LENGTH: 86
<212> TYPE: PRT
<213> ORGANISM: Artificial Sequence
<220> FEATURE:
<223> OTHER INFORMATION: synthetic construct

<400> SEQUENCE: 80

Ile Glu Val Glu Asp Val Thr Asp Thr Thr Ala Leu Ile Thr Trp Thr
1               5                   10                  15

Asn Arg Ser Leu Tyr Ala Asn Phe His Gly Cys Glu Leu Thr Tyr Gly
            20                  25                  30

Ile Lys Asp Val Pro Gly Asp Arg Thr Thr Ile Asp Leu Glu Gln Val
        35                  40                  45

Tyr Val His Tyr Ser Ile Gly Asn Leu Lys Pro Asp Thr Glu Tyr Glu
    50                  55                  60
```

```
Val Ser Leu Ile Cys Leu Thr Thr Asp Gly Thr Tyr Ser Asn Pro Ala
 65                  70                  75                  80

Lys Glu Thr Phe Thr Thr
                 85
```

<210> SEQ ID NO 81
<211> LENGTH: 101
<212> TYPE: PRT
<213> ORGANISM: Artificial Sequence
<220> FEATURE:
<223> OTHER INFORMATION: synthetic construct

<400> SEQUENCE: 81

```
Ala Ile Glu Val Glu Asp Val Thr Asp Thr Thr Ala Leu Ile Thr Trp
 1               5                  10                  15

Thr Asn Arg Ser Ser Tyr Ser Asn Leu Pro Gly Cys Glu Leu Thr Tyr
                 20                  25                  30

Gly Ile Lys Asp Val Pro Gly Asp Arg Thr Thr Ile Asp Leu Asn Gln
             35                  40                  45

Val Tyr Val His Tyr Ser Ile Gly Asn Leu Lys Pro Asp Thr Glu Tyr
 50                  55                  60

Glu Val Ser Leu Ile Cys Leu Thr Thr Asp Gly Thr Tyr Ser Asn Pro
 65                  70                  75                  80

Ala Lys Glu Thr Phe Thr Thr Gly Gly Gly Thr Leu Gly His His
                 85                  90                  95

His His His His His
             100
```

<210> SEQ ID NO 82
<211> LENGTH: 86
<212> TYPE: PRT
<213> ORGANISM: Artificial Sequence
<220> FEATURE:
<223> OTHER INFORMATION: synthetic construct

<400> SEQUENCE: 82

```
Ile Glu Val Glu Asp Val Thr Asp Thr Thr Ala Leu Ile Thr Trp Thr
 1               5                  10                  15

Asn Arg Ser Ser Tyr Ser Asn Leu Pro Gly Cys Glu Leu Thr Tyr Gly
                 20                  25                  30

Ile Lys Asp Val Pro Gly Asp Arg Thr Thr Ile Asp Leu Asn Gln Val
             35                  40                  45

Tyr Val His Tyr Ser Ile Gly Asn Leu Lys Pro Asp Thr Glu Tyr Glu
 50                  55                  60

Val Ser Leu Ile Cys Leu Thr Thr Asp Gly Thr Tyr Ser Asn Pro Ala
 65                  70                  75                  80

Lys Glu Thr Phe Thr Thr
                 85
```

<210> SEQ ID NO 83
<211> LENGTH: 9
<212> TYPE: PRT
<213> ORGANISM: Artificial Sequence
<220> FEATURE:
<223> OTHER INFORMATION: synthetic construct

<400> SEQUENCE: 83

```
Ser Asp Glu Phe Gly His Tyr Asp Gly
 1               5
```

```
<210> SEQ ID NO 84
<211> LENGTH: 9
<212> TYPE: PRT
<213> ORGANISM: Artificial Sequence
<220> FEATURE:
<223> OTHER INFORMATION: synthetic construct

<400> SEQUENCE: 84

Ser Asp Asp Phe Asp Asn Tyr Glu Trp
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic construct

<400> SEQUENCE: 85

Ser Asp Asp Phe Ala Asp Tyr Val Trp
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic construct

<400> SEQUENCE: 86

Ser Asp Asp Phe Gly Glu Tyr Val Trp
1               5

<210> SEQ ID NO 87
<211> LENGTH: 9
<212> TYPE: PRT
<213> ORGANISM: Artificial Sequence
<220> FEATURE:
<223> OTHER INFORMATION: synthetic construct

<400> SEQUENCE: 87

Leu Asp Asp Trp Gly Ser Tyr His Val
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic construct

<400> SEQUENCE: 88

Ser Asp Glu Val Gly Asp Tyr Val Val
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic construct

<400> SEQUENCE: 89

Ser Asp Asp Phe Ala Glu Tyr Val Gly
1               5

<210> SEQ ID NO 90
```

```
<211> LENGTH: 9
<212> TYPE: PRT
<213> ORGANISM: Artificial Sequence
<220> FEATURE:
<223> OTHER INFORMATION: synthetic construct

<400> SEQUENCE: 90

Ser Asp Asp Phe Glu Glu Tyr Val Val
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic construct

<400> SEQUENCE: 91

Ser Asp Glu Val Gly Gln Tyr Val Gly
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic construct

<400> SEQUENCE: 92

Ser Asp Asp Ile Gly Leu Tyr Val Trp
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic construct

<400> SEQUENCE: 93

Ser Asp Glu His Ala Glu Phe Ile Gly
1               5

<210> SEQ ID NO 94
<211> LENGTH: 6
<212> TYPE: PRT
<213> ORGANISM: Artificial Sequence
<220> FEATURE:
<223> OTHER INFORMATION: synthetic construct

<400> SEQUENCE: 94

Trp Trp His Ser Ala Trp
1               5

<210> SEQ ID NO 95
<211> LENGTH: 6
<212> TYPE: PRT
<213> ORGANISM: Artificial Sequence
<220> FEATURE:
<223> OTHER INFORMATION: synthetic construct

<400> SEQUENCE: 95

Trp Tyr His Met Ala Trp
1               5

<210> SEQ ID NO 96
<211> LENGTH: 6
```

<212> TYPE: PRT
<213> ORGANISM: Artificial Sequence
<220> FEATURE:
<223> OTHER INFORMATION: synthetic construct

<400> SEQUENCE: 96

Trp Tyr His His Ala His
1               5

<210> SEQ ID NO 97
<211> LENGTH: 6
<212> TYPE: PRT
<213> ORGANISM: Artificial Sequence
<220> FEATURE:
<223> OTHER INFORMATION: synthetic construct

<400> SEQUENCE: 97

Trp Tyr His Gln Ala Trp
1               5

<210> SEQ ID NO 98
<211> LENGTH: 6
<212> TYPE: PRT
<213> ORGANISM: Artificial Sequence
<220> FEATURE:
<223> OTHER INFORMATION: synthetic construct

<400> SEQUENCE: 98

Trp Phe His Gln Ala Trp
1               5

<210> SEQ ID NO 99
<211> LENGTH: 10
<212> TYPE: PRT
<213> ORGANISM: Artificial Sequence
<220> FEATURE:
<223> OTHER INFORMATION: synthetic construct

<400> SEQUENCE: 99

Tyr Thr Asp Gln Glu Ala Gly Asn Pro Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: synthetic construct

<400> SEQUENCE: 100

Thr Asn Arg Ser Ser Tyr Tyr Asn Leu His Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthetic construct

<400> SEQUENCE: 101

Ile Asn Arg Ser Tyr Tyr Ala Asp Leu His Gly
1               5                   10

<210> SEQ ID NO 102
<211> LENGTH: 11
<212> TYPE: PRT

<213> ORGANISM: Artificial Sequence
<220> FEATURE:
<223> OTHER INFORMATION: synthetic construct

<400> SEQUENCE: 102

Thr Asn Arg Ser Ser Tyr Ser His Leu Asp Gly
1               5                   10

<210> SEQ ID NO 103
<211> LENGTH: 11
<212> TYPE: PRT
<213> ORGANISM: Artificial Sequence
<220> FEATURE:
<223> OTHER INFORMATION: synthetic construct

<400> SEQUENCE: 103

Ile Asn Arg Ser Ser Tyr His Asn Phe Pro His
1               5                   10

<210> SEQ ID NO 104
<211> LENGTH: 11
<212> TYPE: PRT
<213> ORGANISM: Artificial Sequence
<220> FEATURE:
<223> OTHER INFORMATION: synthetic construct

<400> SEQUENCE: 104

Thr Asn Arg Ser Ser Tyr Ser Asn His Leu Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic construct

<400> SEQUENCE: 105

Thr Asn Arg Ser Ser Tyr Ser Asn Phe His Gly
1               5                   10

<210> SEQ ID NO 106
<211> LENGTH: 11
<212> TYPE: PRT
<213> ORGANISM: Artificial Sequence
<220> FEATURE:
<223> OTHER INFORMATION: synthetic construct

<400> SEQUENCE: 106

Thr Asn Arg Ser Phe Tyr Ser Asn Leu His Gly
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic construct

<400> SEQUENCE: 107

Thr Asn Arg Ser Ser Tyr Ala Tyr Leu His Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic construct

<400> SEQUENCE: 108

Ile Asn Arg Ser Ser Tyr Ala Asn Leu His Gly
1               5                   10

<210> SEQ ID NO 109
<211> LENGTH: 11
<212> TYPE: PRT
<213> ORGANISM: Artificial Sequence
<220> FEATURE:
<223> OTHER INFORMATION: synthetic construct

<400> SEQUENCE: 109

Thr Asn Arg Ser Ser Tyr Ala Asn Tyr His Gly
1               5                   10

<210> SEQ ID NO 110
<211> LENGTH: 11
<212> TYPE: PRT
<213> ORGANISM: Artificial Sequence
<220> FEATURE:
<223> OTHER INFORMATION: synthetic construct

<400> SEQUENCE: 110

Thr Asn Arg Ser Ser Tyr Ala Asn Leu Pro Gly
1               5                   10

<210> SEQ ID NO 111
<211> LENGTH: 11
<212> TYPE: PRT
<213> ORGANISM: Artificial Sequence
<220> FEATURE:
<223> OTHER INFORMATION: synthetic construct

<400> SEQUENCE: 111

Thr Asn Arg Ser Ser Tyr Ser Asn Leu His Gly
1               5                   10

<210> SEQ ID NO 112
<211> LENGTH: 11
<212> TYPE: PRT
<213> ORGANISM: Artificial Sequence
<220> FEATURE:
<223> OTHER INFORMATION: synthetic construct

<400> SEQUENCE: 112

Thr Ala Arg Ser Ala Tyr Ser His His His Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: synthetic construct

<400> SEQUENCE: 113

Thr Asn Arg Ser Ser Tyr Ala Asn Tyr His His
1               5                   10

<210> SEQ ID NO 114
<211> LENGTH: 11
<212> TYPE: PRT
<213> ORGANISM: Artificial Sequence
<220> FEATURE:

<223> OTHER INFORMATION: synthetic construct

<400> SEQUENCE: 114

Thr Asn Arg Ser Ser Tyr Ser Asp Leu Pro Gly
1               5                   10

<210> SEQ ID NO 115
<211> LENGTH: 11
<212> TYPE: PRT
<213> ORGANISM: Artificial Sequence
<220> FEATURE:
<223> OTHER INFORMATION: synthetic construct

<400> SEQUENCE: 115

Thr His Arg Ser Ala Tyr Ser Asn His Ser Phe
1               5                   10

<210> SEQ ID NO 116
<211> LENGTH: 11
<212> TYPE: PRT
<213> ORGANISM: Artificial Sequence
<220> FEATURE:
<223> OTHER INFORMATION: synthetic construct

<400> SEQUENCE: 116

Thr Asn Arg Ser Leu Tyr Ala Asn Phe His Gly
1               5                   10

<210> SEQ ID NO 117
<211> LENGTH: 11
<212> TYPE: PRT
<213> ORGANISM: Artificial Sequence
<220> FEATURE:
<223> OTHER INFORMATION: synthetic construct

<400> SEQUENCE: 117

Thr Asn Arg Ser Ser Tyr Ser Asn Leu Pro Gly
1               5                   10

<210> SEQ ID NO 118
<211> LENGTH: 6
<212> TYPE: PRT
<213> ORGANISM: Artificial Sequence
<220> FEATURE:
<223> OTHER INFORMATION: synthetic construct

<400> SEQUENCE: 118

Ser Ser Pro Tyr Val His
1               5

<210> SEQ ID NO 119
<211> LENGTH: 6
<212> TYPE: PRT
<213> ORGANISM: Artificial Sequence
<220> FEATURE:
<223> OTHER INFORMATION: synthetic construct

<400> SEQUENCE: 119

Asp Gln Ile Tyr Val His
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic construct

```
<400> SEQUENCE: 120

Ser Ala Ala Ile Tyr Val His
1               5

<210> SEQ ID NO 121
<211> LENGTH: 6
<212> TYPE: PRT
<213> ORGANISM: Artificial Sequence
<220> FEATURE:
<223> OTHER INFORMATION: synthetic construct

<400> SEQUENCE: 121

Asn Ser Pro Tyr Val His
1               5

<210> SEQ ID NO 122
<211> LENGTH: 6
<212> TYPE: PRT
<213> ORGANISM: Artificial Sequence
<220> FEATURE:
<223> OTHER INFORMATION: synthetic construct

<400> SEQUENCE: 122

Asn Asn Ile Tyr Val His
1               5

<210> SEQ ID NO 123
<211> LENGTH: 6
<212> TYPE: PRT
<213> ORGANISM: Artificial Sequence
<220> FEATURE:
<223> OTHER INFORMATION: synthetic construct

<400> SEQUENCE: 123

Asn Gln Pro Tyr Val His
1               5

<210> SEQ ID NO 124
<211> LENGTH: 6
<212> TYPE: PRT
<213> ORGANISM: Artificial Sequence
<220> FEATURE:
<223> OTHER INFORMATION: synthetic construct

<400> SEQUENCE: 124

Arg Gln Pro Tyr Val His
1               5

<210> SEQ ID NO 125
<211> LENGTH: 5
<212> TYPE: PRT
<213> ORGANISM: Artificial Sequence
<220> FEATURE:
<223> OTHER INFORMATION: synthetic construct

<400> SEQUENCE: 125

Glu Leu Tyr Val His
1               5

<210> SEQ ID NO 126
<211> LENGTH: 6
<212> TYPE: PRT
<213> ORGANISM: Artificial Sequence
<220> FEATURE:
<223> OTHER INFORMATION: synthetic construct
```

<400> SEQUENCE: 126

Asn Thr Pro Tyr Val His
1               5

<210> SEQ ID NO 127
<211> LENGTH: 6
<212> TYPE: PRT
<213> ORGANISM: Artificial Sequence
<220> FEATURE:
<223> OTHER INFORMATION: synthetic construct

<400> SEQUENCE: 127

Glu Gln Val Tyr Val His
1               5

<210> SEQ ID NO 128
<211> LENGTH: 6
<212> TYPE: PRT
<213> ORGANISM: Artificial Sequence
<220> FEATURE:
<223> OTHER INFORMATION: synthetic construct

<400> SEQUENCE: 128

Asn Gln Val Tyr Val His
1               5

<210> SEQ ID NO 129
<211> LENGTH: 11
<212> TYPE: PRT
<213> ORGANISM: Artificial Sequence
<220> FEATURE:
<223> OTHER INFORMATION: synthetic construct

<400> SEQUENCE: 129

Leu Thr Thr Asp Gly Thr Tyr Ser Asn Pro Ala
1               5                   10

<210> SEQ ID NO 130
<211> LENGTH: 11
<212> TYPE: PRT
<213> ORGANISM: Artificial Sequence
<220> FEATURE:
<223> OTHER INFORMATION: synthetic construct

<400> SEQUENCE: 130

Leu Thr Thr Asp Gly Thr Tyr Asn Asn Pro Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: synthetic construct

<400> SEQUENCE: 131

Gly Gly Gly Gly Ser Gly Gly Gly Gly Ser
1               5                   10

<210> SEQ ID NO 132
<211> LENGTH: 15
<212> TYPE: PRT
<213> ORGANISM: Artificial Sequence
<220> FEATURE:
<223> OTHER INFORMATION: synthetic construct

<400> SEQUENCE: 132

```
Gly Gly Gly Gly Ser Gly Gly Gly Ser Gly Gly Gly Ser
1               5               10              15
```

<210> SEQ ID NO 133
<211> LENGTH: 585
<212> TYPE: PRT
<213> ORGANISM: Artificial Sequence
<220> FEATURE:
<223> OTHER INFORMATION: synthetic construct

<400> SEQUENCE: 133

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 134
<211> LENGTH: 680
<212> TYPE: PRT
<213> ORGANISM: Artificial Sequence
<220> FEATURE:
<223> OTHER INFORMATION: synthetic construct

<400> SEQUENCE: 134

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
                20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
        50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Ser Gly Gly Gly Gly Ser Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

```
Ser Pro Phe Glu Asp His Val Lys Leu Val Asn Val Thr Glu Phe
    130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
                180                 185                 190

Arg Asn Glu Cys Phe Leu Gln His Lys Asp Asp Asn Pro Asn Leu Pro
            195                 200                 205

Arg Leu Val Arg Pro Glu Val Asp Val Met Cys Thr Ala Phe His Asp
    210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

Lys Ala Ala Phe Thr Glu Cys Cys Gln Ala Ala Asp Lys Ala Ala Cys
                260                 265                 270

Leu Leu Pro Lys Leu Asp Glu Leu Arg Asp Glu Gly Lys Ala Ser Ser
            275                 280                 285

Ala Lys Gln Arg Leu Lys Cys Ala Ser Leu Gln Lys Phe Gly Glu Arg
    290                 295                 300

Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
                325                 330                 335

His Thr Glu Cys Cys His Gly Asp Leu Leu Glu Cys Ala Asp Asp Arg
            340                 345                 350

Ala Asp Leu Ala Lys Tyr Ile Cys Glu Asn Gln Asp Ser Ile Ser Ser
    355                 360                 365

Lys Leu Lys Glu Cys Cys Glu Lys Pro Leu Leu Glu Lys Ser His Cys
370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
                405                 410                 415

Ala Lys Asp Val Phe Leu Gly Met Phe Leu Tyr Glu Tyr Ala Arg Arg
                420                 425                 430

His Pro Asp Tyr Ser Val Val Leu Leu Leu Arg Leu Ala Lys Thr Tyr
            435                 440                 445

Glu Thr Thr Leu Glu Lys Cys Cys Ala Ala Ala Asp Pro His Glu Cys
    450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
                485                 490                 495

Lys Phe Gln Asn Ala Leu Leu Val Arg Tyr Thr Lys Lys Val Pro Gln
                500                 505                 510

Val Ser Thr Pro Thr Leu Val Glu Val Ser Arg Asn Leu Gly Lys Val
            515                 520                 525

Gly Ser Lys Cys Cys Lys His Pro Glu Ala Lys Arg Met Pro Cys Ala
    530                 535                 540
```

```
Glu Asp Tyr Leu Ser Val Val Leu Asn Gln Leu Cys Val Leu His Glu
545                 550                 555                 560

Lys Thr Pro Val Ser Asp Arg Val Thr Lys Cys Cys Thr Glu Ser Leu
                565                 570                 575

Val Asn Arg Arg Pro Cys Phe Ser Ala Leu Glu Val Asp Glu Thr Tyr
            580                 585                 590

Val Pro Lys Glu Phe Asn Ala Glu Thr Phe Thr Phe His Ala Asp Ile
        595                 600                 605

Cys Thr Leu Ser Glu Lys Glu Arg Gln Ile Lys Lys Gln Thr Ala Leu
    610                 615                 620

Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
                645                 650                 655

Asp Asp Lys Glu Thr Cys Phe Ala Glu Glu Gly Lys Lys Leu Val Ala
                660                 665                 670

Ala Ser Gln Ala Ala Leu Gly Leu
        675                 680

<210> SEQ ID NO 135
<211> LENGTH: 785
<212> TYPE: PRT
<213> ORGANISM: Artificial Sequence
<220> FEATURE:
<223> OTHER INFORMATION: synthetic construct

<400> SEQUENCE: 135

Ser Gln Ile Glu Val Lys Asp Val Thr Asp Thr Ala Leu Ile Thr
1               5                   10                  15

Trp Ser Asp Asp Phe Gly Glu Tyr Val Trp Cys Glu Leu Thr Tyr Gly
                20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Ser Gly Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Phe Gly Glu
        115                 120                 125

Tyr Val Trp Cys Glu Leu Thr Tyr Gly Ile Lys Asp Val Pro Gly Asp
130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
                165                 170                 175

Gly Asp Met Ser Ser Asn Pro Ala Lys Glu Thr Phe Thr Thr Gly Gly
            180                 185                 190

Gly Gly Ser Gly Gly Gly Gly Ser Asp Ala His Lys Ser Glu Val Ala
        195                 200                 205

His Arg Phe Lys Asp Leu Gly Glu Glu Asn Phe Lys Ala Leu Val Leu
    210                 215                 220
```

-continued

```
Ile Ala Phe Ala Gln Tyr Leu Gln Gln Ser Pro Phe Glu Asp His Val
225                 230                 235                 240

Lys Leu Val Asn Glu Val Thr Glu Phe Ala Lys Thr Cys Val Ala Asp
                245                 250                 255

Glu Ser Ala Glu Asn Cys Asp Lys Ser Leu His Thr Leu Phe Gly Asp
            260                 265                 270

Lys Leu Cys Thr Val Ala Thr Leu Arg Glu Thr Tyr Gly Glu Met Ala
        275                 280                 285

Asp Cys Cys Ala Lys Gln Glu Pro Glu Arg Asn Glu Cys Phe Leu Gln
    290                 295                 300

His Lys Asp Asp Asn Pro Asn Leu Pro Arg Leu Val Arg Pro Glu Val
305                 310                 315                 320

Asp Val Met Cys Thr Ala Phe His Asp Asn Glu Glu Thr Phe Leu Lys
                325                 330                 335

Lys Tyr Leu Tyr Glu Ile Ala Arg Arg His Pro Tyr Phe Tyr Ala Pro
                340                 345                 350

Glu Leu Leu Phe Phe Ala Lys Arg Tyr Lys Ala Ala Phe Thr Glu Cys
            355                 360                 365

Cys Gln Ala Ala Asp Lys Ala Ala Cys Leu Leu Pro Lys Leu Asp Glu
        370                 375                 380

Leu Arg Asp Glu Gly Lys Ala Ser Ser Ala Lys Gln Arg Leu Lys Cys
385                 390                 395                 400

Ala Ser Leu Gln Lys Phe Gly Glu Arg Ala Phe Lys Ala Trp Ala Val
                405                 410                 415

Ala Arg Leu Ser Gln Arg Phe Pro Lys Ala Glu Phe Ala Glu Val Ser
            420                 425                 430

Lys Leu Val Thr Asp Leu Thr Lys Val His Thr Glu Cys Cys His Gly
        435                 440                 445

Asp Leu Leu Glu Cys Ala Asp Asp Arg Ala Asp Leu Ala Lys Tyr Ile
    450                 455                 460

Cys Glu Asn Gln Asp Ser Ile Ser Ser Lys Leu Lys Glu Cys Cys Glu
465                 470                 475                 480

Lys Pro Leu Leu Glu Lys Ser His Cys Ile Ala Glu Val Glu Asn Asp
                485                 490                 495

Glu Met Pro Ala Asp Leu Pro Ser Leu Ala Ala Asp Phe Val Glu Ser
            500                 505                 510

Lys Asp Val Cys Lys Asn Tyr Ala Glu Ala Lys Asp Val Phe Leu Gly
        515                 520                 525

Met Phe Leu Tyr Glu Tyr Ala Arg Arg His Pro Asp Tyr Ser Val Val
    530                 535                 540

Leu Leu Leu Arg Leu Ala Lys Thr Tyr Glu Thr Thr Leu Glu Lys Cys
545                 550                 555                 560

Cys Ala Ala Ala Asp Pro His Glu Cys Tyr Ala Lys Val Phe Asp Glu
                565                 570                 575

Phe Lys Pro Leu Val Glu Glu Pro Gln Asn Leu Ile Lys Gln Asn Cys
            580                 585                 590

Glu Leu Phe Glu Gln Leu Gly Glu Tyr Lys Phe Gln Asn Ala Leu Leu
        595                 600                 605

Val Arg Tyr Thr Lys Lys Val Pro Gln Val Ser Thr Pro Thr Leu Val
    610                 615                 620

Glu Val Ser Arg Asn Leu Gly Lys Val Gly Ser Lys Cys Cys Lys His
625                 630                 635                 640

Pro Glu Ala Lys Arg Met Pro Cys Ala Glu Asp Tyr Leu Ser Val Val
```

-continued

```
                645                 650                 655
Leu Asn Gln Leu Cys Val Leu His Glu Lys Thr Pro Val Ser Asp Arg
            660                 665                 670
Val Thr Lys Cys Cys Thr Glu Ser Leu Val Asn Arg Arg Pro Cys Phe
        675                 680                 685
Ser Ala Leu Glu Val Asp Glu Thr Tyr Val Pro Lys Glu Phe Asn Ala
    690                 695                 700
Glu Thr Phe Thr Phe His Ala Asp Ile Cys Thr Leu Ser Glu Lys Glu
705                 710                 715                 720
Arg Gln Ile Lys Lys Gln Thr Ala Leu Val Glu Leu Val Lys His Lys
                725                 730                 735
Pro Lys Ala Thr Lys Glu Gln Leu Lys Ala Val Met Asp Asp Phe Ala
            740                 745                 750
Ala Phe Val Glu Lys Cys Cys Lys Ala Asp Asp Lys Glu Thr Cys Phe
        755                 760                 765
Ala Glu Glu Gly Lys Lys Leu Val Ala Ala Ser Gln Ala Ala Leu Gly
    770                 775                 780
Leu
785
```

<210> SEQ ID NO 136
<211> LENGTH: 7
<212> TYPE: PRT
<213> ORGANISM: Artificial Sequence
<220> FEATURE:
<223> OTHER INFORMATION: synthetic construct

<400> SEQUENCE: 136

```
Glu Asp Val Thr Asp Thr Thr
1               5
```

<210> SEQ ID NO 137
<211> LENGTH: 8
<212> TYPE: PRT
<213> ORGANISM: Artificial Sequence
<220> FEATURE:
<223> OTHER INFORMATION: synthetic construct

<400> SEQUENCE: 137

```
Gly Asn Leu Lys Pro Asp Thr Lys
1               5
```

<210> SEQ ID NO 138
<211> LENGTH: 585
<212> TYPE: PRT
<213> ORGANISM: Homo sapiens

<400> SEQUENCE: 138

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
        50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
```

```
                    85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
            130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
                195                 200                 205
Arg Ala Phe Lys Ala Trp Ala Val Ala Arg Leu Ser Gln Arg Phe Pro
            210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
            325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
            485                 490                 495
Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 139
<211> LENGTH: 10
<212> TYPE: PRT
<213> ORGANISM: Artificial Sequence
<220> FEATURE:
<223> OTHER INFORMATION: synthetic construct

<400> SEQUENCE: 139

Arg Ser Gly Asp Met Ser Ser Asn Pro Ala
1               5                   10

<210> SEQ ID NO 140
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa  is any of Ala, Gly, Leu, Ile and Val
<220> FEATURE:
<221> NAME/KEY: MISC_FEATURE
<222> LOCATION: (10)..(10)
<223> OTHER INFORMATION: Xaa  is any of Ala, Gly, Leu, Ile and Val

<400> SEQUENCE: 140

Gly Gly Gly Gly Xaa Gly Gly Gly Gly Xaa
1               5                   10

<210> SEQ ID NO 141
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is any of Ala, Gly, Leu, Ile and Val
<220> FEATURE:
<221> NAME/KEY: MISC_FEATURE
<222> LOCATION: (10)..(10)
<223> OTHER INFORMATION: Xaa is any of Ala, Gly, Leu, Ile and Val
<220> FEATURE:
<221> NAME/KEY: MISC_FEATURE
<222> LOCATION: (15)..(15)
<223> OTHER INFORMATION: Xaa is any of Ala, Gly, Leu, Ile and Val

<400> SEQUENCE: 141

Gly Gly Gly Gly Xaa Gly Gly Gly Gly Xaa Gly Gly Gly Gly Xaa
1               5                   10                  15

<210> SEQ ID NO 142
<211> LENGTH: 10
<212> TYPE: PRT
```

<213> ORGANISM: Artificial Sequence
<220> FEATURE:
<223> OTHER INFORMATION: synthetic construct

<400> SEQUENCE: 142

Gly Gly Gly Gly Gly Gly Gly Gly Gly Gly
1               5                   10

<210> SEQ ID NO 143
<211> LENGTH: 15
<212> TYPE: PRT
<213> ORGANISM: Artificial Sequence
<220> FEATURE:
<223> OTHER INFORMATION: synthetic construct

<400> SEQUENCE: 143

Gly Gly Gly Gly Gly Gly Gly Gly Gly Gly Gly Gly Gly Gly Gly
1               5                   10                  15

<210> SEQ ID NO 144
<211> LENGTH: 680
<212> TYPE: PRT
<213> ORGANISM: Artificial Sequence
<220> FEATURE:
<223> OTHER INFORMATION: synthetic construct

<400> SEQUENCE: 144

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
                20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
        50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Gly Gly Gly Gly Gly Gly Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Ser Pro Phe Glu Asp His Val Lys Leu Val Asn Glu Val Thr Glu Phe
    130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190

Arg Asn Glu Cys Phe Leu Gln His Lys Asp Asp Asn Pro Asn Leu Pro
        195                 200                 205

Arg Leu Val Arg Pro Glu Val Asp Val Met Cys Thr Ala Phe His Asp
    210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

```
Lys Ala Ala Phe Thr Glu Cys Cys Gln Ala Ala Asp Lys Ala Ala Cys
            260                 265                 270

Leu Leu Pro Lys Leu Asp Glu Leu Arg Asp Glu Gly Lys Ala Ser Ser
            275                 280                 285

Ala Lys Gln Arg Leu Lys Cys Ala Ser Leu Gln Lys Phe Gly Glu Arg
290                 295                 300

Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
                325                 330                 335

His Thr Glu Cys Cys His Gly Asp Leu Leu Glu Cys Ala Asp Asp Arg
            340                 345                 350

Ala Asp Leu Ala Lys Tyr Ile Cys Glu Asn Gln Asp Ser Ile Ser Ser
            355                 360                 365

Lys Leu Lys Glu Cys Cys Glu Lys Pro Leu Leu Glu Lys Ser His Cys
            370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
                405                 410                 415

Ala Lys Asp Val Phe Leu Gly Met Phe Leu Tyr Glu Tyr Ala Arg Arg
                420                 425                 430

His Pro Asp Tyr Ser Val Val Leu Leu Leu Arg Leu Ala Lys Thr Tyr
            435                 440                 445

Glu Thr Thr Leu Glu Lys Cys Cys Ala Ala Ala Asp Pro His Glu Cys
            450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
                485                 490                 495

Lys Phe Gln Asn Ala Leu Leu Val Arg Tyr Thr Lys Lys Val Pro Gln
            500                 505                 510

Val Ser Thr Pro Thr Leu Val Glu Val Ser Arg Asn Leu Gly Lys Val
            515                 520                 525

Gly Ser Lys Cys Cys Lys His Pro Glu Ala Lys Arg Met Pro Cys Ala
530                 535                 540

Glu Asp Tyr Leu Ser Val Val Leu Asn Gln Leu Cys Val Leu His Glu
545                 550                 555                 560

Lys Thr Pro Val Ser Asp Arg Val Thr Lys Cys Cys Thr Glu Ser Leu
                565                 570                 575

Val Asn Arg Arg Pro Cys Phe Ser Ala Leu Glu Val Asp Glu Thr Tyr
            580                 585                 590

Val Pro Lys Glu Phe Asn Ala Glu Thr Phe Thr Phe His Ala Asp Ile
            595                 600                 605

Cys Thr Leu Ser Glu Lys Glu Arg Gln Ile Lys Lys Gln Thr Ala Leu
            610                 615                 620

Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
                645                 650                 655

Asp Asp Lys Glu Thr Cys Phe Ala Glu Glu Gly Lys Lys Leu Val Ala
            660                 665                 670
```

Ala Ser Gln Ala Ala Leu Gly Leu
        675                 680

<210> SEQ ID NO 145
<211> LENGTH: 785
<212> TYPE: PRT
<213> ORGANISM: Artificial Sequence
<220> FEATURE:
<223> OTHER INFORMATION: synthetic construct

<400> SEQUENCE: 145

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
        35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Gly Gly Gly Gly Gly Gly Gly
                85                  90                  95

Gly Gly Gly Gly Arg Leu Asp Ala Pro Ser Gln Ile Glu Val Lys Asp
            100                 105                 110

Val Thr Asp Thr Thr Ala Leu Ile Thr Trp Ser Asp Asp Phe Gly Glu
        115                 120                 125

Tyr Val Trp Cys Glu Leu Thr Tyr Gly Ile Lys Asp Val Pro Gly Asp
    130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
                165                 170                 175

Gly Asp Met Ser Ser Asn Pro Ala Lys Glu Thr Phe Thr Thr Gly Gly
            180                 185                 190

Gly Gly Gly Gly Gly Gly Gly Asp Ala His Lys Ser Glu Val Ala
        195                 200                 205

His Arg Phe Lys Asp Leu Gly Glu Glu Asn Phe Lys Ala Leu Val Leu
    210                 215                 220

Ile Ala Phe Ala Gln Tyr Leu Gln Gln Ser Pro Phe Glu Asp His Val
225                 230                 235                 240

Lys Leu Val Asn Glu Val Thr Glu Phe Ala Lys Thr Cys Val Ala Asp
                245                 250                 255

Glu Ser Ala Glu Asn Cys Asp Lys Ser Leu His Thr Leu Phe Gly Asp
            260                 265                 270

Lys Leu Cys Thr Val Ala Thr Leu Arg Glu Thr Tyr Gly Glu Met Ala
        275                 280                 285

Asp Cys Cys Ala Lys Gln Glu Pro Glu Arg Asn Glu Cys Phe Leu Gln
    290                 295                 300

His Lys Asp Asp Asn Pro Asn Leu Pro Arg Leu Val Arg Pro Glu Val
305                 310                 315                 320

Asp Val Met Cys Thr Ala Phe His Asp Asn Glu Glu Thr Phe Leu Lys
                325                 330                 335

Lys Tyr Leu Tyr Glu Ile Ala Arg Arg His Pro Tyr Phe Tyr Ala Pro
            340                 345                 350

```
Glu Leu Leu Phe Phe Ala Lys Arg Tyr Lys Ala Ala Phe Thr Glu Cys
            355                 360                 365

Cys Gln Ala Ala Asp Lys Ala Ala Cys Leu Leu Pro Lys Leu Asp Glu
        370                 375                 380

Leu Arg Asp Glu Gly Lys Ala Ser Ser Ala Lys Gln Arg Leu Lys Cys
385                 390                 395                 400

Ala Ser Leu Gln Lys Phe Gly Glu Arg Ala Phe Lys Ala Trp Ala Val
                405                 410                 415

Ala Arg Leu Ser Gln Arg Phe Pro Lys Ala Glu Phe Ala Glu Val Ser
            420                 425                 430

Lys Leu Val Thr Asp Leu Thr Lys Val His Thr Glu Cys Cys His Gly
            435                 440                 445

Asp Leu Leu Glu Cys Ala Asp Asp Arg Ala Asp Leu Ala Lys Tyr Ile
        450                 455                 460

Cys Glu Asn Gln Asp Ser Ile Ser Ser Lys Leu Lys Glu Cys Cys Glu
465                 470                 475                 480

Lys Pro Leu Leu Glu Lys Ser His Cys Ile Ala Glu Val Glu Asn Asp
                485                 490                 495

Glu Met Pro Ala Asp Leu Pro Ser Leu Ala Ala Asp Phe Val Glu Ser
            500                 505                 510

Lys Asp Val Cys Lys Asn Tyr Ala Glu Ala Lys Asp Val Phe Leu Gly
            515                 520                 525

Met Phe Leu Tyr Glu Tyr Ala Arg Arg His Pro Asp Tyr Ser Val Val
        530                 535                 540

Leu Leu Leu Arg Leu Ala Lys Thr Tyr Glu Thr Thr Leu Glu Lys Cys
545                 550                 555                 560

Cys Ala Ala Ala Asp Pro His Glu Cys Tyr Ala Lys Val Phe Asp Glu
                565                 570                 575

Phe Lys Pro Leu Val Glu Glu Pro Gln Asn Leu Ile Lys Gln Asn Cys
            580                 585                 590

Glu Leu Phe Glu Gln Leu Gly Glu Tyr Lys Phe Gln Asn Ala Leu Leu
            595                 600                 605

Val Arg Tyr Thr Lys Lys Val Pro Gln Val Ser Thr Pro Thr Leu Val
        610                 615                 620

Glu Val Ser Arg Asn Leu Gly Lys Val Gly Ser Lys Cys Cys Lys His
625                 630                 635                 640

Pro Glu Ala Lys Arg Met Pro Cys Ala Glu Asp Tyr Leu Ser Val Val
                645                 650                 655

Leu Asn Gln Leu Cys Val Leu His Glu Lys Thr Pro Val Ser Asp Arg
            660                 665                 670

Val Thr Lys Cys Cys Thr Glu Ser Leu Val Asn Arg Arg Pro Cys Phe
            675                 680                 685

Ser Ala Leu Glu Val Asp Glu Thr Tyr Val Pro Lys Glu Phe Asn Ala
        690                 695                 700

Glu Thr Phe Thr Phe His Ala Asp Ile Cys Thr Leu Ser Glu Lys Glu
705                 710                 715                 720

Arg Gln Ile Lys Lys Gln Thr Ala Leu Val Glu Leu Val Lys His Lys
                725                 730                 735

Pro Lys Ala Thr Lys Glu Gln Leu Lys Ala Val Met Asp Asp Phe Ala
            740                 745                 750

Ala Phe Val Glu Lys Cys Cys Lys Ala Asp Asp Lys Glu Thr Cys Phe
            755                 760                 765

Ala Glu Glu Gly Lys Lys Leu Val Ala Ala Ser Gln Ala Ala Leu Gly
```

Leu
785

<210> SEQ ID NO 146
<211> LENGTH: 83
<212> TYPE: PRT
<213> ORGANISM: Artificial Sequence
<220> FEATURE:
<223> OTHER INFORMATION: synthetic construct

<400> SEQUENCE: 146

Ile Glu Val Lys Asp Val Thr Asp Thr Thr Ala Leu Ile Thr Trp Ser
1               5                   10                  15

Asp Asp Phe Gly Glu Tyr Val Trp Cys Glu Leu Thr Tyr Gly Ile Lys
            20                  25                  30

Asp Val Pro Gly Asp Arg Thr Thr Ile Asp Leu Trp Tyr His His Ala
        35                  40                  45

His Tyr Ser Ile Gly Asn Leu Lys Pro Asp Thr Glu Tyr Glu Val Ser
    50                  55                  60

Leu Ile Cys Arg Ser Gly Asp Met Ser Ser Asn Pro Ala Lys Glu Thr
65                  70                  75                  80

Phe Thr Thr

<210> SEQ ID NO 147
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is any of Ser, Ala, Gly, Leu, Ile, and Val

<400> SEQUENCE: 147

Gly Gly Gly Gly Xaa
1               5

<210> SEQ ID NO 148
<211> LENGTH: 5
<212> TYPE: PRT
<213> ORGANISM: Artificial Sequence
<220> FEATURE:
<223> OTHER INFORMATION: synthetic construct

<400> SEQUENCE: 148

Gly Gly Gly Gly Ser
1               5

<210> SEQ ID NO 149
<211> LENGTH: 5
<212> TYPE: PRT
<213> ORGANISM: Artificial Sequence
<220> FEATURE:
<223> OTHER INFORMATION: synthetic construct

<400> SEQUENCE: 149

Gly Gly Gly Gly Gly
1               5

<210> SEQ ID NO 150
<211> LENGTH: 5
<212> TYPE: PRT

-continued

```
<213> ORGANISM: Artificial Sequence
<220> FEATURE:
<223> OTHER INFORMATION: synthetic construct

<400> SEQUENCE: 150

Gly Gly Gly Gly Ala
1               5

<210> SEQ ID NO 151
<211> LENGTH: 8
<212> TYPE: PRT
<213> ORGANISM: Artificial Sequence
<220> FEATURE:
<223> OTHER INFORMATION: synthetic construct

<400> SEQUENCE: 151

His His His His His His His His
1               5

<210> SEQ ID NO 152
<211> LENGTH: 13
<212> TYPE: PRT
<213> ORGANISM: Artificial Sequence
<220> FEATURE:
<223> OTHER INFORMATION: synthetic construct

<400> SEQUENCE: 152

Gly Gly Gly Gly Ser His His His His His His His
1               5                   10

<210> SEQ ID NO 153
<211> LENGTH: 584
<212> TYPE: PRT
<213> ORGANISM: mus muscus

<400> SEQUENCE: 153

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Cys Ser Tyr Asp Glu His Ala Lys Leu Val Gln Glu Val Thr Asp
            35                  40                  45

Phe Ala Lys Thr Cys Val Ala Asp Glu Ser Ala Ala Asn Cys Asp Lys
        50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190
```

```
Ser Val Arg Gln Arg Met Lys Cys Ser Ser Met Gln Lys Phe Gly Glu
            195                 200                 205

Arg Ala Phe Lys Ala Trp Ala Val Ala Arg Leu Ser Gln Thr Phe Pro
        210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
        290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
        370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
        450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
        530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580

<210> SEQ ID NO 154
<211> LENGTH: 584
<212> TYPE: PRT
```

<213> ORGANISM: Artificial Sequence
<220> FEATURE:
<223> OTHER INFORMATION: synthetic construct

<400> SEQUENCE: 154

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Ser Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
```

```
                385                 390                 395                 400
Tyr Gly Phe Gln Asn Ala Ile Leu Val Arg Tyr Thr Gln Lys Ala Pro
                    405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
            435                 440                 445

Val Glu Asp Tyr Leu Ser Ala Ile Leu Asn Arg Val Cys Leu Leu His
        450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Ser Lys Asp Ala Leu Ala
            580

<210> SEQ ID NO 155
<211> LENGTH: 84
<212> TYPE: PRT
<213> ORGANISM: Artificial Sequence
<220> FEATURE:
<223> OTHER INFORMATION: synthetic construct

<400> SEQUENCE: 155

Ile Glu Val Lys Asp Val Thr Asp Thr Thr Ala Leu Ile Thr Trp His
1               5                   10                  15

Asp Ala Phe Gly Tyr Asp Phe Gly Cys Glu Leu Thr Tyr Gly Ile Lys
                20                  25                  30

Asp Val Pro Gly Asp Arg Thr Thr Ile Asp Leu Pro Asp His Phe His
            35                  40                  45

Asn Tyr Ser Ile Gly Asn Leu Lys Pro Asp Thr Glu Tyr Glu Val Ser
        50                  55                  60

Leu Ile Cys Ala Asn Asp His Gly Phe Asp Ser Asn Pro Ala Lys Glu
65                  70                  75                  80

Thr Phe Thr Thr

<210> SEQ ID NO 156
<211> LENGTH: 84
<212> TYPE: PRT
<213> ORGANISM: Artificial Sequence
<220> FEATURE:
<223> OTHER INFORMATION: synthetic construct

<400> SEQUENCE: 156

Ile Glu Val Lys Asp Val Thr Asp Thr Thr Ala Leu Ile Thr Trp His
1               5                   10                  15

Asp Ala Phe Gly Tyr Asp Phe Gly Cys Glu Leu Thr Tyr Gly Ile Lys
```

```
            20                  25                  30
Asp Val Pro Gly Asp Arg Thr Thr Ile Asp Leu Pro Asp His Phe His
        35                  40                  45

Gln Tyr Ser Ile Gly Asn Leu Lys Pro Asp Thr Glu Tyr Glu Val Ser
    50                  55                  60

Leu Ile Cys Ala Asn Asp His Gly Phe Asp Ser Asn Pro Ala Lys Glu
65                  70                  75                  80

Thr Phe Thr Thr

<210> SEQ ID NO 157
<211> LENGTH: 183
<212> TYPE: PRT
<213> ORGANISM: Artificial Sequence
<220> FEATURE:
<223> OTHER INFORMATION: synthetic construct

<400> SEQUENCE: 157

Ser Gln Ile Glu Val Lys Asp Val Thr Asp Thr Thr Ala Leu Ile Thr
1               5                   10                  15

Trp His Asp Ala Phe Gly Tyr Asp Phe Gly Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Asn Pro Ala
65                  70                  75                  80

Lys Glu Thr Phe Thr Thr Gly Gly Gly Ser Arg Leu Asp Ala
            85                  90                  95

Pro Ser Gln Ile Glu Val Lys Asp Val Thr Asp Thr Thr Ala Leu Ile
            100                 105                 110

Thr Trp His Asp Ala Phe Gly Tyr Asp Phe Gly Cys Glu Leu Thr Tyr
        115                 120                 125

Gly Ile Lys Asp Val Pro Gly Asp Arg Thr Thr Ile Asp Leu Pro Asp
    130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Asn Pro
                165                 170                 175

Ala Lys Glu Thr Phe Thr Thr
            180

<210> SEQ ID NO 158
<211> LENGTH: 685
<212> TYPE: PRT
<213> ORGANISM: Artificial Sequence
<220> FEATURE:
<223> OTHER INFORMATION: synthetic construct

<400> SEQUENCE: 158

Ser Gln Ile Glu Val Lys Asp Val Thr Asp Thr Thr Ala Leu Ile Thr
1               5                   10                  15

Trp His Asp Ala Phe Gly Tyr Asp Phe Gly Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
```

-continued

```
            50                  55                  60
Val Ser Leu Ile Cys Ala Asn Asp His Gly Phe Asp Ser Asn Pro Ala
 65                  70                  75                  80

Lys Glu Thr Phe Thr Thr Gly Gly Gly Ser Gly Gly Gly Gly Gly Ser
                     85                  90                  95

Gly Gly Gly Gly Ser Glu Ala His Lys Ser Glu Ile Ala His Arg Tyr
                    100                 105                 110

Asn Asp Leu Gly Glu Gln His Phe Lys Gly Leu Val Leu Ile Ala Phe
                    115                 120                 125

Ser Gln Tyr Leu Gln Lys Ser Ser Tyr Asp Glu His Ala Lys Leu Val
                    130                 135                 140

Gln Glu Val Thr Asp Phe Ala Lys Thr Cys Val Ala Asp Glu Ser Ala
145                 150                 155                 160

Ala Asn Cys Asp Lys Ser Leu His Thr Leu Phe Gly Asp Lys Leu Cys
                    165                 170                 175

Ala Ile Pro Asn Leu Arg Glu Asn Tyr Gly Glu Leu Ala Asp Cys Cys
                    180                 185                 190

Thr Lys Gln Glu Pro Glu Arg Asn Glu Cys Phe Leu Gln His Lys Asp
                    195                 200                 205

Asp Asn Pro Ser Leu Pro Pro Phe Glu Arg Pro Glu Ala Glu Ala Met
210                 215                 220

Cys Thr Ser Phe Lys Glu Asn Pro Thr Thr Phe Met Gly His Tyr Leu
225                 230                 235                 240

His Glu Val Ala Arg Arg His Pro Tyr Phe Tyr Ala Pro Glu Leu Leu
                    245                 250                 255

Tyr Tyr Ala Glu Gln Tyr Asn Glu Ile Leu Thr Gln Cys Cys Ala Glu
                    260                 265                 270

Ala Asp Lys Glu Ser Cys Leu Thr Pro Lys Leu Asp Gly Val Lys Glu
                    275                 280                 285

Lys Ala Leu Val Ser Ser Val Arg Gln Arg Met Lys Cys Ser Ser Met
                    290                 295                 300

Gln Lys Phe Gly Glu Arg Ala Phe Lys Ala Trp Ala Val Ala Arg Leu
305                 310                 315                 320

Ser Gln Thr Phe Pro Asn Ala Asp Phe Ala Glu Ile Thr Lys Leu Ala
                    325                 330                 335

Thr Asp Leu Thr Lys Val Asn Lys Glu Cys Cys His Gly Asp Leu Leu
                    340                 345                 350

Glu Cys Ala Asp Asp Arg Ala Glu Leu Ala Lys Tyr Met Cys Glu Asn
                    355                 360                 365

Gln Ala Thr Ile Ser Ser Lys Leu Gln Thr Cys Cys Asp Lys Pro Leu
                    370                 375                 380

Leu Lys Lys Ala His Cys Leu Ser Glu Val His Asp Thr Met Pro
385                 390                 395                 400

Ala Asp Leu Pro Ala Ile Ala Ala Asp Phe Val Glu Asp Gln Glu Val
                    405                 410                 415

Cys Lys Asn Tyr Ala Glu Ala Lys Asp Val Phe Leu Gly Thr Phe Leu
                    420                 425                 430

Tyr Glu Tyr Ser Arg Arg His Pro Asp Tyr Ser Val Ser Leu Leu Leu
                    435                 440                 445

Arg Leu Ala Lys Lys Tyr Glu Ala Thr Leu Glu Lys Cys Cys Ala Glu
                    450                 455                 460

Ala Asn Pro Pro Ala Cys Tyr Gly Thr Val Leu Ala Glu Phe Gln Pro
465                 470                 475                 480
```

```
Leu Val Glu Glu Pro Lys Asn Leu Val Lys Thr Asn Cys Asp Leu Tyr
            485                 490                 495

Glu Lys Leu Gly Glu Tyr Gly Phe Gln Asn Ala Ile Leu Val Arg Tyr
            500                 505                 510

Thr Gln Lys Ala Pro Gln Val Ser Thr Pro Thr Leu Val Glu Ala Ala
            515                 520                 525

Arg Asn Leu Gly Arg Val Gly Thr Lys Cys Cys Thr Leu Pro Glu Asp
            530                 535                 540

Gln Arg Leu Pro Cys Val Glu Asp Tyr Leu Ser Ala Ile Leu Asn Arg
545                 550                 555                 560

Val Cys Leu Leu His Glu Lys Thr Pro Val Ser Glu His Val Thr Lys
            565                 570                 575

Cys Cys Ser Gly Ser Leu Val Glu Arg Arg Pro Cys Phe Ser Ala Leu
            580                 585                 590

Thr Val Asp Glu Thr Tyr Val Pro Lys Glu Phe Lys Ala Glu Thr Phe
            595                 600                 605

Thr Phe His Ser Asp Ile Cys Thr Leu Pro Glu Lys Glu Lys Gln Ile
            610                 615                 620

Lys Lys Gln Thr Ala Leu Ala Glu Leu Val Lys His Lys Pro Lys Ala
625                 630                 635                 640

Thr Ala Glu Gln Leu Lys Thr Val Met Asp Asp Phe Ala Gln Phe Leu
            645                 650                 655

Asp Thr Cys Cys Lys Ala Ala Asp Lys Asp Thr Cys Phe Ser Thr Glu
            660                 665                 670

Gly Pro Asn Leu Val Thr Arg Ser Lys Asp Ala Leu Ala
            675                 680                 685

<210> SEQ ID NO 159
<211> LENGTH: 782
<212> TYPE: PRT
<213> ORGANISM: Artificial Sequence
<220> FEATURE:
<223> OTHER INFORMATION: synthetic construct

<400> SEQUENCE: 159

Ser Gln Ile Glu Val Lys Asp Val Thr Asp Thr Thr Ala Leu Ile Thr
1               5                   10                  15

Trp His Asp Ala Phe Gly Tyr Asp Phe Gly Cys Glu Leu Thr Tyr Gly
            20                  25                  30

Ile Lys Asp Val Pro Gly Asp Arg Thr Thr Ile Asp Leu Pro Asp His
            35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Asn Pro Ala
65                  70                  75                  80

Lys Glu Thr Phe Thr Thr Thr Gly Gly Gly Ser Arg Leu Asp Ala
            85                  90                  95

Pro Ser Gln Ile Glu Val Lys Asp Val Thr Asp Thr Thr Ala Leu Ile
            100                 105                 110

Thr Trp His Asp Ala Phe Gly Tyr Asp Phe Gly Cys Glu Leu Thr Tyr
            115                 120                 125

Gly Ile Lys Asp Val Pro Gly Asp Arg Thr Thr Ile Asp Leu Pro Asp
            130                 135                 140

His Phe His Gln Tyr Ser Ile Gly Asn Leu Lys Pro Asp Thr Glu Tyr
145                 150                 155                 160
```

```
Glu Val Ser Leu Ile Cys Ala Asn Asp His Gly Phe Asp Ser Asn Pro
                165                 170                 175

Ala Lys Glu Thr Phe Thr Thr Gly Gly Gly Ser Gly Gly Gly Gly
            180                 185                 190

Ser Gly Gly Gly Ser Glu Ala His Lys Ser Glu Ile Ala His Arg
        195                 200                 205

Tyr Asn Asp Leu Gly Glu Gln His Phe Lys Gly Leu Val Leu Ile Ala
        210                 215                 220

Phe Ser Gln Tyr Leu Gln Lys Ser Ser Tyr Asp Glu His Ala Lys Leu
225                 230                 235                 240

Val Gln Glu Val Thr Asp Phe Ala Lys Thr Cys Val Ala Asp Glu Ser
                245                 250                 255

Ala Ala Asn Cys Asp Lys Ser Leu His Thr Leu Phe Gly Asp Lys Leu
                260                 265                 270

Cys Ala Ile Pro Asn Leu Arg Glu Asn Tyr Gly Glu Leu Ala Asp Cys
                275                 280                 285

Cys Thr Lys Gln Glu Pro Glu Arg Asn Glu Cys Phe Leu Gln His Lys
            290                 295                 300

Asp Asp Asn Pro Ser Leu Pro Pro Phe Glu Arg Pro Glu Ala Glu Ala
305                 310                 315                 320

Met Cys Thr Ser Phe Lys Glu Asn Pro Thr Thr Phe Met Gly His Tyr
                325                 330                 335

Leu His Glu Val Ala Arg Arg His Pro Tyr Phe Tyr Ala Pro Glu Leu
                340                 345                 350

Leu Tyr Tyr Ala Glu Gln Tyr Asn Glu Ile Leu Thr Gln Cys Cys Ala
                355                 360                 365

Glu Ala Asp Lys Glu Ser Cys Leu Thr Pro Lys Leu Asp Gly Val Lys
            370                 375                 380

Glu Lys Ala Leu Val Ser Ser Val Arg Gln Arg Met Lys Cys Ser Ser
385                 390                 395                 400

Met Gln Lys Phe Gly Glu Arg Ala Phe Lys Ala Trp Ala Val Ala Arg
                405                 410                 415

Leu Ser Gln Thr Phe Pro Asn Ala Asp Phe Ala Glu Ile Thr Lys Leu
                420                 425                 430

Ala Thr Asp Leu Thr Lys Val Asn Lys Glu Cys Cys His Gly Asp Leu
            435                 440                 445

Leu Glu Cys Ala Asp Asp Arg Ala Glu Leu Ala Lys Tyr Met Cys Glu
    450                 455                 460

Asn Gln Ala Thr Ile Ser Ser Lys Leu Gln Thr Cys Cys Asp Lys Pro
465                 470                 475                 480

Leu Leu Lys Lys Ala His Cys Leu Ser Glu Val Glu His Asp Thr Met
                485                 490                 495

Pro Ala Asp Leu Pro Ala Ile Ala Ala Asp Phe Val Glu Asp Gln Glu
                500                 505                 510

Val Cys Lys Asn Tyr Ala Glu Ala Lys Asp Val Phe Leu Gly Thr Phe
            515                 520                 525

Leu Tyr Glu Tyr Ser Arg Arg His Pro Asp Tyr Ser Val Ser Leu Leu
    530                 535                 540

Leu Arg Leu Ala Lys Lys Tyr Glu Ala Thr Leu Glu Lys Cys Cys Ala
545                 550                 555                 560

Glu Ala Asn Pro Pro Ala Cys Tyr Gly Thr Val Leu Ala Glu Phe Gln
                565                 570                 575
```

```
Pro Leu Val Glu Glu Pro Lys Asn Leu Val Lys Thr Asn Cys Asp Leu
            580                 585                 590

Tyr Glu Lys Leu Gly Glu Tyr Gly Phe Gln Asn Ala Ile Leu Val Arg
        595                 600                 605

Tyr Thr Gln Lys Ala Pro Gln Val Ser Thr Pro Thr Leu Val Glu Ala
    610                 615                 620

Ala Arg Asn Leu Gly Arg Val Gly Thr Lys Cys Cys Thr Leu Pro Glu
625                 630                 635                 640

Asp Gln Arg Leu Pro Cys Val Glu Asp Tyr Leu Ser Ala Ile Leu Asn
                645                 650                 655

Arg Val Cys Leu Leu His Glu Lys Thr Pro Val Ser Glu His Val Thr
                660                 665                 670

Lys Cys Cys Ser Gly Ser Leu Val Glu Arg Arg Pro Cys Phe Ser Ala
                675                 680                 685

Leu Thr Val Asp Glu Thr Tyr Val Pro Lys Glu Phe Lys Ala Glu Thr
            690                 695                 700

Phe Thr Phe His Ser Asp Ile Cys Thr Leu Pro Glu Lys Glu Lys Gln
705                 710                 715                 720

Ile Lys Lys Gln Thr Ala Leu Ala Glu Leu Val Lys His Lys Pro Lys
                725                 730                 735

Ala Thr Ala Glu Gln Leu Lys Thr Val Met Asp Asp Phe Ala Gln Phe
            740                 745                 750

Leu Asp Thr Cys Cys Lys Ala Ala Asp Lys Asp Thr Cys Phe Ser Thr
                755                 760                 765

Glu Gly Pro Asn Leu Val Thr Arg Ser Lys Asp Ala Leu Ala
            770                 775                 780

<210> SEQ ID NO 160
<211> LENGTH: 84
<212> TYPE: PRT
<213> ORGANISM: Artificial Sequence
<220> FEATURE:
<223> OTHER INFORMATION: synthetic construct

<400> SEQUENCE: 160

Ile Glu Val Lys Asp Val Thr Asp Thr Thr Ala Leu Ile Thr Trp His
1               5                   10                  15

Asp Pro Ser Gly Tyr Asp Phe Trp Cys Glu Leu Thr Tyr Gly Ile Lys
            20                  25                  30

Asp Val Pro Gly Asp Arg Thr Thr Ile Asp Leu Pro Asp His Phe His
        35                  40                  45

Asn Tyr Ser Ile Gly Asn Leu Lys Pro Asp Thr Glu Tyr Glu Val Ser
    50                  55                  60

Leu Ile Cys Ala Asn Asp His Gly Phe Asp Ser Tyr Pro Ala Lys Glu
65                  70                  75                  80

Thr Phe Thr Thr

<210> SEQ ID NO 161
<211> LENGTH: 84
<212> TYPE: PRT
<213> ORGANISM: Artificial Sequence
<220> FEATURE:
<223> OTHER INFORMATION: synthetic construct

<400> SEQUENCE: 161

Ile Glu Val Lys Asp Val Thr Asp Thr Thr Ala Leu Ile Thr Trp His
1               5                   10                  15
```

```
Asp Pro Ser Gly Tyr Asp Phe Trp Cys Glu Leu Thr Tyr Gly Ile Lys
            20                  25                  30

Asp Val Pro Gly Asp Arg Thr Thr Ile Asp Leu Pro Asp His Phe His
        35                  40                  45

Gln Tyr Ser Ile Gly Asn Leu Lys Pro Asp Thr Glu Tyr Glu Val Ser
 50                  55                  60

Leu Ile Cys Ala Asn Asp His Gly Phe Asp Ser Tyr Pro Ala Lys Glu
65                  70                  75                  80

Thr Phe Thr Thr

<210> SEQ ID NO 162
<211> LENGTH: 183
<212> TYPE: PRT
<213> ORGANISM: Artificial Sequence
<220> FEATURE:
<223> OTHER INFORMATION: synthetic construct

<400> SEQUENCE: 162

Ser Gln Ile Glu Val Lys Asp Val Thr Asp Thr Thr Ala Leu Ile Thr
1               5                   10                  15

Trp His Asp Pro Ser Gly Tyr Asp Phe Trp Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
 50                  55                  60

Val Ser Leu Ile Cys Ala Asn Asp His Gly Phe Asp Ser Tyr Pro Ala
65                  70                  75                  80

Lys Glu Thr Phe Thr Thr Thr Gly Gly Gly Ser Arg Leu Asp Ala
            85                  90                  95

Pro Ser Gln Ile Glu Val Lys Asp Val Thr Asp Thr Thr Ala Leu Ile
            100                 105                 110

Thr Trp His Asp Pro Ser Gly Tyr Asp Phe Trp Cys Glu Leu Thr Tyr
        115                 120                 125

Gly Ile Lys Asp Val Pro Gly Asp Arg Thr Thr Ile Asp Leu Pro Asp
130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Tyr Pro
                165                 170                 175

Ala Lys Glu Thr Phe Thr Thr
            180

<210> SEQ ID NO 163
<211> LENGTH: 685
<212> TYPE: PRT
<213> ORGANISM: Artificial Sequence
<220> FEATURE:
<223> OTHER INFORMATION: synthetic construct

<400> SEQUENCE: 163

Ser Gln Ile Glu Val Lys Asp Val Thr Asp Thr Thr Ala Leu Ile Thr
1               5                   10                  15

Trp His Asp Pro Ser Gly Tyr Asp Phe Trp Cys Glu Leu Thr Tyr Gly
            20                  25                  30

Ile Lys Asp Val Pro Gly Asp Arg Thr Thr Ile Asp Leu Pro Asp His
        35                  40                  45
```

-continued

```
Phe His Gln Tyr Ser Ile Gly Asn Leu Lys Pro Asp Thr Glu Tyr Glu
 50                  55                  60

Val Ser Leu Ile Cys Ala Asn Asp His Gly Phe Asp Ser Tyr Pro Ala
 65                  70                  75                  80

Lys Glu Thr Phe Thr Thr Gly Gly Gly Ser Gly Gly Gly Gly Gly Ser
                 85                  90                  95

Gly Gly Gly Gly Ser Glu Ala His Lys Ser Glu Ile Ala His Arg Tyr
            100                 105                 110

Asn Asp Leu Gly Glu Gln His Phe Lys Gly Leu Val Leu Ile Ala Phe
            115                 120                 125

Ser Gln Tyr Leu Gln Lys Ser Ser Tyr Asp Glu His Ala Lys Leu Val
130                 135                 140

Gln Glu Val Thr Asp Phe Ala Lys Thr Cys Val Ala Asp Glu Ser Ala
145                 150                 155                 160

Ala Asn Cys Asp Lys Ser Leu His Thr Leu Phe Gly Asp Lys Leu Cys
                165                 170                 175

Ala Ile Pro Asn Leu Arg Glu Asn Tyr Gly Glu Leu Ala Asp Cys Cys
            180                 185                 190

Thr Lys Gln Glu Pro Glu Arg Asn Glu Cys Phe Leu Gln His Lys Asp
            195                 200                 205

Asp Asn Pro Ser Leu Pro Pro Phe Glu Arg Pro Glu Ala Glu Ala Met
210                 215                 220

Cys Thr Ser Phe Lys Glu Asn Pro Thr Thr Phe Met Gly His Tyr Leu
225                 230                 235                 240

His Glu Val Ala Arg Arg His Pro Tyr Phe Tyr Ala Pro Glu Leu Leu
                245                 250                 255

Tyr Tyr Ala Glu Gln Tyr Asn Glu Ile Leu Thr Gln Cys Cys Ala Glu
            260                 265                 270

Ala Asp Lys Glu Ser Cys Leu Thr Pro Lys Leu Asp Gly Val Lys Glu
            275                 280                 285

Lys Ala Leu Val Ser Ser Val Arg Gln Arg Met Lys Cys Ser Ser Met
290                 295                 300

Gln Lys Phe Gly Glu Arg Ala Phe Lys Ala Trp Ala Val Ala Arg Leu
305                 310                 315                 320

Ser Gln Thr Phe Pro Asn Ala Asp Phe Ala Glu Ile Thr Lys Leu Ala
                325                 330                 335

Thr Asp Leu Thr Lys Val Asn Lys Glu Cys Cys His Gly Asp Leu Leu
            340                 345                 350

Glu Cys Ala Asp Asp Arg Ala Glu Leu Ala Lys Tyr Met Cys Glu Asn
            355                 360                 365

Gln Ala Thr Ile Ser Ser Lys Leu Gln Thr Cys Cys Asp Lys Pro Leu
370                 375                 380

Leu Lys Lys Ala His Cys Leu Ser Glu Val Glu His Asp Thr Met Pro
385                 390                 395                 400

Ala Asp Leu Pro Ala Ile Ala Ala Asp Phe Val Glu Asp Gln Glu Val
                405                 410                 415

Cys Lys Asn Tyr Ala Glu Ala Lys Asp Val Phe Leu Gly Thr Phe Leu
            420                 425                 430

Tyr Glu Tyr Ser Arg Arg His Pro Asp Tyr Ser Val Ser Leu Leu Leu
            435                 440                 445

Arg Leu Ala Lys Lys Tyr Glu Ala Thr Leu Glu Lys Cys Cys Ala Glu
450                 455                 460

Ala Asn Pro Pro Ala Cys Tyr Gly Thr Val Leu Ala Glu Phe Gln Pro
```

```
                465                 470                 475                 480
Leu Val Glu Glu Pro Lys Asn Leu Val Lys Thr Asn Cys Asp Leu Tyr
                    485                 490                 495
Glu Lys Leu Gly Glu Tyr Gly Phe Gln Asn Ala Ile Leu Val Arg Tyr
                500                 505                 510
Thr Gln Lys Ala Pro Gln Val Ser Thr Pro Thr Leu Val Glu Ala Ala
                515                 520                 525
Arg Asn Leu Gly Arg Val Gly Thr Lys Cys Cys Thr Leu Pro Glu Asp
530                 535                 540
Gln Arg Leu Pro Cys Val Glu Asp Tyr Leu Ser Ala Ile Leu Asn Arg
545                 550                 555                 560
Val Cys Leu Leu His Glu Lys Thr Pro Val Ser Glu His Val Thr Lys
                565                 570                 575
Cys Cys Ser Gly Ser Leu Val Glu Arg Arg Pro Cys Phe Ser Ala Leu
                580                 585                 590
Thr Val Asp Glu Thr Tyr Val Pro Lys Glu Phe Lys Ala Glu Thr Phe
                595                 600                 605
Thr Phe His Ser Asp Ile Cys Thr Leu Pro Glu Lys Glu Lys Gln Ile
                610                 615                 620
Lys Lys Gln Thr Ala Leu Ala Glu Leu Val Lys His Lys Pro Lys Ala
625                 630                 635                 640
Thr Ala Glu Gln Leu Lys Thr Val Met Asp Asp Phe Ala Gln Phe Leu
                645                 650                 655
Asp Thr Cys Cys Lys Ala Ala Asp Lys Asp Thr Cys Phe Ser Thr Glu
                660                 665                 670
Gly Pro Asn Leu Val Thr Arg Ser Lys Asp Ala Leu Ala
                675                 680                 685

<210> SEQ ID NO 164
<211> LENGTH: 782
<212> TYPE: PRT
<213> ORGANISM: Artificial Sequence
<220> FEATURE:
<223> OTHER INFORMATION: synthetic construct

<400> SEQUENCE: 164

Ser Gln Ile Glu Val Lys Asp Val Thr Asp Thr Thr Ala Leu Ile Thr
1               5                   10                  15
Trp His Asp Pro Ser Gly Tyr Asp Phe Trp Cys Glu Leu Thr Tyr Gly
                20                  25                  30
Ile Lys Asp Val Pro Gly Asp Arg Thr Ile Asp Leu Pro Asp His
                35                  40                  45
Phe His Gln Tyr Ser Ile Gly Asn Leu Lys Pro Asp Thr Glu Tyr Glu
            50                  55                  60
Val Ser Leu Ile Cys Ala Asn Asp His Gly Phe Asp Ser Tyr Pro Ala
65                  70                  75                  80
Lys Glu Thr Phe Thr Thr Thr Gly Gly Gly Ser Arg Leu Asp Ala
                85                  90                  95
Pro Ser Gln Ile Glu Val Lys Asp Val Thr Asp Thr Thr Ala Leu Ile
                100                 105                 110
Thr Trp His Asp Pro Ser Gly Tyr Asp Phe Trp Cys Glu Leu Thr Tyr
                115                 120                 125
Gly Ile Lys Asp Val Pro Gly Asp Arg Thr Thr Ile Asp Leu Pro Asp
                130                 135                 140
His Phe His Gln Tyr Ser Ile Gly Asn Leu Lys Pro Asp Thr Glu Tyr
```

```
            145                 150                 155                 160
Glu Val Ser Leu Ile Cys Ala Asn Asp His Gly Phe Asp Ser Tyr Pro
                165                 170                 175
Ala Lys Glu Thr Phe Thr Thr Gly Gly Gly Ser Gly Gly Gly
            180                 185                 190
Ser Gly Gly Gly Ser Glu Ala His Lys Ser Glu Ile Ala His Arg
        195                 200                 205
Tyr Asn Asp Leu Gly Glu Gln His Phe Lys Gly Leu Val Leu Ile Ala
        210                 215                 220
Phe Ser Gln Tyr Leu Gln Lys Ser Ser Tyr Asp Glu His Ala Lys Leu
225                 230                 235                 240
Val Gln Glu Val Thr Asp Phe Ala Lys Thr Cys Val Ala Asp Glu Ser
            245                 250                 255
Ala Ala Asn Cys Asp Lys Ser Leu His Thr Leu Phe Gly Asp Lys Leu
            260                 265                 270
Cys Ala Ile Pro Asn Leu Arg Glu Asn Tyr Gly Glu Leu Ala Asp Cys
        275                 280                 285
Cys Thr Lys Gln Glu Pro Glu Arg Asn Glu Cys Phe Leu Gln His Lys
        290                 295                 300
Asp Asp Asn Pro Ser Leu Pro Pro Phe Glu Arg Pro Glu Ala Glu Ala
305                 310                 315                 320
Met Cys Thr Ser Phe Lys Glu Asn Pro Thr Thr Phe Met Gly His Tyr
            325                 330                 335
Leu His Glu Val Ala Arg Arg His Pro Tyr Phe Tyr Ala Pro Glu Leu
            340                 345                 350
Leu Tyr Tyr Ala Glu Gln Tyr Asn Glu Ile Leu Thr Gln Cys Cys Ala
        355                 360                 365
Glu Ala Asp Lys Glu Ser Cys Leu Thr Pro Lys Leu Asp Gly Val Lys
        370                 375                 380
Glu Lys Ala Leu Val Ser Ser Val Arg Gln Arg Met Lys Cys Ser Ser
385                 390                 395                 400
Met Gln Lys Phe Gly Glu Arg Ala Phe Lys Ala Trp Ala Val Ala Arg
            405                 410                 415
Leu Ser Gln Thr Phe Pro Asn Ala Asp Phe Ala Glu Ile Thr Lys Leu
            420                 425                 430
Ala Thr Asp Leu Thr Lys Val Asn Lys Glu Cys Cys His Gly Asp Leu
        435                 440                 445
Leu Glu Cys Ala Asp Asp Arg Ala Glu Leu Ala Lys Tyr Met Cys Glu
        450                 455                 460
Asn Gln Ala Thr Ile Ser Ser Lys Leu Gln Thr Cys Cys Asp Lys Pro
465                 470                 475                 480
Leu Leu Lys Lys Ala His Cys Leu Ser Glu Val Glu His Asp Thr Met
            485                 490                 495
Pro Ala Asp Leu Pro Ala Ile Ala Ala Asp Phe Val Glu Asp Gln Glu
            500                 505                 510
Val Cys Lys Asn Tyr Ala Glu Ala Lys Asp Val Phe Leu Gly Thr Phe
            515                 520                 525
Leu Tyr Glu Tyr Ser Arg Arg His Pro Asp Tyr Ser Val Ser Leu Leu
            530                 535                 540
Leu Arg Leu Ala Lys Lys Tyr Glu Ala Thr Leu Glu Lys Cys Cys Ala
545                 550                 555                 560
Glu Ala Asn Pro Pro Ala Cys Tyr Gly Thr Val Leu Ala Glu Phe Gln
            565                 570                 575
```

```
Pro Leu Val Glu Glu Pro Lys Asn Leu Val Lys Thr Asn Cys Asp Leu
            580                 585                 590

Tyr Glu Lys Leu Gly Glu Tyr Gly Phe Gln Asn Ala Ile Leu Val Arg
        595                 600                 605

Tyr Thr Gln Lys Ala Pro Gln Val Ser Thr Pro Thr Leu Val Glu Ala
    610                 615                 620

Ala Arg Asn Leu Gly Arg Val Gly Thr Lys Cys Cys Thr Leu Pro Glu
625                 630                 635                 640

Asp Gln Arg Leu Pro Cys Val Glu Asp Tyr Leu Ser Ala Ile Leu Asn
                645                 650                 655

Arg Val Cys Leu Leu His Glu Lys Thr Pro Val Ser Glu His Val Thr
            660                 665                 670

Lys Cys Cys Ser Gly Ser Leu Val Glu Arg Arg Pro Cys Phe Ser Ala
        675                 680                 685

Leu Thr Val Asp Glu Thr Tyr Val Pro Lys Glu Phe Lys Ala Glu Thr
    690                 695                 700

Phe Thr Phe His Ser Asp Ile Cys Thr Leu Pro Glu Lys Glu Lys Gln
705                 710                 715                 720

Ile Lys Lys Gln Thr Ala Leu Ala Glu Leu Val Lys His Lys Pro Lys
                725                 730                 735

Ala Thr Ala Glu Gln Leu Lys Thr Val Met Asp Asp Phe Ala Gln Phe
            740                 745                 750

Leu Asp Thr Cys Cys Lys Ala Ala Asp Lys Asp Thr Cys Phe Ser Thr
        755                 760                 765

Glu Gly Pro Asn Leu Val Thr Arg Ser Lys Asp Ala Leu Ala
    770                 775                 780

<210> SEQ ID NO 165
<211> LENGTH: 86
<212> TYPE: PRT
<213> ORGANISM: Artificial Sequence
<220> FEATURE:
<223> OTHER INFORMATION: synthetic construct

<400> SEQUENCE: 165

Ile Glu Val Lys Asp Val Thr Asp Thr Thr Ala Leu Ile Thr Trp Ser
1               5                   10                  15

Pro Gly Glu Arg Ile Trp Met Phe Thr Gly Cys Glu Leu Thr Tyr Gly
            20                  25                  30

Ile Lys Asp Val Pro Gly Asp Arg Thr Thr Ile Asp Leu Thr Glu Asp
        35                  40                  45

Glu Asn Gln Tyr Ser Ile Gly Asn Leu Lys Pro Asp Thr Glu Tyr Glu
    50                  55                  60

Val Ser Leu Ile Cys Pro Asn Tyr Glu Arg Ile Ser Asn Pro Ala Lys
65                  70                  75                  80

Glu Thr Phe Thr Thr Thr
                85

<210> SEQ ID NO 166
<211> LENGTH: 784
<212> TYPE: PRT
<213> ORGANISM: Artificial Sequence
<220> FEATURE:
<223> OTHER INFORMATION: synthetic construct

<400> SEQUENCE: 166

Ser Gln Ile Glu Val Lys Asp Val Thr Asp Thr Thr Ala Leu Ile Thr
```

-continued

```
1               5                   10                  15
Trp Ser Pro Gly Glu Arg Ile Trp Met Phe Thr Gly Cys Glu Leu Thr
            20                  25                  30
Tyr Gly Ile Lys Asp Val Pro Gly Asp Arg Thr Thr Ile Asp Leu Thr
            35                  40                  45
Glu Asp Glu Asn Gln Tyr Ser Ile Gly Asn Leu Lys Pro Asp Thr Glu
            50                  55                  60
Tyr Glu Val Ser Leu Ile Cys Pro Asn Tyr Glu Arg Ile Ser Asn Pro
65                  70                  75                  80
Ala Lys Glu Thr Phe Thr Thr Thr Gly Gly Gly Ser Arg Leu Asp
            85                  90                  95
Ala Pro Ser Gln Ile Glu Val Lys Asp Val Thr Asp Thr Thr Ala Leu
            100                 105                 110
Ile Thr Trp Ser Pro Gly Glu Arg Ile Trp Met Phe Thr Gly Cys Glu
            115                 120                 125
Leu Thr Tyr Gly Ile Lys Asp Val Pro Gly Asp Arg Thr Thr Ile Asp
            130                 135                 140
Leu Thr Glu Asp Glu Asn Gln Tyr Ser Ile Gly Asn Leu Lys Pro Asp
145                 150                 155                 160
Thr Glu Tyr Glu Val Ser Leu Ile Cys Pro Asn Tyr Glu Arg Ile Ser
            165                 170                 175
Asn Pro Ala Lys Glu Thr Phe Thr Thr Gly Gly Gly Ser Gly Gly
            180                 185                 190
Gly Gly Ser Gly Gly Gly Gly Ser Glu Ala His Lys Ser Glu Ile Ala
            195                 200                 205
His Arg Tyr Asn Asp Leu Gly Glu Gln His Phe Lys Gly Leu Val Leu
            210                 215                 220
Ile Ala Phe Ser Gln Tyr Leu Gln Lys Ser Ser Tyr Asp Glu His Ala
225                 230                 235                 240
Lys Leu Val Gln Glu Val Thr Asp Phe Ala Lys Thr Cys Val Ala Asp
            245                 250                 255
Glu Ser Ala Ala Asn Cys Asp Lys Ser Leu His Thr Leu Phe Gly Asp
            260                 265                 270
Lys Leu Cys Ala Ile Pro Asn Leu Arg Glu Asn Tyr Gly Glu Leu Ala
            275                 280                 285
Asp Cys Cys Thr Lys Gln Glu Pro Glu Arg Asn Glu Cys Phe Leu Gln
            290                 295                 300
His Lys Asp Asp Asn Pro Ser Leu Pro Pro Phe Glu Arg Pro Glu Ala
305                 310                 315                 320
Glu Ala Met Cys Thr Ser Phe Lys Glu Asn Pro Thr Thr Phe Met Gly
            325                 330                 335
His Tyr Leu His Glu Val Ala Arg His Pro Tyr Phe Tyr Ala Pro
            340                 345                 350
Glu Leu Leu Tyr Tyr Ala Glu Gln Tyr Asn Glu Ile Leu Thr Gln Cys
            355                 360                 365
Cys Ala Glu Ala Asp Lys Glu Ser Cys Leu Thr Pro Lys Leu Asp Gly
            370                 375                 380
Val Lys Glu Lys Ala Leu Val Ser Ser Val Arg Gln Arg Met Lys Cys
385                 390                 395                 400
Ser Ser Met Gln Lys Phe Gly Glu Arg Ala Phe Lys Ala Trp Ala Val
            405                 410                 415
Ala Arg Leu Ser Gln Thr Phe Pro Asn Ala Asp Phe Ala Glu Ile Thr
            420                 425                 430
```

```
Lys Leu Ala Thr Asp Leu Thr Lys Val Asn Lys Glu Cys Cys His Gly
            435                 440                 445
Asp Leu Leu Glu Cys Ala Asp Asp Arg Ala Glu Leu Ala Lys Tyr Met
        450                 455                 460
Cys Glu Asn Gln Ala Thr Ile Ser Ser Lys Leu Gln Thr Cys Cys Asp
465                 470                 475                 480
Lys Pro Leu Leu Lys Ala His Cys Leu Ser Glu Val Glu His Asp
                485                 490                 495
Thr Met Pro Ala Asp Leu Pro Ala Ile Ala Ala Asp Phe Val Glu Asp
            500                 505                 510
Gln Glu Val Cys Lys Asn Tyr Ala Glu Ala Lys Asp Val Phe Leu Gly
        515                 520                 525
Thr Phe Leu Tyr Glu Tyr Ser Arg Arg His Pro Asp Tyr Ser Val Ser
    530                 535                 540
Leu Leu Leu Arg Leu Ala Lys Lys Tyr Glu Ala Thr Leu Glu Lys Cys
545                 550                 555                 560
Cys Ala Glu Ala Asn Pro Pro Ala Cys Tyr Gly Thr Val Leu Ala Glu
                565                 570                 575
Phe Gln Pro Leu Val Glu Glu Pro Lys Asn Leu Val Lys Thr Asn Cys
            580                 585                 590
Asp Leu Tyr Glu Lys Leu Gly Glu Tyr Gly Phe Gln Asn Ala Ile Leu
        595                 600                 605
Val Arg Tyr Thr Gln Lys Ala Pro Gln Val Ser Thr Pro Thr Leu Val
    610                 615                 620
Glu Ala Ala Arg Asn Leu Gly Arg Val Gly Thr Lys Cys Cys Thr Leu
625                 630                 635                 640
Pro Glu Asp Gln Arg Leu Pro Cys Val Glu Asp Tyr Leu Ser Ala Ile
                645                 650                 655
Leu Asn Arg Val Cys Leu Leu His Glu Lys Thr Pro Val Ser Glu His
            660                 665                 670
Val Thr Lys Cys Cys Ser Gly Ser Leu Val Glu Arg Arg Pro Cys Phe
        675                 680                 685
Ser Ala Leu Thr Val Asp Glu Thr Tyr Val Pro Lys Glu Phe Lys Ala
    690                 695                 700
Glu Thr Phe Thr Phe His Ser Asp Ile Cys Thr Leu Pro Glu Lys Glu
705                 710                 715                 720
Lys Gln Ile Lys Lys Gln Thr Ala Leu Ala Glu Leu Val Lys His Lys
                725                 730                 735
Pro Lys Ala Thr Ala Glu Gln Leu Lys Thr Val Met Asp Asp Phe Ala
            740                 745                 750
Gln Phe Leu Asp Thr Cys Cys Lys Ala Ala Asp Lys Asp Thr Cys Phe
        755                 760                 765
Ser Thr Glu Gly Pro Asn Leu Val Thr Arg Ser Lys Asp Ala Leu Ala
    770                 775                 780

<210> SEQ ID NO 167
<211> LENGTH: 83
<212> TYPE: PRT
<213> ORGANISM: Artificial Sequence
<220> FEATURE:
<223> OTHER INFORMATION: synthetic construct

<400> SEQUENCE: 167

Ile Glu Val Lys Asp Val Thr Asp Thr Thr Ala Leu Ile Thr Trp Ser
1               5                   10                  15
```

-continued

```
Asp Asp Phe Gly Glu Tyr Val Trp Cys Glu Leu Thr Tyr Gly Ile Lys
            20                  25                  30

Asp Val Pro Gly Asp Arg Thr Thr Ile Asp Leu Trp Tyr His His Ala
        35                  40                  45

His Tyr Ser Ile Gly Asn Leu Lys Pro Asp Thr Glu Tyr Glu Val Ser
 50                  55                  60

Leu Ile Cys Arg Ser Gly Asp Met Ser Ser Asn Pro Ala Lys Glu Thr
65                  70                  75                  80

Phe Thr Thr

<210> SEQ ID NO 168
<211> LENGTH: 83
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (16)..(16)
<223> OTHER INFORMATION: Xaa is Ser or Leu
<220> FEATURE:
<221> NAME/KEY: MISC_FEATURE
<222> LOCATION: (18)..(18)
<223> OTHER INFORMATION: Xaa is Asp or  Glu
<220> FEATURE:
<221> NAME/KEY: MISC_FEATURE
<222> LOCATION: (19)..(19)
<223> OTHER INFORMATION: Xaa is any of His, Ile, Val, Phe or Trp
<220> FEATURE:
<221> NAME/KEY: MISC_FEATURE
<222> LOCATION: (20)..(20)
<223> OTHER INFORMATION: Xaa is any of Ala, Gly, Glu or Asp
<220> FEATURE:
<221> NAME/KEY: MISC_FEATURE
<222> LOCATION: (21)..(21)
<223> OTHER INFORMATION: Xaa is any of Glu, Leu, Gln, Ser, Asp or Asn
<220> FEATURE:
<221> NAME/KEY: MISC_FEATURE
<222> LOCATION: (22)..(22)
<223> OTHER INFORMATION: Xaa is any of Phe or Tyr
<220> FEATURE:
<221> NAME/KEY: MISC_FEATURE
<222> LOCATION: (23)..(23)
<223> OTHER INFORMATION: Xaa is any of Ile, Val, His, Glu or Asp
<220> FEATURE:
<221> NAME/KEY: MISC_FEATURE
<222> LOCATION: (24)..(24)
<223> OTHER INFORMATION: Xaa is any of Gly, Trp or Val
<220> FEATURE:
<221> NAME/KEY: MISC_FEATURE
<222> LOCATION: (45)..(45)
<223> OTHER INFORMATION: Xaa is any of Trp, Phe or Tyr
<220> FEATURE:
<221> NAME/KEY: MISC_FEATURE
<222> LOCATION: (47)..(47)
<223> OTHER INFORMATION: Xaa is any of Ser, Gln, Met or His
<220> FEATURE:
<221> NAME/KEY: MISC_FEATURE
<222> LOCATION: (49)..(49)
<223> OTHER INFORMATION: Xaa is any Trp or His
<220> FEATURE:
<221> NAME/KEY: MISC_FEATURE
<222> LOCATION: (69)..(69)
<223> OTHER INFORMATION: Xaa is any of Arg or Ser

<400> SEQUENCE: 168

Ile Glu Val Lys Asp Val Thr Asp Thr Thr Ala Leu Ile Thr Trp Xaa
1               5                   10                  15

Asp Xaa Xaa Xaa Xaa Xaa Xaa Xaa Cys Glu Leu Thr Tyr Gly Ile Lys
            20                  25                  30
```

-continued

```
Asp Val Pro Gly Asp Arg Thr Thr Ile Asp Leu Trp Xaa His Xaa Ala
         35                  40                  45

Xaa Tyr Ser Ile Gly Asn Leu Lys Pro Asp Thr Glu Tyr Glu Val Ser
 50                  55                  60

Leu Ile Cys Arg Xaa Gly Asp Met Ser Ser Asn Pro Ala Lys Glu Thr
 65                  70                  75                  80

Phe Thr Thr

<210> SEQ ID NO 169
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is any of Ser or Leu
<220> FEATURE:
<221> NAME/KEY: MISC_FEATURE
<222> LOCATION: (3)..(3)
<223> OTHER INFORMATION: Xaa is any of Asp or Glu
<220> FEATURE:
<221> NAME/KEY: MISC_FEATURE
<222> LOCATION: (4)..(4)
<223> OTHER INFORMATION: Xaa is any of His, Ile, Val, Phe or Trp
<220> FEATURE:
<221> NAME/KEY: MISC_FEATURE
<222> LOCATION: (5)..(5)
<223> OTHER INFORMATION: Xaa is any of Ala, Gly, Glu or Asp
<220> FEATURE:
<221> NAME/KEY: MISC_FEATURE
<222> LOCATION: (6)..(6)
<223> OTHER INFORMATION: Xaa is any of Glu, Leu, Gln, Ser, Asp or Asn
<220> FEATURE:
<221> NAME/KEY: MISC_FEATURE
<222> LOCATION: (7)..(7)
<223> OTHER INFORMATION: Xaa is any of Phe or Tyr
<220> FEATURE:
<221> NAME/KEY: MISC_FEATURE
<222> LOCATION: (8)..(8)
<223> OTHER INFORMATION: Xaa is any of Ile, Val, His, Glu or Asp
<220> FEATURE:
<221> NAME/KEY: MISC_FEATURE
<222> LOCATION: (9)..(9)
<223> OTHER INFORMATION: Xaa is any of Gly, Trp or Val

<400> SEQUENCE: 169

Xaa Asp Xaa Xaa Xaa Xaa Xaa Xaa Xaa
 1               5

<210> SEQ ID NO 170
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is any of Trp, Phe or Tyr
<220> FEATURE:
<221> NAME/KEY: MISC_FEATURE
<222> LOCATION: (4)..(4)
<223> OTHER INFORMATION: Xaa is any of Ser, Gln, Met or His
<220> FEATURE:
<221> NAME/KEY: MISC_FEATURE
<222> LOCATION: (6)..(6)
<223> OTHER INFORMATION: Xaa is any of Trp or His

<400> SEQUENCE: 170

Trp Xaa His Xaa Ala Xaa
```

```
<210> SEQ ID NO 171
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is Arg or Ser

<400> SEQUENCE: 171

Arg Xaa Gly Asp Met Ser Ser Asn Pro Ala
1               5                   10

<210> SEQ ID NO 172
<211> LENGTH: 87
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is Lys or Glu
<220> FEATURE:
<221> NAME/KEY: MISC_FEATURE
<222> LOCATION: (16)..(16)
<223> OTHER INFORMATION: Xaa is Thr or Ile
<220> FEATURE:
<221> NAME/KEY: MISC_FEATURE
<222> LOCATION: (17)..(17)
<223> OTHER INFORMATION: Xaa is Asn or Ala
<220> FEATURE:
<221> NAME/KEY: MISC_FEATURE
<222> LOCATION: (20)..(20)
<223> OTHER INFORMATION: Xaa is any of Ser, Leu, Ala, Phe and Tyr
<220> FEATURE:
<221> NAME/KEY: MISC_FEATURE
<222> LOCATION: (21)..(21)
<223> OTHER INFORMATION: Xaa is any of Tyr, Ala, Gly, Val, Ile and Ser
<220> FEATURE:
<221> NAME/KEY: MISC_FEATURE
<222> LOCATION: (22)..(22)
<223> OTHER INFORMATION: Xaa is any of Tyr, Ser, Ala and His
<220> FEATURE:
<221> NAME/KEY: MISC_FEATURE
<222> LOCATION: (23)..(23)
<223> OTHER INFORMATION: Xaa is any of Asn, Asp, His and Tyr
<220> FEATURE:
<221> NAME/KEY: MISC_FEATURE
<222> LOCATION: (24)..(24)
<223> OTHER INFORMATION: Xaa is any of Leu, Phe, His and Tyr
<220> FEATURE:
<221> NAME/KEY: MISC_FEATURE
<222> LOCATION: (25)..(25)
<223> OTHER INFORMATION: Xaa is any of His, Pro, Ser, Leu and Asp
<220> FEATURE:
<221> NAME/KEY: MISC_FEATURE
<222> LOCATION: (26)..(26)
<223> OTHER INFORMATION: Xaa is any of Gly, Phe, His and Tyr
<220> FEATURE:
<221> NAME/KEY: MISC_FEATURE
<222> LOCATION: (30)..(30)
<223> OTHER INFORMATION: Xaa is Ala or Thr
<220> FEATURE:
<221> NAME/KEY: MISC_FEATURE
<222> LOCATION: (46)..(46)
<223> OTHER INFORMATION: Xaa is any of Ser, Asn, Glu, Arg and Asp
<220> FEATURE:
<221> NAME/KEY: MISC_FEATURE
<222> LOCATION: (47)..(47)
<223> OTHER INFORMATION: Xaa is any of Ser, Gln, Thr, Asn and Ala
<220> FEATURE:
```

```
<221> NAME/KEY: MISC_FEATURE
<222> LOCATION: (48)..(48)
<223> OTHER INFORMATION: Xaa is absent or is any of Pro, Val, Ile and
      Ala
<220> FEATURE:
<221> NAME/KEY: MISC_FEATURE
<222> LOCATION: (49)..(49)
<223> OTHER INFORMATION: Xaa is absent or is Ile
<220> FEATURE:
<221> NAME/KEY: MISC_FEATURE
<222> LOCATION: (63)..(63)
<223> OTHER INFORMATION: Xaa is Glu or Lys
<220> FEATURE:
<221> NAME/KEY: MISC_FEATURE
<222> LOCATION: (78)..(78)
<223> OTHER INFORMATION: Xaa is any of

<400> SEQUENCE: 172

Ile Glu Val Xaa Asp Val Thr Asp Thr Thr Ala Leu Ile Thr Trp Xaa
1               5                   10                  15

Xaa Arg Ser Xaa Xaa Xaa Xaa Xaa Xaa Cys Glu Leu Xaa Tyr Gly
            20                  25                  30

Ile Lys Asp Val Pro Gly Asp Arg Thr Thr Ile Asp Leu Xaa Xaa Xaa
            35                  40                  45

Xaa Tyr Val His Tyr Ser Ile Gly Asn Leu Lys Pro Asp Thr Xaa Tyr
    50                  55                  60

Glu Val Ser Leu Ile Cys Leu Thr Thr Asp Gly Thr Tyr Xaa Asn Pro
65                  70                  75                  80

Ala Lys Glu Thr Phe Thr Thr
                85

<210> SEQ ID NO 173
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is Ala or Thr

<400> SEQUENCE: 173

Cys Glu Leu Xaa Tyr Gly Ile
1               5

<210> SEQ ID NO 174
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is Lys or Glu

<400> SEQUENCE: 174

Xaa Asp Val Thr Asp Thr Thr
1               5

<210> SEQ ID NO 175
<211> LENGTH: 11
<212> TYPE: PRT
<213> ORGANISM: Artificial Sequence
<220> FEATURE:
<223> OTHER INFORMATION: synthetic construct
<220> FEATURE:
```

-continued

```
<221> NAME/KEY: MISC_FEATURE
<222> LOCATION: (1)..(1)
<223> OTHER INFORMATION: Xaa is Thr or Ile
<220> FEATURE:
<221> NAME/KEY: MISC_FEATURE
<222> LOCATION: (2)..(2)
<223> OTHER INFORMATION: Xaa is Asn or Ala
<220> FEATURE:
<221> NAME/KEY: MISC_FEATURE
<222> LOCATION: (5)..(5)
<223> OTHER INFORMATION: Xaa is any of Ser, Leu, Ala, Phe and Tyr
<220> FEATURE:
<221> NAME/KEY: MISC_FEATURE
<222> LOCATION: (6)..(6)
<223> OTHER INFORMATION: Xaa is any of Tyr, Ala, Gly, Val, Ile and Ser
<220> FEATURE:
<221> NAME/KEY: MISC_FEATURE
<222> LOCATION: (7)..(7)
<223> OTHER INFORMATION: Xaa is any of Tyr, Ser, Ala and His
<220> FEATURE:
<221> NAME/KEY: MISC_FEATURE
<222> LOCATION: (8)..(8)
<223> OTHER INFORMATION: Xaa is any of Asn, Asp, His and Tyr
<220> FEATURE:
<221> NAME/KEY: MISC_FEATURE
<222> LOCATION: (9)..(9)
<223> OTHER INFORMATION: Xaa is any of Leu, Phe, His and Tyr
<220> FEATURE:
<221> NAME/KEY: MISC_FEATURE
<222> LOCATION: (10)..(10)
<223> OTHER INFORMATION: Xaa is any of His, Pro, Ser, Leu and Asp
<220> FEATURE:
<221> NAME/KEY: MISC_FEATURE
<222> LOCATION: (11)..(11)
<223> OTHER INFORMATION: Xaa is any of Gly, Phe, His and Tyr

<400> SEQUENCE: 175

Xaa Xaa Arg Ser Xaa Xaa Xaa Xaa Xaa Xaa Xaa
1               5                   10

<210> SEQ ID NO 176
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is any of Ser, Asn, Glu, Arg and Asp
<220> FEATURE:
<221> NAME/KEY: MISC_FEATURE
<222> LOCATION: (2)..(2)
<223> OTHER INFORMATION: Xaa is any of Ser, Gln, Thr, Asn and Ala
<220> FEATURE:
<221> NAME/KEY: MISC_FEATURE
<222> LOCATION: (3)..(3)
<223> OTHER INFORMATION: Xaa is not present or is any of Pro, Val, Ile
     and Ala
<220> FEATURE:
<221> NAME/KEY: MISC_FEATURE
<222> LOCATION: (4)..(4)
<223> OTHER INFORMATION: Xaa is not present or is Ile

<400> SEQUENCE: 176

Xaa Xaa Xaa Xaa Tyr Val His
1               5

<210> SEQ ID NO 177
<211> LENGTH: 8
<212> TYPE: PRT
<213> ORGANISM: Artificial Sequence
<220> FEATURE:
<223> OTHER INFORMATION: synthetic construct
<220> FEATURE:
```

```
<221> NAME/KEY: MISC_FEATURE
<222> LOCATION: (8)..()
<223> OTHER INFORMATION: Xaa is Glu or Lys
<220> FEATURE:
<221> NAME/KEY: misc_feature
<222> LOCATION: (8)..(8)
<223> OTHER INFORMATION: Xaa can be any naturally occurring amino acid

<400> SEQUENCE: 177

Gly Asn Leu Lys Pro Asp Thr Xaa
1               5

<210> SEQ ID NO 178
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Xaa is Ser or Asn

<400> SEQUENCE: 178

Leu Thr Thr Asp Gly Thr Tyr Xaa Asn Pro Ala
1               5                   10

<210> SEQ ID NO 179
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T, and C
<220> FEATURE:
<221> NAME/KEY: misc_feature
<222> LOCATION: (22)..(22)
<223> OTHER INFORMATION: N is any of G, A, T, and C
<220> FEATURE:
<221> NAME/KEY: misc_feature
<222> LOCATION: (28)..(28)
<223> OTHER INFORMATION: N is any of G, A, T, and C
<220> FEATURE:
<221> NAME/KEY: misc_feature
<222> LOCATION: (34)..(34)
<223> OTHER INFORMATION: N is any of G, A, T, and C
<220> FEATURE:
<221> NAME/KEY: misc_feature
<222> LOCATION: (37)..(37)
<223> OTHER INFORMATION: N is any of G, A, T, and C
<220> FEATURE:
<221> NAME/KEY: misc_feature
<222> LOCATION: (40)..(40)
<223> OTHER INFORMATION: N is any of G, A, T, and C

<400> SEQUENCE: 179
accgcgctga ttacctggnh tnhtscgnht gstnhtnhtn htggctgtga actgacctat      60
ggcattaaa                                                             69

<210> SEQ ID NO 180
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
```

<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:
<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C

<400> SEQUENCE: 180
accgcgctga ttacctggnh tnhtbstnht nhtnhtnhtn htnhtnhtgg ctgtgaactg      60
acctatggca ttaaa                                                      75

<210> SEQ ID NO 181
<211> LENGTH: 78
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of A, G, T and C
<220> FEATURE:
<221> NAME/KEY: misc_feature
<222> LOCATION: (28)..(28)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C
<220> FEATURE:
<221> NAME/KEY: misc_feature
<222> LOCATION: (49)..(49)
<223> OTHER INFORMATION: N is any of A, G, T and C

<400> SEQUENCE: 181
accgcgctga ttacctggnh tvmaccgnht nhtnhtrrcr gcnhtvttnh tggctgtgaa      60
ctgacctatg gcattaaa                                                   78

<210> SEQ ID NO 182

-continued

```
<211> LENGTH: 64
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (23)..(23)
<223> OTHER INFORMATION: N is any of A, G, T and C
<220> FEATURE:
<221> NAME/KEY: misc_feature
<222> LOCATION: (26)..(26)
<223> OTHER INFORMATION: N is any of A, G, T and C
<220> FEATURE:
<221> NAME/KEY: misc_feature
<222> LOCATION: (29)..(29)
<223> OTHER INFORMATION: N is any of A, G, T and C
<220> FEATURE:
<221> NAME/KEY: misc_feature
<222> LOCATION: (32)..(32)
<223> OTHER INFORMATION: N is any of A, G, T and C
<220> FEATURE:
<221> NAME/KEY: misc_feature
<222> LOCATION: (35)..(35)
<223> OTHER INFORMATION: N is any of A, G, T and C
<220> FEATURE:
<221> NAME/KEY: misc_feature
<222> LOCATION: (38)..(38)
<223> OTHER INFORMATION: N is any of A, G, T and C

<400> SEQUENCE: 182
cgatcgcacc accatagatc tgnhtnhtnh tnhtnhtnht tatagcattg gtaacctgaa      60
accg                                                                  64

<210> SEQ ID NO 183
<211> LENGTH: 73
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C
<220> FEATURE:
<221> NAME/KEY: misc_feature
<222> LOCATION: (46)..(46)
<223> OTHER INFORMATION: N is any of A, G, T and C

<400> SEQUENCE: 183
gaatatgaag tgagcctgat ttgcnhtams nhtnhtggtn htnhtnhtkc gaaagaaacc      60
tttaccaccg gtg                                                        73

<210> SEQ ID NO 184
<211> LENGTH: 76
<212> TYPE: DNA
<213> ORGANISM: Artificial Sequence
```

```
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (37)..(37)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (46)..(46)
<223> OTHER INFORMATION: N is any of A, G, T and C

<400> SEQUENCE: 184
gaatatgaag tgagcctgat ttgcnhtams nhtnhtnhtn htrgcnhtcc ggcgaaagaa    60
acctttacca ccggtg                                                   76

<210> SEQ ID NO 185
<211> LENGTH: 79
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C

<400> SEQUENCE: 185
gaatatgaag tgagcctgat ttgcnhtams nhtnhtggtn htnhtagcaa cccggcgaaa    60 gaaacccttta ccaccggtg                                               79

<210> SEQ ID NO 186
<211> LENGTH: 57
<212> TYPE: DNA
<213> ORGANISM: Artificial Sequence
<220> FEATURE:
<223> OTHER INFORMATION: synthetic construct

<400> SEQUENCE: 186
cagatctatg gtggtgcgat cgcccggcac atctttaatg ccataggtca gttcaca      57
```

```
<210> SEQ ID NO 187
<211> LENGTH: 53
<212> TYPE: DNA
<213> ORGANISM: Artificial Sequence
<220> FEATURE:
<223> OTHER INFORMATION: synthetic construct

<400> SEQUENCE: 187
gcaaatcagg ctcacttcat attcggtatc cggtttcagg ttaccaatgc tat        53

<210> SEQ ID NO 188
<211> LENGTH: 42
<212> TYPE: DNA
<213> ORGANISM: Artificial Sequence
<220> FEATURE:
<223> OTHER INFORMATION: synthetic construct

<400> SEQUENCE: 188
cgggtcggtt ggggtaccgc caccggtggt aaaggtttct tt                    42

<210> SEQ ID NO 189
<211> LENGTH: 16
<212> TYPE: DNA
<213> ORGANISM: Artificial Sequence
<220> FEATURE:
<223> OTHER INFORMATION: synthetic construct

<400> SEQUENCE: 189
cgggtcggtt ggggta                                                 16

<210> SEQ ID NO 190
<211> LENGTH: 67
<212> TYPE: DNA
<213> ORGANISM: Artificial Sequence
<220> FEATURE:
<223> OTHER INFORMATION: synthetic construct

<400> SEQUENCE: 190
ggcccagccg gccatggccg ccattgaagt gaaagatgtg accgatacca ccgcgctgat  60
tacctgg                                                           67

<210> SEQ ID NO 191
<211> LENGTH: 73
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(24)
<223> OTHER INFORMATION: NNN encodes for all amino acids except Cys
<220> FEATURE:
<221> NAME/KEY: misc_feature
<222> LOCATION: (25)..(27)
<223> OTHER INFORMATION: NNN encodes for Ala or Pro
<220> FEATURE:
<221> NAME/KEY: misc_feature
<222> LOCATION: (28)..(30)
<223> OTHER INFORMATION: NNN encodes for all amino acids except Cys
<220> FEATURE:
<221> NAME/KEY: misc_feature
<222> LOCATION: (31)..(33)
<223> OTHER INFORMATION: NNN encodes for Ala or Gly
<220> FEATURE:
<221> NAME/KEY: misc_feature
<222> LOCATION: (34)..(36)
<223> OTHER INFORMATION: NNN encodes for all amino acids except Cys
<220> FEATURE:
<221> NAME/KEY: misc_feature
```

<222> LOCATION: (37)..(39)
<223> OTHER INFORMATION: NNN encodes for all amino acids except Cys
<220> FEATURE:
<221> NAME/KEY: misc_feature
<222> LOCATION: (40)..(42)
<223> OTHER INFORMATION: NNN encodes for all amino acids except Cys

<400> SEQUENCE: 191
accgcgctga ttacctggtc tnnnnnnnnn nnnnnnnnnn nnggctgtga actgacctat    60
ggcattaaag atg                                                      73

<210> SEQ ID NO 192
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(20)
<223> OTHER INFORMATION: each N is any of A, G, T and C
<220> FEATURE:
<221> NAME/KEY: misc_feature
<222> LOCATION: (22)..(23)
<223> OTHER INFORMATION: each N is any of A, G, T and C
<220> FEATURE:
<221> NAME/KEY: misc_feature
<222> LOCATION: (28)..(29)
<223> OTHER INFORMATION: each N is any of A, G, T and C
<220> FEATURE:
<221> NAME/KEY: misc_feature
<222> LOCATION: (34)..(35)
<223> OTHER INFORMATION: each N is any of A, G, T and C
<220> FEATURE:
<221> NAME/KEY: misc_feature
<222> LOCATION: (37)..(38)
<223> OTHER INFORMATION: each N is any of A, G, T and C
<220> FEATURE:
<221> NAME/KEY: misc_feature
<222> LOCATION: (40)..(41)
<223> OTHER INFORMATION: each N is any of A, G, T and C

<400> SEQUENCE: 192
accgcgctga ttacctggnn knnksmgnnk gstnnknnkn nkggctgtga actgacctat    60
ggcattaaa                                                           69

<210> SEQ ID NO 193
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(20)
<223> OTHER INFORMATION: each N is any of A, T, C or T
<220> FEATURE:
<221> NAME/KEY: misc_feature
<222> LOCATION: (22)..(23)
<223> OTHER INFORMATION: each N is any of G, A, C and T
<220> FEATURE:
<221> NAME/KEY: misc_feature
<222> LOCATION: (25)..(26)
<223> OTHER INFORMATION: each N is any of G, A, C and T
<220> FEATURE:
<221> NAME/KEY: misc_feature
<222> LOCATION: (28)..(29)
<223> OTHER INFORMATION: each N is any of G, A, C and T
<220> FEATURE:
<221> NAME/KEY: misc_feature
<222> LOCATION: (31)..(32)
<223> OTHER INFORMATION: each N is any of G, A, C and T
<220> FEATURE:

```
<221> NAME/KEY: misc_feature
<222> LOCATION: (34)..(35)
<223> OTHER INFORMATION: each N is any of G, A, C and T
<220> FEATURE:
<221> NAME/KEY: misc_feature
<222> LOCATION: (37)..(37)
<223> OTHER INFORMATION: N is any of G, A, C and T
<220> FEATURE:
<221> NAME/KEY: misc_feature
<222> LOCATION: (40)..(41)
<223> OTHER INFORMATION: each N is any of G, A, C and T
<220> FEATURE:
<221> NAME/KEY: misc_feature
<222> LOCATION: (43)..(44)
<223> OTHER INFORMATION: each N is any of G, A, C and T

<400> SEQUENCE: 193
accgcgctga ttacctggnn knnknnknnk nnknnknhtn nknnktgtga actgacctat      60
ggcattaaa                                                             69

<210> SEQ ID NO 194
<211> LENGTH: 76
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (34)..(36)
<223> OTHER INFORMATION: NNN encodes for all amino acids except Cys
<220> FEATURE:
<221> NAME/KEY: misc_feature
<222> LOCATION: (37)..(39)
<223> OTHER INFORMATION: NNN encodes for all amino acids except Cys
<220> FEATURE:
<221> NAME/KEY: misc_feature
<222> LOCATION: (40)..(42)
<223> OTHER INFORMATION: NNN encodes for all amino acids except Cys
<220> FEATURE:
<221> NAME/KEY: misc_feature
<222> LOCATION: (43)..(45)
<223> OTHER INFORMATION: NNN encodes for all amino acids except Cys
<220> FEATURE:
<221> NAME/KEY: misc_feature
<222> LOCATION: (46)..(49)
<223> OTHER INFORMATION: NNN encodes for all amino acids except Cys
<220> FEATURE:
<221> NAME/KEY: misc_feature
<222> LOCATION: (50)..(51)
<223> OTHER INFORMATION: NNN encodes for all amino acids except Cys

<400> SEQUENCE: 194
gatgtgccgg gcgatcgcac caccatagat ctgnnnnnnn nnnnnnnnnn ntatagcatt      60
ggtaacctga aaccgg                                                     76

<210> SEQ ID NO 195
<211> LENGTH: 23
<212> TYPE: DNA
<213> ORGANISM: Artificial Sequence
<220> FEATURE:
<223> OTHER INFORMATION: synthetic construct

<400> SEQUENCE: 195
ccaggtaatc agcgcggtgg tat                                             23

<210> SEQ ID NO 196
<211> LENGTH: 23
<212> TYPE: DNA
<213> ORGANISM: Artificial Sequence
<220> FEATURE:
<223> OTHER INFORMATION: synthetic construct
```

<400> SEQUENCE: 196
cagatctatg gtggtgcgat cgc                                                    23

<210> SEQ ID NO 197
<211> LENGTH: 29
<212> TYPE: DNA
<213> ORGANISM: Artificial Sequence
<220> FEATURE:
<223> OTHER INFORMATION: synthetic construct

<400> SEQUENCE: 197
tgtgaactga cctatggcat taaagatgt                                              29

<210> SEQ ID NO 198
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature
<222> LOCATION: (26)..(26)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:
<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (38)..(38)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C

<400> SEQUENCE: 198
accgcgctga ttacctggnh tnhtvntnht nhtnhtnhtn htnhtnhtgg ctgtgaactg            60
acctatggca ttaaa                                                            75

<210> SEQ ID NO 199
<211> LENGTH: 75
<212> TYPE: DNA

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature
<222> LOCATION: (26)..(26)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:
<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C
<220> FEATURE:
<221> NAME/KEY: misc_feature
<222> LOCATION: (49)..(49)
<223> OTHER INFORMATION: N is any of G, A, T and C

<400> SEQUENCE: 199
accgcgctga ttacctggnh tnhtvntnht nhtnhtnhtn htnhtnhtnh ttgtgaactg    60
acctatggca ttaaa                                                    75

<210> SEQ ID NO 200
<211> LENGTH: 67
<212> TYPE: DNA
<213> ORGANISM: Artificial Sequence
<220> FEATURE:
<223> OTHER INFORMATION: synthetic construct

<400> SEQUENCE: 200
ggcccagccg gccatggccg ccattgaagt ggaagatgtg accgatacca ccgcgctgat    60
tacctgg                                                             67

<210> SEQ ID NO 201
<211> LENGTH: 585
<212> TYPE: PRT
<213> ORGANISM: Artificial Sequence
<220> FEATURE:
<223> OTHER INFORMATION: synthetic construct

<400> SEQUENCE: 201

Asp Ala His Lys Ser Glu Val Ala His Arg Phe Lys Asp Leu Gly Glu
```

```
1               5                    10                   15
Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
                35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
                210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430
```

```
Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Asn His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Leu Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 202
<211> LENGTH: 683
<212> TYPE: PRT
<213> ORGANISM: Artificial Sequence
<220> FEATURE:
<223> OTHER INFORMATION: synthetic construct

<400> SEQUENCE: 202

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Ala
            20                  25                  30

Tyr Gly Ile Lys Asp Val Pro Gly Asp Arg Thr Thr Ile Asp Leu Asn
        35                  40                  45

Gln Pro Tyr Val His Tyr Ser Ile Gly Asn Leu Lys Pro Asp Thr Glu
    50                  55                  60

Tyr Glu Val Ser Leu Ile Cys Leu Thr Thr Asp Gly Thr Tyr Asn Asn
65                  70                  75                  80

Pro Ala Lys Glu Thr Phe Thr Thr Gly Gly Gly Ser Gly Gly Gly Gly
                85                  90                  95

Gly Ser Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205
```

```
Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
                260                 265                 270

Ala Ala Cys Leu Leu Pro Lys Leu Asp Glu Leu Arg Asp Glu Gly Lys
            275                 280                 285

Ala Ser Ser Ala Lys Gln Arg Leu Lys Cys Ala Ser Leu Gln Lys Phe
    290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
    355                 360                 365

Ile Ser Ser Lys Leu Lys Glu Cys Cys Glu Lys Pro Leu Leu Glu Lys
370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
                420                 425                 430

Ala Arg Arg His Pro Asp Tyr Ser Val Val Leu Leu Leu Arg Leu Ala
            435                 440                 445

Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
                500                 505                 510

Val Pro Gln Val Ser Thr Pro Thr Leu Val Glu Val Ser Arg Asn Leu
            515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
                580                 585                 590

Glu Thr Tyr Val Pro Lys Glu Phe Asn Ala Glu Thr Phe Thr Phe His
            595                 600                 605

Ala Asp Ile Cys Thr Leu Ser Glu Lys Glu Arg Gln Ile Lys Lys Gln
    610                 615                 620
```

```
Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
            645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu
        675                 680

<210> SEQ ID NO 203
<211> LENGTH: 683
<212> TYPE: PRT
<213> ORGANISM: Artificial Sequence
<220> FEATURE:
<223> OTHER INFORMATION: synthetic construct

<400> SEQUENCE: 203

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Thr
            20                  25                  30

Tyr Gly Ile Lys Asp Val Pro Gly Asp Arg Thr Thr Ile Asp Leu Asn
        35                  40                  45

Gln Pro Tyr Val His Tyr Ser Ile Gly Asn Leu Lys Pro Asp Thr Glu
    50                  55                  60

Tyr Glu Val Ser Leu Ile Cys Leu Thr Thr Asp Gly Thr Tyr Asn Asn
65                  70                  75                  80

Pro Ala Lys Glu Thr Phe Thr Thr Gly Gly Gly Gly Gly Gly Gly Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
        275                 280                 285

Ala Ser Ser Ala Lys Gln Arg Leu Lys Cys Ala Ser Leu Gln Lys Phe
    290                 295                 300
```

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
            325                 330                 335

Thr Lys Val His Thr Glu Cys Cys His Gly Asp Leu Leu Glu Cys Ala
        340                 345                 350

Asp Asp Arg Ala Asp Leu Ala Lys Tyr Ile Cys Glu Asn Gln Asp Ser
    355                 360                 365

Ile Ser Ser Lys Leu Lys Glu Cys Cys Glu Lys Pro Leu Leu Glu Lys
370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
            405                 410                 415

Tyr Ala Glu Ala Lys Asp Val Phe Leu Gly Met Phe Leu Tyr Glu Tyr
        420                 425                 430

Ala Arg Arg His Pro Asp Tyr Ser Val Val Leu Leu Leu Arg Leu Ala
    435                 440                 445

Lys Thr Tyr Glu Thr Thr Leu Glu Lys Cys Cys Ala Ala Ala Asp Pro
450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
            485                 490                 495

Gly Glu Tyr Lys Phe Gln Asn Ala Leu Leu Val Arg Tyr Thr Lys Lys
        500                 505                 510

Val Pro Gln Val Ser Thr Pro Thr Leu Val Glu Val Ser Arg Asn Leu
    515                 520                 525

Gly Lys Val Gly Ser Lys Cys Cys Lys His Pro Glu Ala Lys Arg Met
530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
            565                 570                 575

Glu Ser Leu Val Asn Arg Arg Pro Cys Phe Ser Ala Leu Glu Val Asp
        580                 585                 590

Glu Thr Tyr Val Pro Lys Glu Phe Asn Ala Glu Thr Phe Thr Phe His
    595                 600                 605

Ala Asp Ile Cys Thr Leu Ser Glu Lys Glu Arg Gln Ile Lys Lys Gln
610                 615                 620

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
            645                 650                 655

Cys Lys Ala Asp Asp Lys Glu Thr Cys Phe Ala Glu Glu Gly Lys Lys
        660                 665                 670

Leu Val Ala Ala Ser Gln Ala Ala Leu Gly Leu
    675                 680

<210> SEQ ID NO 204
<211> LENGTH: 791
<212> TYPE: PRT
<213> ORGANISM: Artificial Sequence
<220> FEATURE:
<223> OTHER INFORMATION: synthetic construct

<400> SEQUENCE: 204

```
Ser Gln Ile Glu Val Glu Asp Val Thr Asp Thr Thr Ala Leu Ile Thr
1               5                   10                  15
Trp Thr Asn Arg Ser Ser Tyr Ser Asn Leu His Gly Cys Glu Leu Ala
            20                  25                  30
Tyr Gly Ile Lys Asp Val Pro Gly Asp Arg Thr Thr Ile Asp Leu Asn
        35                  40                  45
Gln Pro Tyr Val His Tyr Ser Ile Gly Asn Leu Lys Pro Asp Thr Glu
    50                  55                  60
Tyr Glu Val Ser Leu Ile Cys Leu Thr Thr Asp Gly Thr Tyr Asn Asn
65                  70                  75                  80
Pro Ala Lys Glu Thr Phe Thr Thr Gly Gly Gly Ser Gly Gly Gly
            85                  90                  95
Gly Ser Gly Gly Gly Ser Arg Leu Asp Ala Pro Ser Gln Ile Glu
        100                 105                 110
Val Glu Asp Val Thr Asp Thr Thr Ala Leu Ile Thr Trp Thr Asn Arg
        115                 120                 125
Ser Ser Tyr Ser Asn Leu His Gly Cys Glu Leu Ala Tyr Gly Ile Lys
130                 135                 140
Asp Val Pro Gly Asp Arg Thr Thr Ile Asp Leu Asn Gln Pro Tyr Val
145                 150                 155                 160
His Tyr Ser Ile Gly Asn Leu Lys Pro Asp Thr Glu Tyr Glu Val Ser
                165                 170                 175
Leu Ile Cys Leu Thr Thr Asp Gly Thr Tyr Asn Asn Pro Ala Lys Glu
            180                 185                 190
Thr Phe Thr Thr Gly Gly Gly Ser Gly Gly Gly Gly Ser Asp Ala
        195                 200                 205
His Lys Ser Glu Val Ala His Arg Phe Lys Asp Leu Gly Glu Glu Asn
210                 215                 220
Phe Lys Ala Leu Val Leu Ile Ala Phe Ala Gln Tyr Leu Gln Gln Ser
225                 230                 235                 240
Pro Phe Glu Asp His Val Lys Leu Val Asn Glu Val Thr Glu Phe Ala
                245                 250                 255
Lys Thr Cys Val Ala Asp Glu Ser Ala Glu Asn Cys Asp Lys Ser Leu
            260                 265                 270
His Thr Leu Phe Gly Asp Lys Leu Cys Thr Val Ala Thr Leu Arg Glu
        275                 280                 285
Thr Tyr Gly Glu Met Ala Asp Cys Cys Ala Lys Gln Glu Pro Glu Arg
    290                 295                 300
Asn Glu Cys Phe Leu Gln His Lys Asp Asp Asn Pro Asn Leu Pro Arg
305                 310                 315                 320
Leu Val Arg Pro Glu Val Asp Val Met Cys Thr Ala Phe His Asp Asn
                325                 330                 335
Glu Glu Thr Phe Leu Lys Lys Tyr Leu Tyr Glu Ile Ala Arg Arg His
            340                 345                 350
Pro Tyr Phe Tyr Ala Pro Glu Leu Leu Phe Phe Ala Lys Arg Tyr Lys
        355                 360                 365
Ala Ala Phe Thr Glu Cys Cys Gln Ala Ala Asp Lys Ala Ala Cys Leu
    370                 375                 380
Leu Pro Lys Leu Asp Glu Leu Arg Asp Glu Gly Lys Ala Ser Ser Ala
385                 390                 395                 400
Lys Gln Arg Leu Lys Cys Ala Ser Leu Gln Lys Phe Gly Glu Arg Ala
```

```
                405                 410                 415
Phe Lys Ala Trp Ala Val Ala Arg Leu Ser Gln Arg Phe Pro Lys Ala
            420                 425                 430

Glu Phe Ala Glu Val Ser Lys Leu Val Thr Asp Leu Thr Lys Val His
            435                 440                 445

Thr Glu Cys Cys His Gly Asp Leu Leu Glu Cys Ala Asp Asp Arg Ala
            450                 455                 460

Asp Leu Ala Lys Tyr Ile Cys Glu Asn Gln Asp Ser Ile Ser Ser Lys
465                 470                 475                 480

Leu Lys Glu Cys Cys Glu Lys Pro Leu Leu Glu Lys Ser His Cys Ile
                485                 490                 495

Ala Glu Val Glu Asn Asp Glu Met Pro Ala Asp Leu Pro Ser Leu Ala
            500                 505                 510

Ala Asp Phe Val Glu Ser Lys Asp Val Cys Lys Asn Tyr Ala Glu Ala
            515                 520                 525

Lys Asp Val Phe Leu Gly Met Phe Leu Tyr Glu Tyr Ala Arg Arg His
530                 535                 540

Pro Asp Tyr Ser Val Val Leu Leu Leu Arg Leu Ala Lys Thr Tyr Glu
545                 550                 555                 560

Thr Thr Leu Glu Lys Cys Cys Ala Ala Ala Asp Pro His Glu Cys Tyr
                565                 570                 575

Ala Lys Val Phe Asp Glu Phe Lys Pro Leu Val Glu Glu Pro Gln Asn
            580                 585                 590

Leu Ile Lys Gln Asn Cys Glu Leu Phe Glu Gln Leu Gly Glu Tyr Lys
            595                 600                 605

Phe Gln Asn Ala Leu Leu Val Arg Tyr Thr Lys Lys Val Pro Gln Val
            610                 615                 620

Ser Thr Pro Thr Leu Val Glu Val Ser Arg Asn Leu Gly Lys Val Gly
625                 630                 635                 640

Ser Lys Cys Cys Lys His Pro Glu Ala Lys Arg Met Pro Cys Ala Glu
                645                 650                 655

Asp Tyr Leu Ser Val Val Leu Asn Gln Leu Cys Val Leu His Glu Lys
            660                 665                 670

Thr Pro Val Ser Asp Arg Val Thr Lys Cys Cys Thr Glu Ser Leu Val
            675                 680                 685

Asn Arg Arg Pro Cys Phe Ser Ala Leu Glu Val Asp Glu Thr Tyr Val
            690                 695                 700

Pro Lys Glu Phe Asn Ala Glu Thr Phe Thr Phe His Ala Asp Ile Cys
705                 710                 715                 720

Thr Leu Ser Glu Lys Glu Arg Gln Ile Lys Lys Gln Thr Ala Leu Val
                725                 730                 735

Glu Leu Val Lys His Lys Pro Lys Ala Thr Lys Glu Gln Leu Lys Ala
            740                 745                 750

Val Met Asp Asp Phe Ala Ala Phe Val Glu Lys Cys Cys Lys Ala Asp
            755                 760                 765

Asp Lys Glu Thr Cys Phe Ala Glu Glu Gly Lys Lys Leu Val Ala Ala
            770                 775                 780

Ser Gln Ala Ala Leu Gly Leu
785                 790

<210> SEQ ID NO 205
<211> LENGTH: 791
<212> TYPE: PRT
<213> ORGANISM: Artificial Sequence
```

```
<220> FEATURE:
<223> OTHER INFORMATION: synthetic construct

<400> SEQUENCE: 205

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Thr
            20                  25                  30

Tyr Gly Ile Lys Asp Val Pro Gly Asp Arg Thr Thr Ile Asp Leu Asn
        35                  40                  45

Gln Pro Tyr Val His Tyr Ser Ile Gly Asn Leu Lys Pro Asp Thr Glu
    50                  55                  60

Tyr Glu Val Ser Leu Ile Cys Leu Thr Thr Asp Gly Thr Tyr Asn Asn
65                  70                  75                  80

Pro Ala Lys Glu Thr Phe Thr Thr Gly Gly Gly Gly Gly Gly Gly Gly
                85                  90                  95

Gly Gly Gly Gly Gly Gly Gly Arg Leu Asp Ala Pro Ser Gln Ile Glu
            100                 105                 110

Val Glu Asp Val Thr Asp Thr Thr Ala Leu Ile Thr Trp Thr Asn Arg
        115                 120                 125

Ser Ser Tyr Ser Asn Leu His Gly Cys Glu Leu Ala Tyr Gly Ile Lys
    130                 135                 140

Asp Val Pro Gly Asp Arg Thr Thr Ile Asp Leu Asn Gln Pro Tyr Val
145                 150                 155                 160

His Tyr Ser Ile Gly Asn Leu Lys Pro Asp Thr Glu Tyr Glu Val Ser
                165                 170                 175

Leu Ile Cys Leu Thr Thr Asp Gly Thr Tyr Asn Asn Pro Ala Lys Glu
            180                 185                 190

Thr Phe Thr Thr Gly Gly Gly Gly Gly Gly Gly Gly Gly Gly Asp Ala
        195                 200                 205

His Lys Ser Glu Val Ala His Arg Phe Lys Asp Leu Gly Glu Glu Asn
    210                 215                 220

Phe Lys Ala Leu Val Leu Ile Ala Phe Ala Gln Tyr Leu Gln Gln Ser
225                 230                 235                 240

Pro Phe Glu Asp His Val Lys Leu Val Asn Glu Val Thr Glu Phe Ala
                245                 250                 255

Lys Thr Cys Val Ala Asp Glu Ser Ala Glu Asn Cys Asp Lys Ser Leu
            260                 265                 270

His Thr Leu Phe Gly Asp Lys Leu Cys Thr Val Ala Thr Leu Arg Glu
        275                 280                 285

Thr Tyr Gly Glu Met Ala Asp Cys Cys Ala Lys Gln Glu Pro Glu Arg
    290                 295                 300

Asn Glu Cys Phe Leu Gln His Lys Asp Asp Asn Pro Asn Leu Pro Arg
305                 310                 315                 320

Leu Val Arg Pro Glu Val Asp Val Met Cys Thr Ala Phe His Asp Asn
                325                 330                 335

Glu Glu Thr Phe Leu Lys Lys Tyr Leu Tyr Glu Ile Ala Arg Arg His
            340                 345                 350

Pro Tyr Phe Tyr Ala Pro Glu Leu Leu Phe Phe Ala Lys Arg Tyr Lys
        355                 360                 365

Ala Ala Phe Thr Glu Cys Cys Gln Ala Ala Asp Lys Ala Ala Cys Leu
    370                 375                 380

Leu Pro Lys Leu Asp Glu Leu Arg Asp Glu Gly Lys Ala Ser Ser Ala
385                 390                 395                 400
```

Lys Gln Arg Leu Lys Cys Ala Ser Leu Gln Lys Phe Gly Glu Arg Ala
                405                 410                 415

Phe Lys Ala Trp Ala Val Ala Arg Leu Ser Gln Arg Phe Pro Lys Ala
            420                 425                 430

Glu Phe Ala Glu Val Ser Lys Leu Val Thr Asp Leu Thr Lys Val His
        435                 440                 445

Thr Glu Cys Cys His Gly Asp Leu Leu Glu Cys Ala Asp Asp Arg Ala
    450                 455                 460

Asp Leu Ala Lys Tyr Ile Cys Glu Asn Gln Asp Ser Ile Ser Ser Lys
465                 470                 475                 480

Leu Lys Glu Cys Cys Glu Lys Pro Leu Leu Glu Lys Ser His Cys Ile
                485                 490                 495

Ala Glu Val Glu Asn Asp Glu Met Pro Ala Asp Leu Pro Ser Leu Ala
            500                 505                 510

Ala Asp Phe Val Glu Ser Lys Asp Val Cys Lys Asn Tyr Ala Glu Ala
        515                 520                 525

Lys Asp Val Phe Leu Gly Met Phe Leu Tyr Glu Tyr Ala Arg Arg His
    530                 535                 540

Pro Asp Tyr Ser Val Val Leu Leu Leu Arg Leu Ala Lys Thr Tyr Glu
545                 550                 555                 560

Thr Thr Leu Glu Lys Cys Cys Ala Ala Ala Asp Pro His Glu Cys Tyr
                565                 570                 575

Ala Lys Val Phe Asp Glu Phe Lys Pro Leu Val Glu Glu Pro Gln Asn
            580                 585                 590

Leu Ile Lys Gln Asn Cys Glu Leu Phe Glu Gln Leu Gly Glu Tyr Lys
        595                 600                 605

Phe Gln Asn Ala Leu Leu Val Arg Tyr Thr Lys Lys Val Pro Gln Val
    610                 615                 620

Ser Thr Pro Thr Leu Val Glu Val Ser Arg Asn Leu Gly Lys Val Gly
625                 630                 635                 640

Ser Lys Cys Cys Lys His Pro Glu Ala Lys Arg Met Pro Cys Ala Glu
                645                 650                 655

Asp Tyr Leu Ser Val Val Leu Asn Gln Leu Cys Val Leu His Glu Lys
            660                 665                 670

Thr Pro Val Ser Asp Arg Val Thr Lys Cys Cys Thr Glu Ser Leu Val
        675                 680                 685

Asn Arg Arg Pro Cys Phe Ser Ala Leu Glu Val Asp Glu Thr Tyr Val
    690                 695                 700

Pro Lys Glu Phe Asn Ala Glu Thr Phe Thr Phe His Ala Asp Ile Cys
705                 710                 715                 720

Thr Leu Ser Glu Lys Glu Arg Gln Ile Lys Lys Gln Thr Ala Leu Val
                725                 730                 735

Glu Leu Val Lys His Lys Pro Lys Ala Thr Lys Glu Gln Leu Lys Ala
            740                 745                 750

Val Met Asp Asp Phe Ala Ala Phe Val Glu Lys Cys Cys Lys Ala Asp
        755                 760                 765

Asp Lys Glu Thr Cys Phe Ala Glu Glu Gly Lys Lys Leu Val Ala Ala
    770                 775                 780

Ser Gln Ala Ala Leu Gly Leu
785                 790

<210> SEQ ID NO 206
<211> LENGTH: 190

```
<212> TYPE: PRT
<213> ORGANISM: Artificial Sequence
<220> FEATURE:
<223> OTHER INFORMATION: synthetic construct

<400> SEQUENCE: 206

Ser Gln Ile Glu Val Lys Asp Val Thr Asp Thr Thr Ala Leu Ile Thr
1               5                   10                  15

Trp Ser Asp Glu Phe Gly His Tyr Asp Gly Cys Glu Leu Thr Tyr Gly
            20                  25                  30

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
    50                  55                  60

Val Ser Leu Ile Cys Tyr Thr Asp Gln Glu Ala Gly Asn Pro Ala Lys
65                  70                  75                  80

Glu Thr Phe Thr Thr Gly Gly Gly Ser Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Glu Phe Gly His
        115                 120                 125

Tyr Asp Gly Cys Glu Leu Thr Tyr Gly Ile Lys Asp Val Pro Gly Asp
    130                 135                 140

Arg Thr Thr Ile Asp Leu Trp Trp His Ser Ala Trp Tyr Ser Ile Gly
145                 150                 155                 160

Asn Leu Lys Pro Asp Thr Glu Tyr Glu Val Ser Leu Ile Cys Tyr Thr
                165                 170                 175

Asp Gln Glu Ala Gly Asn Pro Ala Lys Glu Thr Phe Thr Thr
            180                 185                 190

<210> SEQ ID NO 207
<211> LENGTH: 680
<212> TYPE: PRT
<213> ORGANISM: Artificial Sequence
<220> FEATURE:
<223> OTHER INFORMATION: synthetic construct

<400> SEQUENCE: 207

Ser Gln Ile Glu Val Lys Asp Val Thr Asp Thr Thr Ala Leu Ile Thr
1               5                   10                  15

Trp Ser Asp Glu Phe Gly His Tyr Asp Gly Cys Glu Leu Thr Tyr Gly
            20                  25                  30

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
    50                  55                  60

Val Ser Leu Ile Cys Tyr Thr Asp Gln Glu Ala Gly Asn Pro Ala Lys
65                  70                  75                  80

Glu Thr Phe Thr Thr Gly Gly Gly Ser Gly Gly Gly Ser Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Ser Pro Phe Glu Asp His Val Lys Leu Val Asn Glu Val Thr Glu Phe
    130                 135                 140
```

```
Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
            165                 170                 175

Glu Thr Tyr Gly Glu Met Ala Asp Cys Cys Ala Lys Gln Glu Pro Glu
                180                 185                 190

Arg Asn Glu Cys Phe Leu Gln His Lys Asp Asp Asn Pro Asn Leu Pro
        195                 200                 205

Arg Leu Val Arg Pro Glu Val Asp Val Met Cys Thr Ala Phe His Asp
    210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
            245                 250                 255

Lys Ala Ala Phe Thr Glu Cys Cys Gln Ala Ala Asp Lys Ala Ala Cys
                260                 265                 270

Leu Leu Pro Lys Leu Asp Glu Leu Arg Asp Glu Gly Lys Ala Ser Ser
        275                 280                 285

Ala Lys Gln Arg Leu Lys Cys Ala Ser Leu Gln Lys Phe Gly Glu Arg
    290                 295                 300

Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
            325                 330                 335

His Thr Glu Cys Cys His Gly Asp Leu Leu Glu Cys Ala Asp Asp Arg
                340                 345                 350

Ala Asp Leu Ala Lys Tyr Ile Cys Glu Asn Gln Asp Ser Ile Ser Ser
        355                 360                 365

Lys Leu Lys Glu Cys Cys Glu Lys Pro Leu Leu Glu Lys Ser His Cys
    370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
            405                 410                 415

Ala Lys Asp Val Phe Leu Gly Met Phe Leu Tyr Glu Tyr Ala Arg Arg
                420                 425                 430

His Pro Asp Tyr Ser Val Val Leu Leu Leu Arg Leu Ala Lys Thr Tyr
        435                 440                 445

Glu Thr Thr Leu Glu Lys Cys Cys Ala Ala Ala Asp Pro His Glu Cys
    450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
            485                 490                 495

Lys Phe Gln Asn Ala Leu Leu Val Arg Tyr Thr Lys Lys Val Pro Gln
                500                 505                 510

Val Ser Thr Pro Thr Leu Val Glu Val Ser Arg Asn Leu Gly Lys Val
        515                 520                 525

Gly Ser Lys Cys Cys Lys His Pro Glu Ala Lys Arg Met Pro Cys Ala
    530                 535                 540

Glu Asp Tyr Leu Ser Val Val Leu Asn Gln Leu Cys Val Leu His Glu
545                 550                 555                 560
```

```
Lys Thr Pro Val Ser Asp Arg Val Thr Lys Cys Cys Thr Glu Ser Leu
                565                 570                 575

Val Asn Arg Arg Pro Cys Phe Ser Ala Leu Glu Val Asp Glu Thr Tyr
            580                 585                 590

Val Pro Lys Glu Phe Asn Ala Glu Thr Phe Thr Phe His Ala Asp Ile
        595                 600                 605

Cys Thr Leu Ser Glu Lys Glu Arg Gln Ile Lys Lys Gln Thr Ala Leu
    610                 615                 620

Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
                645                 650                 655

Asp Asp Lys Glu Thr Cys Phe Ala Glu Glu Gly Lys Lys Leu Val Ala
            660                 665                 670

Ala Ser Gln Ala Ala Leu Gly Leu
        675                 680

<210> SEQ ID NO 208
<211> LENGTH: 785
<212> TYPE: PRT
<213> ORGANISM: Artificial Sequence
<220> FEATURE:
<223> OTHER INFORMATION: synthetic construct

<400> SEQUENCE: 208

Ser Gln Ile Glu Val Lys Asp Val Thr Asp Thr Thr Ala Leu Ile Thr
1               5                   10                  15

Trp Ser Asp Glu Phe Gly His Tyr Asp Gly Cys Glu Leu Thr Tyr Gly
            20                  25                  30

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
    50                  55                  60

Val Ser Leu Ile Cys Tyr Thr Asp Gln Glu Ala Gly Asn Pro Ala Lys
65                  70                  75                  80

Glu Thr Phe Thr Thr Gly Gly Gly Ser Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Glu Phe Gly His
        115                 120                 125

Tyr Asp Gly Cys Glu Leu Thr Tyr Gly Ile Lys Asp Val Pro Gly Asp
    130                 135                 140

Arg Thr Thr Ile Asp Leu Trp Trp His Ser Ala Trp Tyr Ser Ile Gly
145                 150                 155                 160

Asn Leu Lys Pro Asp Thr Glu Tyr Glu Val Ser Leu Ile Cys Tyr Thr
                165                 170                 175

Asp Gln Glu Ala Gly Asn Pro Ala Lys Glu Thr Phe Thr Thr Gly Gly
            180                 185                 190

Gly Gly Ser Gly Gly Gly Gly Ser Asp Ala His Lys Ser Glu Val Ala
        195                 200                 205

His Arg Phe Lys Asp Leu Gly Glu Glu Asn Phe Lys Ala Leu Val Leu
    210                 215                 220

Ile Ala Phe Ala Gln Tyr Leu Gln Gln Ser Pro Phe Glu Asp His Val
225                 230                 235                 240
```

-continued

```
Lys Leu Val Asn Glu Val Thr Glu Phe Ala Lys Thr Cys Val Ala Asp
                245                 250                 255
Glu Ser Ala Glu Asn Cys Asp Lys Ser Leu His Thr Leu Phe Gly Asp
            260                 265                 270
Lys Leu Cys Thr Val Ala Thr Leu Arg Glu Thr Tyr Gly Glu Met Ala
        275                 280                 285
Asp Cys Cys Ala Lys Gln Glu Pro Glu Arg Asn Glu Cys Phe Leu Gln
    290                 295                 300
His Lys Asp Asp Asn Pro Asn Leu Pro Arg Leu Val Arg Pro Glu Val
305                 310                 315                 320
Asp Val Met Cys Thr Ala Phe His Asp Asn Glu Glu Thr Phe Leu Lys
                325                 330                 335
Lys Tyr Leu Tyr Glu Ile Ala Arg Arg His Pro Tyr Phe Tyr Ala Pro
            340                 345                 350
Glu Leu Leu Phe Phe Ala Lys Arg Tyr Lys Ala Ala Phe Thr Glu Cys
        355                 360                 365
Cys Gln Ala Ala Asp Lys Ala Ala Cys Leu Leu Pro Lys Leu Asp Glu
    370                 375                 380
Leu Arg Asp Glu Gly Lys Ala Ser Ser Ala Lys Gln Arg Leu Lys Cys
385                 390                 395                 400
Ala Ser Leu Gln Lys Phe Gly Glu Arg Ala Phe Lys Ala Trp Ala Val
                405                 410                 415
Ala Arg Leu Ser Gln Arg Phe Pro Lys Ala Glu Phe Ala Glu Val Ser
            420                 425                 430
Lys Leu Val Thr Asp Leu Thr Lys Val His Thr Glu Cys Cys His Gly
        435                 440                 445
Asp Leu Leu Glu Cys Ala Asp Asp Arg Ala Asp Leu Ala Lys Tyr Ile
    450                 455                 460
Cys Glu Asn Gln Asp Ser Ile Ser Ser Lys Leu Lys Glu Cys Cys Glu
465                 470                 475                 480
Lys Pro Leu Leu Glu Lys Ser His Cys Ile Ala Glu Val Glu Asn Asp
                485                 490                 495
Glu Met Pro Ala Asp Leu Pro Ser Leu Ala Ala Asp Phe Val Glu Ser
            500                 505                 510
Lys Asp Val Cys Lys Asn Tyr Ala Glu Ala Lys Asp Val Phe Leu Gly
        515                 520                 525
Met Phe Leu Tyr Glu Tyr Ala Arg Arg His Pro Asp Tyr Ser Val Val
    530                 535                 540
Leu Leu Leu Arg Leu Ala Lys Thr Tyr Glu Thr Thr Leu Glu Lys Cys
545                 550                 555                 560
Cys Ala Ala Ala Asp Pro His Glu Cys Tyr Ala Lys Val Phe Asp Glu
                565                 570                 575
Phe Lys Pro Leu Val Glu Glu Pro Gln Asn Leu Ile Lys Gln Asn Cys
            580                 585                 590
Glu Leu Phe Glu Gln Leu Gly Glu Tyr Lys Phe Gln Asn Ala Leu Leu
        595                 600                 605
Val Arg Tyr Thr Lys Lys Val Pro Gln Val Ser Thr Pro Thr Leu Val
    610                 615                 620
Glu Val Ser Arg Asn Leu Gly Lys Val Gly Ser Lys Cys Cys Lys His
625                 630                 635                 640
Pro Glu Ala Lys Arg Met Pro Cys Ala Glu Asp Tyr Leu Ser Val Val
                645                 650                 655
Leu Asn Gln Leu Cys Val Leu His Glu Lys Thr Pro Val Ser Asp Arg
```

```
                    660                 665                 670
Val Thr Lys Cys Cys Thr Glu Ser Leu Val Asn Arg Arg Pro Cys Phe
                675                 680                 685

Ser Ala Leu Glu Val Asp Glu Thr Tyr Val Pro Lys Glu Phe Asn Ala
            690                 695                 700

Glu Thr Phe Thr Phe His Ala Asp Ile Cys Thr Leu Ser Glu Lys Glu
705                 710                 715                 720

Arg Gln Ile Lys Lys Gln Thr Ala Leu Val Glu Leu Val Lys His Lys
                725                 730                 735

Pro Lys Ala Thr Lys Glu Gln Leu Lys Ala Val Met Asp Asp Phe Ala
            740                 745                 750

Ala Phe Val Glu Lys Cys Cys Lys Ala Asp Asp Lys Glu Thr Cys Phe
            755                 760                 765

Ala Glu Glu Gly Lys Lys Leu Val Ala Ala Ser Gln Ala Ala Leu Gly
            770                 775                 780

Leu
785

<210> SEQ ID NO 209
<211> LENGTH: 190
<212> TYPE: PRT
<213> ORGANISM: Artificial Sequence
<220> FEATURE:
<223> OTHER INFORMATION: synthetic construct

<400> SEQUENCE: 209

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
        35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Ser Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Asp Phe Gly Glu
            115                 120                 125

Tyr Val Trp Cys Glu Leu Thr Tyr Gly Ile Lys Asp Val Pro Gly Asp
        130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
                165                 170                 175

Gly Asp Met Ser Ser Asn Pro Ala Lys Glu Thr Phe Thr Thr
            180                 185                 190

<210> SEQ ID NO 210
<211> LENGTH: 26
<212> TYPE: PRT
<213> ORGANISM: Artificial Sequence
<220> FEATURE:
<223> OTHER INFORMATION: synthetic construct
```

```
<400> SEQUENCE: 210

Met Thr Asn Ile Thr Lys Arg Ser Leu Val Ala Ala Gly Val Leu Ala
1               5                   10                  15

Ala Leu Met Ala Gly Asn Val Ala Met Ala
            20                  25
```